US007048930B2

(12) United States Patent
Bosman et al.

(10) Patent No.: US 7,048,930 B2
(45) Date of Patent: May 23, 2006

(54) EXPRESSION OF CORE-GLYCOSYLATED HCV ENVELOPE PROTEINS IN YEAST

(75) Inventors: Fons Bosman, Opwijk (BE); Erik Depla, Destelbergen (BE); Geert Deschamps, Aalter (BE); Erwin Sablon, Merchtem (BE); Isabelle Samson, Heule (BE); Annie Van Broekhoven, Berchem (BE); Joost Haelewyn, Ghent (BE)

(73) Assignee: Innogenetics N.V., Ghent (BE)

( * ) Notice: Subject to any disclaimer, the term of this patent is extended or adjusted under 35 U.S.C. 154(b) by 277 days.

(21) Appl. No.: 10/128,578

(22) Filed: Apr. 24, 2002

(65) Prior Publication Data

US 2003/0211597 A1 Nov. 13, 2003

Related U.S. Application Data

(60) Provisional application No. 60/305,604, filed on Jul. 17, 2001.

(30) Foreign Application Priority Data

Apr. 24, 2001 (EP) .................................. 01870088

(51) Int. Cl.
*A61K 39/29* (2006.01)
*C12N 15/51* (2006.01)
*C12N 7/06* (2006.01)
*C12N 7/00* (2006.01)
*C12Q 1/70* (2006.01)

(52) U.S. Cl. .............................. 424/189.1; 424/228.1; 424/193.1; 424/194.1; 424/196.11; 435/5; 435/69.3; 435/235.1; 435/238; 435/239; 530/404; 530/412; 530/415; 530/422

(58) Field of Classification Search ............ 435/235.1, 435/5, 69.3, 238, 239; 424/186.1, 189.1, 424/193.1, 194.1, 196.11, 228.1; 530/412, 530/404, 415, 422

See application file for complete search history.

(56) References Cited

U.S. PATENT DOCUMENTS

| | | | | |
|---|---|---|---|---|
| 5,135,854 A | | 8/1992 | Mackay et al. | |
| 6,150,134 A | * | 11/2000 | Maertens et al. | 435/69.3 |
| 6,245,503 B1 | * | 6/2001 | Maertens et al. | 435/5 |
| 6,613,333 B1 | | 9/2003 | Leroux-Roels et al. | |
| 2002/0182706 A1 | * | 12/2002 | Maertens et al. | 435/239 |
| 2003/0036110 A1 | * | 2/2003 | Maertens et al. | 435/69.1 |
| 2003/0108561 A1 | * | 6/2003 | Bosman et al. | 424/186.1 |

FOREIGN PATENT DOCUMENTS

| | | |
|---|---|---|
| EP | 0288198 | 10/1988 |
| WO | WO 94/01132 | 1/1994 |
| WO | WO 9/5/12677 | 5/1995 |
| WO | WO 96/04385 | 2/1996 |
| WO | WO 99/54735 | 10/1999 |
| WO | WO 99/67285 | 12/1999 |
| WO | WO 01/30815 | 5/2001 |
| WO | WO 02/055548 | 7/2002 |
| WO | WO 03/051912 | 6/2003 |

OTHER PUBLICATIONS

Johnson et al (Current Opinion in Structural Biology 10:229-235, 2000).*
Kuroda et al, The Journal of Biological Chemistry, 1992, vol. 267, No. 3, issue of Jan. 25, pp. 1953-1961.
Kuroda et al, Applied Microbiology Biotechnology, 1993, 40:333-340.
Helenius, Molecular Biology of the Cell, 1994, vol. 5, 253-265, Mar.
Liang et al, Ann Intern Med, 2000, 132:296-305.
Rosa et al, PNAS, 1996, 93, pp. 1759-1763, Mar.
Ralston et al, J. Virology, 1993, No. pp. 6753-6761, vol. 67, No. 11.
Fransca et al, The Journal of Immunology, 1999, 163: 650-658.
Lechmann et al, Hepatology, 1996, 24:790-795.
Klenerman et al, Science, 2000, vol. 289, Sep. 22, p. 2003a.
Mustilli et al, Res Microbiol, 1999, 150 (1999) 179-187.
Diminsky etal, Vaccine, 1997, Apr.-May; 15(6-7):637-47 (Abstract only).
Sarobe, Journal of Virology, 2003, p. 10862-10871, vol. 77, No. 20.
Choo et al, PNAS, 1994, pp. 1294-1298.
Ghany, Hepatology, 2003, 38, 1092-1094.
Lerous-Roels et al, Hepatology, 2003, 34, 449A.
Nevens et al, Hepatology, 2003, 38, 1289-1296.
Pawlotsky, Hepatology, 2003, 39, 554-567.
Forns, J. Hepatol, 2002, 37, 684-695.
Major, J. Virology, 2002, 76, 6586-6595.
Bassett, Hepatology, 2001, 33, 1479-1487.
Weiner, J. Virology, 2001,75, 7142-7148.
Mehta, Lancet, 2002, 359, 1478-1483.
Herscovics, FASEB, 1993, 7, 540-550.
Botarelli et al, Gastroenterology, 1993, 104:580-587.
Houghton et al, Prospects for Prophylactic and Therapeutic Hepatitis C Virus Vaccines, 1995, pp. 237-243.

* cited by examiner

*Primary Examiner*—Mary E. Mosher
(74) *Attorney, Agent, or Firm*—Nixon & Vanderhye P.C.

(57) ABSTRACT

The present invention relates to the general field of recombinant protein expression, purification of recombinant proteins, diagnosis of HCV infection, prophylactic treatment against HCV infection and to the prognosing/monitoring of the clinical efficiency of treatment of an individual with chronic hepatitis, or the prognosing/monitoring of the natural disease. In particular, the present invention relates to the use of yeast, i.e. *Hansenula* or *Saccharomyces* glycosylation minus strains, for the efficient expression of HCV envelope proteins that are core-glycosylated, purification methods for these proteins, and the use in various applications, such as the use in diagnosis, prophylaxis or therapy of HCV envelope proteins purified according to the present invention.

34 Claims, 54 Drawing Sheets

BspLU11I

Ecl136II
SacI
MunI
BsgI
NaeI
NgoMIV
BsaAI

BclI

SpeI

E1

CL pUC18-FMD-CL-E1 (p57-7)
4234 bps

FMD-P

DsaI
SacII
EcoRV
XcmI
ApaI
PspOMI

PsiI

PshAI ampR

XmnI

AatII
EcoO109I

BstAPI
NdeI

BseRI
HincII
SalI
SphI
HindIII

A

B

EXPRESSION OF CORE-GLYCOSYLATED HCV ENVELOPE PROTEINS IN YEAST

This application claims the benefit of Provisional Application No. 60/305,604, filed Jul. 17, 2001, the entire content of which is hereby incorporated by reference in this application.

FIELD OF THE INVENTION

The present invention relates to the general field of recombinant protein expression, purification of recombinant proteins, diagnosis of HCV infection, prophylactic treatment against HCV infection and to the prognosing/monitoring of the clinical efficiency of treatment of an individual with chronic hepatitis, or the prognosing/monitoring of the natural disease.

More particularly, the present invention relates to the expression of hepatitis C virus envelope proteins in yeast, expression constructs for the efficient expression of HCV envelope proteins, yeast strains for the expression of core-glycosylated viral envelope proteins, purification methods for these proteins, and the use in diagnosis, prophylaxis or therapy of HCV envelope proteins purified according to the present invention,

BACKGROUND OF THE INVENTION

Hepatitis C virus (HCV) infection is a major health problem in both developed and developing countries. It is estimated that about 1 to 5% of the world population is affected by the virus. HCV infection appears to be the most important cause of transfusion-associated hepatitis and frequently progresses to chronic liver damage. Moreover, there is evidence implicating HCV in induction of hepatocellular carcinoma. Consequently, the demand for reliable diagnostic methods and effective therapeutic agents is high. Also sensitive and specific screening methods of HCV-contaminated blood-products and improved methods to culture HCV are needed.

HCV is a positive stranded RNA virus of approximately 9,600 bases which encode a single polyprotein precursor of about 3000 amino acids. Proteolytic cleavage of the precursor coupled to co- and posttranslational modifications has been shown to result in at least three structural and six non-structural proteins. Based on sequence homology, the structural proteins have been functionally assigned as one single core protein and two envelope glycoproteins: E1 and E2. The E1 protein consists of 192 amino acids and contains 5 to 6 N-glycosylation sites, depending on the HCV genotype. The E2 protein consists of 363 to 370 amino acids and contains 9–11 N-glycosylation sites, depending on the HCV genotype (for reviews see: Major and Feinstone, 1997; Maertens and Stuyver, 1997). The E1 protein contains various variable domains (Maertens and Stuyver, 1997), while the E2 protein contains three hypervariable domains, of which the major domain is located at the N-terminus of the protein (Maertens and Stuyver, 1997). The HCV glycoproteins localize predominantly in the ER where they are modified and assembled into oligomeric complexes.

In eukaryotes, sugar residues are commonly linked to four different amino acid residues. These amino acid residues are classified as O-linked (serine, threonine, and hydroxylysine) and N-linked (asparagine). The O-linked sugars are synthesized in the Golgi or rough Endoplasmic Reticulum (ER) from nucleotide sugars. The N-linked sugars are synthesized from a common precursor, and subsequently processed. It is believed that HCV envelope proteins are N-glycosylated. It is known in the art that addition of N-linked carbohydrate chains is important for stabilization of folding intermediates and thus for efficient folding, prevention of malfolding and degradation in the endoplasmic reticulum, oligomerization, biological activity, and transport of glycoproteins (see reviews by Rose et al., 1988; Doms et al., 1993; Helenius, 1994). The tripeptide sequences Asn-X-Ser and Asn-X-Thr (in which X can be any amino acid) on polypeptides are the consensus sites for binding N-linked oligosaccharides. After addition of the N-linked oligosaccharide to the polypeptide, the oligosaccharide is further processed into the complex type (containing N-acetylglucosamine, mannose, fucose, galactose and sialic acid) or the high-mannose type (containing N-acetylglucosamine and mannose). HCV envelope proteins are believed to be of the high-mannose type. N-linked oligosaccharide processing in yeast is very different from mammalian Golgi processing. In yeast the oligosaccharide chains are elongated in the Golgi through stepwise addition of mannose, leading to elaborate high mannose structures, which do not contain sialic acid. In contrast therewith, proteins expressed in prokaryotes are never glycosylated.

To date, vaccination against disease has been proven to be the most cost effective and efficient method for controlling diseases. Despite promising results, efforts to develop an efficacious HCV vaccine, however, have been plagued with difficulties. A conditio sine qua none for vaccines is the induction of an immune response in patients. Consequently, HCV antigenic determinants should be identified, and administered to patients in a proper setting. Antigenic determinants can be divided in at least two forms, i.e. lineair and conformational epitopes. Conformational epitopes result from the folding of a molecule in a three-dimensional space, including co- and posttranslational modifications, such as glycosylation. In general, it is believed that conformational epitopes will realize the most efficacious vaccines, since they represent epitopes which resemble native-like HCV epitopes, and which may be better conserved than the actual linear amino acid sequence. Hence, the eventual degree of glycosylation of the HCV envelope proteins is of the utmost importance for generating native-like HCV antigenic determinants. However, there are seemingly insurmountable problems with culturing HCV, that result in only minute amounts of virions. In addition, there are vast problems with the expression and purification of recombinant proteins, that result in either low amounts of proteins, hyperglycosylated proteins, or proteins that are not glycosylated.

The HCV envelope proteins have been produced by recombinant techniques in *Escherichia coli*, insect cells, yeast cells and mammalian cells. However, expression in higher eukaryotes has been characterised by the difficulty of obtaining large amounts of antigens for eventual vaccine production. Expression in prokaryotes, such as *E. coli* results in HCV envelope proteins that are not glycosylated. Expression of HCV envelope proteins in yeast resulted in hyperglycosylation. As already demonstrated in WO 96/04385, the expression of HCV envelope protein E2 in *Saccharomyces cerevisiae* leads to proteins which are heavily glycosylated. This hyperglycosylation leads to shielding of protein epitopes. Although Mustilli et al. (1999) claims that expression of HCV E2 in *S. cerevisiae* results in core-glycosylation, the results of the intracellularly expressed material demonstrate that part of it is at least hyperglycosylated, while the correct processing of the remainder of this material has not been shown. The need for HCV envelope proteins derived from an intracellular source is well accepted (WO 96/04385 to Maertens et al. and Heile et al., 2000). This result is exemplified by the poor reactivity of this material with sera of chimpanzee immunized with mammalian cell culture derived E2 protein (see FIG. 5). This is further documented by Rosa and colleagues (1996) who show that immunization with yeast derived HCV envelope proteins fails to protect from challenge.

Consequently, there is a need for efficient expression systems resulting in large and cost-effective amounts of HCV envelope proteins that at the same time have a native-like glycosylation pattern.

SUMMARY OF THE INVENTION/AIMS

It thus appears that due to the absence of or inefficient expression and purification systems the production of large amounts of correctly glycosylated HCV envelope proteins is impaired. Such hyperglycosylated or non-glycosylated proteins are often not biologically active and/or have an incorrect protein structure. As a consequence, native anti-HCV antibodies fail to recognize an important subset of antigenic determinants on these proteins, see for example Houghton (1997).

The present invention overcomes these problems, since it describes and makes for the first time in yeast, large amounts HCV proteins with a native-like glycosylation pattern.

It is an aim of the present invention to use *Hansenula* or *Saccharomyces* glycosylation minus strains for HCV E1 and/or HCV E2 protein expression, or any part thereof, characterised in that said HCV E1 and/or HCV E2 proteins, or said parts thereof, are core-glycosylated.

It is another aim of the present invention to provide a method for producing core-glycosylated hepatitis C virus (HCV) envelope proteins, or any part thereof, suitable for use in an immunoassay or vaccine, which method comprising: (i) growing *Hansenula* or *Saccharomyces* glycosylation minus strains transformed with an envelope gene encoding an HCV E1 and/or HCV E2 protein, or any part thereof, in a suitable culture medium; (ii) causing expression of said HCV E1 and/or HCV E2 gene, or any part thereof; and (iii) purifying said core-glycosylated HCV E1 and/or HCV E2 protein, or any part thereof, from said cell culture, or alternatively (iii) purifying said intracellularly expressed core-glycosylated HCV E1 and/or HCV E2 protein, or any part thereof, upon lysing the transformed host cell. More particularly, it is also an aim of the present invention to provide a method as described above in which the said gene, or any part thereof, contains a CL-leader or a functional equivalent thereof.

It is an aim of the present invention to provide a method for purifying core-glycosylated hepatitis C virus (HCV) envelope proteins, or any part thereof, suitable for use in an immunoassay or vaccine, which method comprising: -i- growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids; -ii- causing expression of said HCV E1 and/or HCV E2 gene, or any part thereof; and -iii- purifying said core-glycosylated HCV E1 and/or HCV E2 protein, or any part thereof, in which said Cys-amino acids are reversibly protected by chemical and/or enzymatic means, from said culture.

It is another aim of the present invention to provide a method for purifying recombinant core-glycosylated HCV yeast proteins, or any part thereof, as described above, which includes heparin affinity chromatography.

It is an aim of the present invention to provide a method for purifying recombinant core-glycosylated HCV yeast proteins, or any part thereof, as described above, in which step said chemical means is sulfonation.

It is an aim of the present invention to provide a method for purifying recombinant core-glycosylated HCV yeast proteins, or any part thereof, as described above, in which said reversibly protection of Cys-amino acids is exchanged for an irreversible protection by chemical and/or enzymatic means, such as iodo-acetamide, NEM or Biotin-NEM or a mixture thereof.

It is also an aim of the present invention to HCV E1 and/or HCV E2 proteins, or any part thereof, according to that aims described above, for use as a medicament.

It is another aim of the present invention to use of HCV E1 and/or HCV E2 proteins, or any part thereof, as described above, for the preparation of a diagnostic kit, or for the manufacture of a vaccine/medicament against HCV infection.

It is an aim of the present invention to provide an immunoassay for detecting HCV antibody in a biological sample, which immunoassay comprises: (i) providing the HCV envelope protein, or any part thereof, according to any of the claims 1 to 10; (ii) incubating a biological sample with said HCV antibody under conditions that allow formation of HCV antibody-HCV protein complex; and (iii) determining whether said HCV antibody-HCV protein complex is formed.

It is an aim of the present invention to provide a kit for detecting HCV antibody in a biological sample, which kit comprises: providing the HCV envelope protein, or any part thereof, as described above.

It is an aim of the present invention to use the CL leader for the expression of viral envelope proteins in yeast.

It is an aim of the present invention to provide a vector suitable for transformation of a yeast and comprising an expression cassette comprising a DNA sequence encoding for a viral envelope protein preceeded by the CL leader or part thereof, as well as a host organism transformed with the vector described above.

It is another aim of the present invention to use of *Hansenula polymorpha* for the expression of viral envelope proteins which become glycosylated upon expression in this yeast species.

All the aims of the present invention are considered to have been met by the embodiments as set out below.

Lane 1: Alkylated E2-H6 before Endo H-treatment

Lane 2: Alkylated E2-H6 after Endo H-treatment.

Figure 40:
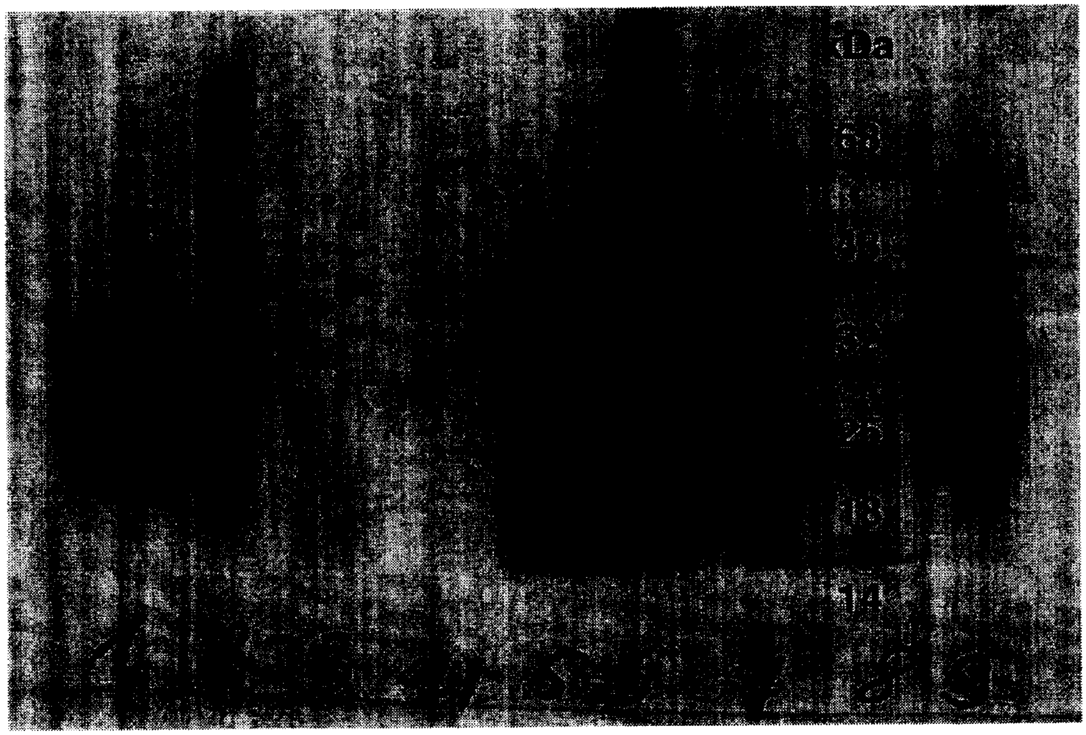

FIG. 40. Western-blot analysis of cell lysates of E1 expressed in *Saccharomyces cerevisiae*. The Western-blot was developed using the E1-specific monoclonal antibody IGH 201.

Lanes 1–4: expression product after 2, 3, 5 or 7 days expression, respectively, in a *Saccharomyces* clone transformed with pSY1YIG7E1s (SEQ ID NO:50, FIG. 28) comprising the nucleotide sequence encoding the chicken lysozyme leader peptide joined to E1-H6.

Lanes 5–7: expression product after 2, 3 or 5 days expression, respectively, in a *Saccharomyces* clone transformed with pSY1aMFE1sH6aYIG1 (SEQ ID NO:44, FIG. 22) comprising the nucleotide sequence encoding the α-mating factor leader peptide joined to E1-H6.

Lane 8: molecular weight markers with sizes as indicated.

Lane 9: purified E1s produced by HCV-recombinant vaccinia virus-infected mammalian cells.

Figure 41:
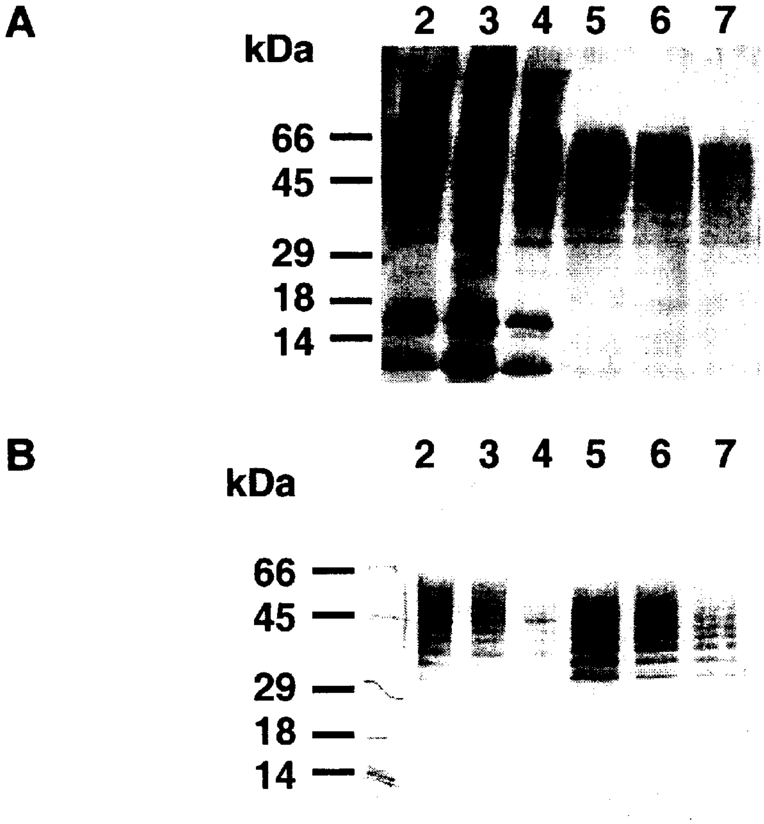

FIG. 41. Analysis of the immobilized metal ion affinity chromatography (IMAC)-purified E2-H6 protein expressed by and processed from CL-E2-H6 to E2-H6 by *H. polymorpha* (see Example 17). Proteins in different wash fractions (lanes 2 to 4) and elution fractions (lanes 5 to 7) were analyzed by reducing SDS-PAGE followed by silver staining of the gel (A, top picture) or by western blot using using a specific monoclonal antibody directed against E2 (B, bottom picture). The sizes of the molecular mass markers are indicated at the left.

Figure 42:
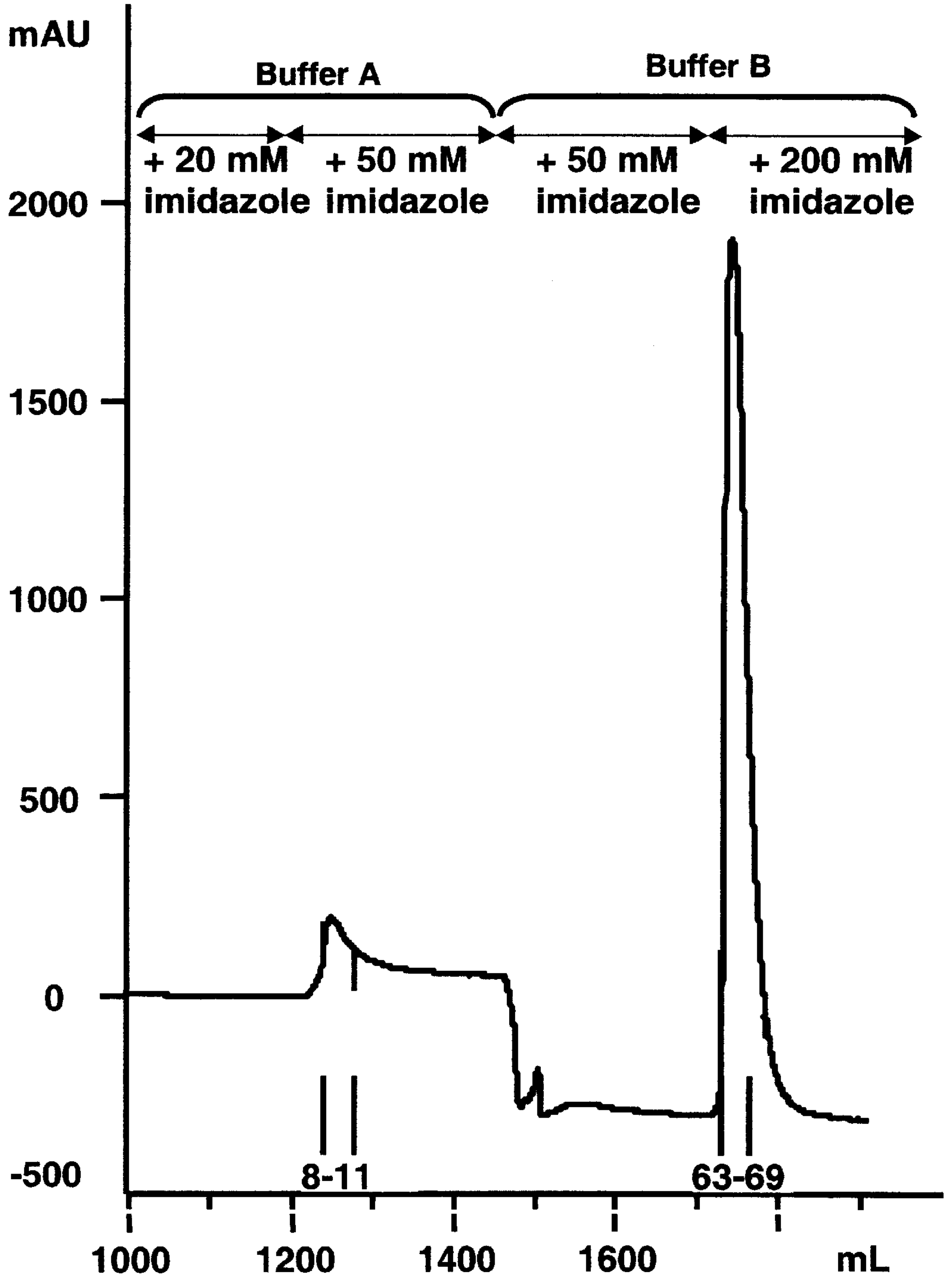

FIG. 42. Elution profile of the first IMAC chromatography step on a Ni-IDA column (Chelating Sepharose FF loaded with $Ni^{2+}$, Pharmacia) for the purification of the sulfonated H6-K-E1 protein produced by *H. polymorpha* (see Example 18). The column was equilibrated with buffer A (50 mM phosphate, 6 M GuHCl, 1% Empigen BB (v/v), pH 7.2) supplemented with 20 mM imidazole. After sample application, the column was washed sequentially with buffer A containing 20 mM and 50 mM imidazole, respectively (as indicated on chromatogram). A further washing and elution step of the His-tagged products was performed by the sequential application of buffer B (PBS, 1% empigen BB, pH 7.2) supplemented with 50 mM imidazole and 200 mM imidazole respectively (as indicated on chromatogram). Following fractions were pooled: the wash pool 1 (fractions 8 to 11, wash with 50 mM imidazole). The eluted material was collected as separate fractions 63 to 72 or an elution pool (fractions 63 to 69) was made. The Y-axis indicates absorbance given in mAU (milli absorbance units). The X-axis indicates the elution volume in mL FIG. 43. Analysis of the IMAC-purified H6-K-E1 protein (see FIG. 42) expressed by and processed from CL-H6-K-E1 to H6-K-E1 by *H. polymorpha*. Proteins in the wash pool 1 (lane 12) and elution fractions 63 to 72 (lanes 2 to 11) were analyzed by reducing SDS-PAGE followed by silver staining of the gel (A, top picture). Proteins present in the sample before IMAC (lane 2), in the flow-through pool (lane 4), in wash pool 1 (lane 5) and in the elution pool (lane 6) were analyzed by western blot using a specific monoclonal antibody directed against E1 (IGH201) (B, bottom picture; no sample was loaded in lane 3). The sizes of the molecular mass markers (lanes M) are indicated at the left.

Figure 44:
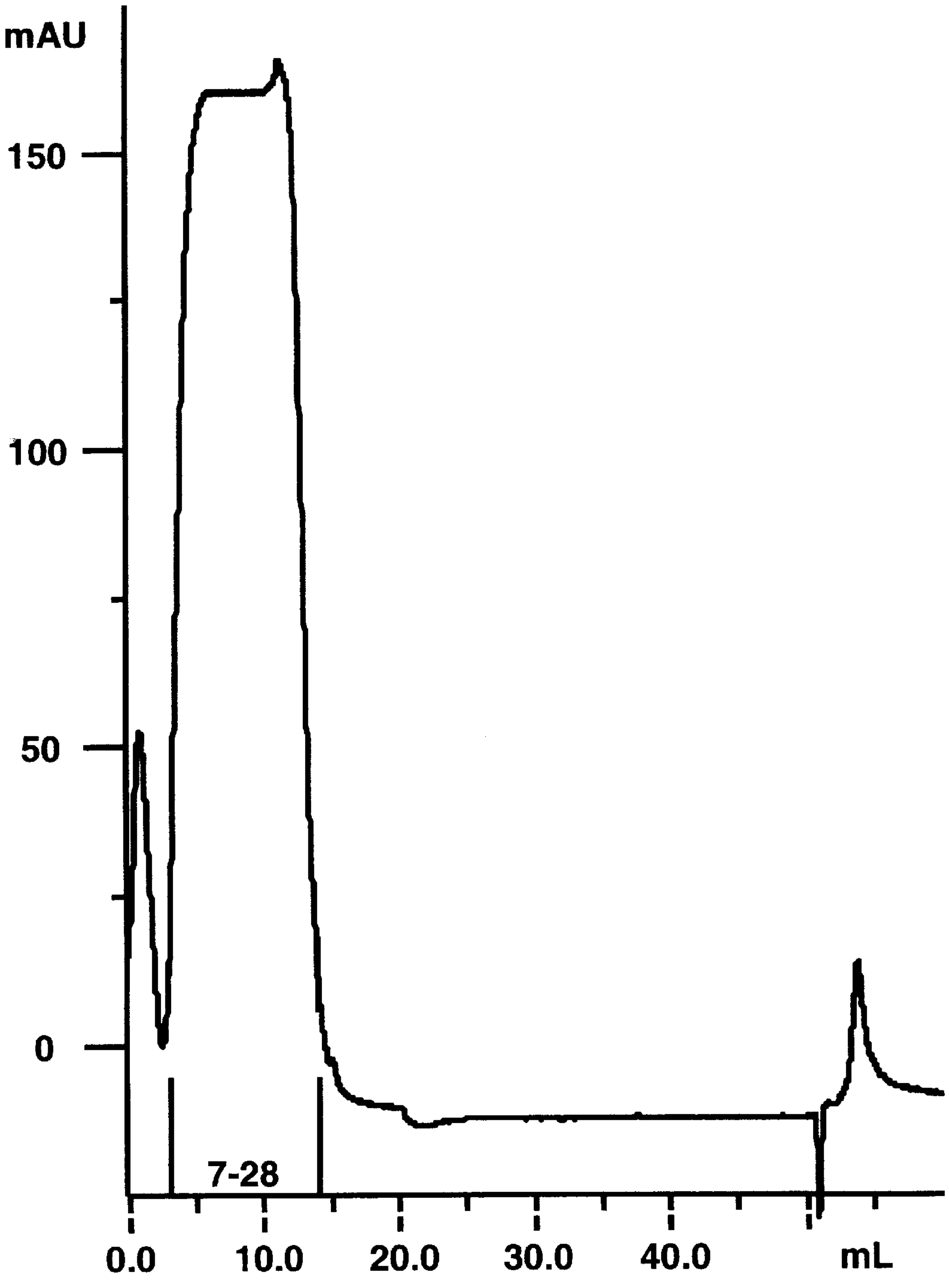

FIG. 44. Elution profile of the second IMAC chromatography step on a Ni-IDA column (Chelating Sepharose FF loaded with $Ni^{2+}$, Pharmacia) for the purification of E1 resulting from the in vitro processing of H6-K-E1 (purification: see FIG. 42) with Endo Lys-C. The flow through was collected in different fractions (1 to 40) that were screened for the presence of E1s-products. The fractions (7 to 28), containing intact E1 processed from H6-K-E1 were pooled. The Y-axis indicates absorbance given in mAU (milli absorbance units). The X-axis indicates the elution volume in mL.

Figure 45:
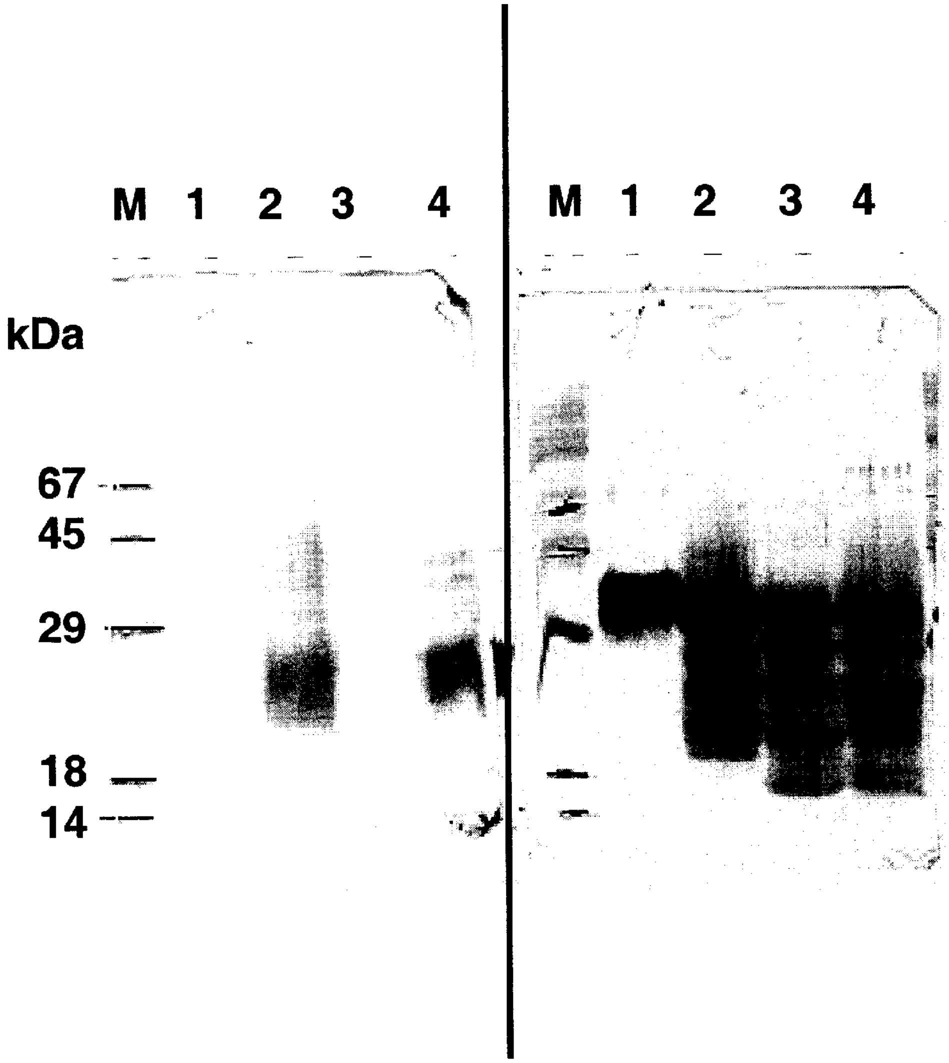

FIG. 45. Western-blot analysis indicating specific E1s proteins bands reacting with biotinylated heparin (see also Example 19). E1s preparations purified from HCV-recombinant vaccinia virus-infected mammalian cell culture or expressed by *H. polymorpha* were analyzed. The panel right from the vertical line shows a Western-blot developed with the biotinylated E1 specific monoclonal IGH 200. The panel left from the vertical line shows a Western-blot developed with biotinylated heparin. From these results it is concluded that mainly the lower-glycosylated E1s has high affinity for heparin.

Lanes M: molecular weight marker (molecular weights indicated at the left).

Lanes 1: E1s from mammalian cells and alkylated during isolation.

Lanes 2: E1s-H6 expressed by *H. polymorpha* and sulphonated during isolation.

Lanes 3: E1s-H6 expressed by *H. polymorpha* and alkylated during isolation.

Lanes 4: same material as loaded in lane 2 but treated with dithiotreitol to convert the sulphonated Cys-thiol groups to Cys-thiol.

Figure 46:
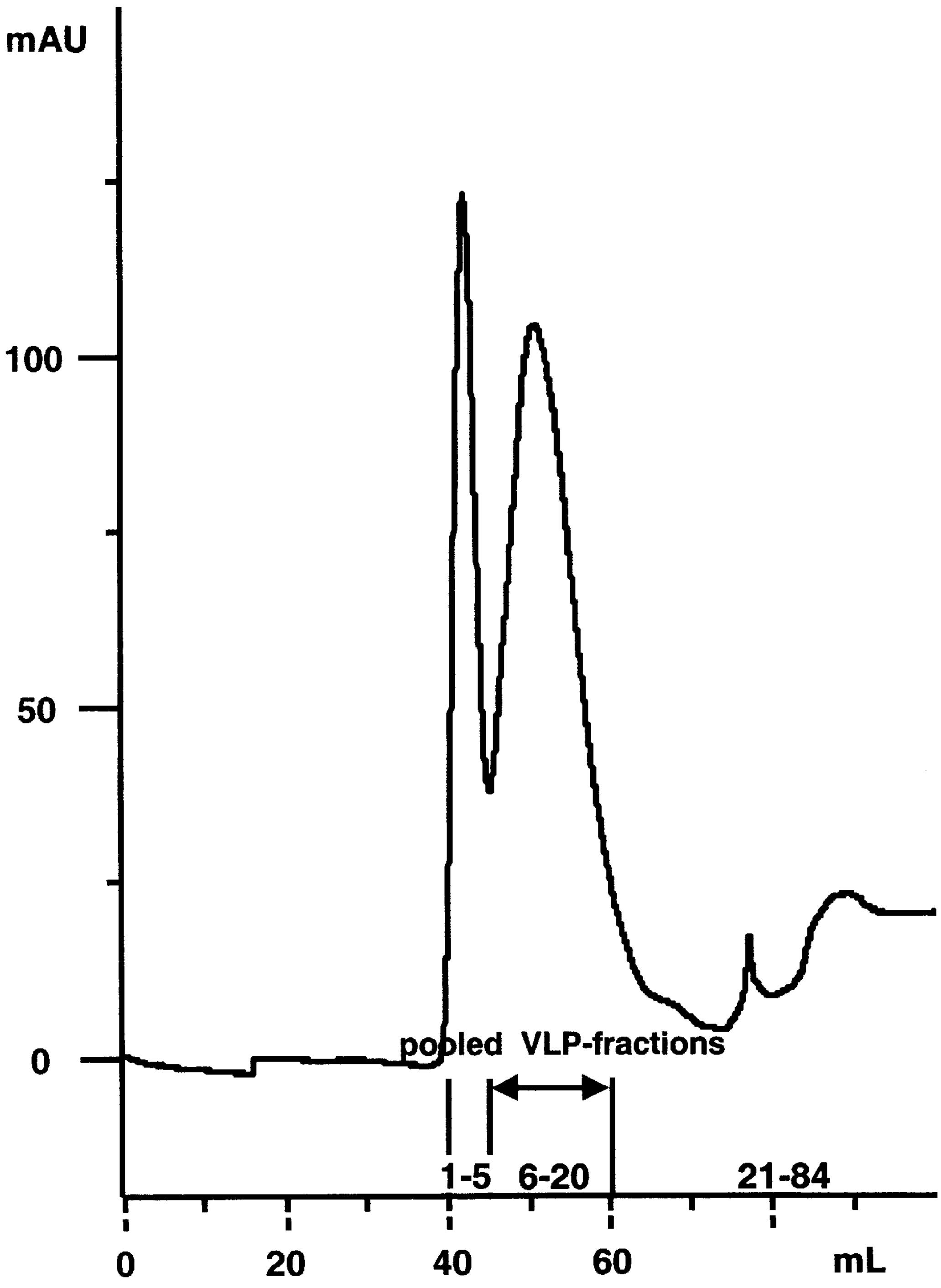

FIG. 46. Size exclusion chromatography (SEC) profile of the purified *H. polymorpha*-expressed E2-H6 in its sulphonated form, submitted to a run in PBS, 3% betain to force virus-like particle formation by exchange of Empigen BB for betain. The pooled fractions containing the VLPs used for further study are indicated by "E". The Y-axis indicates absorbance given in mAU (milli absorbance units). The X-axis indicates the elution volume in mL. See also Example 20.

Figure 47:
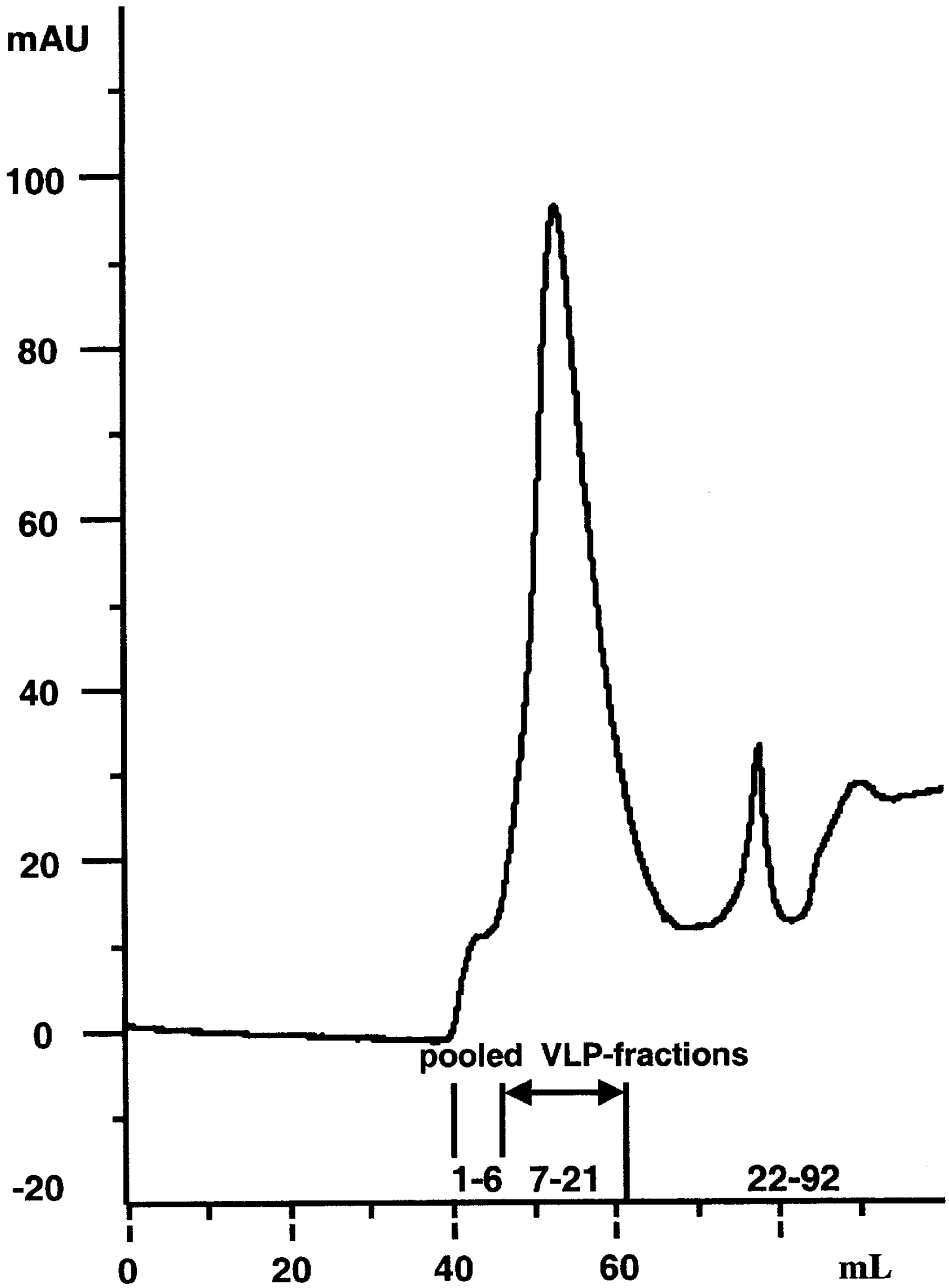

FIG. 47. Size exclusion chromatography (SEC) profile of the purified *H. polymorpha*-expressed E2-H6 in its alkylated form, submitted to a run in PBS, 3% betain to force virus-like particle formation by exchange of Empigen BB for betain. The pooled fractions containing the VLPs are indicated by "E". The Y-axis indicates absorbance given in mAU (milli absorbance units). The X-axis indicates the elution volume in mL. See also Example 20.

Figure 48:
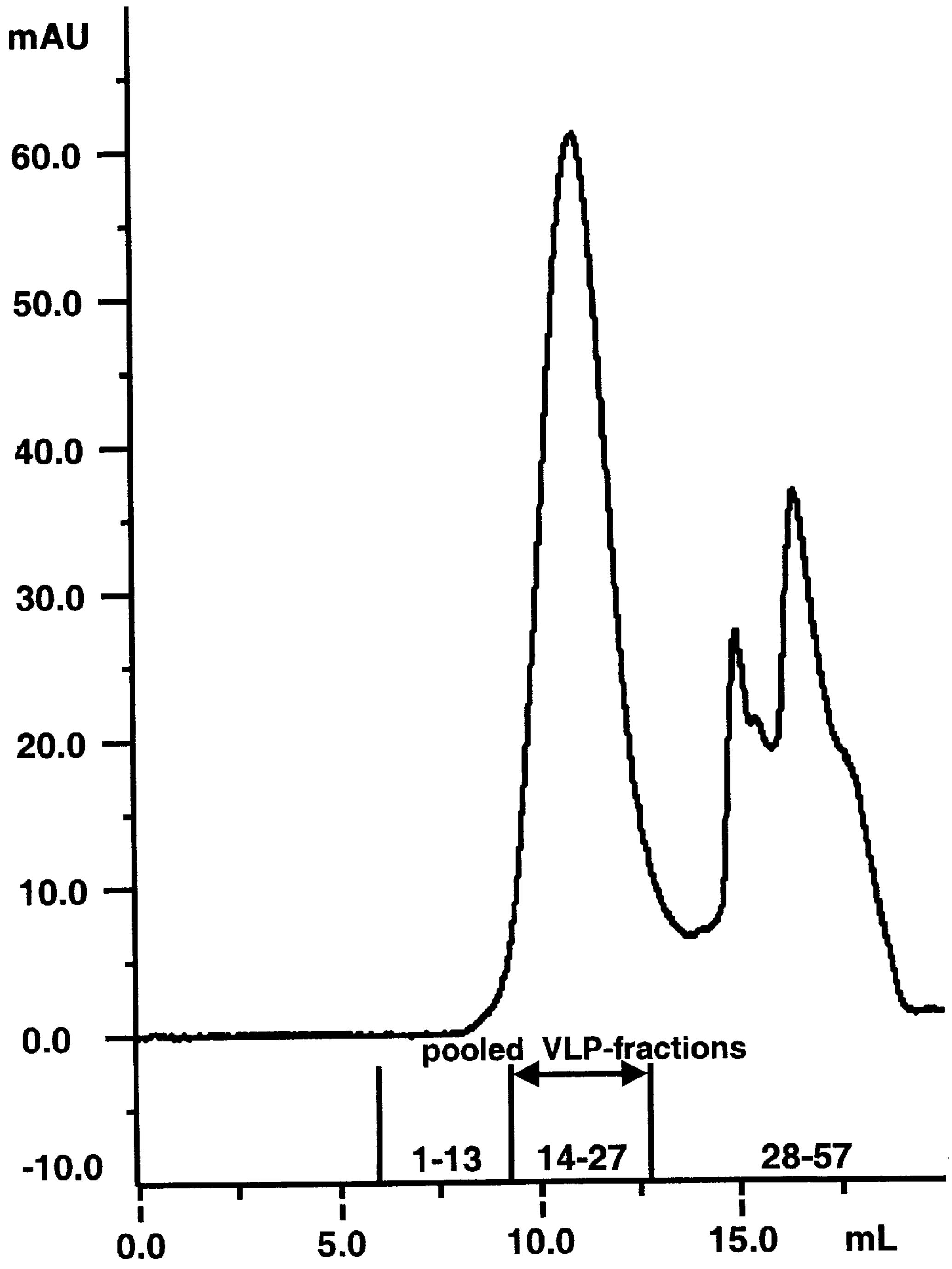

FIG. 48. Size exclusion chromatography (SEC) profile of the purified *H. polymorpha*-expressed E1 in its sulphonated form, submitted to a run in PBS, 3% betain to force virus-like particle formation by exchange of Empigen BB for betain. The pooled fractions containing the VLPs are indicated by "E". The Y-axis indicates absorbance given in mAU (milli absorbance units). The X-axis indicates the elution volume in mL. See also Example 20.

Figure 49:
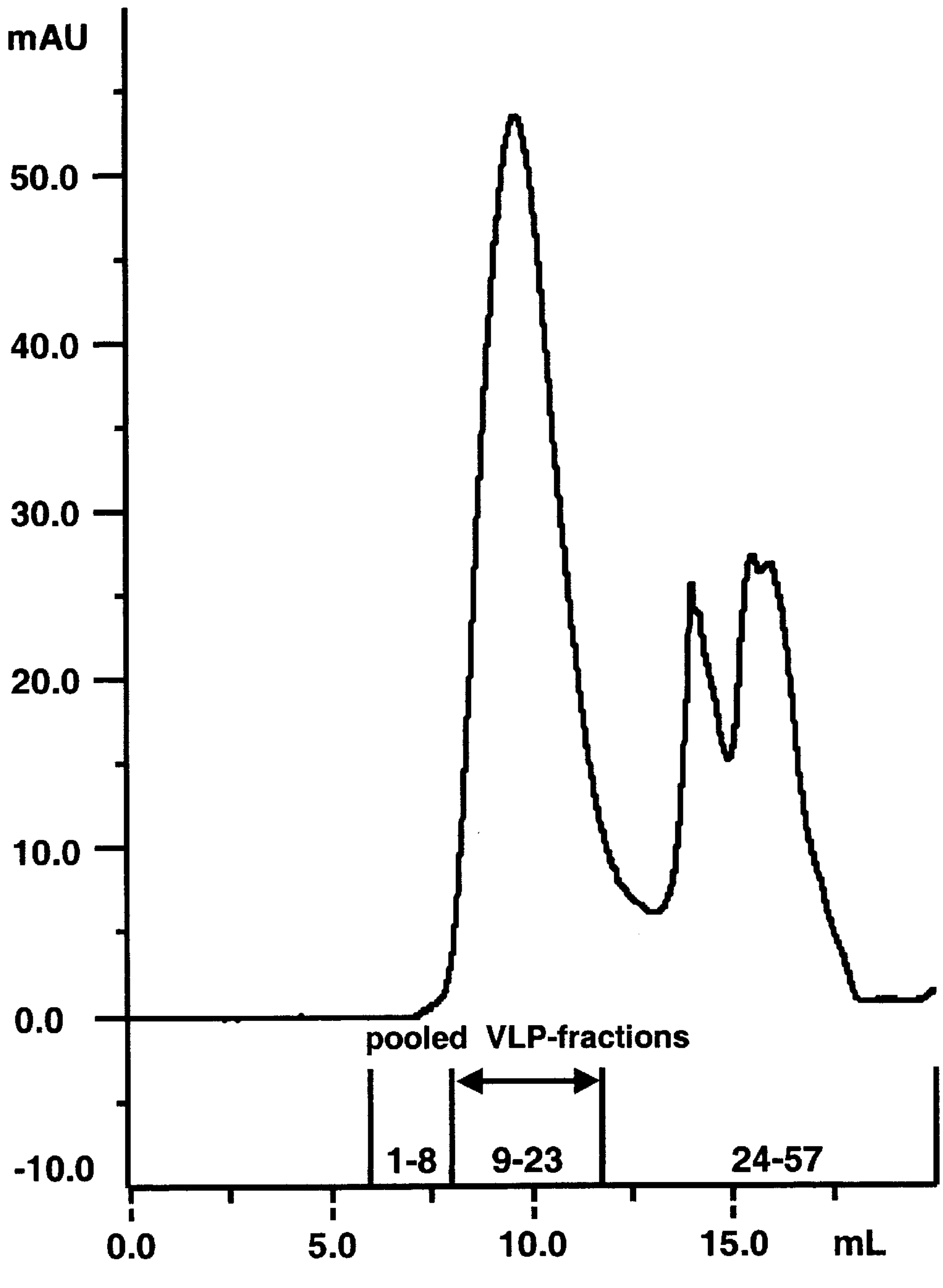

FIG. 49. Size exclusion chromatography (SEC) profile of the purified *H. polymorpha*-expressed E1 in its alkylated form, submitted to a run in PBS, 3% betain to force virus-like particle formation by exchange of Empigen BB for betain. The pooled fractions containing the VLPs are indicated by "E". The Y-axis indicates absorbance given in mAU (milli absorbance units). The X-axis indicates the elution volume in mL. See also Example 20.

Figure 50:
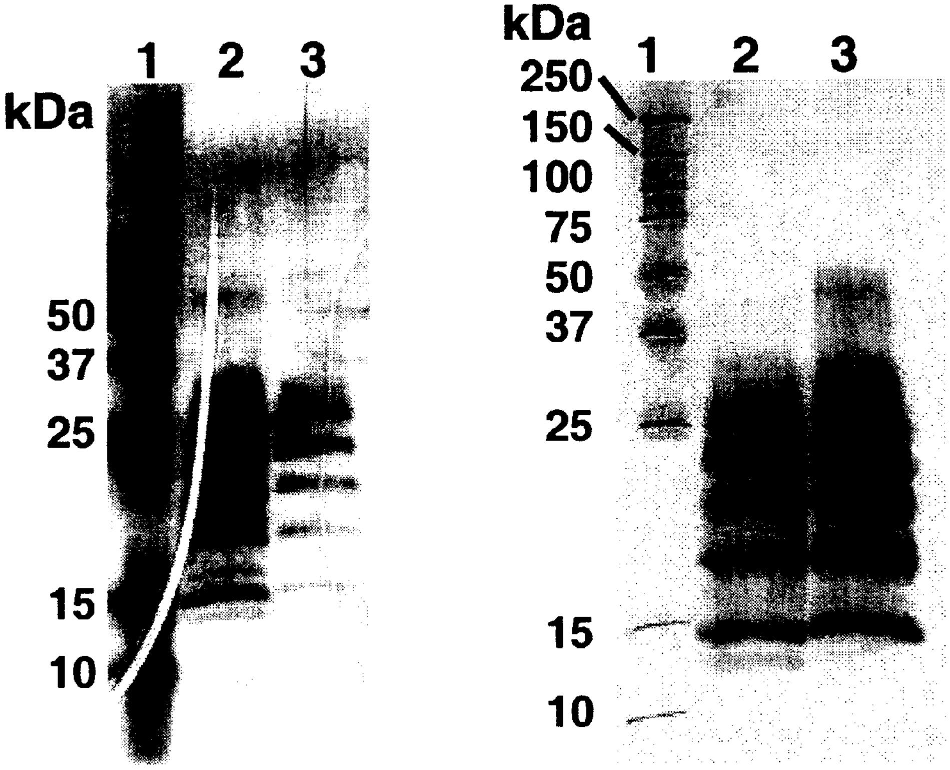

FIG. 50. SDS-PAGE (under reducing conditions) and western blot analysis of VLPs as isolated after size exclusion chromatography (SEC) as described in FIGS. 48 and 49. Left panel: silver-stained SDS-PAGE gel. Right panel: western blot using a specific monoclonal antibody directed against E1 (IGH201). Lanes 1: molecular weight markers (molecular weights indicated at the left); lanes 2: pool of VLPs containing sulphonated E1 (cfr. FIG. 48); lanes 3: pool of VLPs containing alkylated E1 (cfr. FIG. 49). See also Example 20.

Figure 51:
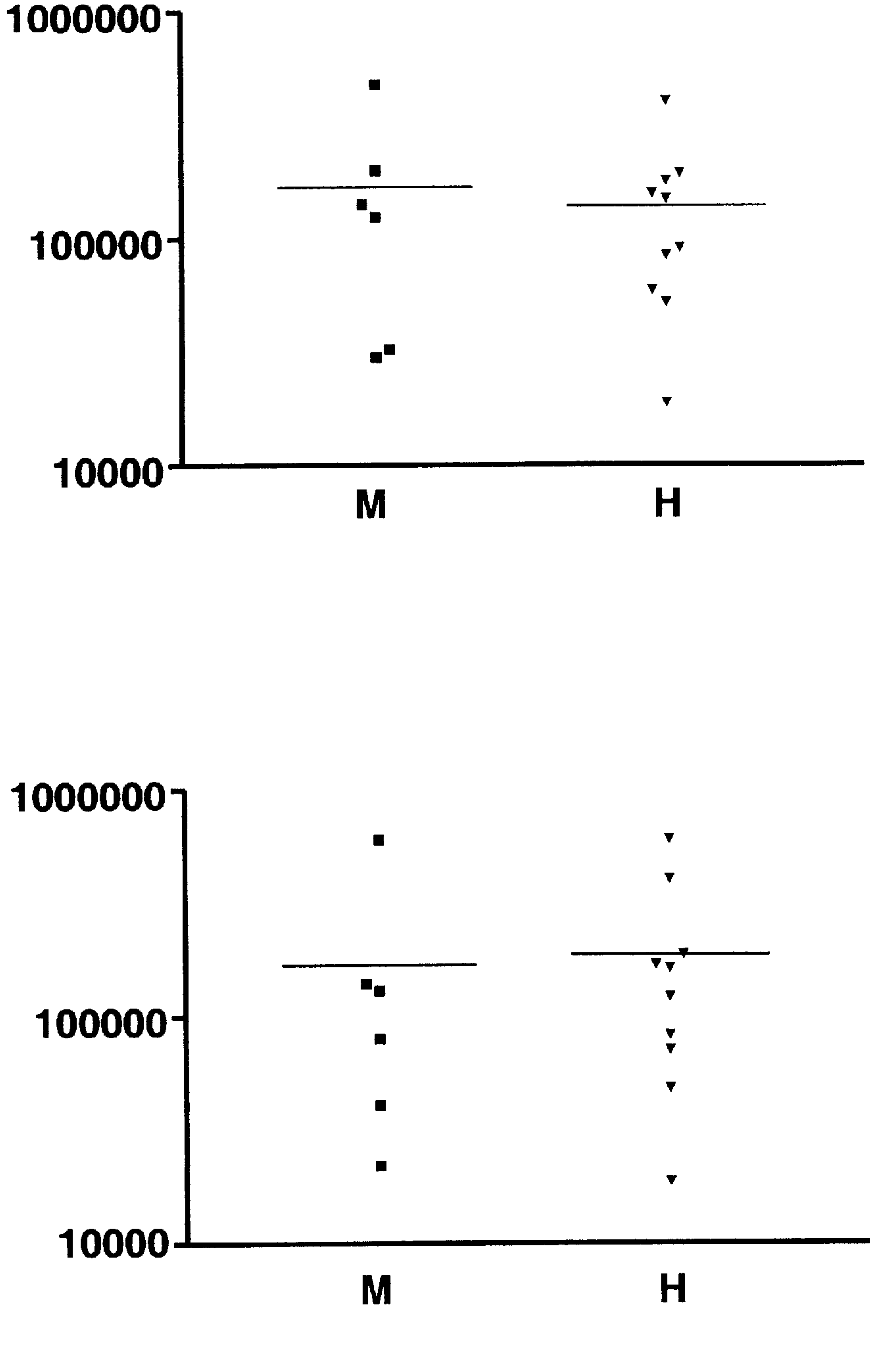

FIG. 51. E1 produced in mammalian cells ("M") or *Hansenula*-produced E1 ("H") were coated on a ELISA solid support to determine the end point titer of antibodies present in sera after vaccination of mice with E1 produced in mammalian cells (top panel), or after vaccination of mice with *Hansenula*-produced E1 (bottom panel). The horizontal bar represents the mean antibody titer. The end-point titers (fold-dilution) are indicated on the Y-axis. See also Example 22.

Figure 52:
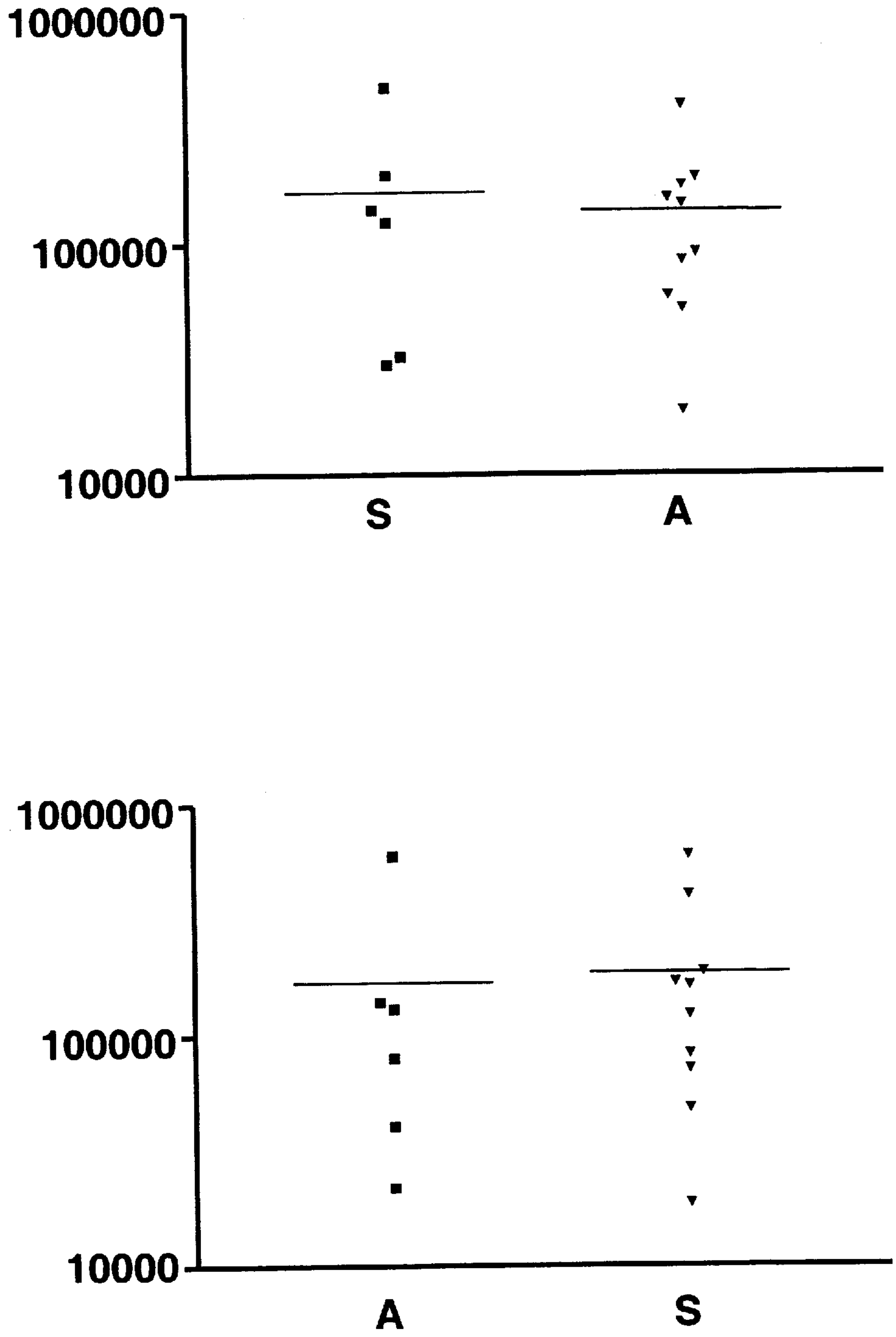

FIG. 52. *Hansenula*-produced E1 was alkylated ("A") or sulphonated ("S") and coated on a ELISA solid support to determine the end point titer of antibodies present in sera after vaccination of mice with *Hansenula*-produced E1 that was alkylated (top panel), or after vaccination of mice with *Hansenula*-produced E1 that was sulphonated (bottom panel). The horizontal bar represents the mean antibody titer. The end-point titers (fold-dilution) are indicated on the Y-axis. See also Example 23.

Figure 53:
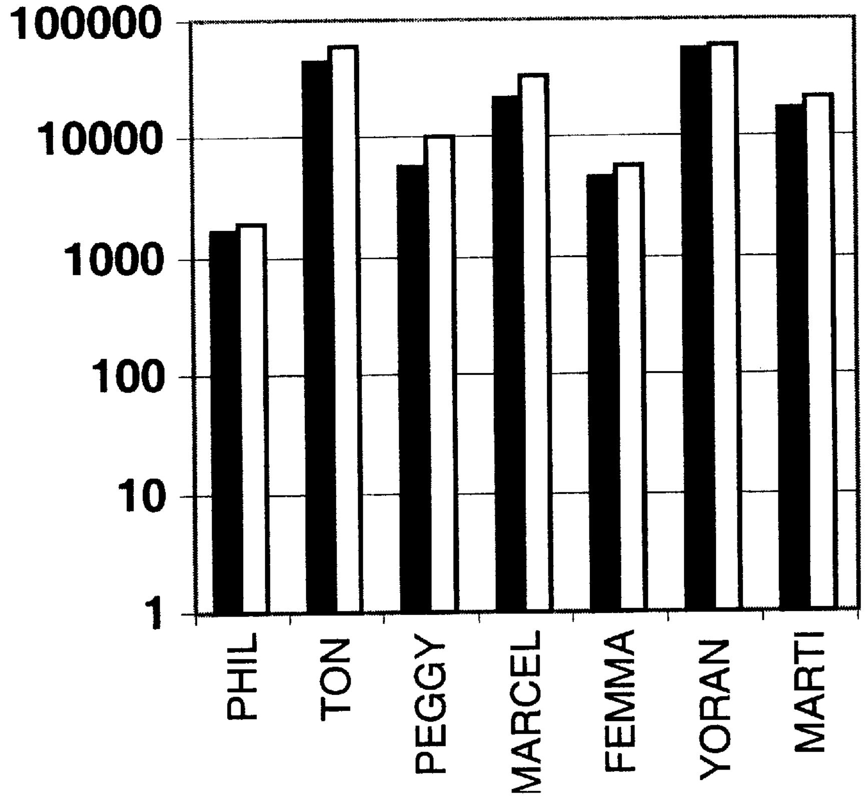
Figure 53:
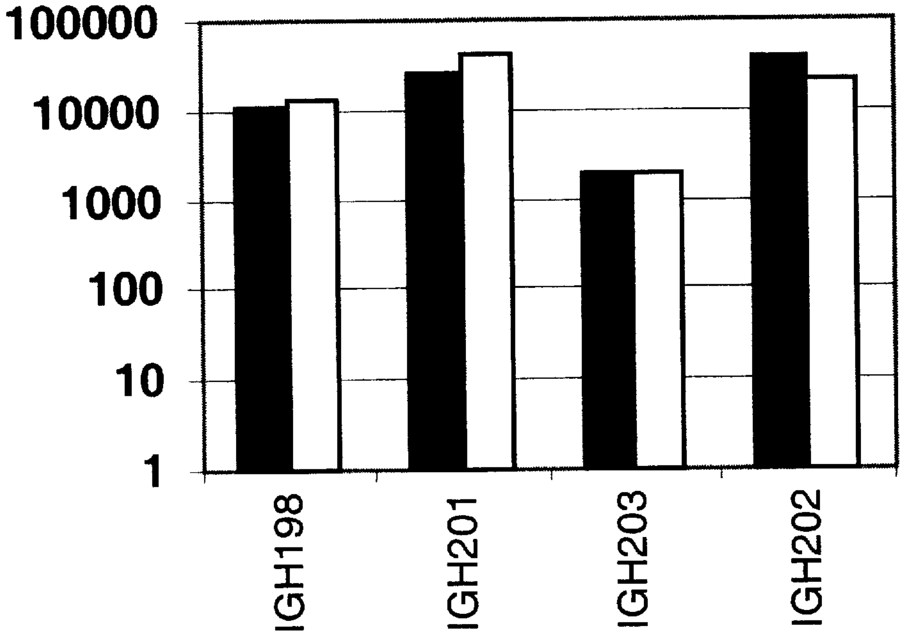

FIG. 53. HCV E1 produced by HCV-recombinant vaccinia virus-infected mammalian cells and HCV E1 produced by *H. polymorpha* were coated directly to ELISA plates. End point titers of antibodies were deteremined in sera of chimpanzees vaccinated with E1 produced by mammalian cells (top panel) and of murine monoclonal antibodies raised against E1 produced by mammalian cells (bottom panel). Chimpanzees Yoran and Marti were prophylactically vaccinated. Chimpanzees Ton, Phil, Marcel, Peggy and Femma were therapeutically vaccinated. Black filled bars: ELISA plate coated with E1 produced by mammalian cells. Open bars: ELISA plate coated with E1 produced by *Hansenula*. The end-point titers (fold-dilution) are indicated on the Y-axis. See also Example 24.

Figure 54:
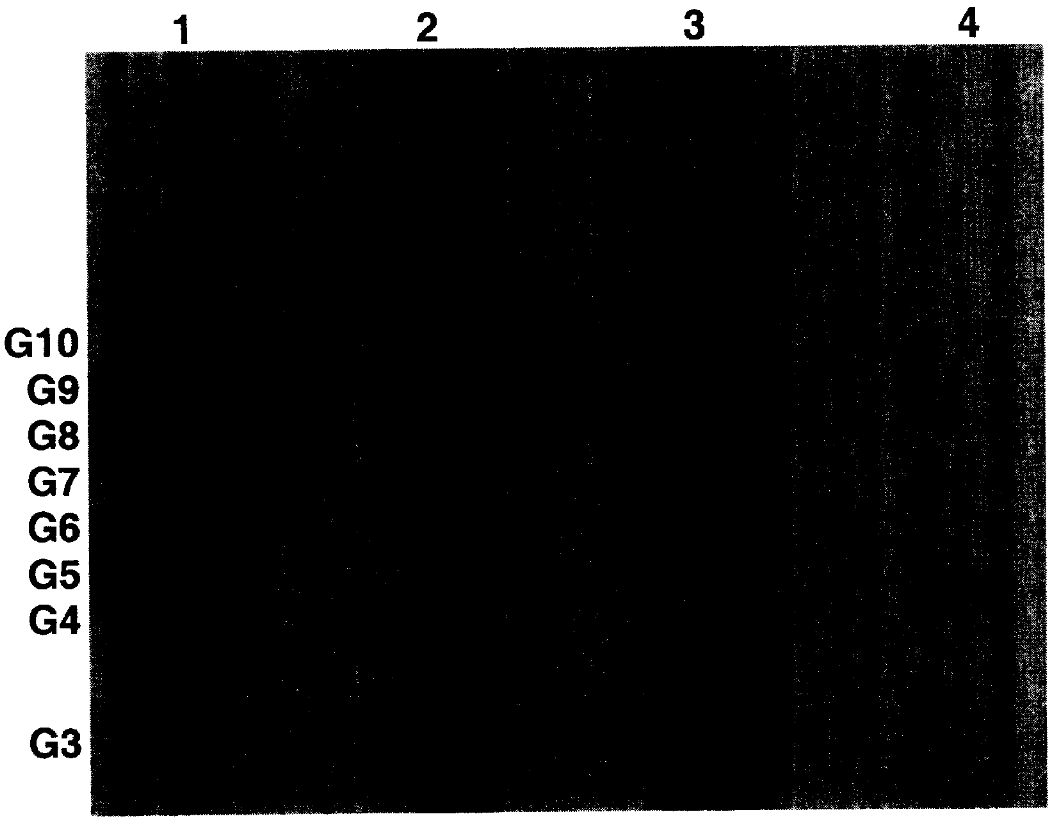

FIG. 54. Fluorophore-assisted carbohydrate gelelectrophoresis of oligosaccharides released from E1 produced by recombinant vaccinia virus-infected mammalian cells and from E1-H6 protein produced by *Hansenula*.

Lane 1: Glucose ladder standard with indication at the left of the number of monosaccharides (3 to 10, indicated by G3 to G10).

Lane 2: 25 μg N-linked oligosaccharides released from (alkylated) E1 produced by mammalian cells.

Lane 3: 25 μg N-linked oligosaccharides released from (alkylated) E1-H6 produced by *Hansenula*.

Lane 4: 100 pmoles maltotetraose.

See also Example 25.

DEFINITIONS

The following definitions serve to illustrate the different terms and expressions used in the present invention.

The present invention relates to HCV envelope proteins that have a native-like glycosylation pattern, while being expressed in yeast.

The term "HCV envelope proteins" relates to a polypeptide or an analogue thereof (e.g. mimotopes) comprising an amino acid sequence (and/or amino acid analogues) defining at least one HCV epitope of either the E1 or the E2 region, in addition to a glycosylation site. These envelope proteins may be both monomeric, hetero-oligomeric or homo-oligomeric forms of recombinantly expressed envelope proteins. Typically, the sequences defining the epitope correspond to the amino acid sequences of either the E1 or the E2 region of HCV (either identically or via substitutions of analogues of the native amino acid residue that do not destroy the epitope).

It will be understood that the HCV epitope may co-locate with the glycosylation site.

In general, the epitope-defining sequence will be 3 or 4 amino acids in length, more typically, 5, 6, or 7 amino acids in length, more typically 8 or 9 amino acids in length, and even more typically 10 or more amino acids in length. With respect to conformational epitopes, the length of the epitope-defining sequence can be subject to wide variations, since it is believed that these epitopes are formed by the three-dimensional shape of the antigen (e.g. folding). Thus, the amino acids defining the epitope can be relatively few in number, but widely dispersed along the length of the molecule being brought into the correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to genotypes 1a, 1b, 1c, 1d, 1e, 1f, 2a, 2b, 2c, 2d, 2e, 2f, 2g, 2h, 2i, 3a, 3b, 3c, 3d, 3e, 3f, 3g, 4a, 4b, 4c, 4d, 4e, 4f, 4g, 4h, 4i, 4j, 4k, 4l, 5a, 5b, 6a, 6b , 6c, 7a, 7b, 7c, 8a, 8b, 9a, 9b, 10a, or any other newly defined HCV (sub)type. It is to be understood that the amino acids constituting the epitope need not be part of a linear sequence, but may be interspersed by any number of amino acids, thus forming a conformational epitope.

The HCV antigens of the present invention comprise conformational epitopes from the E1 and/or E2 (envelope) domains of HCV. The E1 domain, which is believed to correspond to the viral envelope protein, is currently estimated to span amino acids 192–383 of the HCV polyprotein (Hijikata et al., 1991). Upon expression in a mammalian system (glycosylated), it is believed to have an approximate molecular weight of 35 kDa as determined via SDS-PAGE. The E2 protein, previously called NS1, is believed to span amino acids 384–809 or 384–746 (Grakoui et al., 1993) of the HCV polyprotein and also to be an envelope protein. Upon expression in a vaccinia system (glycosylated), it is believed to have an apparent gel molecular weight of about 72 kDa. It is understood that these protein endpoints are approximations (e.g. the carboxy terminal end of E2 could lie somewhere in the 730–820 amino acid region, e.g. ending at amino acid 730, 735, 740, 742, 744, 745, preferably 746, 747, 748, 750, 760, 770, 780, 790, 800, 809, 810, 820). The E2 protein may also be expressed together with the E1, and/or core (aa 1–191), and/or P7 (aa 747–809), and/or NS2 (aa 810–1026), and/or NS3 (aa 1027–1657), and/or NS4A (aa 1658–1711) and/or NS4B (aa 1712–1972) and/or NS5A (aa 1973–2420), and/or NS5B (aa 2421–3011). Likewise, the E1 protein may also be expressed together with the E2, and/or core (aa 1–191), and/or P7 (aa 747–809), and/or NS2 (aa 810–1026), and/or NS3 (aa 1027–1657), and/or NS4A (aa 1658–1711) and/or NS4B (aa 1712–1972), and/or NS5A (aa 1973–2420), and/or NS5B (aa 2421–3011). Expression together with these other HCV proteins may be important for obtaining the correct protein folding.

The term 'E1' as used herein also includes analogs and truncated forms that are immunologically cross-reactive with natural E1, and includes E1 proteins of genotypes 1, 2, 3, 4, 5, 6, 7, 8, 9, 10, or any other newly identified HCV type or subtype. The term 'E2' as used herein also includes analogs and truncated forms that are immunologically cross-reactive with natural E2, and includes E2 proteins of genotypes 1, 2, 3, 4, 5, 6, 7, 8, 9, 10, or any other newly identified HCV type or subtype. For example, insertions of multiple codons between codon 383 and 384, as well as deletions of amino acids 384–387 have been reported by Kato et al. (1992). It is thus also understood that the isolates used in the examples section of the present invention were not intended to limit the scope of the invention and that any HCV isolate from type 1, 2, 3, 4, 5, 6, 7, 8, 9, 10 or any other new genotype of HCV is a suitable source of E1 and/or E2 sequence for the practice of the present invention. Similarly, as described above, the HCV proteins that are co-expressed with the HCV envelope proteins of the present invention, can be derived from any HCV type, thus also from the same type as the HCV envelope proteins of the present invention.

'E1/E2' as used herein refers to an oligomeric form of envelope proteins containing at least one E1 component and at least one E2 component.

The term 'specific oligomeric' E1 and/or E2 and/or E1/E2 envelope proteins refers to all possible oligomeric forms of recombinantly expressed E1 and/or E2 envelope proteins which are not aggregates. E1 and/or E2 specific oligomeric envelope proteins are also referred to as homo-oligomeric E1 or E2 envelope proteins (see below). The term 'single or specific oligomeric' E1 and/or E2 and/or E1/E2 envelope proteins refers to single monomeric E1 or E2 proteins (single in the strict sense of the word) as well as specific oligomeric E1 and/or E2 and/or E1/E2 recombinantly expressed proteins. These single or specific oligomeric envelope proteins according to the present invention can be further defined by the following formula $(E1)_x(E2)_y$ wherein x can be a number between 0 and 100, and y can be a number between 0 and 100, provided that x and y are not both 0. With x=1 and y=1 said envelope proteins include monomeric E1.

The term 'homo-oligomer' as used herein refers to a complex of E1 or E2 containing more than one E1 or E2 monomer, e.g. E1/E1 dimers, E1/E1/E1 trimers or E1/E1/E1/E1 tetramers and E2/E2 dimers, E2/E2/E2 trimers or E2/E2/E2/E2 tetramers, E1 pentamers and hexamers, E2 pentamers and hexamers or any higher-order homo-oligomers of E1 or E2 are all 'homo-oligomers' within the scope of this definition. The oligomers may contain one, two, or several different monomers of E1 or E2 obtained from different types or subtypes of hepatitis C virus including for example those described in an international application published under WO 94/25601 and European application No. 94870166.9 both by the present applicants. Such mixed oligomers are still homo-oligomers within the scope of this invention, and may allow more universal diagnosis, prophylaxis or treatment of HCV.

The E1 and E2 antigens used in the present invention may be full-length viral proteins, substantially full-length versions thereof, or functional fragments thereof (e.g. fragments comprising at least one epitope and/or glycosylation site). Furthermore, the HCV antigens of the present invention can also include other sequences that do not block or prevent the formation of the conformational epitope of interest. The presence or absence of a conformational epitope can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to adsorb the polyclonal serum first with the denatured antigen and see if it retains antibodies to the antigen of interest.

The term 'protein' refers to a polymer of amino acids and does not refer to a specific length of the product; thus, peptides, oligopeptides, and polypeptides are included within the definition of protein. This term also does not refer to or exclude post-expression modifications of the protein, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The proteins of the present invention are glycosylated. Glycosylated proteins intend proteins that contain one or more carbohydrate groups, in particular sugar groups. In general, all eukaryotic cells are able to glycosylate proteins. After alignment of the different envelope protein sequences of HCV genotypes, it may be inferred that not all 6 glycosylation sites on the HCV E1 protein are required for proper folding and reactivity. For instance, HCV subtype 1b E1 protein contains 6 glycosylation sites, but some of these glycosylation sites are absent in certain other (sub)types. The fourth carbohydrate motif (on Asn250), present in types 1b, 6a, 7, 8, and 9, is absent in all other types know today. This sugar-addition motif may be mutated to yield a type 1b E1 protein with improved reactivity. Also, the type 2b sequences show an extra glycosylation site in the V5 region (on Asn299). The isolate S83, belonging to genotype 2c, even lacks the first carbohydrate motif in the VI region (on Asn), while it is present on all other isolates (Stuyver et al., 1994) However, even among the completely conserved sugar-addition motifs, the presence of the carbohydrate may not be required for folding, but may have a role in evasion of immune surveillance. Thus, the identification of the role of glycosylation can be further tested by mutagenesis of the glycosylation motifs. Mutagenesis of a glycosylation motif (NXS or NXT sequences) can be achieved by either mutating the codons for N, S, or T, in such a way that these codons encode amino acids different from N in the case of N, and/or amino acids different from S or T in the case of S and in the case of T. Alternatively, the X position may be mutated into P, since it is known that NPS or NPT are not frequently modified with carbohydrates. After establishing which carbohydrate-addition motifs are required for folding and/or reactivity and which are not, combinations of such mutations may be made. Such experiments have been described extensively in WO 96/04385 (Example 8), which is included herein specifically by reference.

The term glycosylation as used in the present invention refers to N-glycsoylation unless otherwise specified.

In particular, the present invention relates to HCV envelope proteins, or parts thereof that are core-glycosylated. In this respect, the term "core-glycosylation" refers to a structure "similar" to the structure as described by Herscovics and Orlean (1993) in FIG. 3 (boxed structure) (i.e.,

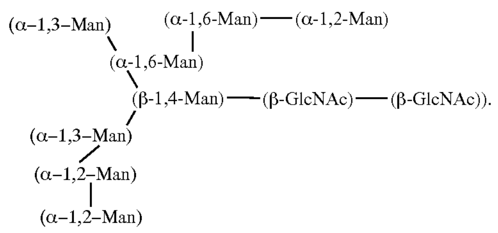

Thus, the carbohydrate structure referred to contains 10 mono-saccharides. Notably, said disclosure is herein incorporated by reference. The term "similar" intends that not more than about 5 additional mono-saccharides have been added to the structure or that not more than about 3 mono-saccharides have been removed from the structure. Consequently, a carbohydrate structure consists most preferentially of 10 mono-saccharides, but minimally of 7, and more preferentially of 8 or 9 mono-sacchariden, and maximally of 15 mono-saccharides, and more preferentially of 14, 13, 12, or 11 mono-saccharides. The mono-saccharides connoted are preferentially glucose, mannose or N-acetyl glucosamine.

The term "signal sequence" intends an amino acid sequence that targets a protein to the rough ER and is in this way a prerequisite for N-glycosylation. The signal sequence is cleaved off on the luminal side of this ER by host specific proteases referred to as signal peptidases. The signal sequence of this invention is correctly removed from HCV envelope proteins by a yeast signal peptidase. The preferrred signal sequence is the signal sequence of lysozyme C (CL-leader; 1,4-beta-N-acetylmuramidase C, EC 3.2.1.17), which has the amino acid sequence as set forth in SEQ ID NO:1.

It is understood that the amino acids of this sequence may be exchanged for others without affecting the functionality, i.e. functional equivalent, which targets HCV envelope proteins to the rough ER, as evidenced by the presence of N-glycosylation of these HCV envelope proteins and the signal sequence being correctly cleaved off.

The present invention relates to "correctly processed" HCV envelope proteins, when expressed in yeast. The term "correctly processed" connotes that at least about 40%, but more preferentially about 50%, 60%, 70%, 75%, 80%, 85%, 90%, 95%, 96%, 97%, 98% or even 99% of the glycoproteins of the present invention is cleaved at exactly the intended site, i.e. that the complete signal sequence is removed, but only the signal sequence. Alternatively, if a substantial part the proteins expressed in yeast is not "correctly processed", the glycosylated envelope proteins of the present invention may still be purified provided sufficiently discriminating biochemical characteristics between the different expression products exist.

In particular, the present invention relates to a method for purifying core glycosylated hepatitis C virus (HCV) envelope proteins, or any part thereof, suitable for use in an immunoassay or vaccine as described above, in which the HCV envelope gene, or any part thereof, contains a CL-leader or a functional equivalent thereof.

In particular, the present invention relates to the use of the CL leader, or a functionally equivalent thereof, for the expression of viral envelope proteins in yeast.

In particular, the present invention relates to a vector suitable for transformation of a yeast and comprising an expression cassette comprising a DNA sequence encoding for a viral envelope protein preceeded by the CL leader, or a functionally equivalent thereof.

In particular, the present invention relates to a host organism transformed with the vector as described above.

Expression of the HCV envelope proteins of the present invention may be achieved by a number of methods. For example, one may express the HCV envelope proteins of the present invention in lower eukaryotes (such as yeast). Other host organisms include higher eukaryotes, such as mammalian cells.

One may use any of a variety of vectors to obtain expression in a host organism. Host organsims, such as lower eukaryotes, in particular yeast, are typically transformed with vectors which may replicate within the host cell independently, or may integrate into the host cell genome. These vectors usually contain selection markers such as URA3, LEU2, ADE2, HIS4, TRP1, ALG7 or resistance genes such as G418 or any other antibiotic. The vector also contains an 'expression cassette' which comprises a promoter, a leader sequence, a coding sequence of interest and a transcription termination sequence. Preferentially, the vectors described in Example 1 are used. Procedures to transform yeast usually vary with the yeast species but are well known in the art and include electroporation, spheroplast transformation and lithium acetate or other alkali cation transformations.

It is preferred in the present invention to obtain intracellularly expressed HCV envelope proteins, or the parts thereof, upon lysing the transformed host cell. Lysis of the transformed host cells can be accomplished by a variety of techniques known in the art. Preferentially, the transformed host cells are subjected to a freeze-thaw cycle followed by resuspension in a solution containing a chaotropic agent, such as, for example, in 6M Gu.HCl, pH 7.4 in 50 mM phosphate.

The terms "expressed" and "recombinantly expressed" are used interchangeably herein. The terms "expressed" and "recombinantly expressed" used within the context of the present invention refers to the fact that the proteins of the present invention are produced by recombinant expression methods in lower eukaryotes. Expression techniques are well known in the art, such as for example described in Sambrook et al (1989). The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluyveromyces, Pichia* (e.g. *Pichia pastoris*), *Hansenula* (e.g. *Hansenula polymorpha*), *Yarowia, Schwaniomyces, Schizosaccharomyces, Zygosaccharomyces* and the like. The present invention contemplates in particular *Saccharomyces cerevisiae* and *Hansenula* as convenient yeast hosts. Preferentially, yeast glycosylation minus strains, and even more preferentially *Saccharomyces* glycosylation minus strains are used in the present invention. Glycosylation minus strains are defined as strains carrying a mutation, in which the nature of the mutation is not necessarily known, but that result in a glycosylation of glycoproteins comparable to the glycosylation in *Hansenula*. In particular, it is contemplated that glycosylation minus strains carry a mutation, that result in a significant shift in mobility on PAGE of the invertase protein. Invertase is a protein which is normally present in *Saccharomyces* in a hyperglycosylated form only (Ballou et al 1991). Glycosylation minus strains include mnn2, and/or OCH1 and/or mnn9 deficient strains.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

In particular, the present invention relates to the use of *Hansenula* for HCV E1 and/or HCV E2 protein expression, or any part thereof, characterised in that said HCV E1 and/or HCV E2 proteins, or said parts thereof, are core-glycosylated.

In particular, the present invention relates to the use of *Hansenula polymorpha* for the expression of viral envelope proteins which become core-glycosylated upon expression in this yeast species.

In particular, the present invention relates to the use of *Saccharomyces* glycosylation minus strains for HCV E1 and/or HCV E2 protein expression, or any part thereof, characterised in that said HCV E1 and/or HCV E2 proteins, or said parts thereof, are core-glycosylated.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, withouth affecting the determination of the percentage purity as used herein. An 'isolated' HCV protein intends an HCV protein composition that is at least 35% pure.

The term 'essentially purified proteins' refers to proteins purified such that they can be used for in vitro diagnostic methods and as a therapeutic compound. These proteins are substantially free from cellular proteins, vector-derived proteins or other HCV viral components. Usually these proteins are purified to homogeneity (at least 80% pure, preferably, 90%, more preferably 95%, more preferably 97%, more preferably 98%, more preferably 99%, even more preferably 99.5%, and most preferably the contaminating proteins should be undetectable by conventional methods like SDS-PAGE and silver staining.

If present, the cysteine residues of the HCV envelope proteins or the parts thereof, of the present invention are protected during the purification procedure. This protection can be via irreversible or via reversible protection. For purification, specific reference is made to the purification protocols as employed and described extensively in WO 99/67285 and WO96/04385, which are herein incorporated specifically by reference.

The invention connotes that HCV envelope proteins as described herein, wherein at least one cysteine residue, but preferably 2 or more of the HCV envelope protein as described above can be irreversibly protected by chemical or enzymatic means. In particular, irreversible protection by chemical means refers to alkylation, preferably alkylation of the HCV envelope proteins by means of alkylating agents, such as, for example, active halogens, ethylenimine or N-(iodoethyl)trifluoro-acetamide. In this respect, it is to be understood that alkylation of cysteines refers to cysteines on which the hydrogen on the sulphur atom is replaced by $(CH_2)_nR$, in which n is 0, 1, 2, 3 or 4 and R~H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine. Other methods of alkylation include the use of NEM (N-ethylmaleimide) or Biotin-NEM, a mixture thereof, or ethylenimine or N-(iodoethyl)trifluoroacetamide both resulting in substitution of —H by $—CH_2—CH_2—NH_2$ (Hermanson, 1996). The term "alkylating agents" as used herein refers to compounds which are able to perform alkylation as described herein. Such alkylations finally result in a modified cysteine, which can mimic other aminoacids. Alkylation by an ethylenimine results in a structure resembling lysine, in such a way that new cleavage sites for trypsine are introduced (Hermanson 1996). Similarly, the usage of methyliodide results in an amino acid resembling methionine, while the usage of iodoacetate and iodoacetamide results in amino acids resembling glutamic acid and glutamine, respectively. In analogy, these amino acids are preferably used in direct mutation of cysteine. Therefore, the present invention pertains to HCV envelope proteins as described herein, wherein at least one cysteine residue of the HCV envelope protein as described herein is mutated to a natural amino acid, preferentially to methionine, glutamic acid, glutamine or lysine. The term "mutated" refers to site-directed mutagenesis of nucleic acids encoding these amino acids, ie to the well known methods in the art, such as, for example, site-directed mutagenesis by means of PCR or via oligonucleotide-mediated mutagenesis as described in Sambrook et al. (1989). It should be understood that for the examples section of the present invention, alkylation refers to the use of iodo-acetamide as an alkylating agent unless otherwise specified.

It is further understood that in the pruification procedure, the cysteine residues of the HCV proteins or the parts thereof of the present invention can reversibly protected. The purpose of reversibly protection is to stabilise the HCV protein. Especially, after reversibly protection the sulfur-containing functional group (eg thiols and disulfides) is retained in a non-reactive condition. The sulfur-containing functional group is thus unable to react with other compounds, e.g. no tendency of forming or exchanging disulfide bonds, such as, for example

| | | |
|---|---|---|
| $R_1$-SH + $R_2$-SH | -x-> | $R_1$-S-S-$R_2$; |
| $R_1$-S-S-$R_2$ + $R_3$-SH | -x-> | $R_1$-S-S-$R_3$ + $R_2$-SH; |
| $R_1$-S-S-$R_2$ + $R_3$-S-S-$R_4$ | -x-> | $R_1$-S-S-$R_3$ + $R_2$-S-S-$R_4$. |

The described reactions between thiols and/or disulphide residues are not limited to intermolecular processes, but may also occur intramolecularly.

The term "reversibly protecting" as used herein contemplates covalently binding of modification agents to the cysteine residue, as well as manipulating the environment of the HCV protein such, that the redox state of the thiol-groups remains unaffected throughout subsequent steps of the purification procedure (shielding).

Reversible protection of the cysteine residues can be carried out chemically or enzymatically.

The term "reversible protection by enzymatical means" as used herein contemplates reversible protection mediated by enzymes, such as for example acyl-transferases, e.g. acyl-transferases that are involved in catalysing thio-esterification, such as palmitoyl acyltransferase (see below and Das et al., 1997).

The term "reversible protection by chemical means" as used herein contemplates reversible protection:

(1) by modification agents that reversibly modify cysteinyls such as for example by sulphonation and thio-esterification;

Sulphonation is a reaction where thiol or cysteines involved in disulfide bridges are modified to S-sulfonate: $RSH \rightarrow RS—SO^{3-}$ (André Darbre ) or $RS—SR \rightarrow 2\ RS—SO_3^-$ (sulfitolysis; Kumar et al, 1986). Reagents for sulfonation are e.g. $Na_2SO_3$, or sodium tetrathionate. The latter reagents for sulfonation are used in a concentration of 10–200 mM, and more preferentially in a concentration of 50–200 mM. Optionally sulfonation can be performed in the presence of a catalysator such as, for example $Cu^{2+}$ (100 μM–1 mM) or cysteine (1–10 mM).

The reaction can be performed under protein denaturing as well as native conditions (Kumar et al., 1985; Kumar et al., 1986).

Thioester bond formation, or thio-esterification is characterised by:

$$RSH + R'COX \rightarrow RS—COR'$$

in which X is preferentially a halogenide in the compound R'CO—X.

(2) by modification agents that reversibly modify the cysteinyls of the present invention such as, for example, by heavy metals, in particular $Zn^{2+}$, $Cd^{2+}$ (Matts et al, 1991), mono-, dithio- and disulfide- compounds (e.g. aryl- and alkylmethanethiosulfonate, dithiopyridine, dithiomorpholine, dihydrolipoamide, Ellmann reagent, aldrothiol™ (Aldrich) (Rein et al, 1996), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulphydryl groups. Thiol containing compounds are preferentially used in a concentration of 0.1–50 mM, more preferentially in a concentration of 1–50 mM, and even more preferentially in a concentration of 10–50 mM;

(3) by the presence of modification agents that preserve the thiol status (stabilise), in particular antioxidantia, such as for example DTT, dihydroascorbate, vitamin s and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM–10 mM, more preferentially in a concentration of 1–10 mM;

(4) by thiol stabilising conditions such as, for example, (i) cofactors as metal ions ($Zn^{2+}$, $Mg^{2+}$), ATP, (ii) pH control (e.g. for proteins in most cases pH ~5 or pH is preferentially thiol $pK_a$−2; e.g. for peptides purified by Reverse Phase Chromatography at pH ~2).

Combinations of reversible protection as described in (1), (2), (3) and (4) may result in similarly pure and refolded HCV proteins. In effect, combination compounds can be used, such as, for example Z103 (Zn camosine), preferentially in a concentration of 1–10 mM. It should be clear that reversible protection also refers to, besides the modification groups or shielding described above, any cysteinyl protection method which may be reversed enzymatically or chemically, without disrupting the peptide backbone. In this respect, the present invention specifically refers to peptides prepared by classical chemical synthesis (see above), in which, for example, thioester bounds are cleaved by thioesterase, basic buffer conditions (Beekman et al., 1997) or by hydroxylamine treatment (Vingerhoeds et al, 1996).

Thiol containing HCV proteins can be purified, for example, on affinity chromatography resins which contain (1) a cleavable connector arm containing a disulfide bond (e.g. immobilised 5,5' dithiobis(2-nitrobenzoic acid) (Jayabaskaran et al., 1987) and covalent chromatography on activated thiol-Sepharose 4B (Pharmacia)) or (2) a aminohexanoyl-4-aminophenylarsine as immobilised ligand. The latter affinity matrix has been used for the purification of proteins, which are subject to redox regulation and dithiol proteins that are targets for oxidative stress (Kalef et al., 1993).

Reversible protection may also be used to increase the solubilisation and extraction of peptides (Pomroy & Deber, 1998).

The reversible protection and thiol stabilizing compounds may be presented under a monomeric, polymeric or liposomic form.

The removal of the reversibly protection state of the cysteine residues can chemically or enzymatically accomplished by e.g.:

- a reductant, in particular DTT, DTE, 2-mercaptoethanol, dithionite, $SnCl_2$, sodium borohydride, hydroxylamine, TCEP, in particular in a concentration of 1–200 mM, more preferentially in a concentration of 50–200 mM;
- removal of the thiol stabilising conditions or agents by e.g. pH increase;
- enzymes, in particular thioesterases, glutaredoxine, thioredoxine, in particular in a concentration of 0.01–5 μM, even more particular in a concentration range of 0.1–5 μM.;
- combinations of the above described chemical and/or enzymatical conditions.

The removal of the reversibly protection state of the cysteine residues can be carried out in vitro or in vivo, e.g. in a cell or in an individual.

It will be appreciated that in the purification procedure, the cysteine residues may or may not be irreversibly blocked, or replaced by any reversible modification agent, as listed above.

A reductant according to the present invention is any agent which achieves reduction of the sulfur in cysteine residues, e.g. "S—S" disulfide bridges, desulphonation of the cysteine residue ($RS—SO_3^-$→RSH). An antioxidant is any reagent which preserves the thiol status or minimises "S—S" formation and/or exchanges. Reduction of the "S—S" disulfide bridges is a chemical reaction whereby the disulfides are reduced to thiol (—SH). The disulfide bridge breaking agents and methods disclosed in WO 96/04385 are hereby incorporated by reference in the present description. "S—S" Reduction can be obtained by (1) enzymatic cascade pathways or by (2) reducing compounds. Enzymes like thioredoxin, glutaredoxin are known to be involved in the in vivo reduction of disulfides and have also been shown to be effective in reducing "S—S" bridges in vitro. Disulfide bonds are rapidly cleaved by reduced thioredoxin at pH 7.0, with an apparent second order rate that is around $10^4$ times larger than the corresponding rate constant for the reaction with DTT. The reduction kinetic can be dramatically increased by preincubation the protein solution with 1 mM DTT or dihydrolipoamide (Holmgren, 1979).

Thiol compounds able to reduce protein disulfide bridges are for instance Dithiothreitol (DTT), Dithioerythritol (DTE), β-mercaptoethanol, thiocarbamates, bis(2-mercaptoethyl)sulfone and N,N'-bis(mercaptoacetyl)hydrazine, and sodium-dithionite.

Reducing agents without thiol groups like ascorbate or stannous chloride ($SnCl_2$), which have been shown to be very useful in the reduction of disulfide bridges in monoclonal antibodies (Thakur et al., 1991), may also be used for the reduction of HCV proteins. In addition, changes in pH values may influence the redox status of HCV proteins. Sodium borohydride treatment has been shown to be effective for the reduction of disulfide bridges in peptides (Gailit, 1993). Tris (2-carboxyethyl)phosphine (TCEP) is able to reduce disulfides at low pH (Bums et al., 1991). Selenol catalyses the reduction of disulfide to thiols when DTT or sodium borohydride is used as reductant. Selenocysteamine, a commercially available diselenide, was used as precursor of the catalyst (Singh and Kats, 1995).

It is stressed again that the whole content, including all definitions of the documents cited above, are incorporated by reference in the present application. Hence, the above mentioned methods and compounds to modify the redox status of HCV proteins are all contemplated in the present invention.

Heparin is known to bind to several viruses and consequently binding to the HCV envelope has already been suggested (Garson et al., 1999). In this respect, in order to analyze potential binding of HCV envelope proteins to heparin, heparin can be biotinylated and subsequently the interaction of heparin with HCV envelope proteins can be analyzed, e.g. on microtiterplates coated with HCV envelope proteins. In this way different expression systems can be scrutinized. For example, a strong binding is observed with part of the HCV E1 expressed in Hansenula, while binding with HCV E1 from mammalian cell culture is absent. In this respect, the term "heparin affinity chromatography" relates to an immobilized heparin, which is able to specifically bind to HCV envelope proteins. Proteins of the high-mannose type bind agglutinins such as Lens culinaris, Galanthus nivalis, Narcissus pseudonarcissus Pisum sativum or Allium ursinum. Moreover, N-acetylglucosamine can be bound by lectins, such as WGA (wheat germ agglutinin) and its equivalents. Therefore, one may employ lectins bound to a solid phase to separate the HCV envelope proteins of the present invention from cell culture supernatants, cell lysates and other fluids, e.g. for purification during the production of antigens for vaccine or immunoassay use (Lectin-chromatography).

In particular, the present invention relates to a method for purifying core glycosylated hepatitis C virus (HCV) envelope proteins, or any part thereof, suitable for use in an immunoassay or vaccine, which method comprising:

- growing *Hansenula* or *Saccharomyces* glycosylation minus strains transformed with an envelope gene encoding an HCV E1 and/or HCV E2 protein, or any part thereof, in a suitable culture medium;

causing expression of said HCV E1 and/or HCV E2 gene, or any part thereof; and, purifying said core-glycosylated HCV E1 and/or HCV E2 protein, or any part thereof, from said cell culture.

The invention further pertains to a method for purifying core-glycosylated hepatitis C virus (HCV) envelope proteins, or any part thereof, suitable for use in an immunoassay or vaccine, which method comprising:

growing *Hansenula* or *Saccharomyces* glycosylation minus strains transformed with an envelope gene encoding an HCV E1 and/or HCV E2 protein, or any part thereof, in a suitable culture medium;

causing expression of said HCV E1 and/or HCV E2 gene, or any part thereof; and purifying said intracellularly expressed core-glycosylated HCV E1 and/or HCV E2 protein, or any part thereof, upon lysing the transformed host cell.

The invention further pertains to a method for purifying core-glycosylated hepatitis C virus (HCV) envelope proteins, or any part thereof, suitable for use in an immunoassay or vaccine, which method comprising:

-i- growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;

-ii- causing expression of said HCV E1 and/or HCV E2 gene, or any part thereof; and -iii- purifying said core-glycosylated HCV E1 and/or HCV E2 protein, or any part thereof, in which said Cys-amino acids are reversibly protected by chemical and/or enzymatic means, from said culture.

The invention further pertains to a method for purifying core-glycosylated hepatitis C virus (HCV) envelope proteins, or any part thereof, suitable for use in an immunoassay or vaccine, which method comprising:

-i- growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;

-ii- causing expression of said HCV E1 and/or HCV E2 gene, or any part thereof; and, -iii- purifying said intra-cellulary expressed core-glycosylated HCV E1 and/or HCV E2 protein, or any part thereof, upon lysing the transformed host cell, in which said Cys-amino acids are reversibly protected by chemical and/or enzymatic means.

The present invention specifically relates to a method for purifying recombinant core-glycosylated HCV yeast proteins, or any part thereof, as described herein, in which said purification includes heparin affinity chromatography.

Hence, the present invention also relates to a method for purifying recombinant core-glycosylated HCV yeast proteins, or any part thereof, as described above, in which said chemical means is sulfonation.

Hence, the present invention also relates to a method for purifying recombinant core-glycosylated HCV yeast proteins, or any part thereof, as described above, in which said reversibly protection of Cys-amino acids is exchanged for an irreversible protection by chemical and/or enzymatic means.

Hence, the present invention also relates to a method for purifying recombinant core-glycosylated HCV yeast proteins, or any part thereof, as described above, in which said irreversible protection by chemical means is iodo-acetamide.

Hence, the present invention also relates to a method for purifying recombinant core-glycosylated HCV yeast proteins, or any part thereof, as described above, in which said irreversible protection by chemical means is NEM or Biotin-NEM or a mixture thereof.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting micro-organisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers.

The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A "vaccine" or "medicament" is an immunogenic composition capable of eliciting protection against HCV, whether partial or complete, whether against acute or chronic disease. A vaccine may also be useful for treatment of an individual, in which case it is called a therapeutic vaccine. A vaccine, therefore, includes HCV peptides, proteins, or polynucleotides. Protection against HCV refers in particular to humans, but refers also to non-human primates, trimera mouse (Zauberman et al., 1999), or other mammals.

The core-glycosylated proteins of the present invention can be used as such, in a biotinylated form (as explained in WO 93/18054) and/or complexed to Neutralite Avidin (Molecular Probes Inc., Eugene, Oreg., USA). It should also be noted that "a vaccine composition" comprises, in addition to an active substance, a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric aa's, aa copolymers and inactive virus particles. Such carriers are well known to those skilled in the art. Preferred adjuvants to enhance effectiveness of the composition include, but are not limited to: aluminium hydroxide, aluminium in combination with 3-0-deacylated monophosphoryl lipid A as described in WO 93/19780, aluminium phosphate as described in WO 93/24148, N-acetyl-muramyl-L-threonyl-D-isoglutamine as described in U.S. Pat. No. 4,606,918, N-acetyl-normuramyl-L-alanyl-D-isoglutamine, N-acetylmuramyl-L-alanyl-D-isoglutamyl-L-alanine2-(1'2'dipalmitoyl-sn-glycero-3-hydroxyphosphoryloxy)ethylamine and RIBI (ImmunoChem Research Inc., Hamilton, Mont., USA) which contains monophosphoryl lipid A, detoxified endotoxin, trehalose-6,6-dimycolate, and cell wall skeleton (MPL+TDM+CWS) in a 2% squalene/Tween 80 emulsion. Any of the three components MPL, TDM or CWS may also be used alone or combined 2 by 2. The MPL may also be replaced by its synthetic analogue referred to as RIBI.529. Additionally, adjuvants such as Stimulon (Cambridge Bioscience, Worcester, Mass., USA) or SAF-1 (Syntex) may be used, as well as adjuvants such as combinations between QS21 and 3-de-O-acetylated monophosphoryl lipid A (WO94/00153), or MF-59 (Chiron), or poly[di(carboxylatophenoxy) phosphazene] based adjuvants (Virus Research Institute), or blockcopolymer based adjuvants such as Optivax (Vaxcel, Cythx) or inulin-based adjuvants, such as Algammulin and GammaInulin (Anutech), Incomplete Freund's Adjuvant (IFA) or Gerbu preparations (Gerbu Biotechnik). It is to be understood that Complete Freund's Adjuvant (CFA) may be used for non-human applications and research purposes as well. "A vaccine composition" will further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS). Vaccine compositions comprise an immunologically effective amount of the polypeptides of the present invention, as well as any other of the above-mentioned components. "Immunologically effective amount" means that the administration of that amount to an individual, either in a single dose or as part of a series, is effective for prevention or treatment. This amount varies depending upon the health and physical condition of the individual to be treated, the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting HCV and other relevant factors. It is expected that the amount will fall in a relatively broad range that can be determined through routine trials. Usually, the amount will vary from 0.01 to 1000 μg/dose, more particularly from 0.1 to 100 μg/dose. The vaccine compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents. Therefore, the instant invention pertains to the use of an oligomeric particle as defined herein for prophylactically inducing immunity against HCV. It should be noted that a vaccine may also be useful for treatment of an individual as pointed-out above, in which case it is called a "therapeutic vaccine".

The present invention also relates to a composition as defined above which also comprises HCV core, E1, E2, P7, NS2, NS3, NS4A, NS4B, NS5A and/or NS5B protein, or parts thereof. The core-glycosylated proteins E1, E2, and/or E1/E2 of the present invention may, for example, be combined with other HCV antigens, such as, for example, core, P7, NS3, NS4A, NS4B, NS5A and/or NS5B. The purification of these NS3 proteins will preferentially include a reversible modification of the cysteine residues, and even more preferentially sulfonation of cysteines. Methods to obtain such a reversible modification, including sulfonation have been described for NS3 proteins in Maertens et al. (PCT/EP99/02547). It should be stressed that the whole content, including all the definitions, of the latter document is incorporated by reference in the present application. It is clear from the above that the present invention also relates to the usage of a core-glycosylated envelope proteins as defined above or a composition as defined above for the manufacture of an HCV vaccine composition. In particular, the present invention relates to the usage of a core-glycosylated envelope protein as defined herein for inducing immunity against HCV in chronic HCV carriers. More in particular, the present invention relates to the usage of a core-glycosylated envelope protein as defined herein for inducing immunity against HCV in chronic HCV carriers prior to, simultaneously to or after any other therapy, such as, for example, the well-known interferon therapy either or not in combination with the administration of small drugs treating HCV, such as, for example, ribavirin. Such composition may also be employed before or after liver transplantation, or after presumed infection, such as, for example, needle-stick injury. In addition, the present invention relates to a kit containing the a core-glycosylated envelope protein of the present invention to detect HCV antibodies present in a biological sample. The term "biological sample" as used herein, refers to a sample of tissue or fluid isolated from an individual, including but not limited to, for example, serum, plasma, lymph fluid, the external sections of the skin, respiratory intestinal, and genitourinary tracts, oocytes, tears, saliva, milk, blood cells, tumors, organs, gastric secretions, mucus, spinal cord fluid, external secretions such as, for example, excrement, urine, sperm, and the like. Since the a core-glycosylated envelope proteins of the present invention are highly immunogenic, and stimulate both the humoral and cellular immune response, the present invention relates also to a kit for detecting HCV related T cell response, comprising the oligomeric particle or the purified single HCV envelope protein of the instant invention. HCV T cell response can for example be measured as described in the examples section, or as described in PCT/EP 94/03555 to Leroux-Roels et al. It should be stressed that the whole content, including all the definitions, of this document is incorporated by reference in the present application In particular, the present invention relates to HCV E1 and/or E2 proteins, or any part thereof, as described herein, for use as medicament.

In particular, the present invention relates to the use of HCV E1 and/or E2 proteins, or any part thereof, as described herein, for the manufacture of a vaccine/medicament against HCV infection.

Also, the present invention relates to the use of a core-glycosylated envelope protein as described herein for inducing immunity against HCV, characterized in that said core-glycosylated envelope protein is used as part of a series of time and compounds. In this regard, it is to be understood that the term "a series of time and compounds" refers to administering with time intervals to an individual the compounds used for eliciting an immune response. The latter compounds may comprise any of the following components: a core-glycosylated envelope protein, HCV DNA vaccine composition, HCV polypeptides.

In this respect, a series comprises administering, either:

(I) an HCV antigen, such as, for example, a core-glycosylated envelope protein, with time intervals, or (II) an HCV antigen, such as, for example, a core-glycosylated envelope protein in combination with a HCV DNA vaccine composition, in which said core-glycosylated envelope protein oligomeric particles and said HCV DNA vaccine composition, can be administered simultaneously, or at different time intervals, including at alternating time intervals, or (III) either (I) or (II), possibly in combination with other HCV peptides, with time intervals.

In this regard, it should be clear that a HCV DNA vaccine composition comprises nucleic acids encoding HCV envelope peptide, including E1-, E2-, E1/E2-peptides, NS3 peptide, other HCV peptides, or parts of said peptides. Moreover, it is to be understood that said HCV peptides comprises HCV envelope peptides, including E1-, E2-, E1/E2-peptides, other HCV peptides, or parts thereof. The term "other HCV peptides" refers to any HCV peptide or fragment thereof. In item II of the above scheme, the HCV DNA vaccine composition comprises preferentially nucleic acids encoding HCV envelope peptides. In item II of the above scheme, the HCV DNA vaccine composition consists even more preferentially of nucleic acids encoding HCV envelope peptides, possibly in combination with a HCV-NS3 DNA vaccine composition. In this regard, it should be clear that an HCV DNA vaccine composition comprises a plasmid vector comprising a polynucleotide sequence encoding an HCV peptide as described above, operably linked to transcription regulatory elements. As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. As used herein, a "polynucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides. As used herein, the term "transcription regulatory elements" refers to a nucleotide sequence which contains essential regulatory elements, such that upon introduction into a living vertebrate cell it is able to direct the cellular machinery to produce translation products encoded by the polynucleotide. The term "operably linked"0 refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used succesfully.

Alternatively, the DNA vaccine may be delivered through a live vector such as adenovirus, canary pox virus, MVA, and the like.

The HCV envelope proteins of the present invention, or the parts thereof, are particularly suited for incorporation into an immunoassay for the detection of HCV, and/or genotyping of HCV, for prognosing/monitoring of HCV disease, or as a therapeutic agent.

The immunoassay methods according to the present invention utilize the HCV envelope proteins of the present invention that maintain linear (in case of peptides) and conformational epitopes, recognized by antibodies in the sera from individuals infected with HCV. The HCV E1 and E2 antigens of the present invention may be employed in virtually any assay format that employs a known antigen to detect antibodies. Of course, a format that denatures the HCV conformational epitope should be avoided or adapted. A common feature of all of these assays is that the antigen is contacted with the body component suspected of containing HCV antibodies under conditions that permit the antigen to bind to any such antibody present in the component. Such conditions will typically be physiologic temperature, pH and ionic strenght using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA and RIA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies in the antibody-antigen complexes is directly monitored. This may be accomplished by determining whether labeled anti-xenogeneic (e.g. anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or in the case of competitive assays, the amount of competing antibody) are detected by any of a number of known techniques, depending on the format. For example, unlabeled HCV antibodies in the complex may be detected using a conjugate of anti-xenogeneic Ig complexed with a label (e.g. an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

The HCV envelope proteins, or specific parts thereof of the present invention comprised of conformational epitopes will typically be packaged in the form of a kit for use in these immunoassays. The kit will normally contain in separate containers the native HCV antigen, control antibody formulations (positive and/or negative), labeled antibody when the assay format requires the same and signal generating reagents (e.g. enzyme substrate) if the label does not generate a signal directly. The native HCV antigen may be already bound to a solid matrix or separate with reagents for binding it to the matrix. Instructions (e.g. written, tape, CD-ROM, etc.) for carrying out the assay usually will be included in the kit.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

In particular, the present invention relates to the use of HCV E1 and/or HCV E2 proteins, or any part thereof, as described herein, for the preparation of a diagnostic kit.

In particular, the present invention relates to an immunoassay for detecting HCV antibody in a biological sample, which immunoassay comprises:

providing the HCV envelope protein, or any part thereof, as described herein;

incubating a biological sample with said HCV antibody under conditions that allow formation of HCV antibody-HCV protein complex; and determining whether said HCV antibody-HCV protein complex is formed.

In particular, the present invention relates to a kit for detecting HCV antibody in a biological sample, which kit comprises providing the HCV envelope protein, or any part thereof, as described herein.

The present invention will now be illustrated by reference to the following examples which set forth particularly advantageous embodiments. However, it should be noted that these embodiments are merely illustrative, and cannot be construed as to restrict the invention in any way.

EXAMPLES

Example 1

Construction of pFPMT-MFα-E1-H6 Shuttle Vector

Plasmids for *Hansenula polymorpha* transformation were constructed as follows. The pFPMT-MFα-E1-H6 shuttle vector has been constructed in a multi-step procedure. Intially the nucleic acid sequence encoding the HCV E1s protein (SEQ ID NO:2) was cloned after a CHH leader sequence (CHH=*Carcinus maenas* hyperglycemic hormone) which was subsequently changed for a MFα leader sequence (MFα=*Saccharomyces cerevisiae* α-mating factor).

At first a pUC18 derivative has been constructed harboring the CHH-E1-H6 unit as a EcoRI/BamHI fragment by the seamless cloning method (Padgett, K. A. and Sorge, J. A. 1996). Thereto, the E1s-H6-encoding DNA fragment and the pCHH-Hir-derived acceptor plasmid were generated by PCR as described below.

Generation of E1s-H6-encoding DNA Fragment

Figure 1:
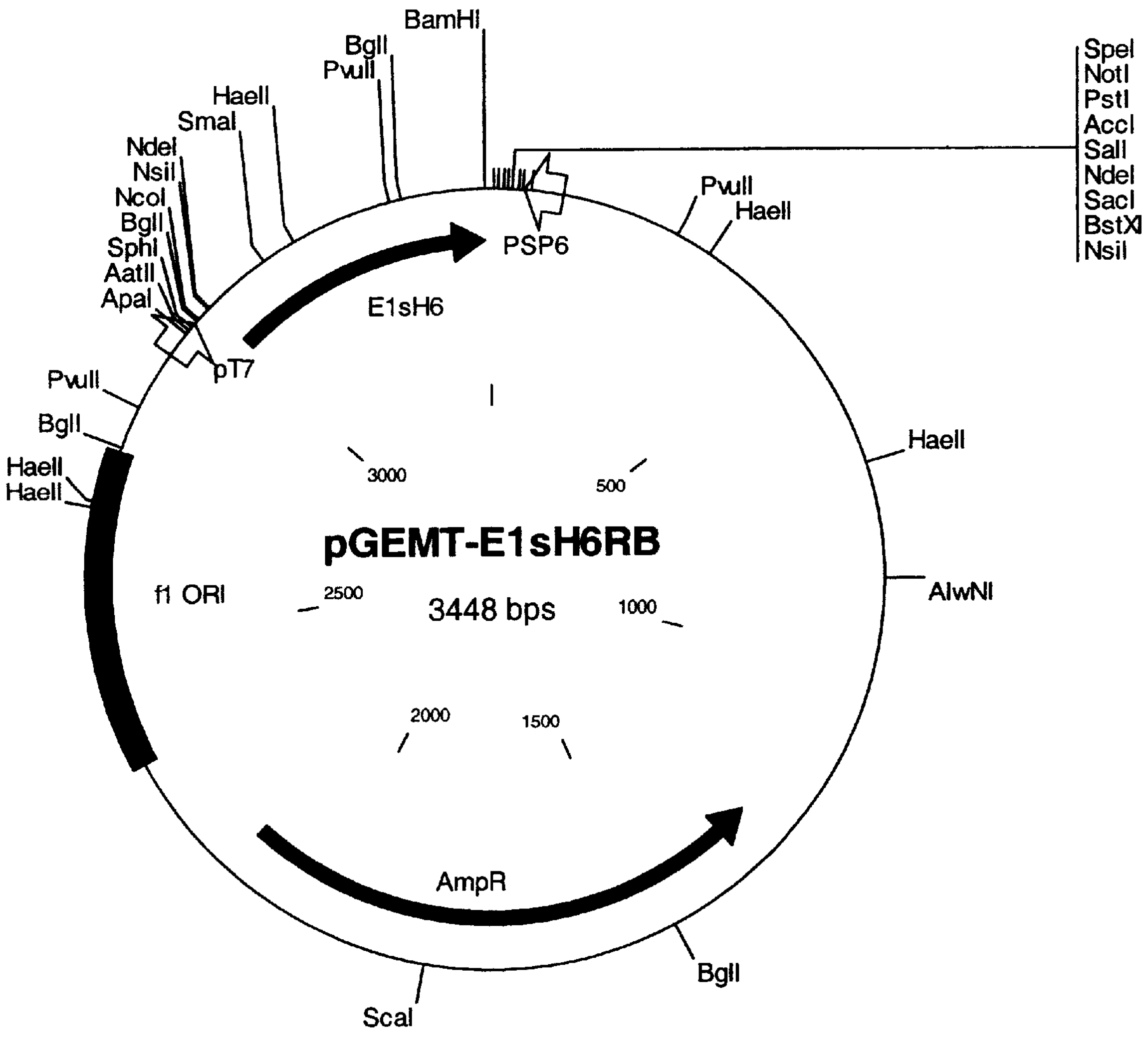
FIG. 1. Schematic map of the vector pGEMT-E1sH6RB which has the sequence as defined in SEQ ID NO:6.

The E1-H6 DNA fragment (coding for HCV type 1b E1s protein consisting of the amino acids 192 to 326 of E1s elongated with 6 His-residues; SEQ ID NO:5) was isolated by PCR from the plasmid pGEMTE1sH6 (SEQ ID NO:6; FIG. 1). The following primers were used thereto:

CHHE1-F: 5'-agttactcttca.agg tatgaggtgcgcaacgtgtccg-3' (SEQ ID NO:7);

The Eam1104I site is underlined, the dot marks the cleavage site. The bold printed bases are complementary to those of primer CHH-links. The non-marked bases anneal within the start region of E1 (192–326) in sense direction; and

CHHE1-R:

5'-agttactcttca.cagggatcctccttaatggtgatggtggtggtgcc-3' (SEQ ID NO:8);

The Eam1104I site is underlined, the dot marks the cleavage site. The bold printed bases are complementary to those of primer MF30-rechts. The bases forming the BamHI site usefull for later cloning procedures are printed in italics. The non-marked bases anneal in antisense direction within the end of the E1-H6 unit, including the stop codon and three additional bases between the stop codon and the BamHI site.

The reaction mixture was constituted as follows: total volume of 50 μL containing 20 ng of Eco311-linearized pGEMTE1sH6, each 0.2 μM of primers CHHE1-F and CHHE1-R, dNTP's (each at 0.2 μM), 1×buffer 2 (Expand Long Template PCR System; Boehringer; Cat No 1681 834), 2.5 U polymerase mix (Expand Long Template PCR System; Boehringer; Cat No 1681 834).

Program 1 was used, said program consisting of the following steps:

1. denaturation: 5 min 95° C.;
2. 10 cycles of 30 sec denaturation at 95° C., 30 sec annealing at 65° C., and 130 sec elongation at 68° C.
3. termination at 4° C.

Then 5 μL 10× buffer 2 (Expand Long Template PCR System; Boeringer; Cat No 1681 834), 40 μL $H_2O$, and 5 μL of [dATP, dGTP, and dTTP (2 mM each); 10 mM 5-methyl-dCTP] were added to the sample derived from program 1, and further amplification was performed following program 2 consisting of the following steps:

1. denataruation: 5 min at 95° C.
2. 5 cycles of 45 sec denaturation at 95° C., 30 sec annealing at 65° C., and 130 sec at 68° C.
3. termination at 4° C.

Generation of pCHH-Hir-derived Acceptor Plasmid

Figure 2:
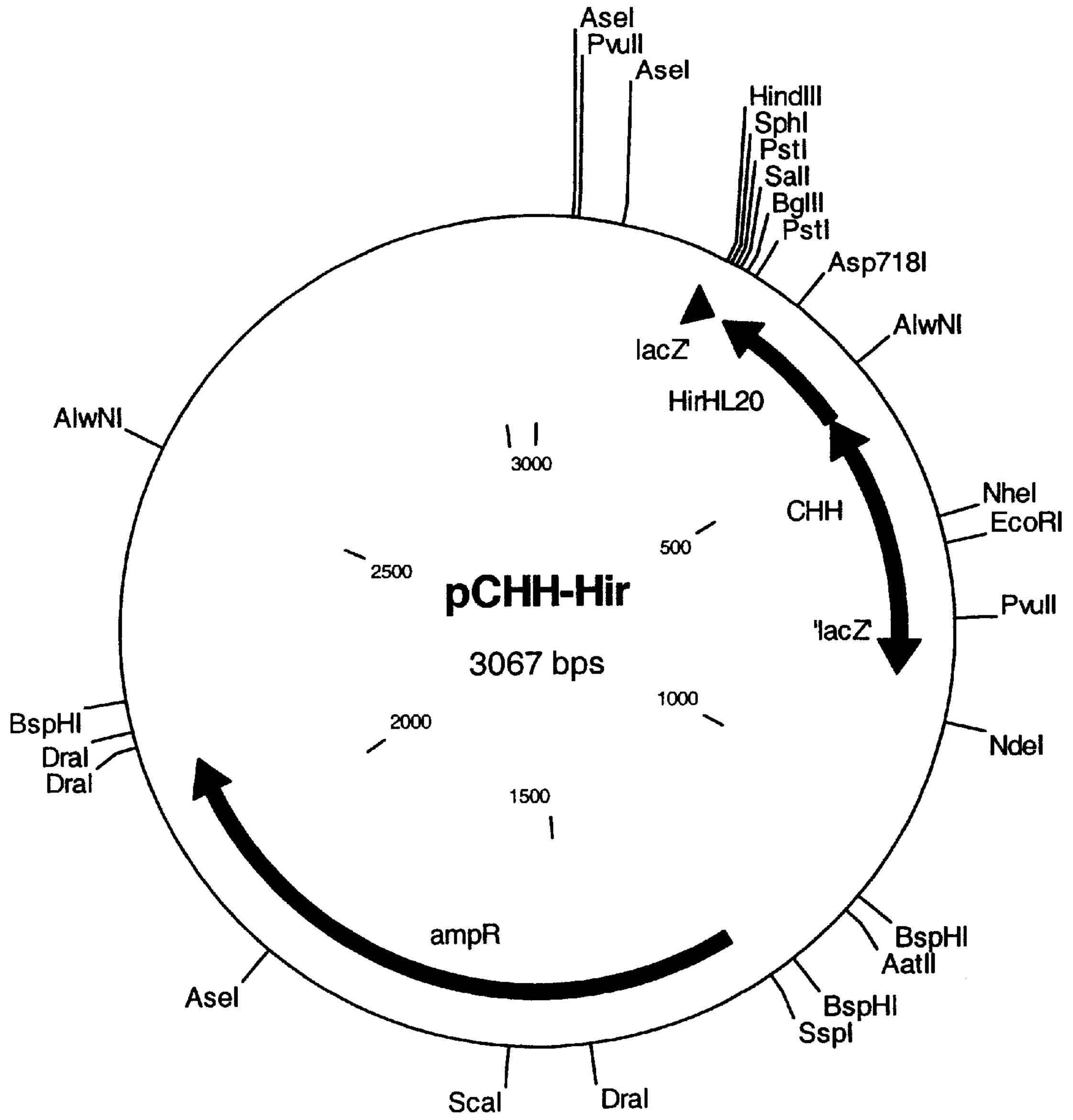
FIG. 2. Schematic map of the vector pCHH-Hir which has the sequence as defined in SEQ ID NO:9.

The acceptor fragment was made by PCR from the pCHH-Hir plasmid (SEQ ID NO:9; FIG. 2) and consists of almost the complete pCHH-Hir plasmid, except that the Hir-coding sequence is not present in the PCR product. Following primers were used for this PCR:

1. CHH-links: 5'-agtta<u>ctcttc</u>a.cctcttttccaacgggtgtgtag-3'; (SEQ ID NO:10)

The Eam1104I site is underlined, the dot marks the cleavage site. The bold printed bases are complementary to those of primer CHHE1-F. The non-marked bases anneal within the end of the CHH sequence in antisense direction; and 2. MF30-rechts: 5'-agtca<u>ctcttc</u>a.ctgcaggcatgcaagcttggcg-3'; (SEQ ID NO:11)

The Eam1104I site is underlined, the dot marks the cleavage site. The bold printed bases are complementary to those of primer CHHE1-R. The non-marked bases anneal within the pUC18 sequences behind the cloned CHH-Hirudin HL20 of pCHH-Hir, pointing away from the insert.

The reaction mixture was constituted as follows: total volume of 50 μL containing 20 ng of Asp718I-linearized pCHH-Hir, each 0.2 μM of primers CHH-links and MF30-rechts, dNTP's (each at 0.2 μM), 1× buffer 2 (Expand Long Template PCR System; Boeringer; Cat No 1681 834), 2.5 U polymerase mix (Expand Long Template PCR System; Boeringer; Cat No 1681 834).

Program 1 was as described above was used.

Then 5 μL 10× buffer 2 (Expand Long Template PCR System; Boeringer; Cat No 1681 834), 40 μL $H_2O$, and 5 μL of [dATP, dGTP, and dTTP (2 mM each); 10 mM 5-methyl-dCTP] were added to the sample derived from program 1, and further amplification was performed following program 2 as described above.

Generation of Vector pCHHE1

The E1s-H6-encoding DNA fragment and the pCHH-Hir-derived acceptor plasmid generated by PCR as described above were purified using the PCR product purification kit (Qiagen) according to the supplier's specifications. Subsequently the purified fragments were digested separately with Eam1104I. Subsequently, the E1s-H6 DNA fragment was ligated into the pCHH-Hir-derived acceptor plasmid using T4 ligase (Boehringer) following the specifications of the supplier.

*E. coli* XL-Gold cells were transformed with the ligation mixture and the plasmid DNA of several ampicillin-resistant colonies were analyzed by digestion with EcoRI and BamHI. A positive clone was selected and denominated as pCHHE1.

Generation of Vector pFPMT-CHH-E1H6

Figure 3:
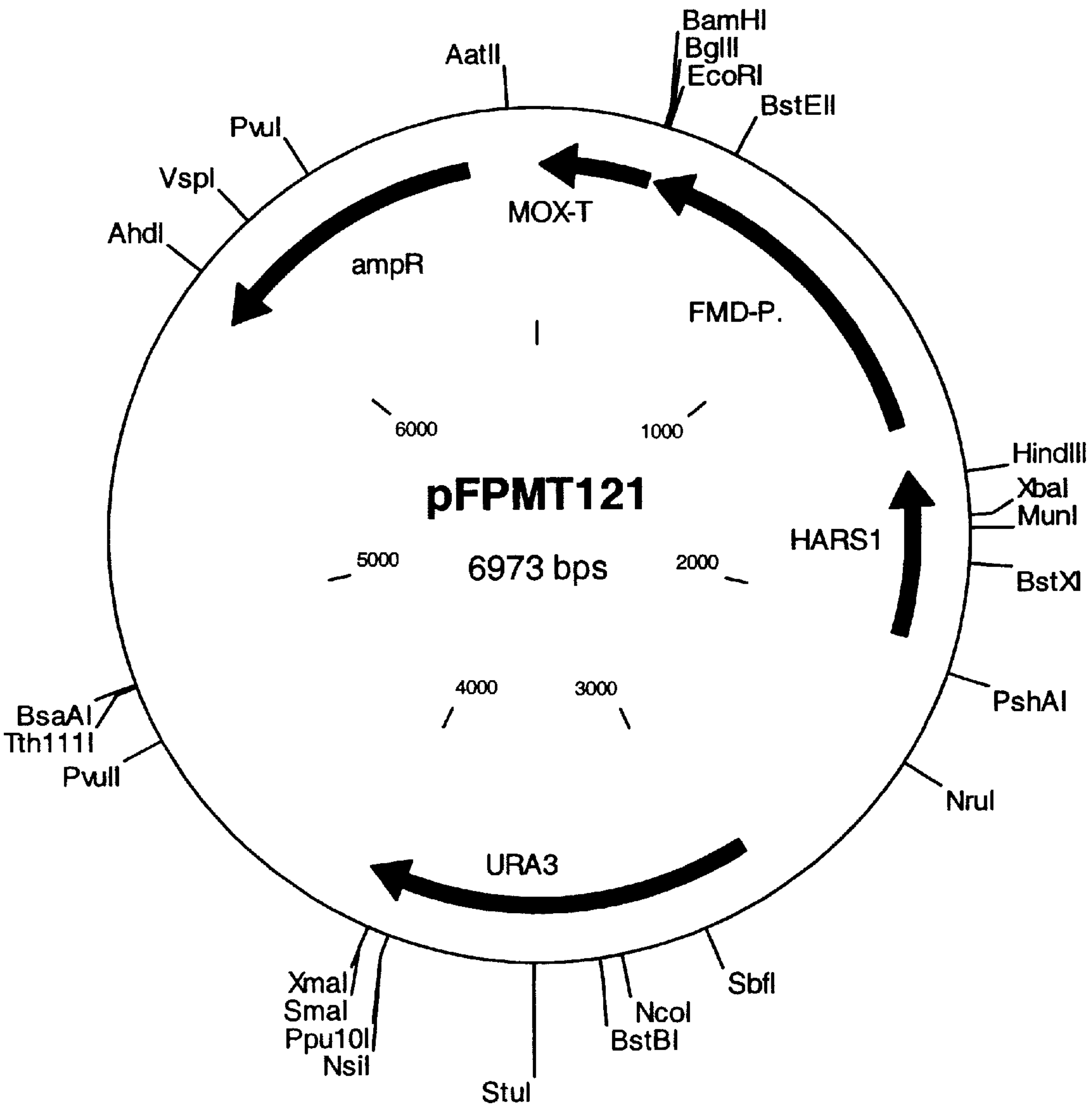
FIG. 3. Schematic map of the vector pFPMT121 which has the sequence as defined in SEQ ID NO:12.
Figure 4:
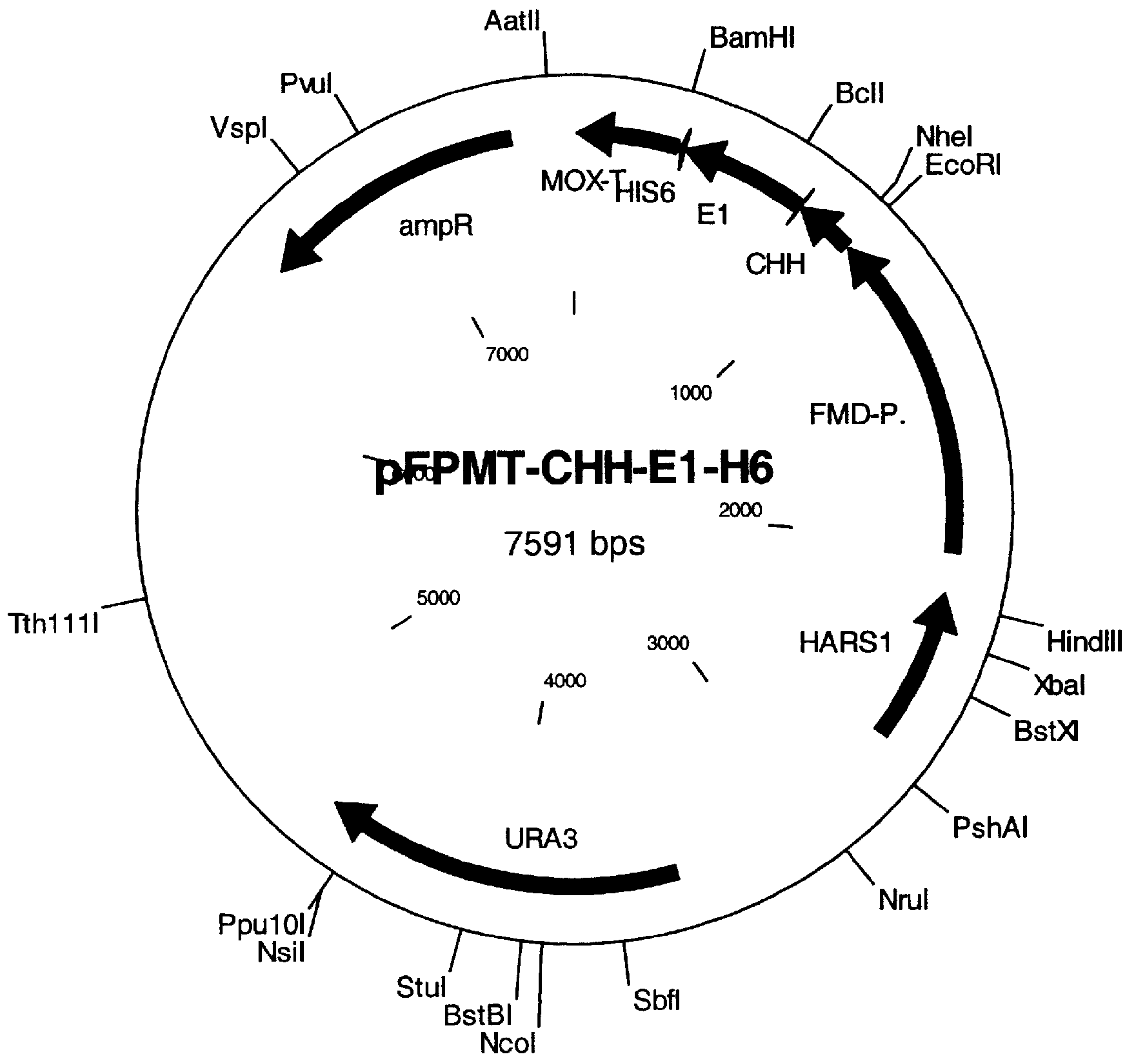
FIG. 4. Schematic map of the vector pFPMT-CHH-E1-H6 which has the sequence as defined in SEQ ID NO:13.

The EcoRI/BamHI fragment of pCHHE1 was ligated with the EcoRI/BamHI digested vector pFPMT121 (SEQ ID NO:12; FIG. 3). T4 ligase (Boehringer) was used according to the supplier's instructions. The ligation mixture was used to transform *E. coli* DH5αF' cells. Several transformants were analyzed on restriction pattern of the plasmid DNA and a positive clone was withheld which was denominated pFPMT-CHH-E1H6 (SEQ ID NO:13; FIG. 4).

Generation of pFPMT-MFα-E1-H6

Figure 36:
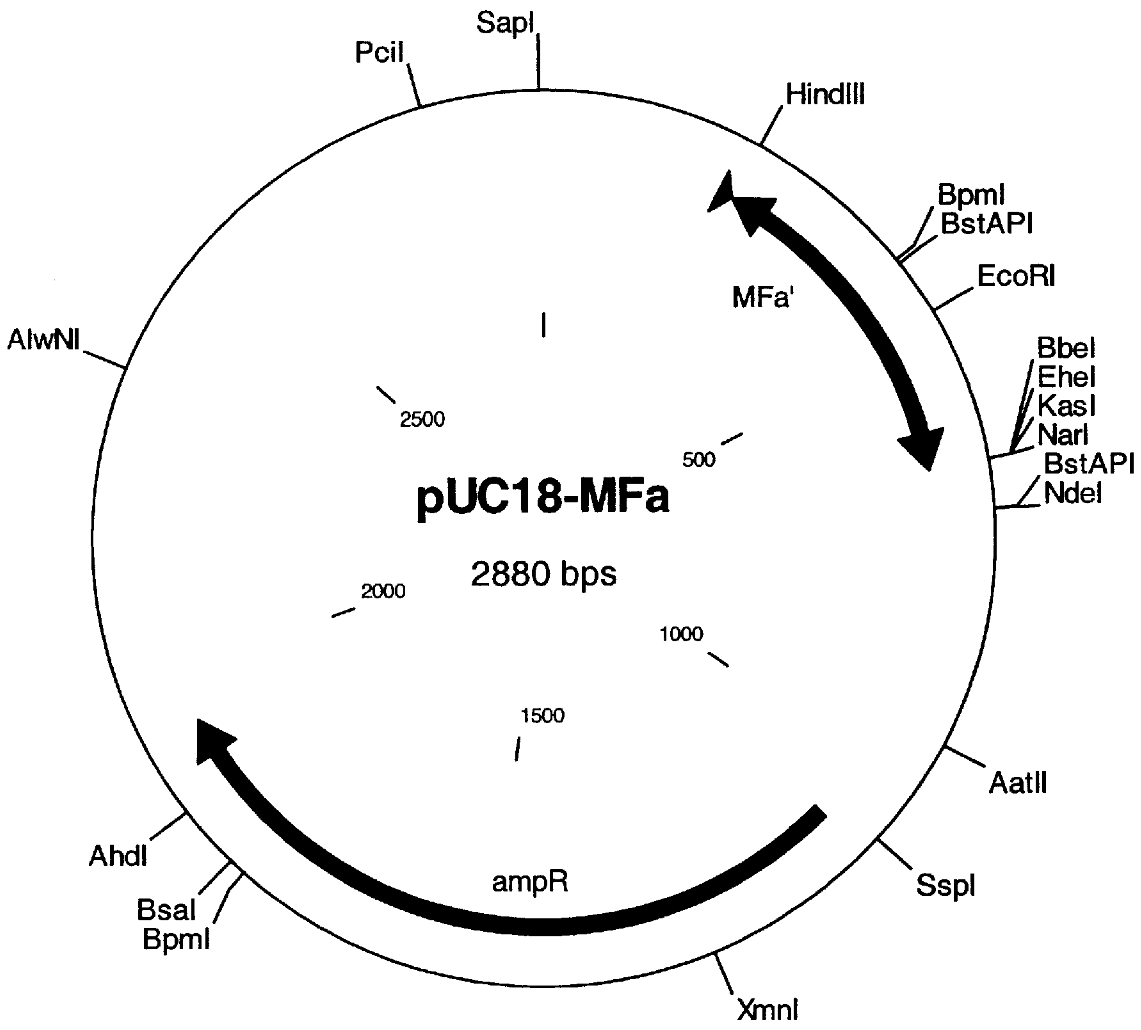
FIG. 36. Schematic map of the vector pUC18MFa which has the sequence as defined in SEQ ID NO:62.

Finally the shuttle vector pFPMT-MFα-E1-H6 was generated by ligation of three fragments, said fragments being:

1. the 6.961 kb EcoRI/BamHI digested pFPMT121 (SEQ ID NO:12; FIG. 3),
2. the 0.245 EcoRI/HindIII fragment of pUC18-MFa (SEQ ID NO:62; FIG. 36), and
3. the 0.442 kb HindIII/BamHI fragment of a 0.454 kb PCR product derived from pFPMT-CHH-E1H6.

The 0.454 kb PCR product giving rise to fragment No.3 was obtained by PCR using the following primers:

```
1. primer MFa-E1 f-Hi:
5'-aggggtaagcttggataaaaggtatgaggtgcgcaacgtgtccgggatgt-3'; (SEQ ID NO:14)
and

2. primer E1 back-Bam:
5'-agttacggatccttaatggtgatggtggtggtgccagttcat-3'.         (SEQ ID NO:15)
```

The reaction mixture was constituted as follows: Reaction mixture volume 50 µL, pFPMT-CHH-E1-H6 (EcoRI-linearized; 15 ng/µL), 0.5 µL; primer MFa-E1 f-Hi (50 µM), 0.25 µL; primer E1 back-Bam (50 µM), 0.25 µL; dNTP's (all at 2 mM), 5 µL; DMSO, 5 µL; $H_2O$, 33.5 µL; Expand Long Template PCR System (Boeringer Mannheim; Cat No 1681 834) Buffer 2 (10× concentrated), 5 µL; Expand Long Template PCR System Polymerase mixture (1 U/µL), 0.5 µL.

The PCR program consisting of the following steps was used:

1. denaturation: 5 min at 95° C.
2. 29 cycles of 45 sec denaturation at 95° C., 45 sec annealing at 55° C., and 40 sec elongation at 68° C.
3. termination at 4° C.

Based on the primers used, the resulting 0.454 kb PCR product contained the codons of E1(192–326) followed by six histidine codons and a "taa" stop codon, upstream flanked by the 22 3'-terminal base pairs of the MFα prepro sequence (including the cloning relevant HindIII site plus a six base pairs overhang) and downstream flanked by a (cloning relevant) BamHI site and a six base pairs overhang.

For the ligation reaction, T4 DNA ligase (Boehringer Mannheim) has been used according to the supplier's conditions (sample volume 20 µL).

Figure 5:
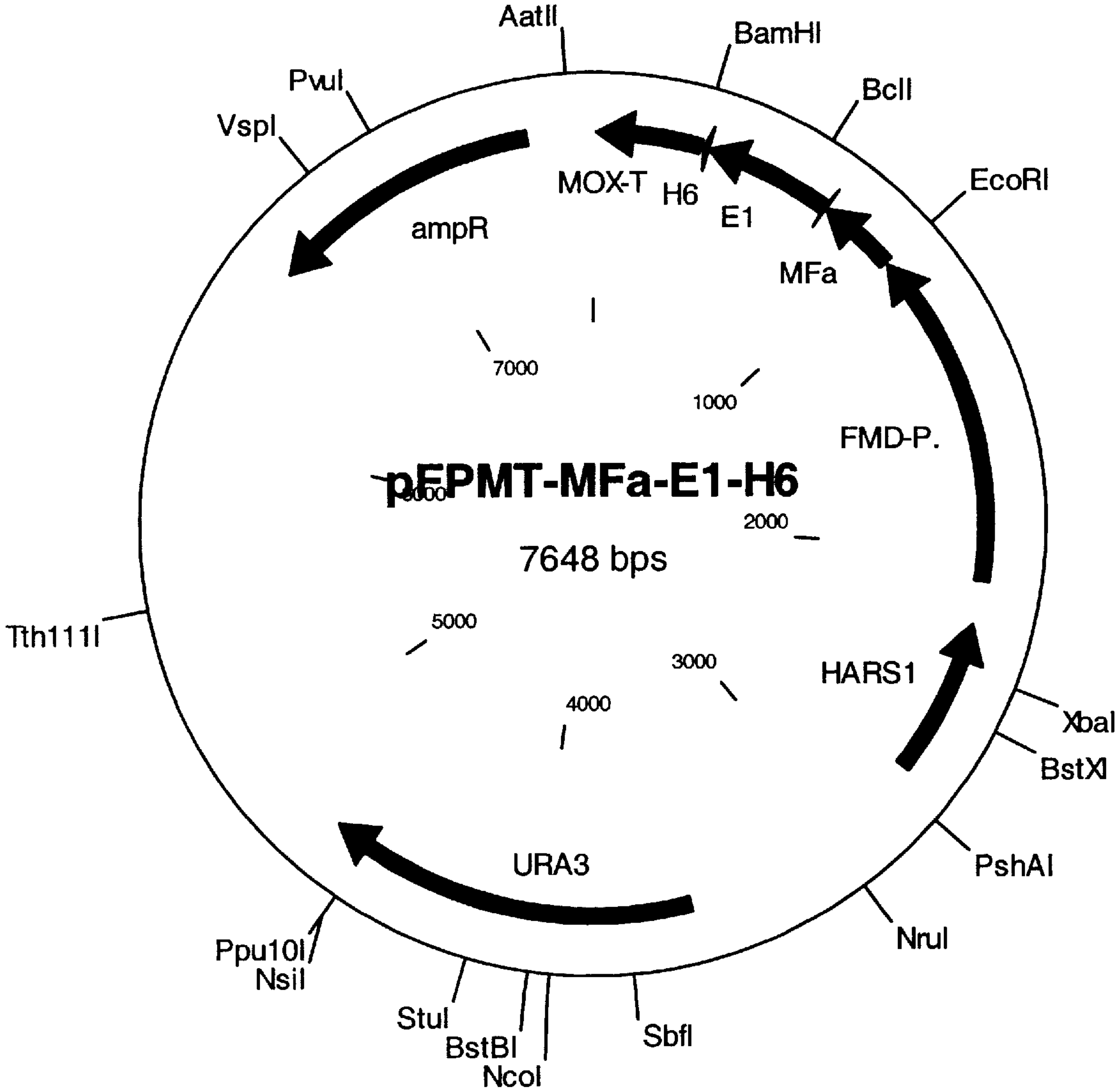
FIG. 5. Schematic map of the vector pFPMT-MFa-E1-H6 which has the sequence as defined in SEQ ID NO:16.

*E. coli* HB101 cells were transformed with the ligation mixture and positive clones withheld after restriction analysis of the plasmids isolated from several transformants. A positive plasmid was selected and denominated as pFPMT-MFα-E1-H6 (SEQ ID NO:16; FIG. 5).

Example 2

Construction of pFPMT-CL-E1-H6 Shuttle Vector

Plasmids for *Hansenula polymorpha* transformation were constructed as follows. The pFPMT-CL-E1-H6 shuttle vector was constructed in three steps starting from pFPMT-MFα-E1-H6 (SEQ ID NO:16, FIG. 5).

Figure 6:
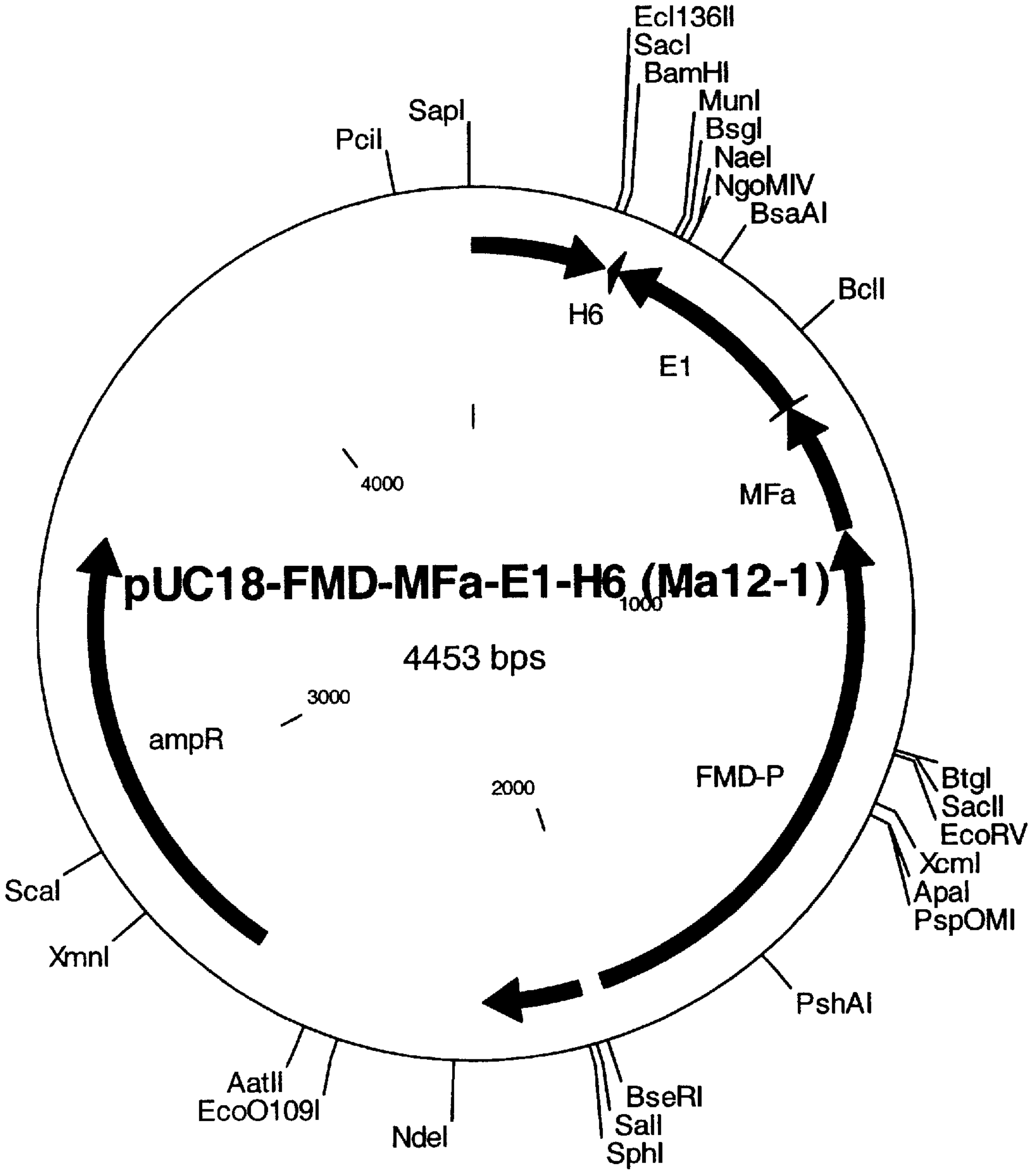
FIG. 6. Schematic map of the vector pUC18-FMD-MFa-E1-H6 which has the sequence as defined in SEQ ID NO:17.

In a first step, the MFα-E1-H6 reading frame of pFPMT-MFα-E1-H6 was subcloned into the pUC18 vector. Therefore a 1.798 kb SalI/BamHI fragment of pFPMT-MFα-E1-H6 (containing the FMD promotor plus MFα-E1-H6) was ligated to the SalI/BamHI vector fragment of pUC18 with T4 ligase (Boehringer) accordig to the supplier's conditions. This resulted in plasmid that is depicted in FIG. 6 (SEQ ID NO:17), and further denominated as pMa12-1 (pUC18-FMD-MFα-E1-H6). The ligation mixture was used to transform *E. coli* DH5αF' cells. Several ampicillin-resistant colonies were picked and analyzed by restriction enzyme digestion of plasmid DNA isolated from the picked clones. A positive clone was further analyzed by determining the DNA sequence of the MFα-E1-H6 coding sequence. A correct clone was used for PCR directed mutagenesis to replace the MFα pre-pro-sequence with the codons of the avian lysozyme pre-sequence ("CL"; corresponding to amino acids 1 to 18 of avian lysozyme; SEQ ID NO:1). The principle of the applied PCR-directed mutagenesis method is based on the amplification of an entire plasmid with the desired alterations located at the 5'-ends of the primers. In downstream steps, the ends of the linear PCR product are modified prior to self-ligation resulting in the desired altered plasmid.

The following primers were used for the PCR reaction:

```
1. primer CL hin: 5'-tgcttcctaccactagcagcactaggatatgaggtgcgcaacgtgtccggg-3';        (SEQ ID NO:18)

2. primer CL her neu: 5'-tagtactagtattagtaggcttcgcatgaattcccgatgaaggcagagagcg-3'.     (SEQ ID NO:19)
```

The underlined 5' regions of the primers contain the codons of about half of the avian lysozyme pre-sequence. Primer CL her neu includes a SpeI restriction site (italic). The non-underlined regions of the primers anneal with the codons for amino acid residues 192 to 199 of E1 (CL hin) or the with the "atg" start codon over the EcoRI site up to position −19 (counted from the EcoRI site) of FMD promoter. The primers are designed to amplify the complete pMa12-1 thereby replacing the codons of the MFa pre-pro-sequence with the codons of the avian lysozyme pre sequence.

The reaction mixture was constituted as follows: pUC18-FMD-Mfα-E1-H6 (pMa12-1; 1.3 ng/µL), 1 µL; primer CL hin (100 µM), 2 µL; primer CL her neu (100 µM), 2 µL; dNTP's (all at 2.5 mM), 8 µL; $H_2O$, 76 µL; Expand Long Template PCR System (Boeringer; Cat No 1681 834) Buffer 2 (10× concentrated), 10 µL; Expand Long Template PCR System Polymerase mixture (1 U/µL), 0.75 µL.

The PCR program consisting of the following steps was applied:

1. denaturation: 15 min at 95° C.
2. 35 cycles of 30 sec denaturation at 95° C., 1 min annealing at 60° C., and 1 min elongation at 72° C.
3. termination at 4° C.

The resulting PCR product was checked by agarose gel electrophoresis for its correct size (3.5 kb). Thereafter the 3'-A overhangs form the PCR product were removed by a T4 polymerase reaction resulting in blunt ends with 3'- and 5'-OH-groups. Therefore, the PCR product was treated with T4 polymerase (Boehringer; 1 U/μL): to the remaining 95 μL of PCR reaction mix were added 1 μL T4 polymerase and 4 μL dNTP's (all at 2.5 mM). The sample was incubated for 20 min at 37° C. Subsequently, the DNA was precipitated with ethanol and taken up in 16 μL $H_2O$.

Subsequently 5'-phosphates were added to the blunt-ended PCR product by a kinase reaction. Therefore, to the 16 μL blunt-ended PCR product were added 1 μL T4 polynucleotide kinase (Boehringer; 1U/μL), 2 μL 10-fold concentrated T4 polynucleotide kinase reaction buffer (Boehringer), and 1 μL ATP (10 mM). The sample was incubated for 30 min at 37° C.

Subsequently the DNA was applied onto a 1% agarose gel and the correct product band was isolated by means of the gel extraction kit (Qiagen) according to the supplier's conditions. Fifty (50) ng of the purified product was then self-ligated by use of T4 ligase (Boehringer) according to the supplier's conditions. After 72 h incubation at 16° C., the DNA in the ligation mix was precipitated with ethanol and dissolved in 20 μL water.

*E. coli* DH5α-F' cells were subsequently transformed with 10 μL of the ligation sample. The plasmid DNA of several ampicillin-resistant clones was checked by means of restriction enzyme digestion. A positive clone was withheld and denominated p27d-3 (pUC18-FMD-CL-E1-H6, SEQ ID NO:20, FIG. 7). Subsequently the CL-E1-H6 reading frame was verified by DNA sequencing.

Figure 8:
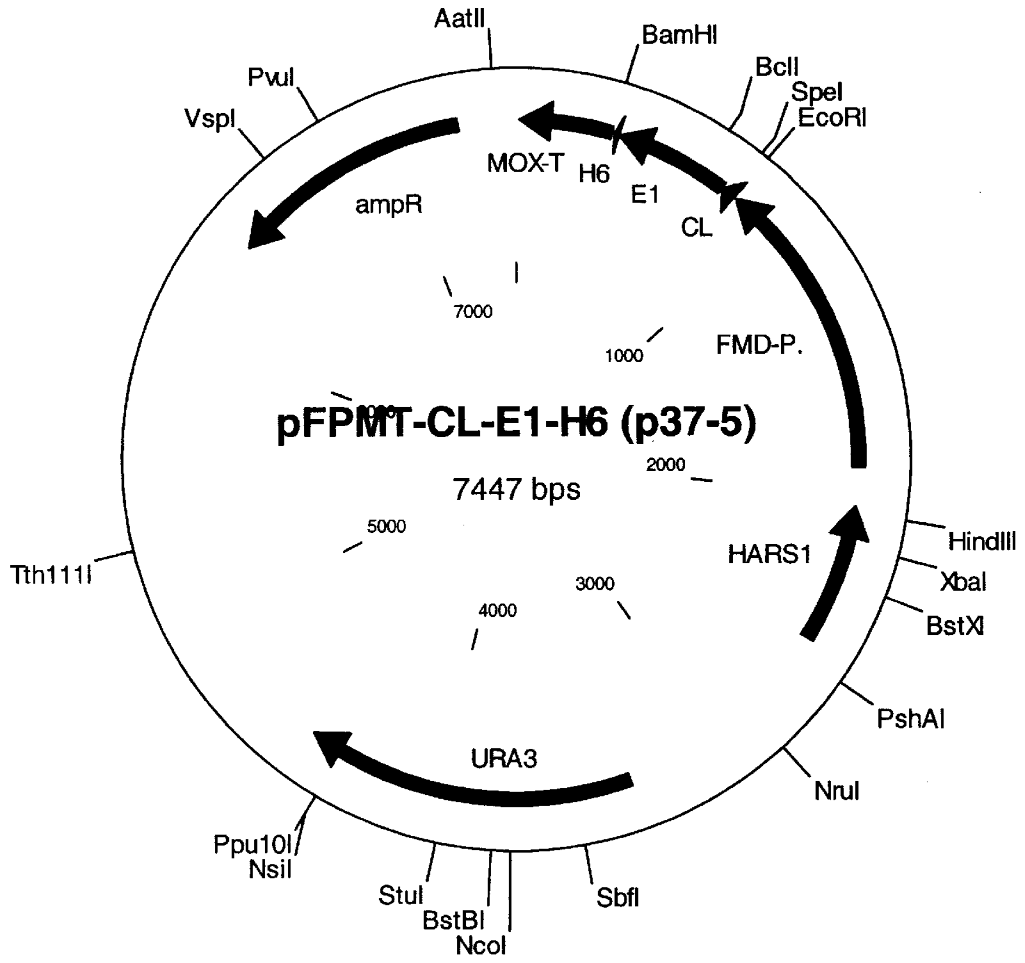
FIG. 8. Schematic map of the vector pFPMT-CL-E1-H6 which has the sequence as defined in SEQ ID NO:21.

In a last step the pFPMT-CL-E1-H6 shuttle vector was constructed as described below. The 0.486 kb EcoRI/BamHI fragment of p27d-3 (harboring CL-E1(192–326)-H6) was ligated with EcoRI/BamHI-digested pFPMT121 (SEQ ID NO:12, FIG. 3). For the reaction, T4 ligase (Boehringer) has been used according to the supplier's recommendations. The DNA in the ligation sample was precipitated with ethanol and dissolved in 10 μL $H_2O$. *E. coli* DH5αF' cells were transformed with 10 μL of the ligation sample, and the plasmid DNA of several ampicillin-resistant colonies were analyzed by digestion with EcoRI and BamHI. Plasmid clone p37-5 (pFPMT-CL-E1-H6; SEQ ID NO:21, FIG. 8) showed the desired fragment sizes of 0.486 kb and 6.961 kb. The correct sequence of CL-E1-H6 of p37-5 was verified by sequencing.

Example 3

Construction of pFPMT-MFα-E2-H6 and pMPT-MFα-E2-H6 Shuttle Vectors

Figure 9:
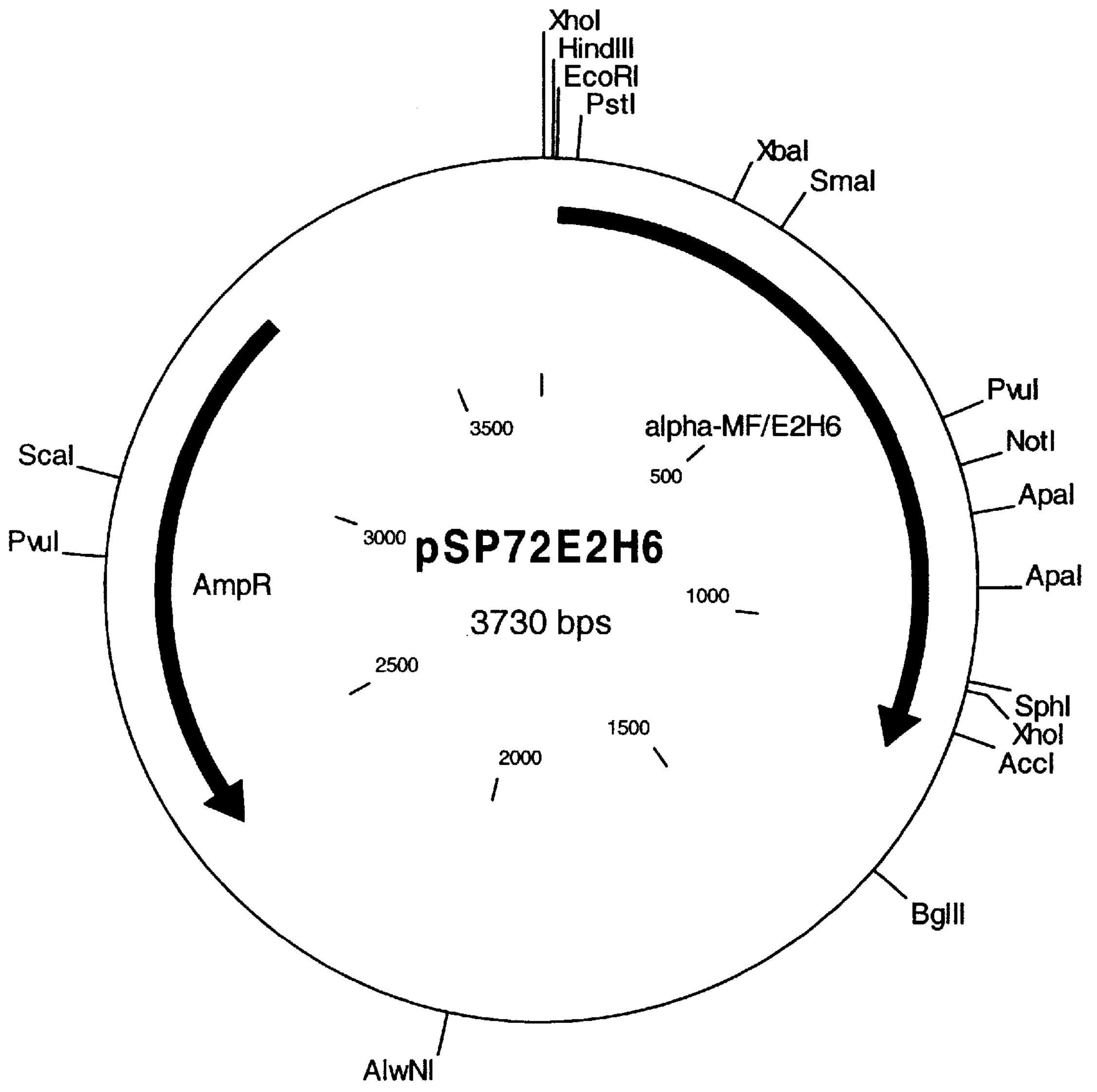
FIG. 9. Schematic map of the vector pSP72E2H6 which has the sequence as defined in SEQ ID NO:22.
Figure 10:
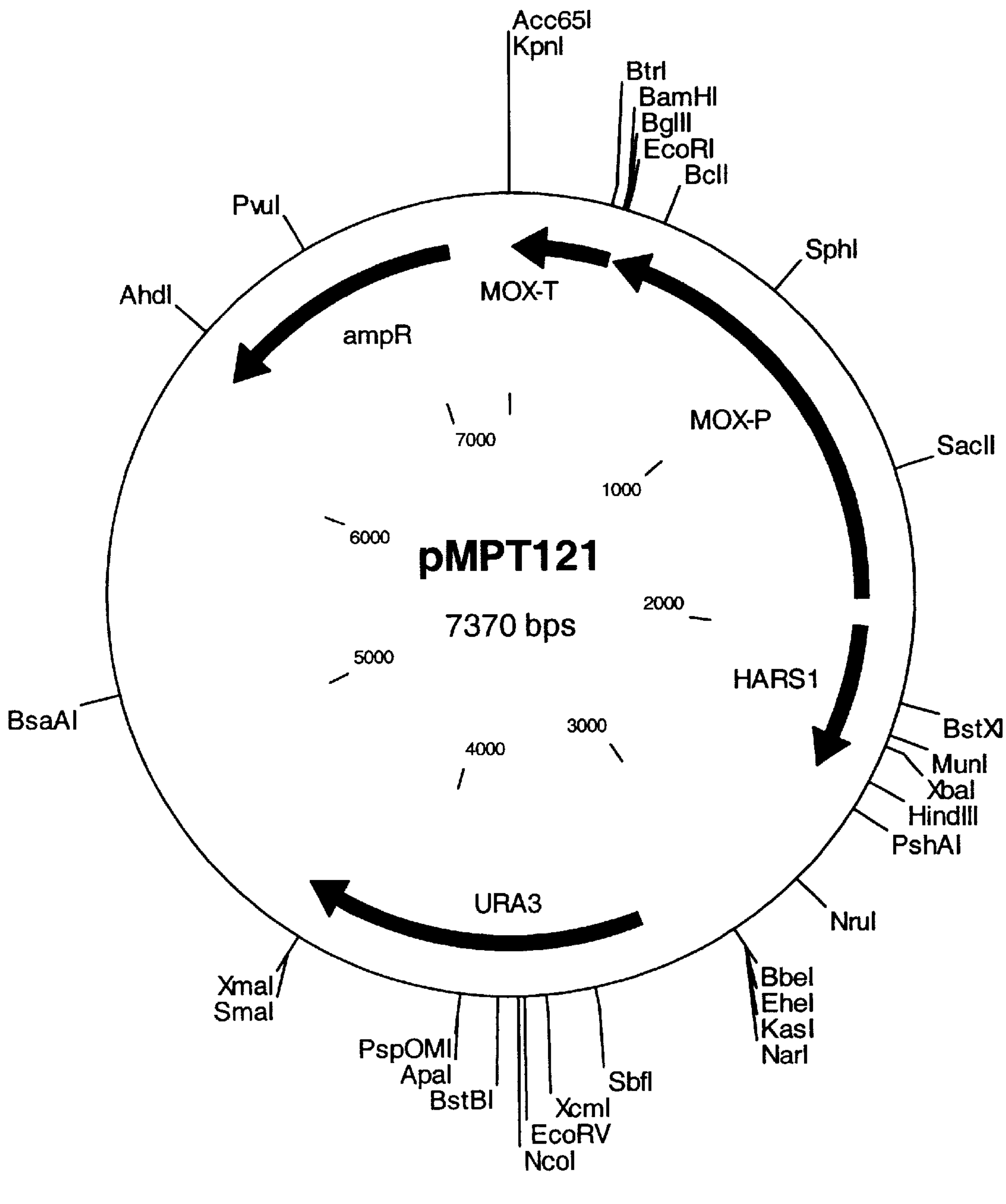
FIG. 10. Schematic map of the vector pMPT121 which has the sequence as defined in SEQ ID NO:23.
Figure 11:
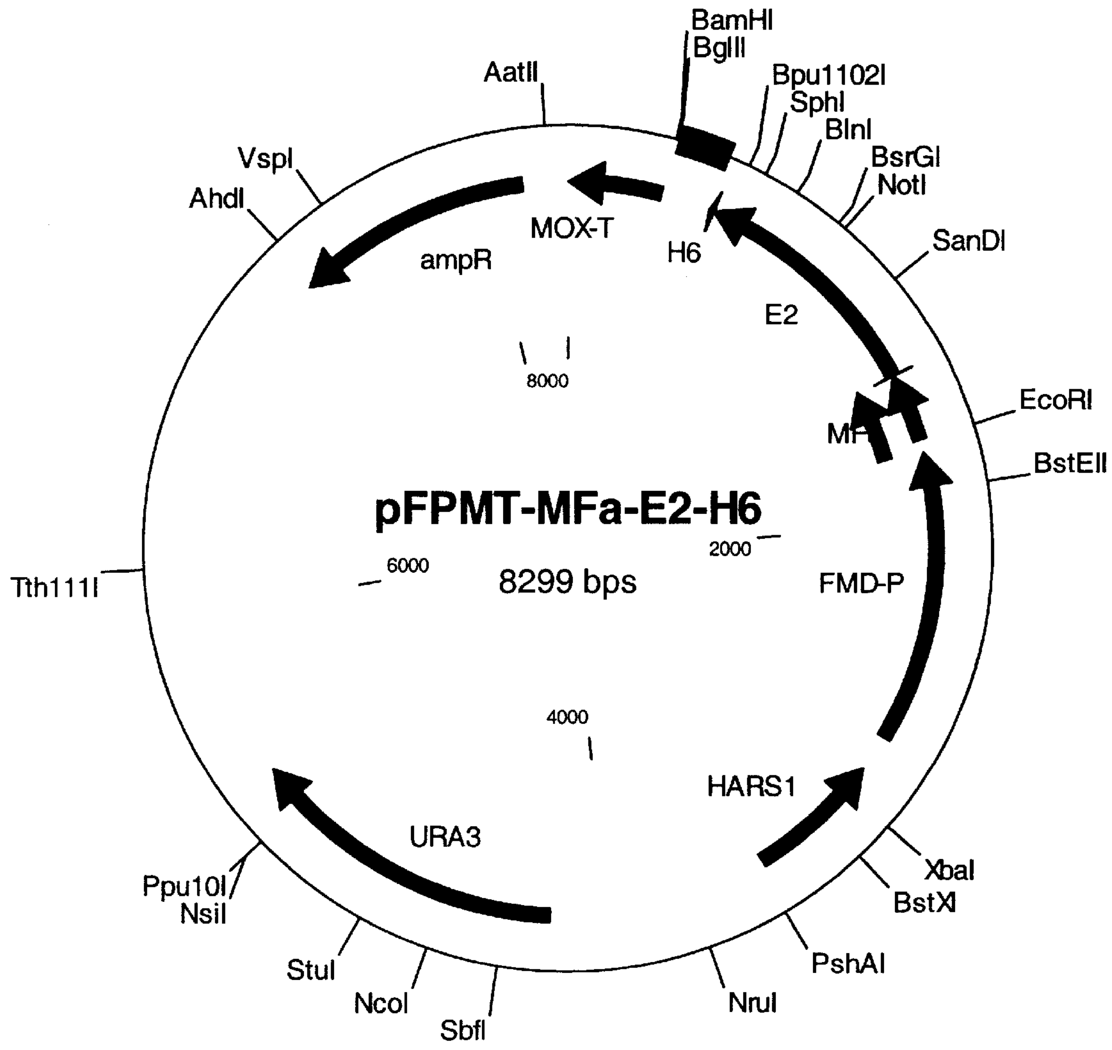
FIG. 11. Schematic map of the vector pFPMT-MFa-E2-H6 which has the sequence as defined in SEQ ID NO:24.
Figure 12:
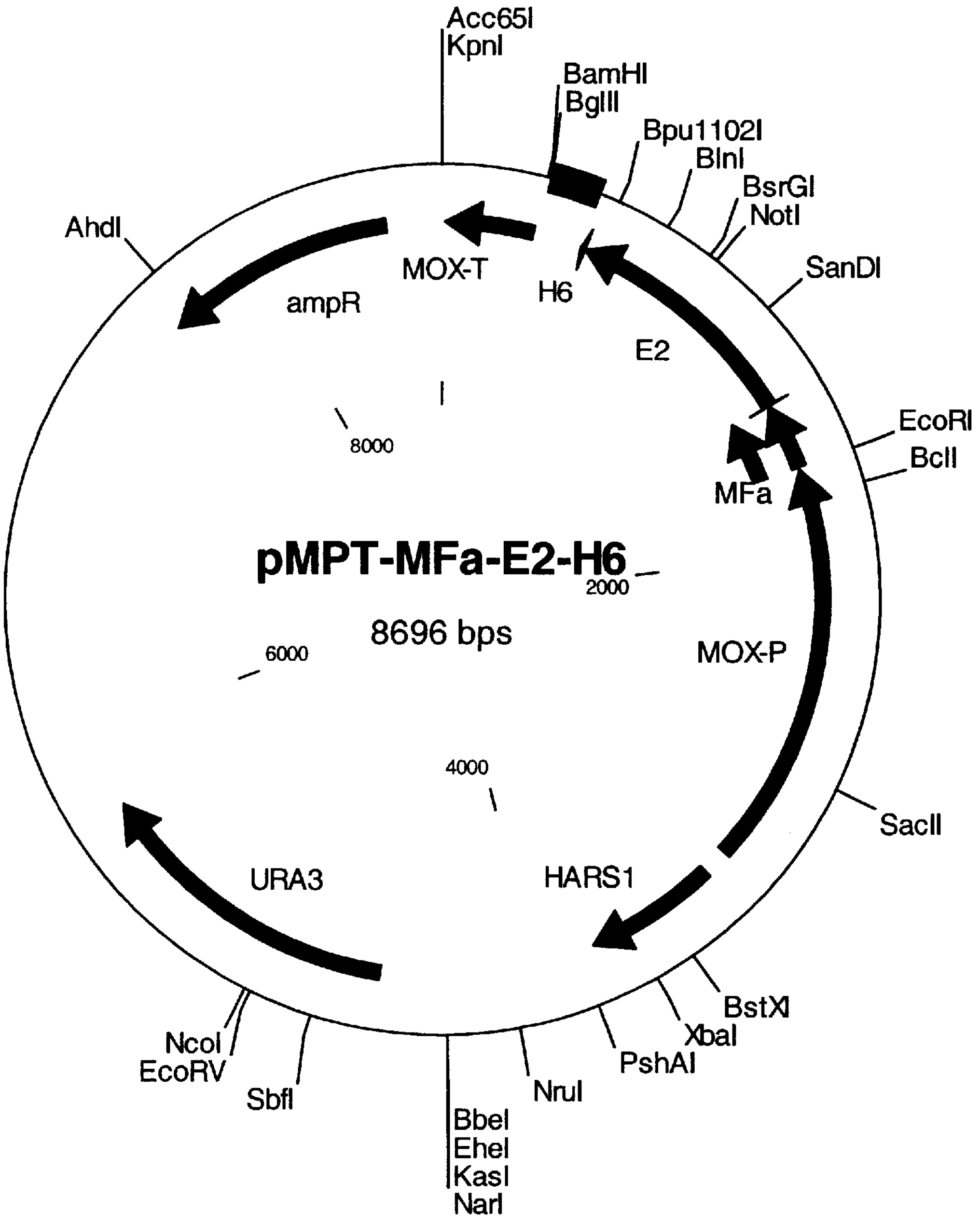
FIG. 12. Schematic map of the vector pMPT-MFa-E2-H6 which has the sequence as defined in SEQ ID NO:25.

Plasmids for *Hansenula polymorpha* transformation were constructed as follows. The DNA sequence encoding the MFα-E2s (amino acids 384–673 of HCV E2)-VIEGR-His6 (SEQ ID NO:5) was isolated as a 1.331 kb EcoRI/BglII fragment from plasmid pSP72E2H6 (SEQ ID NO:22, FIG. 9). This fragment was ligated with either the EcoRI/BglII-digested vectors pFPMT121 (SEQ ID NO:12, FIG. C+2) or pMPT121 (SEQ ID NO:23, FIG. 10) using T4 DNA ligase (Boehringer Mannheim) according to the supplier's recommendations. After transformation of *E. coli* and checking of plasmid DNA isolated from different transformants by restriction enzyme digestion, positive clones were withheld and the resulting shuttle vectors are denominated pFPMT-MFα-E2-H6 (SEQ ID NO:22, FIG. 11) and pMPT-MFα-E2-H6 (SEQ ID NO:23, FIG. 12), respectively.

Example 4

Construction of pFPMT-CL-E6-H6 Shuttle Vector

The shuttle vector pFPMT-CL-E2-H6 was assembled in a three-step procedure. An intermediate construct was prepared in which the E2 coding sequence was cloned behind the signal sequence of α-amylase of *Schwanniomyces accidentalis*. This was done by the seamless cloning method (Padgett, K. A. and Sorge, J. A. 1996).

Generation of E2s-H6 Encoding DNA Fragment

At first the DNA sequence encoding E2-H6 (amino acids 384 to 673 of HCV E2 extended with the linker peptide "VIEGR" and with 6 His residues, SEQ ID NO:5) was amplified from the pSP72E2H6 plasmid (SEQ ID NO:24, FIG. 11) by PCR. The used primers were denoted MF30E2/F and MF30E2/R and have the following sequences:

primer MF30E2/F: 5'-agtca<u>ctctt</u>ca.aggcatacccgcgtgtcaggaggg-3' (SEQ ID NO:26; the Eam1104I site is underlined, the dot marks the enzyme's cleavage site; the last codon of the *S. occidentalis* signal sequence is printed in bold; the non-marked bases anneal with the codons of E2 (amino acids 384–390 of HCV E2);

primer MF30E2/R:

5'-agtca<u>ctcttc</u>a.cagggatccttagtgatggtggtgatg-3' (SEQ ID NO:27; the Eam1104I site is underlined, the dot marks the enzyme's cleavage site; the bold printed bases are complementary to the bold printed bases of primer MF30-Rechts (see below); a BamHI site to be introduced into the construct is printed in italic; the non-marked sequence anneals with the stop codon and the six terminal His codons of E2 (384–673)-VIEGR-H6 (SEQ ID NO:5).

The reaction mixture was constituted as follows: total volume of 50 μL containing 20 ng of the 1.33 kb EcoRI/BglII fragment of pSP72E2H6, each 0.2 μM of primers MF30E2/F and MF30E2/R, dNTP's (each 0.2 μM), 1× buffer 2 (Expand Long Template PCR System; Boeringer; Cat No 1681 834), 2.5 U polymerase mix (Expand Long Template PCR System; Boeringer; Cat No 1681 834).

The PCR program 3 consisting of the following steps was used:

1. denaturation: 5 min at 95° C.
2. 10 cycles of 30 sec denaturation at 95° C., 30 sec annealing at 65° C., and 1 min elongation at 68° C.
3. termination at 4° C.

Then 10 μL 10× buffer 2 (Expand Long Template PCR System; Boeringer; Cat No 1681 834), 40 μL $H_2O$, and 5 μL of [dATP, dGTP, and dTTP (2 mM each); 10 mM 5-methyl-dCTP] have been added to the sample derived from PCR program 3, and it has been continued with PCR program 4 consisting of the following steps:

1. denaturation: 5 min at 95° C.
2. 5 cycles of 45 sec denaturation at 95° C., 30 sec annealing at 65° C., and 1 min elongation at 68° C.
3. termination at 4° C.

Generation of pMF30-derived Acceptor Plasmid

Figure 13:
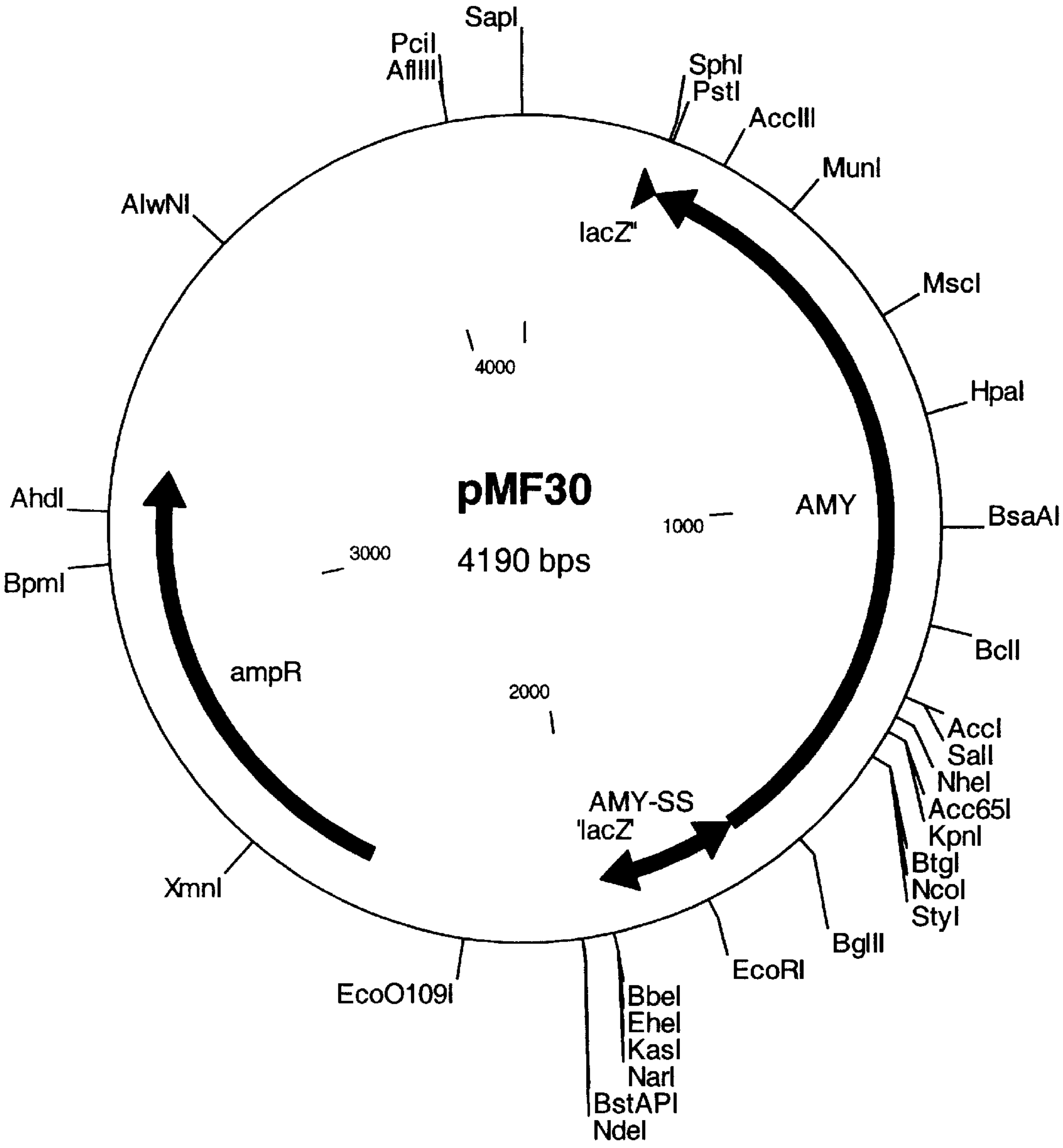
FIG. 13. Schematic map of the vector pMF30 which has the sequence as defined in SEQ ID NO:28.

The second fragment originated from the plasmid pMF30 (SEQ ID NO:28, FIG. 13), the amplicon was almost the complete pMF30 plasmid excluding the codons of the mature α-amylase of *S. occidentalis*, modifications relevant for cloning were introduced by primer design. The following set of primers was used:

primer MF30-Links:

5'-agtcactcttca.cctcttgtcaaaaataatcggttgag-3' (SEQ ID NO:29; the Eam1104I site is underlined, the dot marks the enzyme's cleavage site; the bold printed "cct" is complementary to the bold printed "agg" of primer MF30E2/F (see above); the non-marked and the bold printed bases anneal with the 26 terminal bases of the codons of the α-Amylase of *S. occidentalis* in pMF30);

primer MF30-Rechts: 5'-agtca ctcttca.ctgcaggcatgcaagcttggcg-3' (SEQ ID NO:11; the Eam1104I site is underlined, the dot marks the enzyme's cleavage site; the bold printed "ctg" is complementary to the bold printed "cag" of primer MF30E2/R (see above); the non-marked bases anneal with pUC18 sequences downstream of the stop codon of the α-Amylase of *S. occidentalis* in pMF30).

The reaction mixture was constituted as follows: total volume of 50 μL containing 20 ng of the BglII-linearized pMF30, each 0.2 μM of primers MF30-Links and MF30-Rechts, dNTP's (each 0.2 μM), 133 buffer 1 (Expand Long Template PCR System; Boeringer; Cat No 1681 834), 2.5 U polymerase mix (Expand Long Template PCR System; Boeringer; Cat No 1681 834). The same PCR programs (programs 3 and 4) as described above were used, except for the elongation times which were extended from 1 minute to 4 minutes in both programs.

Generation of Vector pAMY-E2

The E2s-H6 encoding DNA fragment and pMF30-derived acceptor plasmid obtained by PCR were controlled on their respective size by gel electrophoresis on a 1% agarose gel. The PCR products were purified with a PCR product purification kit (Qiagen) according to the supplier's instructions. Subsequently the purified fragments were digested separately with Eam1104I. Ligation of the E2s-H6 fragment with the pMF30-derived acceptor plasmid was performed by using T4 ligase (Boehringer) according to the supplier's recommendations. The ligation mixture was used to transform *E. coli* DH5αF' cells and the plasmid DNA of several clones was analyzed by EcoRI/BamHI digestion. A positive clone was selected, its plasmid further denominated as pAMY-E2, and utilized for further modifications as described below.

Generation of Vector pUC18-CL-E2-H6

The pAMY-E2 was subjected to PCR-directed mutagenesis in order to replace the codons of the α-amylase signal sequence with the codons of the avian lysozyme pre sequence. This is further denominated as "CL", corresponding to the first 18 amino acids of avian lysozyme ORF (SEQ ID NO:1). For this mutagenesis following primers were used:

regions of the primers anneal with the codons of amino acid residues 384 to 392 of E2 (CL2 hin) or the with the "atg" start codon over the EcoRI site up to position −19 (counted from the EcoRI site) of FMD promoter. The primers are designed to amplify the complete pAMY-E2 vector thereby replacing the codons of the α-amylase signal sequence with the codons of the avian lysozyme pre-sequence.

The PCR reaction was performed according to the following program:

1. denaturation: 15 min at 95° C.
2. 35 cycles of 30 sec denaturation at 95° C., 1 min annealing at 60° C., and 1 min elongation at 72° C.
3. termination at 4° C.

The following reaction mixture was used: pAMY-E2 (1 ng/μL), 1 μL; primer CL2 hin (100 μM), 2 μL; primer CL2 her (100 μM), 2 μL; dNTP's (2.5mM each), 8 μL; $H_2O$, 76 μL; Expand Long Template PCR System (Boeringer; Cat No 1681 834) Buffer 2 (10× concentrated), 10 μL; Expand Long Template PCR System Polymerase mixture (1U/μL), 0.75 μL.

The resulting PCR product was checked by gel electrophoresis on a 1% agarose gel. Prior to ligation the PCR fragment was modified as follows. The 3'-A overhangs were removed by T4 polymerase resulting in blunt ends with 3'- and 5'-OH-groups. Thereto 1 μL T4 polymerase (Boehringer, 1U/μL) was added to the residual 95 μL PCR reaction mixture along with 4 μL dNTP's (2.5 mM each). The sample was incubated for 20 min at 37° c. Subsequently the DNA was precipitated with ethanol and dissolved in 16 μL deionized water. This was followed by a kinase treatment to add 5'-phosphates to the blunt-ended PCR product. To the 16 μL dissolved blunt-ended PCR product were added 1 μL T4 polynucleotide kinase (Boehringer, 1U/μL), 2 μL 10-fold concentrated T4 polynucleotide kinase reaction buffer (Boehringer) and 1 μL ATP (10 mM). The sample was incubated for 30 min at 37° C.

The kinase treated sample was subsequently separated on a 1% agarose gel. The product band was isolated. The DNA was extracted from the agarose slice by means of the Gel Extraction kit (Qiagen) according to the supplier's recommendations. Fifty (50) ng of the purified product was then self-ligated by use of T4 ligase (Boehringer) according to the supplier's conditions. After 16 h incubation at 16° C., the DNA in the ligation mix was precipitated with ethanol and dissolved in 20 μL $H_2O$ (ligation sample).

*E.coli* DH5αF' cells were transformed with 10 μL of the ligation sample. Several ampicillin-resistant clones were further characterized via restriction analysis of the isolated plasmid DNA. A positive clone was denominated as pUC18-CL-E2-H6 and was used for further modifications as described below.

```
primer CL2 hin:
5'-tgcttcctaccactagcagcactaggacatacccgcgtgtcaggaggggcag-3';        (SEQ ID NO:30)
and

primer CL2 her:
5'-tagtactagtattagtaggcttcgcatggaattcactggccgtcgttttacaacgtc-3'.   (SEQ ID NO:31)
```

The underlined 5'-regions of the primers contain the DNA sequence of about half of the avian lysozyme pre sequence. Primer CL2 her includes SpeI (italic) and EcoRI (italic, double underlined) restriction sites. The non-underlined Generation of Shuttle Vector pFPMT-CL-E2-H6

Figure 14:
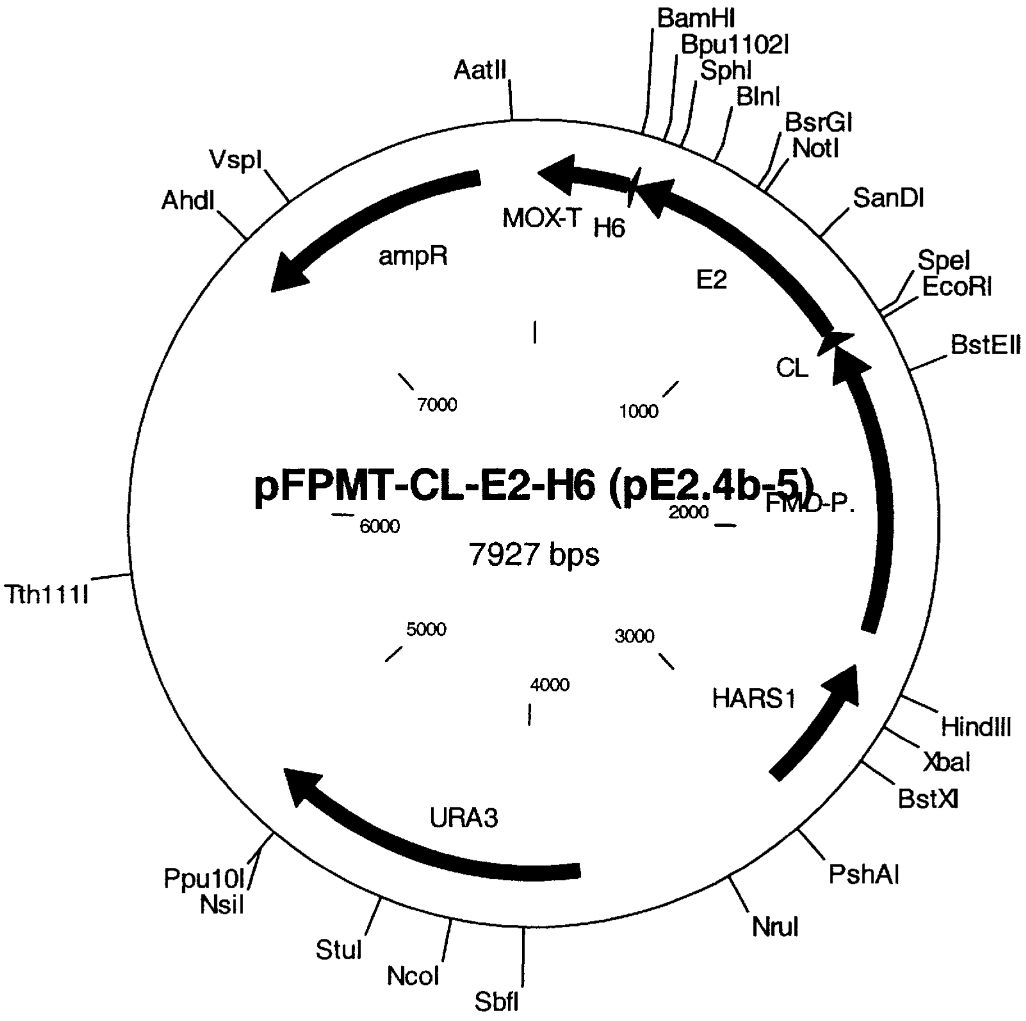
FIG. 14. Schematic map of the vector pFPMT-CL-E2-H6 which has the sequence as defined in SEQ ID NO:32.
Figure 15:
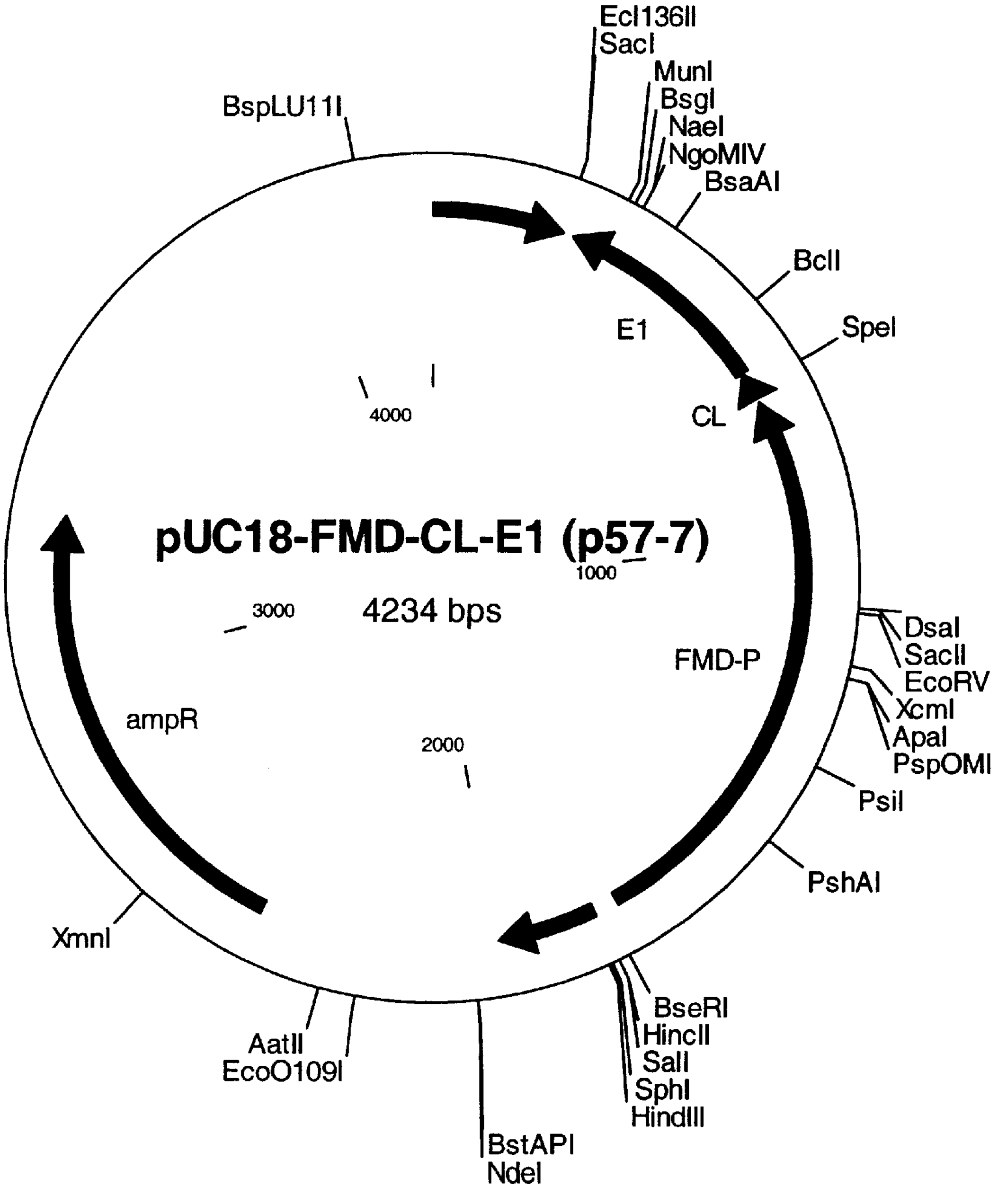
FIG. 15. Schematic map of the vector pUC18-FMD-CL-E1 which has the sequence as defined in SEQ ID NO:35.

A 0.966 kb EcoRI/BamHI fragment was isolated from pUC18-CL-E2-H6 (harboring CL-E2(384–673)-VIEGR-H6) and was ligated into the EcoRI/BamHI-digested pFPMT121 (SEQ ID NO:12, FIG. 3). For the reaction, T4 ligase (Boehringer) was used according to the supplier's conditions. The ligation sample was precipitated with ethanol and dissolved in 10 μL water. This was used to transform *E.coli* DH5αF' cells, a positive clone was withheld after restriction analysis and the respective plasmid is denominated pFPMT-CL-E2-H6 (SEQ ID NO:32, FIG. 14).

Example 5

Construction of pFPMT-CL-K-H6-E1 Shuttle Vector

Figure 7:
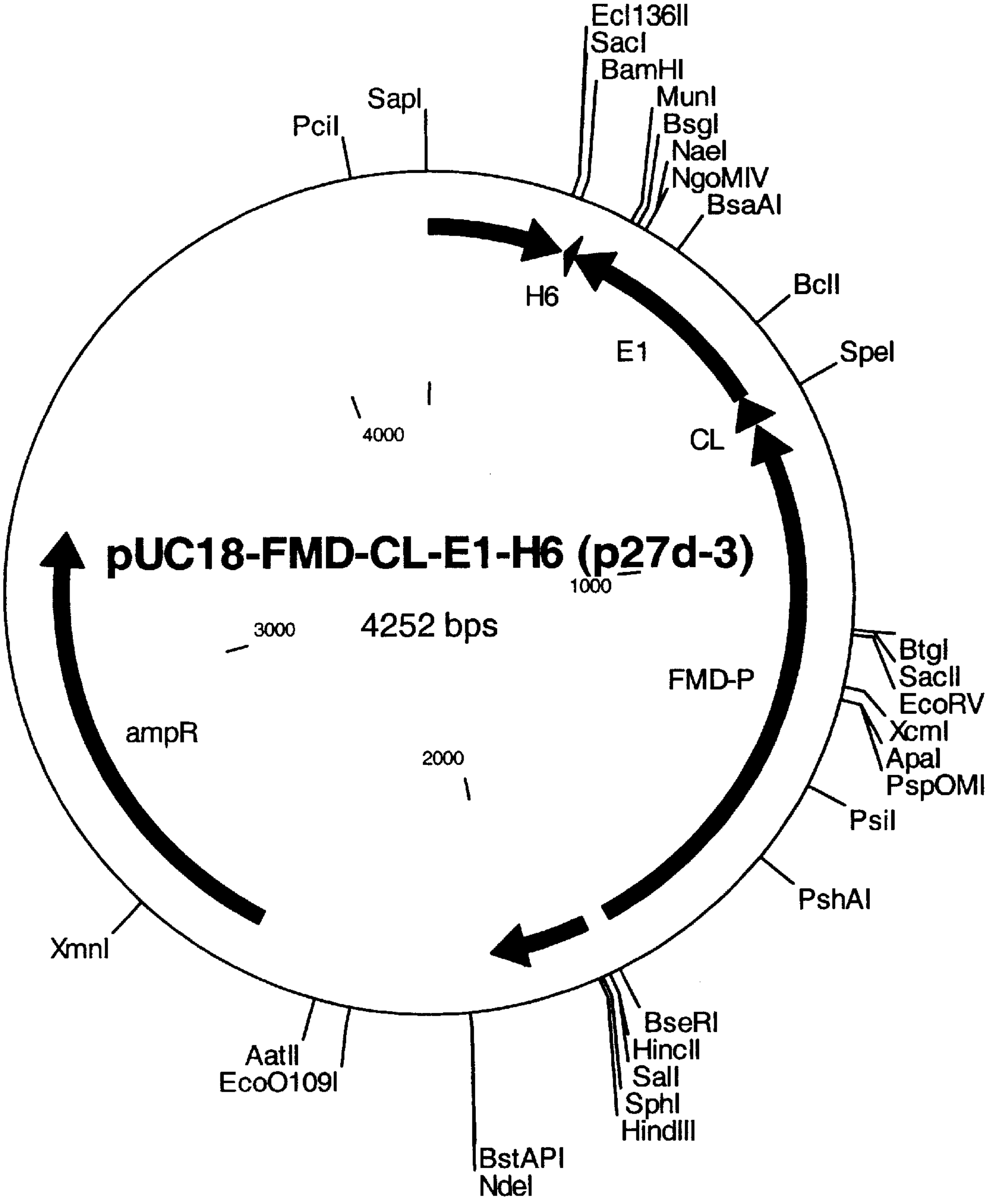
FIG. 7. Schematic map of the vector pUC18-FMD-CL-E1-H6 which has the sequence as defined in SEQ ID NO:20.

The construction of the shuttle vector was comprised of two steps. In a first step the pUC18-FMD-CL-H6-K-E1-H6 construct was constructed by site-directed mutagenesis. The pUC18-FMD-CL-E1-H6 was used as template (SEQ ID NO:20; FIG. 7). The following primers were used:

```
Primer H6K hin neu: 5'-catcacaaatatgaggtgcgcaacgtgtccgggatgtac-3'.  (SEQ ID NO:37)

Primer H6KRK her neu:
5'-gtgatggtggtgtcctagtgctgctagtggtaggaagcatag-3' (SEQ ID NO:38).
```

(The bases providing additional codons are underlined.)

The PCR reaction mixture was constituted as follows: pUC18-FMD-CL-E1-H6 (2 ng/μL), 1 μL; primer H6K hin neu (100 μM), 2 μL; primer H6KRK her neu (100 μM), 2 μL; dNTP's (2.5 mM each), 8 μL; $H_2O$, 76 μL; Expand Long Template PCR System (Boeringer; Cat No 1681 834) Buffer 2 (10× concentrated), 10 μL; Expand Long Template PCR System Polymerase mixture (1 U/μL), 0.75 μL.

The PCR program used consisted of the following steps:

denaturation step: 15 min at 95° C.

35 cycles of 30 sec denaturation at 95° C., 1 min annealing at 60° C., and 5 min elongation at 72° C.

termination at 4° C.

An aliquot of the PCR sample was analyzed on a 1% agarose gel to check its size, which was correct (~4.2 kb).

Thereafter the 3'-A overhangs from the PCR product were removed by a T4 polymerase reaction resulting in blunt ends with 3'- and 5'-OH groups. Therefore, to the remaining 95 μL of the PCR reaction were added 1 μL T4 polymerase (Boehringer; 1 U/μL) and 4 μL dNTP's (2.5 mM each). The sample was incubated for 20 min at 37° C. Subsequently, the DNA in the sample was precipitated with ethanol and dissolved in 16 μL $H_2O$.

Subsequently 5'-phosphates were added to the blunt-ended PCR product by a kinase reaction. Therefore, to the 16 μL dissolved blunt-ended PCR product were added 1 μL T4 polynucleotide kinase (Boehringer; 1 U/μL), 2 μL 10-fold concentrated T4 polynucleotide kinase reaction buffer (Boehringer), and 1 μL ATP (10 mM). The sample was incubated for 30 min at 37° C.

Subsequently the sample was applied onto a 1% agarose gel and the correct product band was isolated, by means of the gel extraction kit (Qiagen) according to the supplier's conditions. Fifty (50) ng of the purified product has then been self-ligated by use of T4 ligase (Boehringer) according to the supplier's recommendations. After 72 h incubation at 16° C. the DNA in the ligation sample was precipitated with ethanol and dissolved in 10 μL water.

Figure 17:
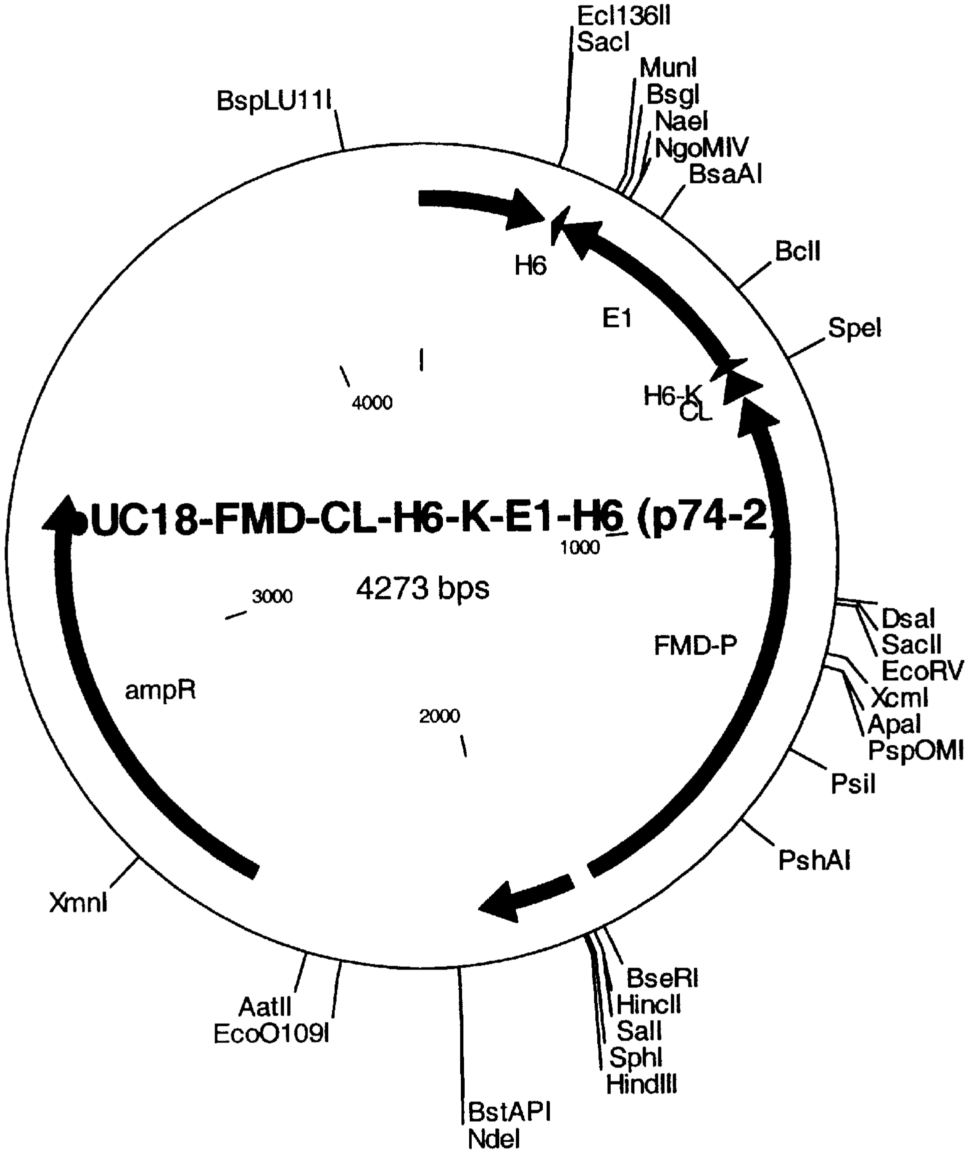
FIG. 17. Schematic map of the vector pUC18-FMD-CL-H6-E1-K-H6 which has the sequence as defined in SEQ ID NO:39.

*E.coli* DH5αF' cells were transformed with 5 μL of the ligation sample. The plasmid DNA of several ampicillin-resitant colonies was analyzed by restriction enzyme digestion, a positive clone was withheld and the corresponding plasmid denominated: pUC18-FMD-CL-H6-E1-K-H6 (SEQ ID NO:39, FIG. 17).

Figure 16:
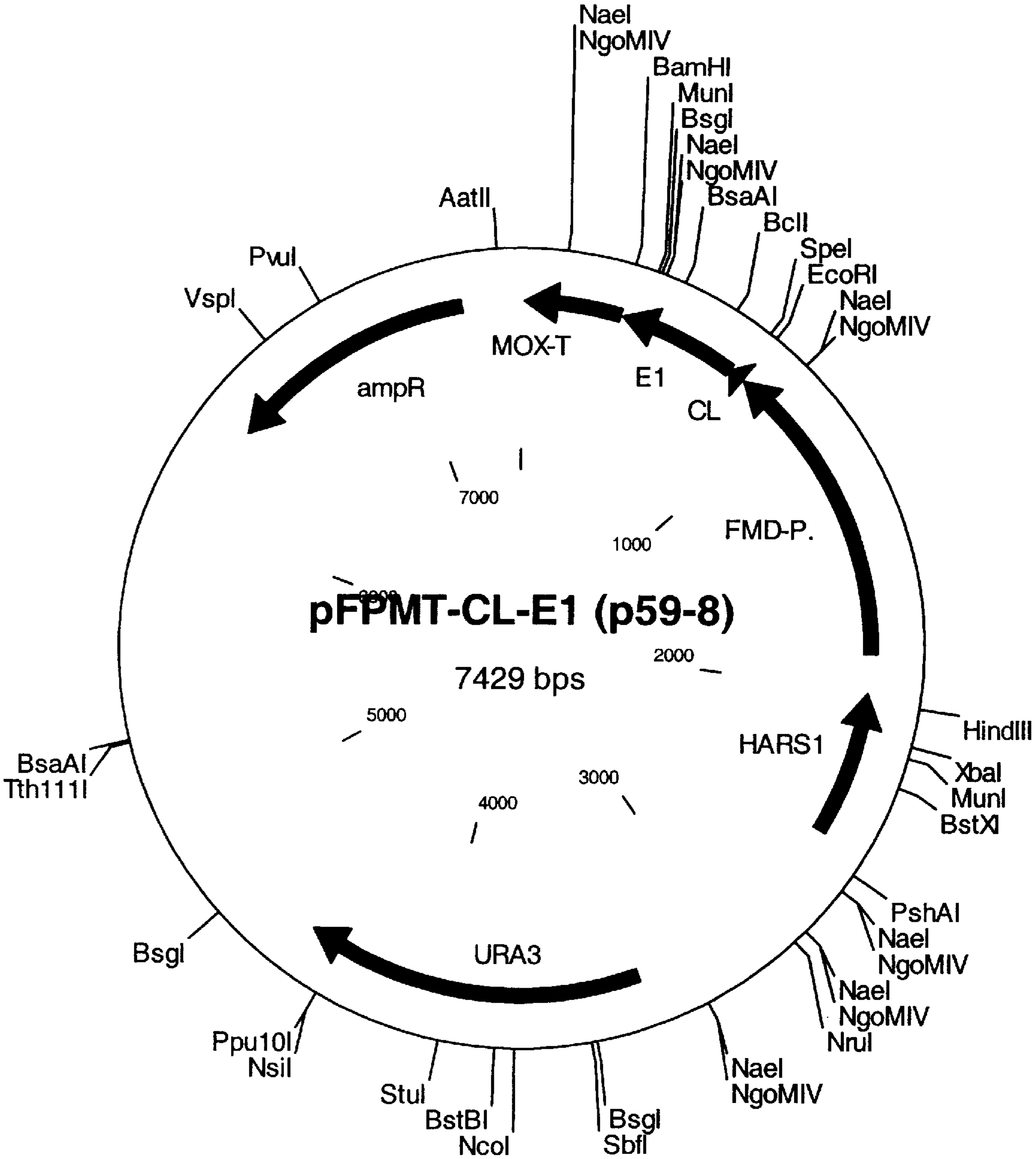
FIG. 16. Schematic map of the vector pFPMT-CL-E1 which has the sequence as defined in SEQ ID NO:36.
Figure 18:
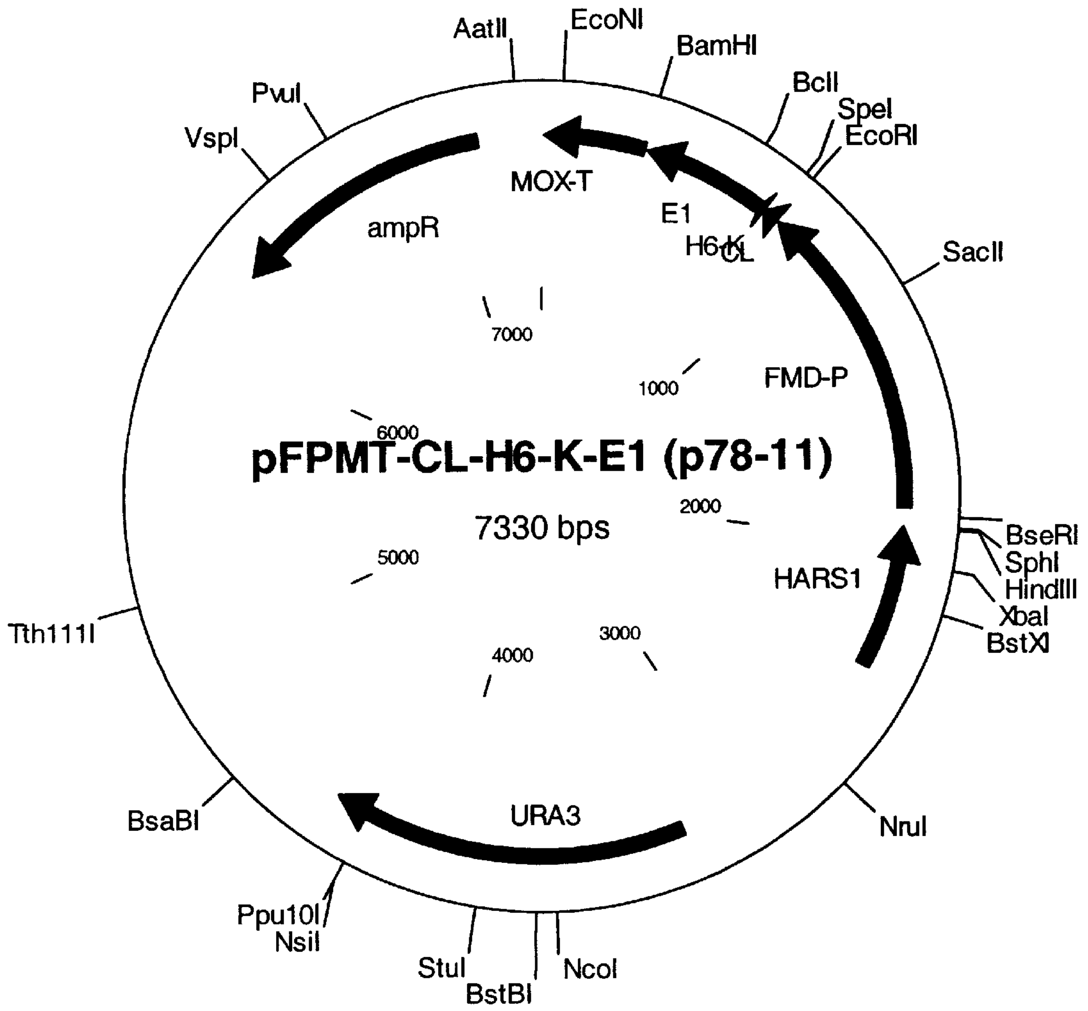
FIG. 18. Schematic map of the vector pFPMT-CL-H6-K-E1 which has the sequence as defined in SEQ ID NO:40.

In a second step the transfer vector was constructed by a two-fragment ligation. In the following construction fragments with BclI cohesive ends were involved. Since BclI can cleave its site only on unmethylated DNA, an *E. coli* dam_ strain was transformed with the involved plasmids pUC18-FMD-CL-H6-K-E1-H6 (SEQ ID NO:39, FIG. 17) and pFPMT-CL-E1 (SEQ ID NO:36, FIG. 16). From each transformation, an ampicillin-resistant colony was picked, grown in a liquid culture and the unmethylated plasmid DNAs were prepared for the further use. The 1.273 kb BclI/HindIII fragment of the unmethylated plasmid pUC18-FMD-CL-H6-K-E1-H6 (harbouring the FMD promoter, the codons of the CL-H6-K unit, and the start of E1) and the 6.057 kb BclI/HindIII fragment of plasmid pFPMT-CL-E1 (harbouring the missing part of the E1 reading frame starting from the BclI site, without C-terminal His tag, as well as the pFPMT121-located elements except for the FMD promoter) were prepared and ligated together for 72 h at 16° C. by use of T4 ligase (Boehringer) in a total volume of 20 μL according to the supplier's specifications. Subsequently, the ligation mixture was placed on a piece of nitrocellulose membrane floating on sterile deionized water in order to desalt the ligation mixture (incubation for 30 min at room temperature). *E. coli* TOP10 cells were transformed by electroporation with 5 μL of the desalted sample. The plasmid DNA of several resulting ampicillin-resistant colonies was analyzed by restriction enzyme digestion. A positive clone was withheld and denominated pFPMT-CL-H6-K-E1 (SEQ ID NO:40, FIG. 18).

Example 6

Transformation of *Hansenula Polymorpha* and Selection of Transformants

*H. polymorpha* strain RB 11 was been transformed (PEG-mediated DNA uptake protocol essentially as described by (Klebe, R. J. et al. 1983) with the modification of (Roggenkamp, R. et al. 1986) with the different parental shuttle vectors as described in Examples 1 to 5. For each transfonnation, 72 uracil-prototrophic colonies were selected and used for strain generation by the following procedure. For each colony, a 2 mL liquid culture was inoculated and grown in test tubes for 48 h (37° C.; 160 rpm; angle 45°) in selective medium (YNB/glucose, Difco). This step is defined as the first passaging step. A 150 μL aliquot of the cultures of the first passaging step were used to inoculate 2 mL fresh YNB/glucose medium. Again, the cultures have been incubated as described above (second passaging step). Together, eight of such passaging steps were carried out. Aliquots of the cultures after the third and the eighth passaging steps were used to inoculate 2 mL of non-selective YPD medium (Difco). After 48 h of incubation at 37° C. (160 rpm; angle 45°; the so-called first stabilization step), 150 μL aliquots of these YPD cultures have been used to inoculate fresh 2 mL YPD cultures which were incubated as described above (second stabilization step). Aliquots of the cultures of the second stabilization step were then streaked on plates containing selective YNB/agar. These plates were incubated for four days until macroscopic colonies became visible. A well-defined single colony of each separation was defined as strain and used for further expression analysis.

Expression analysis was performed on small-scale shake flask cultures. A colony was picked from the above mentioned YNB/agar plate and inoculated in 2 mL YPD and incubated for 48 h as mentioned above. This 2 mL-aliquot was used as seed culture for 20 mL shake flask culture. YPGlycerol (1%) was used as medium and the shake flask was incubated on a rotary shaker (200 rpm, 37° C.). After 48 h of growth 1% MeOH was added to the culture for induction of the expression cassette. At different time intervals cell pellets of 1 mL aliquots were collected and stored at −20° C. until further analysis. Specific protein expression was analyzed by SDS-PAGE/Western blotting. Therefore cell pellets were solubilized in sample-buffer (TrisHCl-SDS) and incubated for >15 minutes at 95° C. Proteins were separated on a 15% polyacryl-amide gel and blotted (wet-blot; bicarbonate buffer) onto nitrocellulose membranes. Blots were developed using a specific murine anti-E1 (IGH 201) or murine anti-E2 (IGH 216, described by Maertens et al. in WO96/04385) as first antibody, Rabbit-Anti-Mouse-AP was used as second antibody. Staining was performed with NBT-BCIP.

Positive strains were withheld for further investigation.

Five of these positive clones were used in a shake flask expression experiment. A colony of the respective strain was picked from YNB plate and used to inoculate 2 mL YPD. These cultures were incubated as described above. This cell suspension was used to inoculate a second seed culture of 100 mL YPD medium in a 500 mL shake flask. This shake flask was incubated on a rotary shaker for 48 h at 37° C. and 200 rpm. A 25 mL aliquot of this seed culture was used to inoculate 250 mL YPGlycerol (1%) medium and was incubated in a baffled 2-1 shake flask under the above described conditions. 48 h after inoculation 1% MeOH (promotor induction) was added and the shake flasks were further incubated under the above described conditions. 24 h post induction, the experiment was stopped and cell pellets collected by centrifugation. The expression level of the five different clones was analyzed by SDS-PAGE/Western blotting (conditions as above). A titration series of each clone was loaded onto the gel and the most productive strain was selected for further fermentation and purification trials.

Surprisingly, *H. polymorpha*, a yeast strain closely related to *Pichia pastoris* (Gellissen, G. 2000), is able to express HCV proteins essentially without hyperglycosylation and thus with sugar moieties comparable in size to the HCV envelope proteins expressed by HCV-recombinant vaccinia virus-infected mammalian cells.

The *Hansenula polymorpha* strain RB 11 was deposited on Apr. 19, 2002 under the conditions of the Budapest Treaty at the Mycothèque de l'UCL (MUCL), Université Catholique de Louvain, Laboratoire de mycologie, Place Croix du Sud 3 bte 6, B-1348 Louvain-la-Neuve, Belgium and has the MUCL accession number MUCL43805.

Example 7

Construction of pSY1aMFE1sH6A Vector

Figure 19:
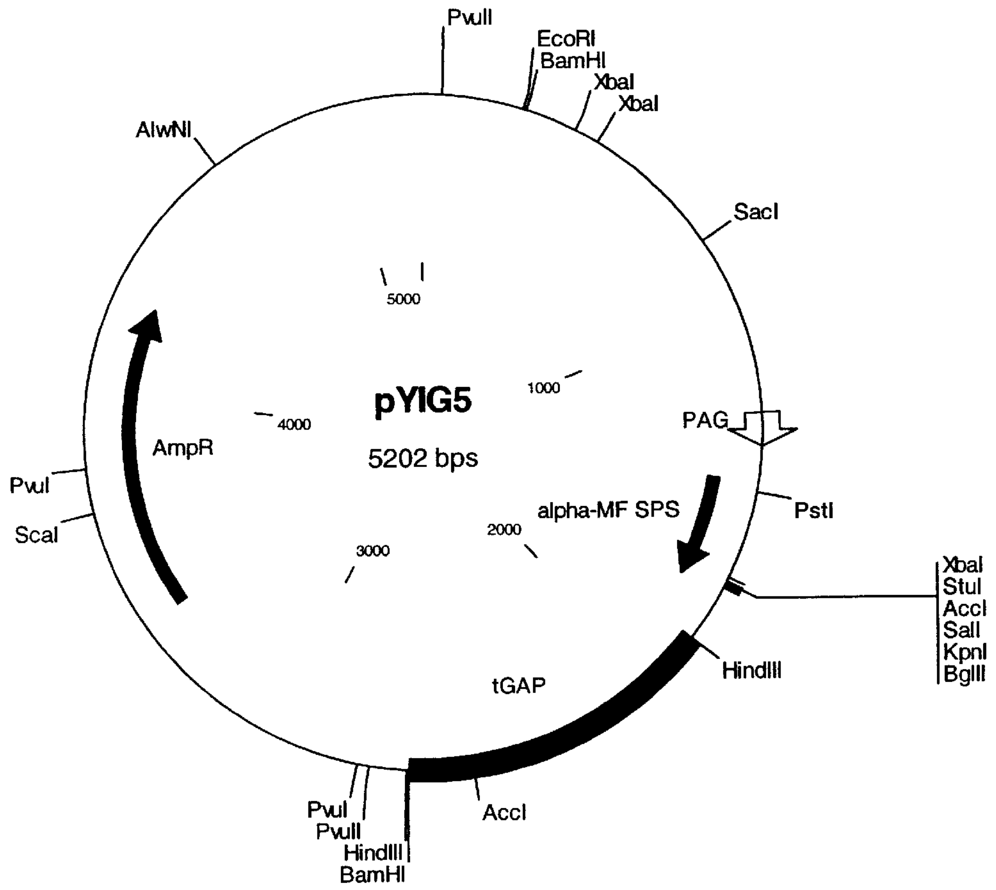
FIG. 19. Schematic map of the vector pYIG5 which has the sequence as defined in SEQ ID NO:41.

The *S. cerevisiae* expression plasmid was constructed as follows. An E1-coding sequence was isolated as a NsI1/Eco52I fragment from pGEMT-E1sH6 (SEQ ID NO:6, FIG. 1) which was made blunt-ended (using T4 DNA polymerase) and cloned in the pYIG5 vector (SEQ ID NO:41, FIG. 19) using T4 DNA ligase (Boehringer) according to the supplier's specifications. The cloning was such that the E1s-H6 encoding fragment was joined directly and in frame to the αMF-coding sequence. The ligation mixture was transformed in *E.coli* DH5αF' cells. Subsequently, the plasmid DNA of several ampicilin resistant clones was analyzed by restriction digestion and a positive clone was withheld and denominated as pYIG5E1H6 (ICCG3470; SEQ ID NO:42, FIG. 20).

Figure 43:
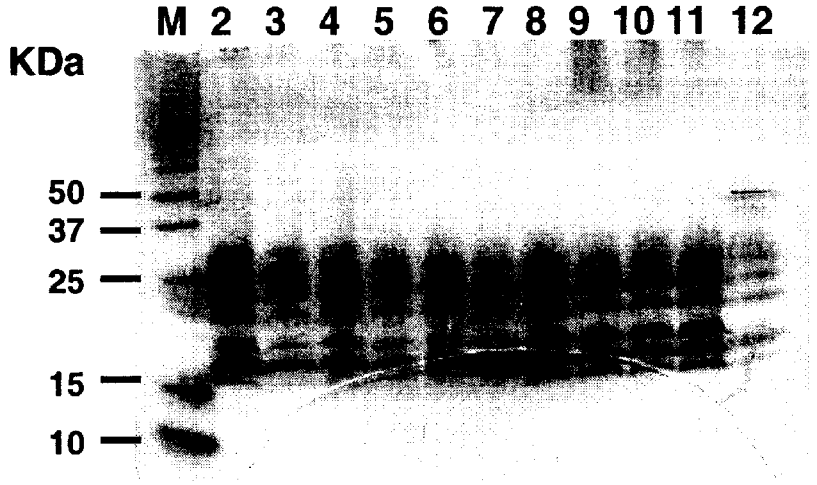
Figure 43:
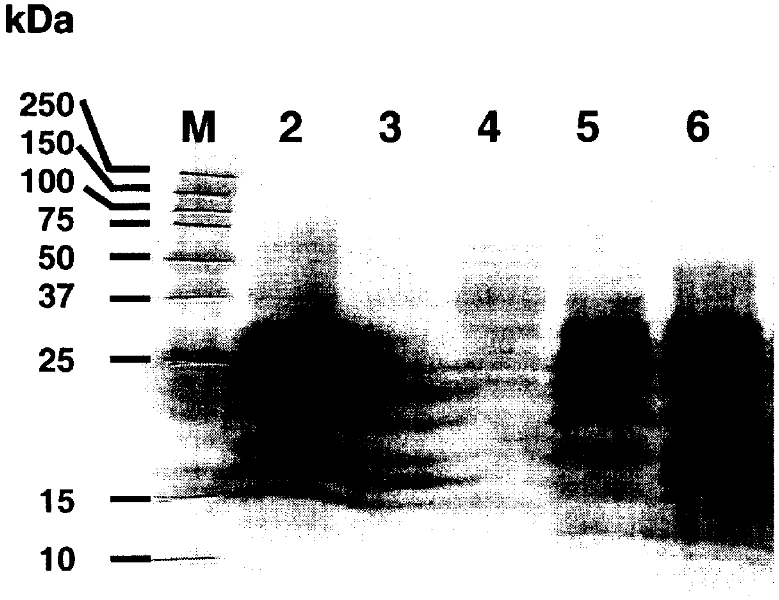

The expression cassette (containing the αMF-sequence and the E1s-coding region with a His-tag) was transferred as a BamHI fragment (2790 bp) of pYIG5E1H6 into the BamHI-digested *E. coli/S. cerevisiae* pSY1 shuttle vector (SEQ ID NO:21, FIG. 43). The ligation was performed with T4 DNA ligase (Boehringer) according to supplier's conditions. The ligation mix was transformed to *E. coli* DH5αF' cells, and the plasmid DNA of several ampicilin resistant colonies was analyzed by restriction enzyme digestion. A positive clone was withheld and denominated pSY1aMFE1sH6a (ICCG3479; SEQ ID NO:44, FIG. 22).

Example 8

Construction of pSYYIGSE2H6 Vector

The *S. cerevisiae* expression plasmid pSYYIGSE2H6 was constructed as follows. An E2 coding sequence was isolated as a SalI/KpnI fragment from pBSK-E2sH6 (SEQ ID NO:45, FIG. 23) which was made blunt-ended (using T4 DNA polymerase) and subsequently cloned in the pYIG5 vector (SEQ ID NO:41, FIG. 19) using T4 DNA ligase (Boehringer) according to the supplier's specifications. The cloning was such that the E2-H6 encoding fragment was joined directly and in frame to the αMF-coding sequence. The ligation mixture was then transformed to *E. coli* DH5αF' cells, the plasmid DNA of several ampicilin resistant clones was analyzed by restriction digestion and a positive clone withheld and denominated as pYIG5HCCL-22aH6 (ICCG2424; SEQ ID NO:46, FIG. 24).

Figure 21:
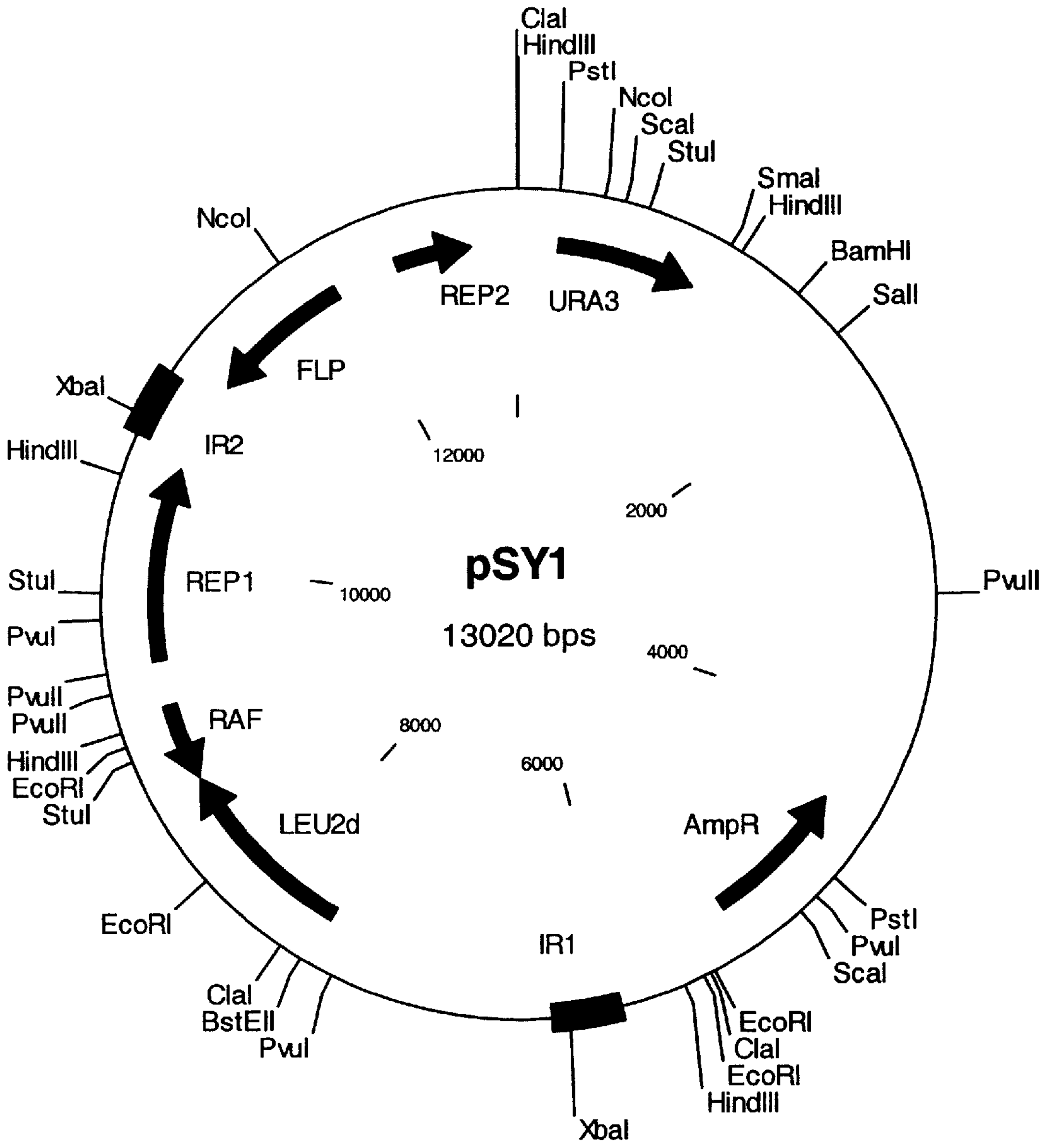
FIG. 21. Schematic map of the vector pSY1 which has the sequence as defined in SEQ ID NO:43.

The expression cassette (containing the αMF-sequence and the E2 (384–673) coding region with a His-tag) was transferred as a BamHI fragment (3281 bp) of pYIG5HCCL-22aH6 into the BamHI opened *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A restriction positive clone was withheld and denominated pSYYIGSE2H6 (ICCG2466; SEQ ID NO:47, FIG. 25).

Example 9

Construction of pSY1YIG7E1s Vector

Figure 26:
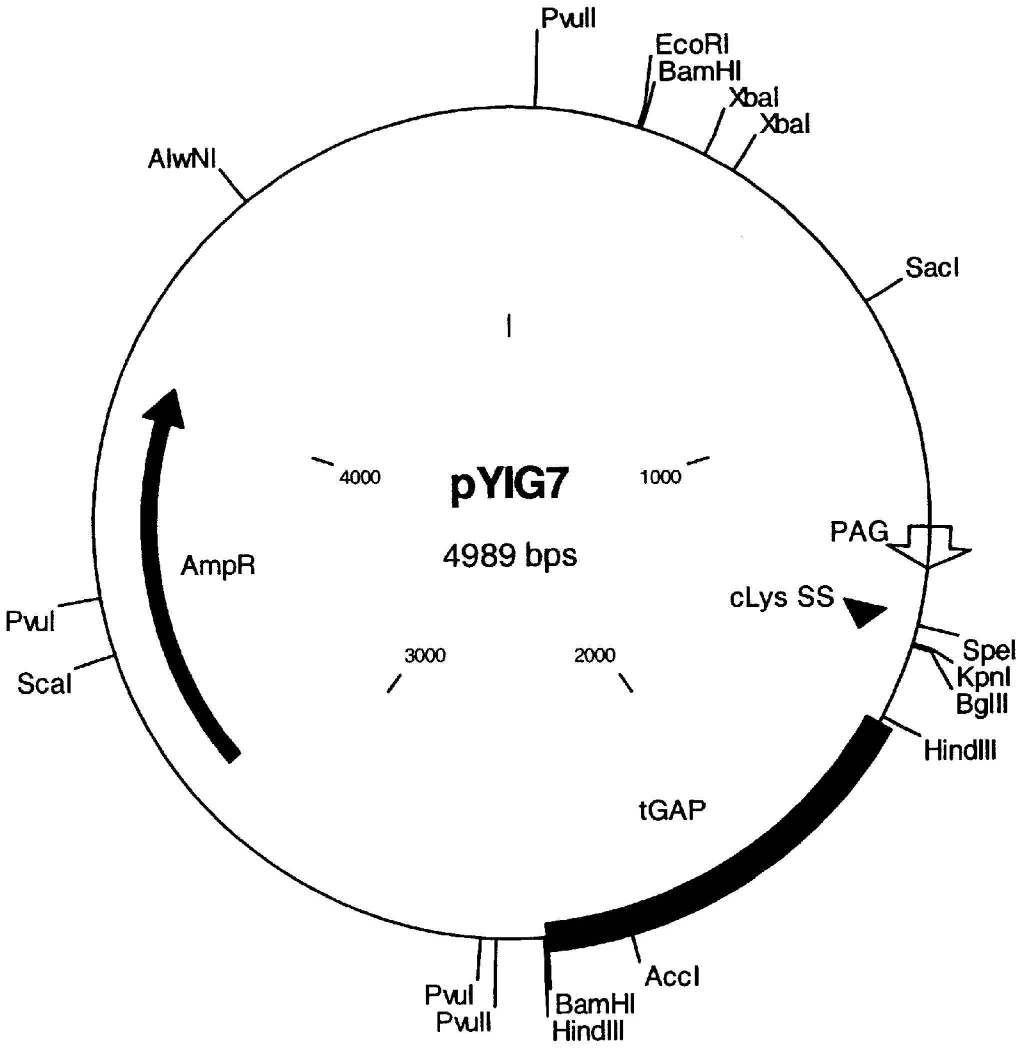
FIG. 26. Schematic map of the vector pYIG7 which has the sequence as defined in SEQ ID NO:48.

The *S. cerevisiae* expression plasmid pSY1YIG7E1s was constructed as follows. An E1 coding sequence was isolated as a NsI1/Eco52I fragment from pGEMT-E1s (SEQ ID NO:6, FIG. 1) which was made blunt-ended and cloned into the pYIG7 vector (SEQ ID NO:48, FIG. 26) using T4 DNA ligase (Boehringer) according to the supplier's specifications. The cloning was such that the E1-encoding fragment was joined directly and in frame to the αMF-coding sequence. The ligation mixture was transformed to *E. coli*

Figure 27:
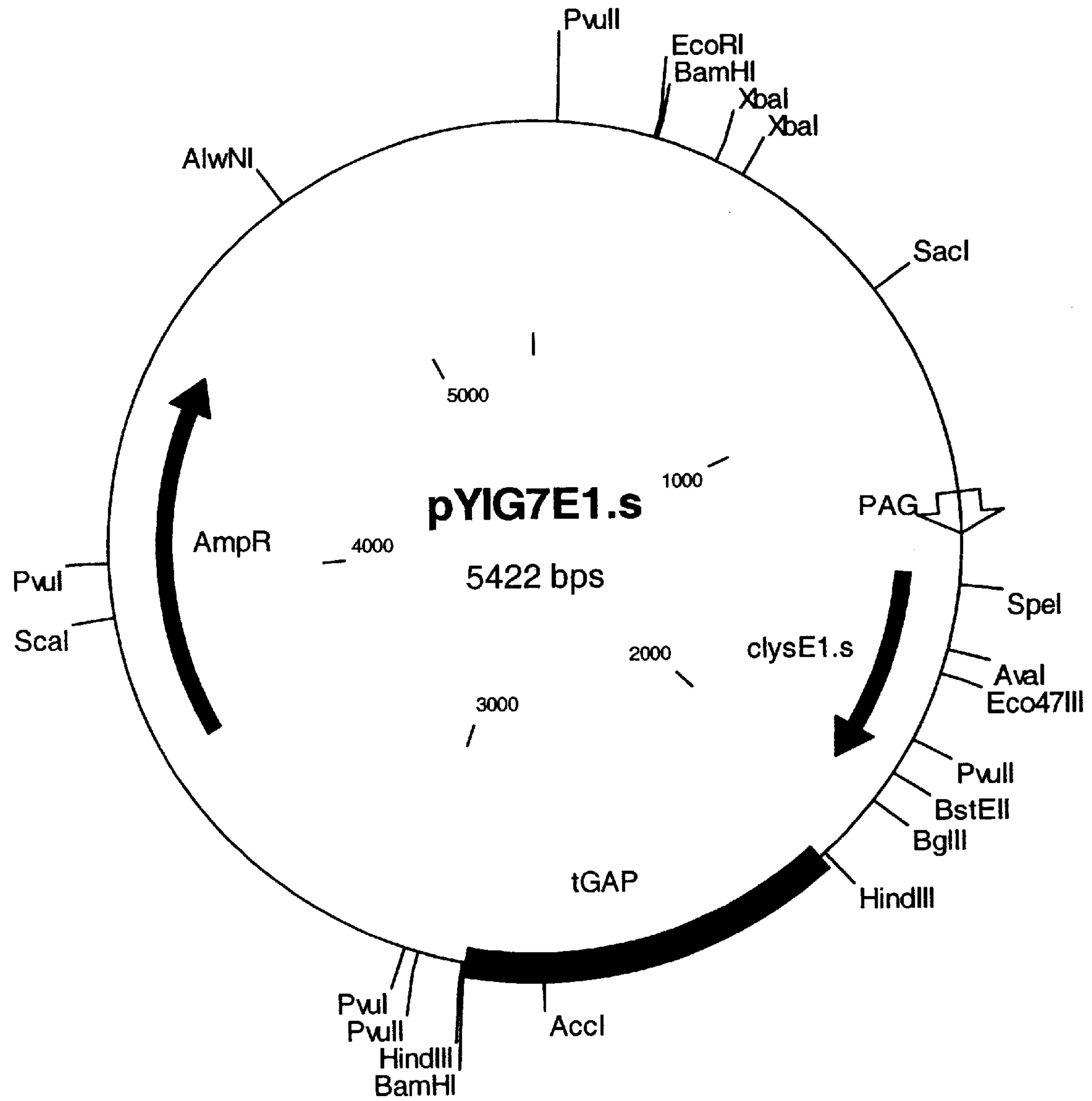
FIG. 27. Schematic map of the vector pYIG7E1 which has the sequence as defined in SEQ ID NO:49.

DH5αF' cells, the plasmid DNA of several ampicilin resistant clones analyzed by restriction digestion and a positive clone withheld and denominated as pYIG7E1 (SEQ ID NO:49, FIG. 27).

The expression cassette (containing the CL leader sequence and the E1 (192–326) coding region) was transferred as a BamHI fragment (2790 bp) of pYIG7E1 into the BamHI-digested *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A positive clone was withheld and denominated pSY1YIG7E1s (SEQ ID NO:50, FIG. 28).

Example 10

Transformation of *Saccaromyces Cerevisiae* and Selection of Transformants

In order to overcome hyper-glycosylation problems, often reported for proteins over-expressed in *Saccharomyces cerevisiae*, a mutant screening was set-up. This screening was based on the method of Ballou (Ballou, L. et al. 1991), whereby spontaneous recessive orthovanadate-resistant mutants were selected. Initial strain selection was performed based on the glycosylation pattern of invertase, as observed after native gel electrophoresis. A strain, reduced in glycosylation capabilities, was withheld for further recombinant protein expression experiments and denominated strain IYCC155. The nature of mutation has not been further studied.

Said glycosylation-deficient strain IYCC155 was transformed with the plasmids as described in Examples 7 to 9 essentially by to the lithium acetate method as described by Elble (Elble, R. 1992). Several Ura complemented strains were picked from a selective YNB+2% agar plate (Difco) and used to inoculate 2 ml YNB+2% glucose. These cultures were incubated for 72 h, 37° C., 200 rpm on orbital shaker, and the culture supernatant and intracellular fractions were analysed for expression of E1 by western blot developed with a E1 specific murine monoclonal antibody (IGH 201). A high producing clone was withheld for further experiments.

The expression of proteins in the *S. cerivisiae* glycosylation deficient mutant used here is hampered by the suboptimal growth characteristics of such strains which leads to a lower biomass yield and thus a lower yield of the desired proteins compared to wild-type *S. cerivisiae* strains. The yield of the desired proteins was still substantially higher than in mammalian cells.

Example 11

Construction of pPICZalphaD'E1sH6 and pPICZalphaE'E1sH6 Vectors

Figure 29:
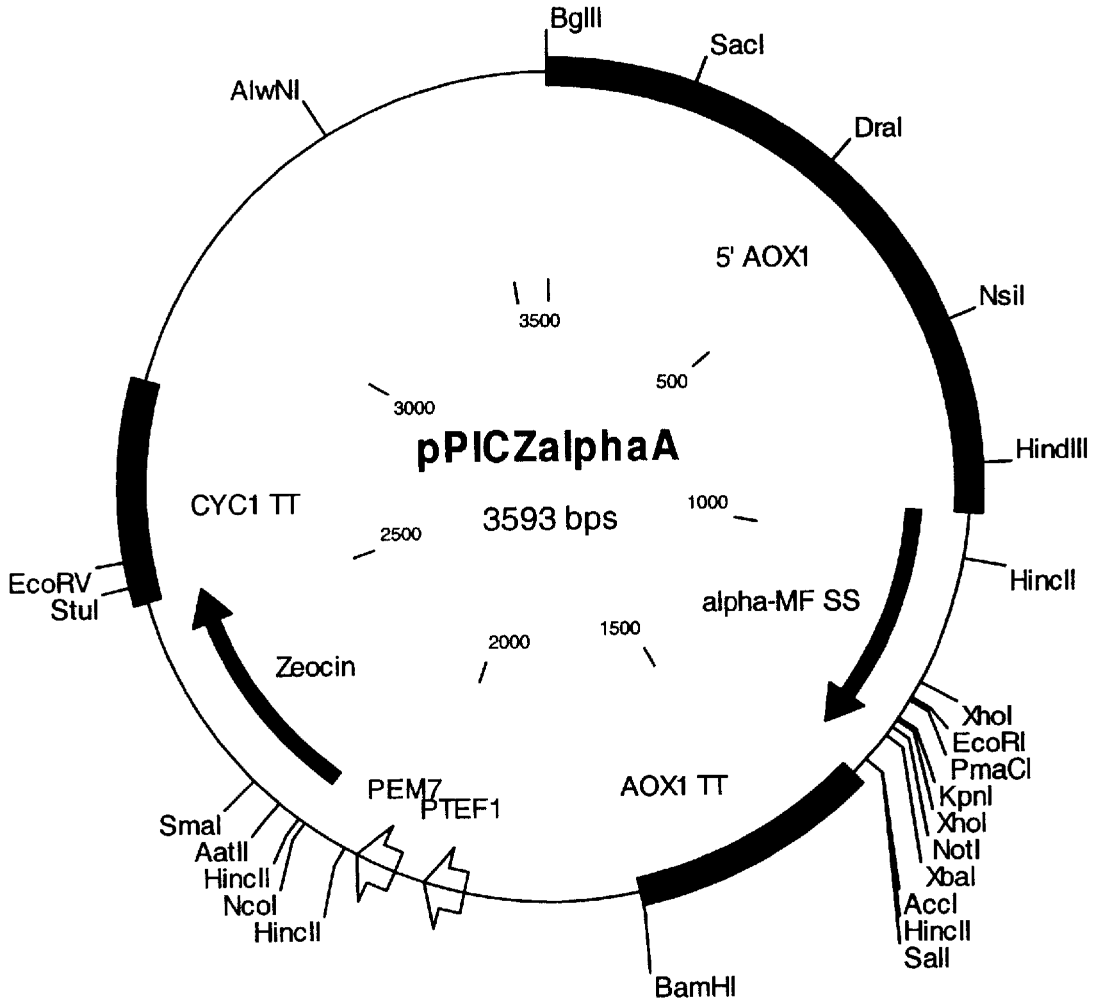
FIG. 29. Schematic map of the vector pPICZalphaA which has the sequence as defined in SEQ ID NO:51.
Figure 30:
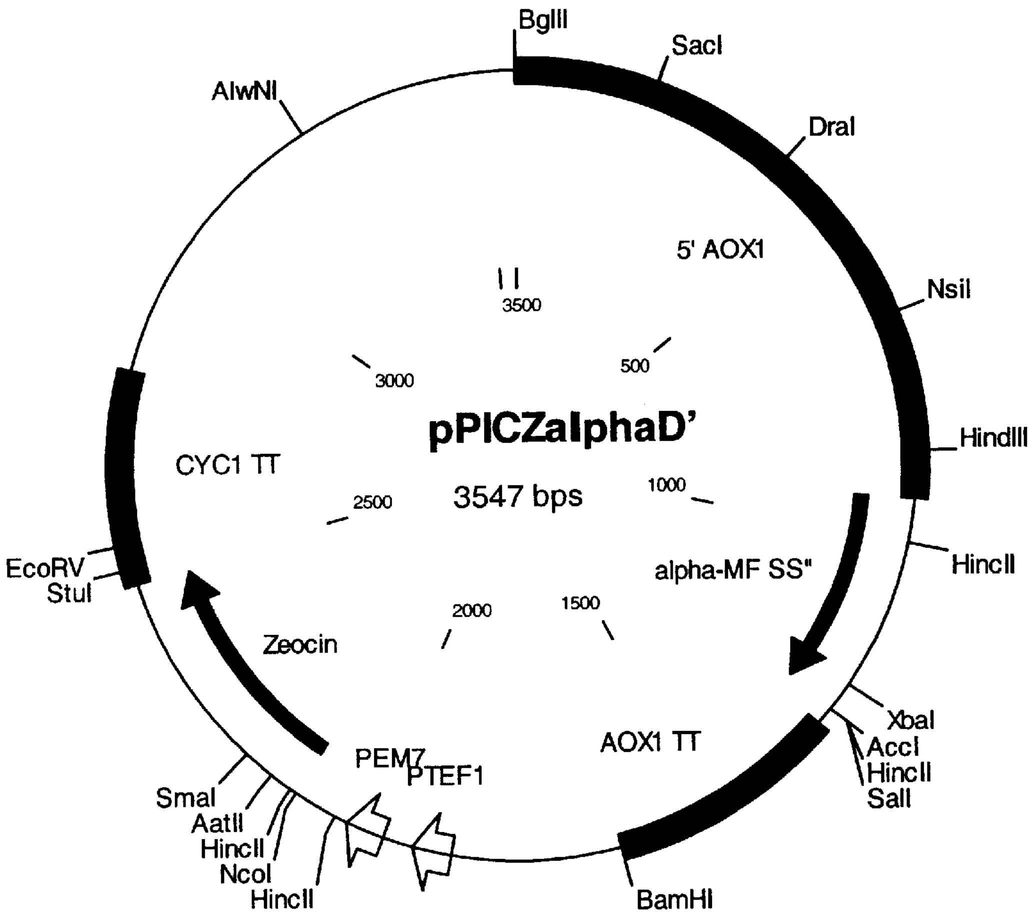
FIG. 30. Schematic map of the vector pPICZalphaD' which has the sequence as defined in SEQ ID NO:52.
Figure 31:
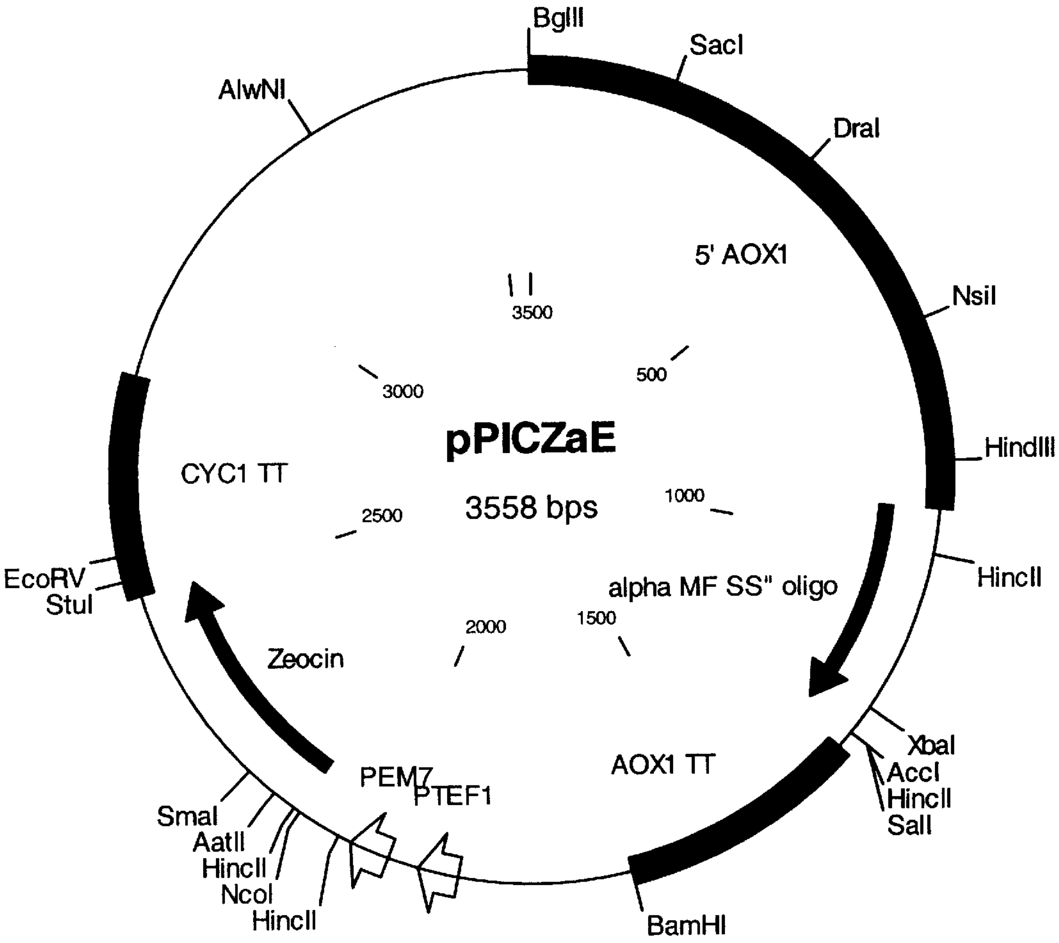
FIG. 31. Schematic map of the vector pPICZalphaE' which has the sequence as defined in SEQ ID NO:53.

The shuttle vector pPICZalphaE'E1sH6 was constructed starting from the pPICZalphaA vector (Invitrogen; SEQ ID NO:51, FIG. 29). In a first step said vector was adapted in order to enable cloning of the E1 coding sequence directly behind the cleavage site of the KEX2 or STE13 processing proteases, respectively. Therefore pPICZalphaA was digested with XhoI and NotI. The digest was separated on a 1% agarose gel and the 3519 kb fragment (major part of vector) was isolated and purified by means of a gel extraction kit (Qiagen). This fragment was then ligated using T4 polymerase (Boehringer) according to the supplier's conditions in presence of specific oligonucleotides yielding pPICZalphaD' (SEQ ID NO:52, FIG. 30) or pPICZalphaE' (SEQ ID NO:53, FIG. 31).

The following oligonucleotides were used:

for constructing pPICZalphaD':

```
                                    (SEQ ID NO:54)
8822: 5'-TCGAGAAAAGGGGCCCGAATTCGCATGC-3';
and
                                    (SEQ ID NO:55)
8823: 5'-GGCCGCATGCGAATTCGGGCCCCTTTTC-3'
```

which yield, after annealing, the linker oligonucleotide:

```
TCGAGAAAAGGGGCCCGAATTCGCATGC       (SEQ ID NO:54)
    CTTTTCCCCGGGCTTAAGCGTACGCCGG   (SEQ ID NO:55)
```

for constructing pPICZalphaE'

```
                                         (SEQ ID NO: 56)
8649: 5'-TCGAGAAAAGAGAGGCTGAAGCCTGCAGCATATGC-3'
                                         (SEQ ID NO: 57)
8650: 5'-GGCCGCATATGCTGCAGGCTTCAGCCTCTCTTTTC-3'
```

which yield, after annealing, the linker oligonucleotide:

```
                                    (SEQ ID NO:56)
TCGAGAAAAGAGAGGCTGAAGCCTGCAGCATATGC
                                    (SEQ ID NO:57)
    CTTTTCTCTCCGACTTCGGACGTCGTATACGCCGG
```

These shuttle vectors pPICZalphaD' and pPICZalphaE' have newly introduced cloning sites directly behind the cleavage site of the respective processing proteases, KEX2 and STE13.

The E1-H6 coding sequence was isolated as a NsI1/Eco52I fragment from pGEMT-E1sH6 (SEQ ID NO:6, FIG. 1). The fragment was purified using a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

Figure 32:
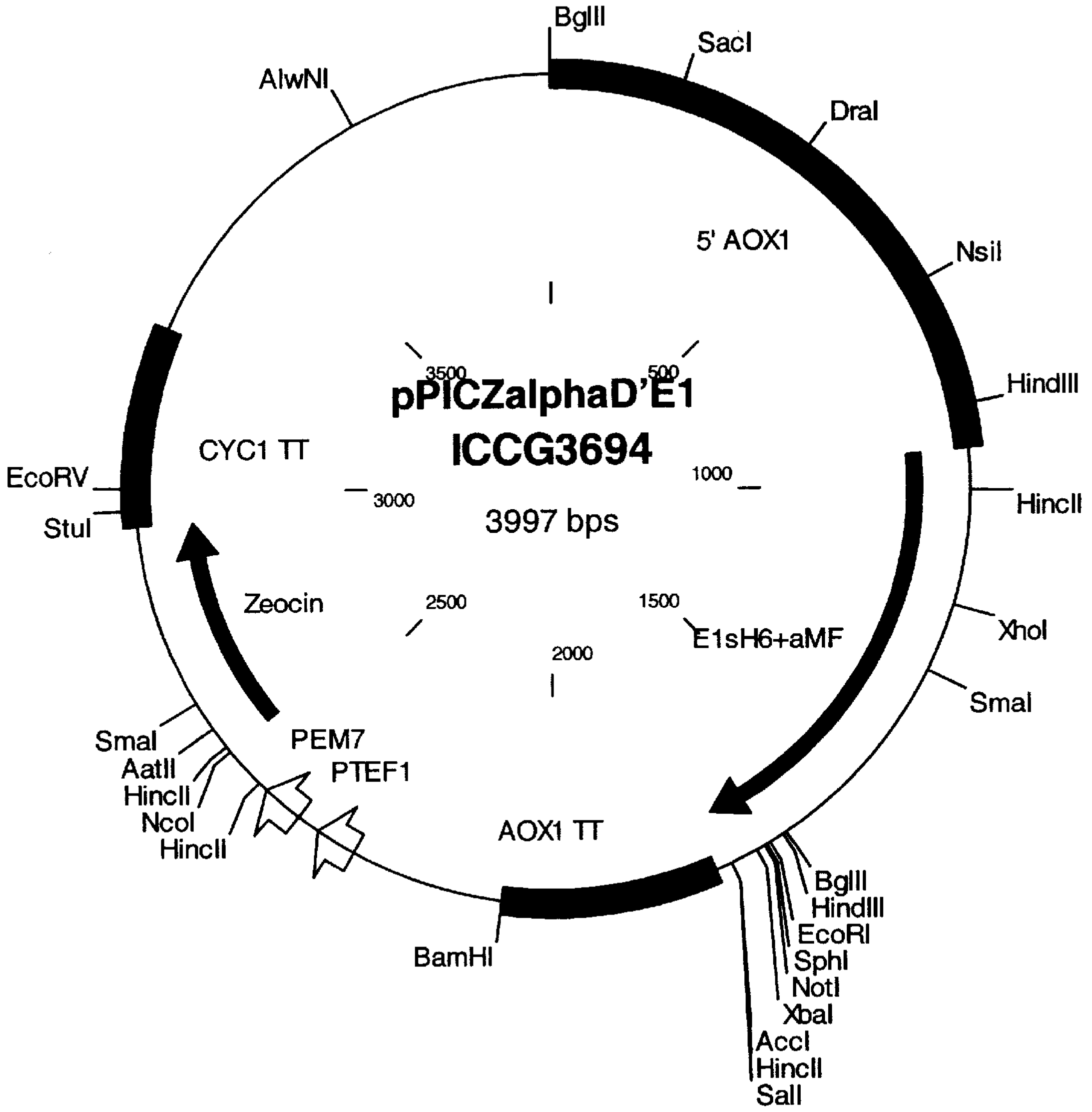
FIG. 32. Schematic map of the vector pPICZalphaD'E1sH6 which has the sequence as defined in SEQ ID NO:58.
Figure 33:
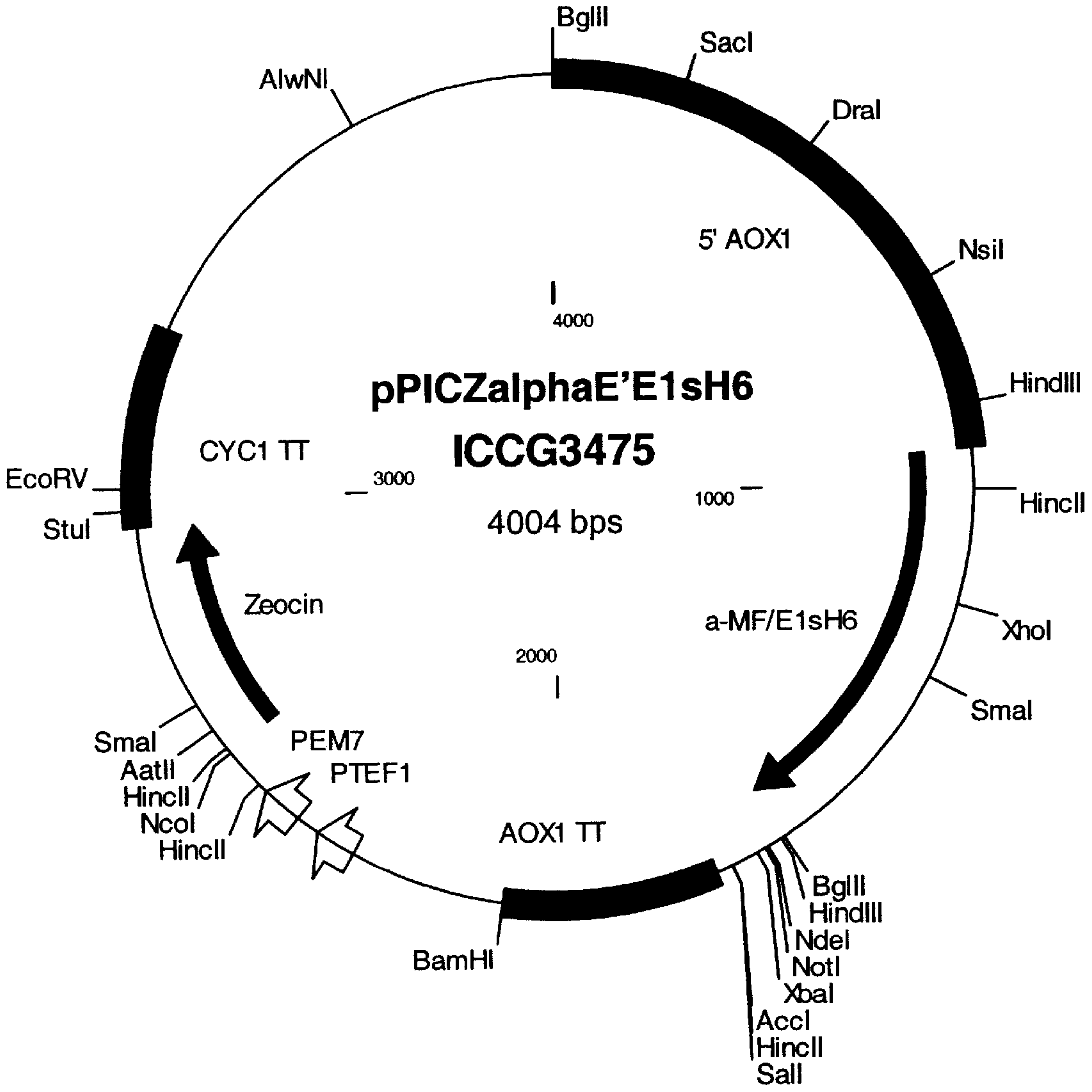
FIG. 33. Schematic map of the vector pPICZalphaE'E1sH6 which has the sequence as defined in SEQ ID NO:59.

The ligation mixtures were transformed to *E. coli* TOP10F' cells and plasmid DNA of several zeocin resistant colonies analyzed by restriction enzyme digestion. Positive clones were withheld and denominated pPICZalphaD'E1sH6 (ICCG3694; SEQ ID NO:58, FIG. 32) and pPICZalphaE'E1sH6 (ICCG3475; SEQ ID NO:59, FIG. 33), respectively.

Example 12

Construction of pPICZalphaD'E2sH6 and pPICZalphaE'E2H6 Vectors

The shuttle vectors pPICZalphaD' and pPICZalphaE' were constructed as described in Example 11.

Figure 23:
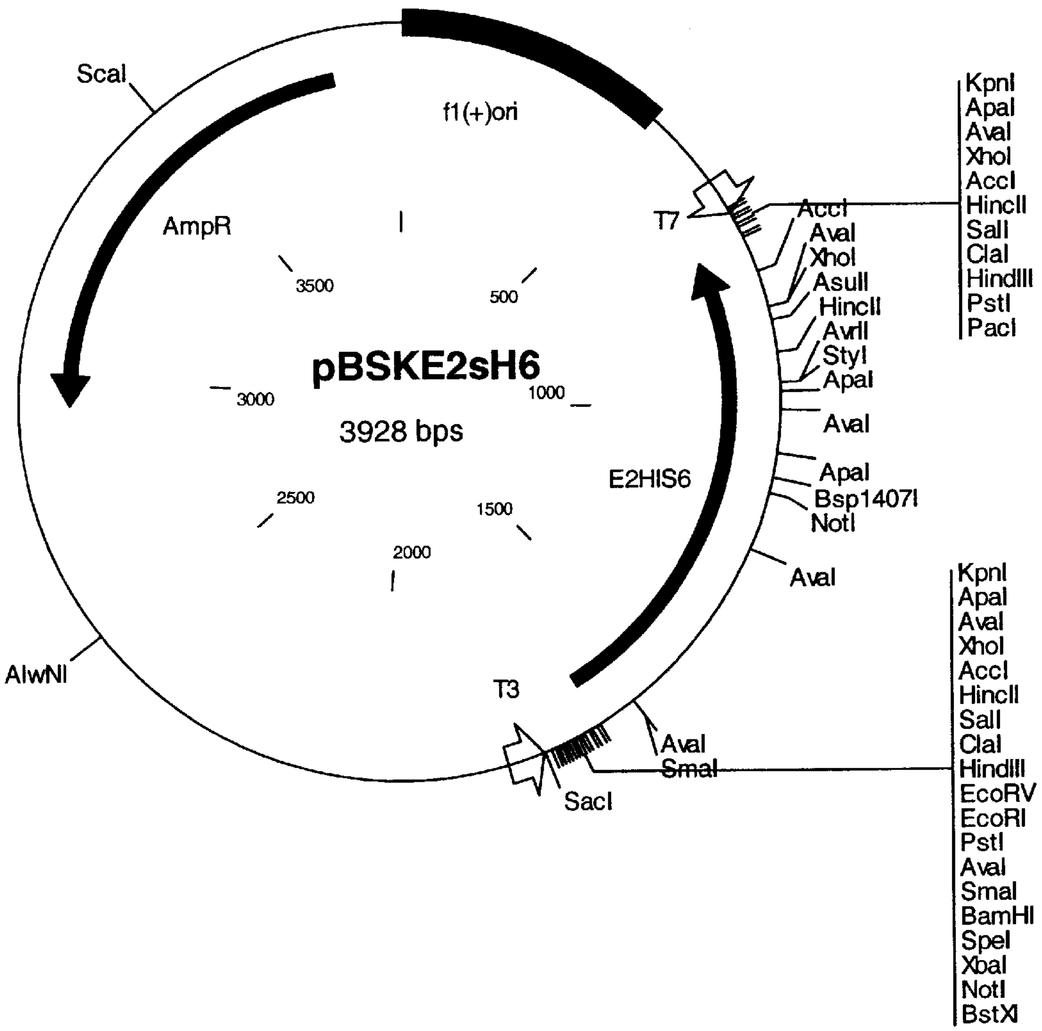
FIG. 23. Schematic map of the vector pBSK-E2sH6 which has the sequence as defined in SEQ ID NO:45.

The E2-H6 coding sequence was isolated as a SalI/KpnI fragment from pBSK-E2sH6 (SEQ ID NO:45, FIG. 23). The fragment was purified with a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

Figure 34:
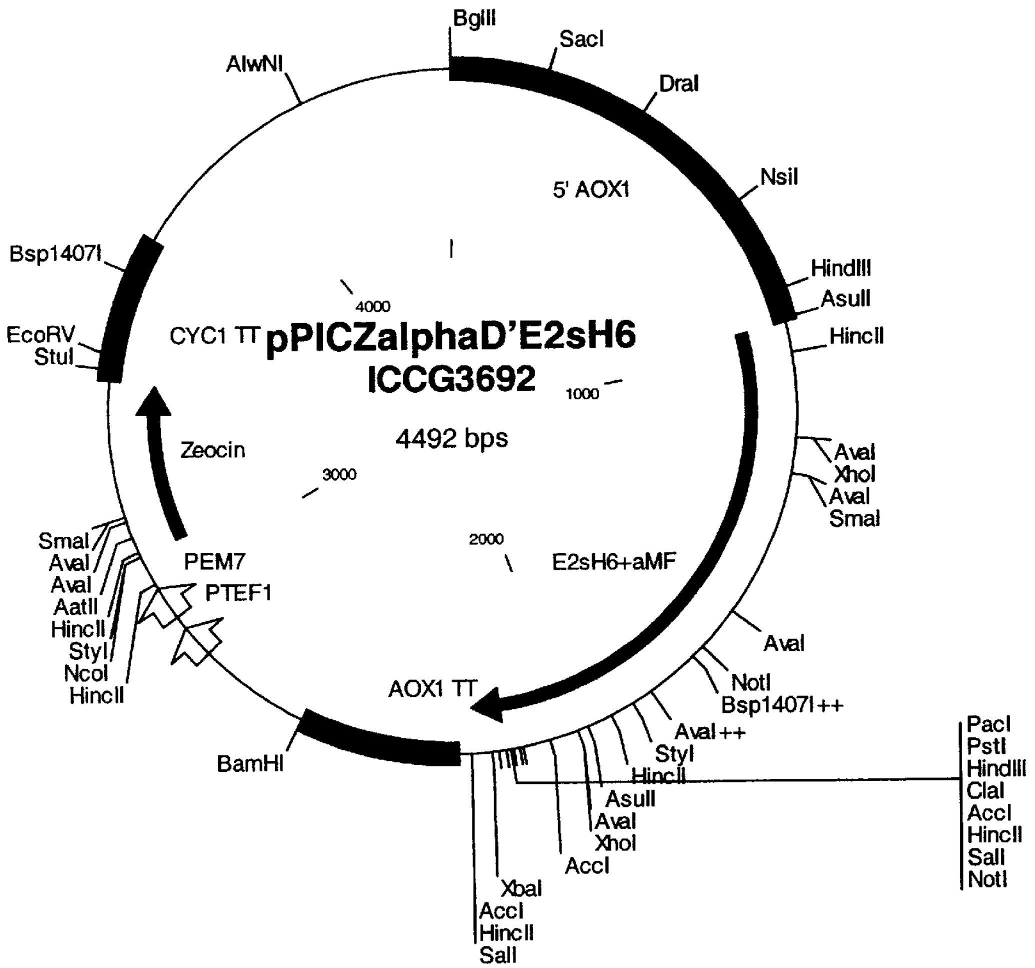
FIG. 34. Schematic map of the vector pPICZalphaD'E2sH6 which has the sequence as defined in SEQ ID NO:60.
Figure 35:
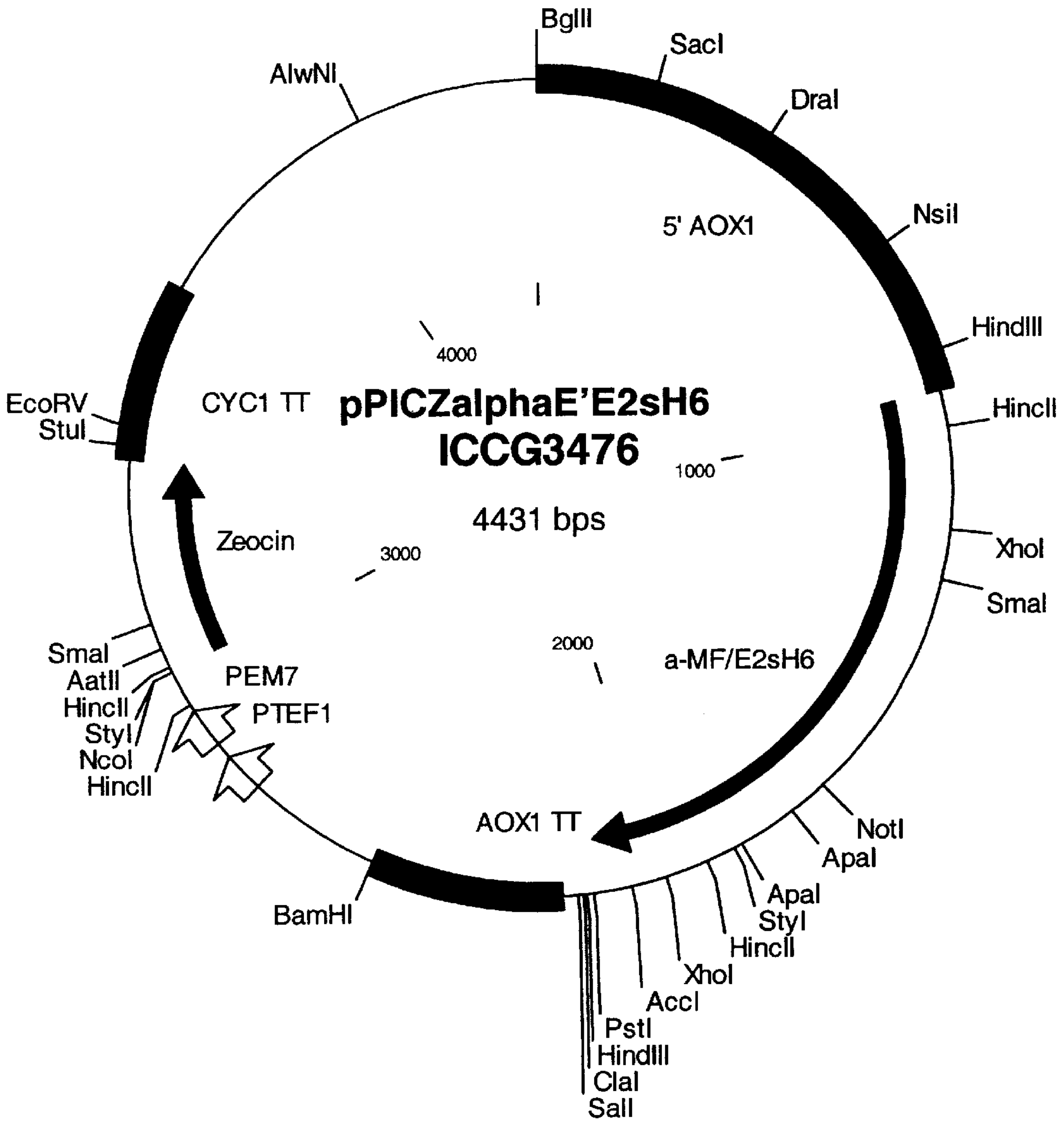
FIG. 35. Schematic map of the vector pPICZalphaE'E2sH6 which has the sequence as defined in SEQ ID NO:61.

The ligation mixture was transformed to *E. coli* TOP10F' cellls and the plasmid DNA of several zeocin resistant colonies was analyzed by restriction enzyme digestion. Positive clone were withheld and denominated pPICZalphaD'E2sH6 (ICCG3692; SEQ ID NO:60, FIG. 34) and pPICZalphaE'E2sH6 (ICGG3476; SEQ ID NO:61, FIG. 35), respectively.

Example 13

Transformation of *Pichia Pastoris* and Selection of Transformants

The *P. pastoris* shuttle plasmids as described in Examples 11 and 12 were transformed to *P. pastoris* cells according to the supplier's conditions (Invitrogen). An E1- and an E2-producing strain were withheld for further characterization.

The HCV envelope proteins were expressed in *P. pastoris*, a yeast strain well known for the fact that hyperglycosylation is normally absent (Gellissen, G. 2000) and previously used to express dengue virus E protein as GST fusion (Sugrue, R. J. et al. 1997). Remarkably, the resulting *P. pastoris*-expressed HCV envelope proteins displayed a comparable glycosylation as is observed in wild-type *Saccharomyces* strains. More specifically, the HCV envelope proteins produced by *P. pastoris* are hyperglycosylated (based on the molecular weight of the expression products detected in western-blots of proteins isolated from transformed *P. pastoris* cells).

Example 14

Culture Conditions for *Saccaromyces Cerevisiae, Hansenula Polymorpha* and *Pichia Pastoris*

*Saccharomyces cerevisiae*

Cell Banking

Of the selected recombinant clone a master cell bank and working cell bank were prepared. Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved working cell bank vial and grown in 500 mL medium (YNB supplemented with 2% sucrose, Difco) in a 2 L Erlenmeyer shake flasks at 37° C., 200 rpm for 48 h.

Fermentations were typically performed in Biostat C fermentors with a working volume of 15 L (B. Braun Int., Melsungen, Germany). The fermentation medium contained 1% Yeast Extract, 2% Peptone and 2% sucrose as carbon source. Poly-ethylene glycol was used as anti-foam agent.

Temperature, pH and dissolved oxygen were typically controlled during the fermentation, applicable set-points are summarised in Table 1. Dissolved oxygen was cascade controlled by agitation/aeration. pH was controlled by addition of NaOH (0.5 M) or $H_3PO_4$ solution (8.5%).

TABLE 1

Typical parameter settings for *S. cerevisiae* fermentations

| Parameter | set-point |
|---|---|
| Temperature | 33–37° C. |
| pH | 4.2–5.0 |
| DO (growth phase) | 10–40% air saturation |
| DO (induction) | 0–5% |
| aeration | 0.5–1.8 vvm* |
| agitation | 150–900 rpm |

*volume replacement per minute

The fermentation was started by the addition of 10% seed-culture. During the growth phase the sucrose concentration was monitored off-line by HPLC analysis (Polysphere Column OAKC Merck).

During the growth phase the dissolved oxygen was controlled by cascade control (agitation/aeration). After complete metabolisation of sucrose the heterologous protein production was driven by the endogenous produced ethanol supplemented with stepwise addition of EtOH in order to maintain the concentration at approximately 0.5% (off-line HPLC analysis, polyspher OAKC column) During this induction phase the dissolved oxygen was controlled below 5% air-saturation, by manual adjustment of airflow rate and agitator speed.

Typically the fermentation was harvested 48 to 72 h post induction by concentration via tangential flow filtration followed by centrifugation of the concentrated cell suspension to obtain cell pellets. If not analyzed immediately, cell pellets were stored at −70° C.

*Hansenula polymorpha*

Cell Banking

Of the selected recombinant clone a master cell bank and working cell bank were prepared. Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved (−70° C.) working cell bank vial and grown in 500 mL medium (YPD, Difco) in a 2 L Erlenmeyer shake flasks at 37° C., 200 rpm for 48 h.

Fermentations were typically performed in Biostat C fermentors with a working volume of 15 L (B. Braun Int., Melsungen, Germany). The fermentation medium contained 1% Yeast Extract, 2% Peptone and 1% glycerol as carbon source. Poly-ethylene glycol was used as anti-foam agent.

Temperature, pH, air-in and dissolved oxygen were typically controlled during the fermentation, applicable set-points are summarised in Table 2. Dissolved oxygen was controlled by agitation. pH was controlled by addition of NaOH (0.5 M) or $H_3PO_4$ solution (8.5%).

TABLE 2

Typical parameter settings for *H. polymorpha* fermentations

| Parameter | set-point |
|---|---|
| Temperature | 30–40° C. |
| pH | 4.2–5.0 |
| DO | 10–40% air saturation |

TABLE 2-continued

| Typical parameter settings for *H. polymorpha* fermentations | |
|---|---|
| Parameter | set-point |
| aeration | 0.5–1.8 vvm* |
| agitation | 150–900 rpm |

*volume replacement per minute

The fermentation was started by the addition of 10% seed-culture. During the growth phase the glycerol concentration was monitored off-line (Polysphere Column OAKC Merck) and 24 h after complete glycerol consumption 1% methanol was added in order to induce the heterologous protein expression. The fermentation was harvested 24 h post induction by concentration via tangential flow filtration followed by centrifugation of the concentrated cell suspension to obtain cell pellets. If not analyzed immediately, cell pellets were stored at −70° C.

*Pichia pastoris*

Small scale protein production experiments with recombinant *Pichia pastoris* were set up in shake flask cultures. Seed cultures were grown overnight in YPD medium (Difco). Initial medium pH was corrected to 4.5. Shake flasks were incubated on a rotary shaker at 200–250 rpm, 37° C.

The small scale production was typically performed at 500 mL scale in 2 L shake flasks and were started with a 10% inoculation in expression medium, containing 1% Yeast extract, 2% Peptone (both Difco), and 2% glycerol as carbon source. Incubation conditions were as for the seed culture. Induction was started by addition of 1% MeOH approximately 72 h after inoculation. The cells were collected 24 h post induction by centrifugation. If not analyzed immediately, cell pellets were stored at −70° C.

Example 15

Leader Peptide Removal from MFα-E1-H6 and MFα-E2-H6Proteins Expressed in Selected Yeast Cells The expression products in *Hansenula polymorpha* and a *Saccharomyces cerevisiae* glycosylation minus strain of the HCV E1 and E2 protein constructs with the α-mating factor (αMF) leader sequence of *S. cerevisiae* were further analyzed. Since both genotype 1b HCV E1s (aa 192–326) and HCV E2s (aa 383–673 extended by the VLEGR (SEQ ID NO:64)-sequence) were expressed as C-terminal his-tagged (H6, HHHHHH, SEQ ID NO:63; said HCV proteins are furtheron in this Example denoted as αMF-E1-H6 and αMF-E2-H6) proteins, a rapid and efficient purification of the expressed products after guanidinium chloride (GuHCl)-solubilization of the yeast cells was performed on Ni-IDA (Ni-iminodiacetic acid). In brief, cell pellets were resuspended in 50 mM phosphate, 6M GuHCl, pH 7.4 (9 vol/g cells). Proteins were sulfonated overnight at room temperature (RT) in the presence of 320 mM (4% wlv) sodium sulfite and 65 mM (2% w/v) sodium tetrathionate. The lysate was cleared after a freeze-thaw cycle by centrifugation (10.000 g, 30 mm, 4° C.) and Empigen (Albright &Wilson, UK) and imidazole were added to the supernatant to final concentrations of 1% (w/v) and 20 mM, respectively. The sample was filtrated (0.22 μM) and loaded on a Ni-IDA Sepharose FF column, which was equilibrated with 50 mM phosphate, 6M GuHCl, 1% Empigen (buffer A) supplemented with 20 mM imidazole. The column was washed sequentially with buffer A containing 20 mM and 50 mM imidazole, respectively, till absorbance at 280 nm reached baseline level. The his-tagged products were eluted by applying buffer D, 50 mM phosphate, 6M GuHCl, 0.2% (for E1) or 1% (for E2) Empigen, 200 mM imidazole. The eluted materials were analyzed by SDS-PAGE and western-blot using a specific monoclonal antibodies directed against E1 (IGH212), or E2 (IGH212).

The E1-products were immediately analyzed by Edman degradation.

Figure 37:
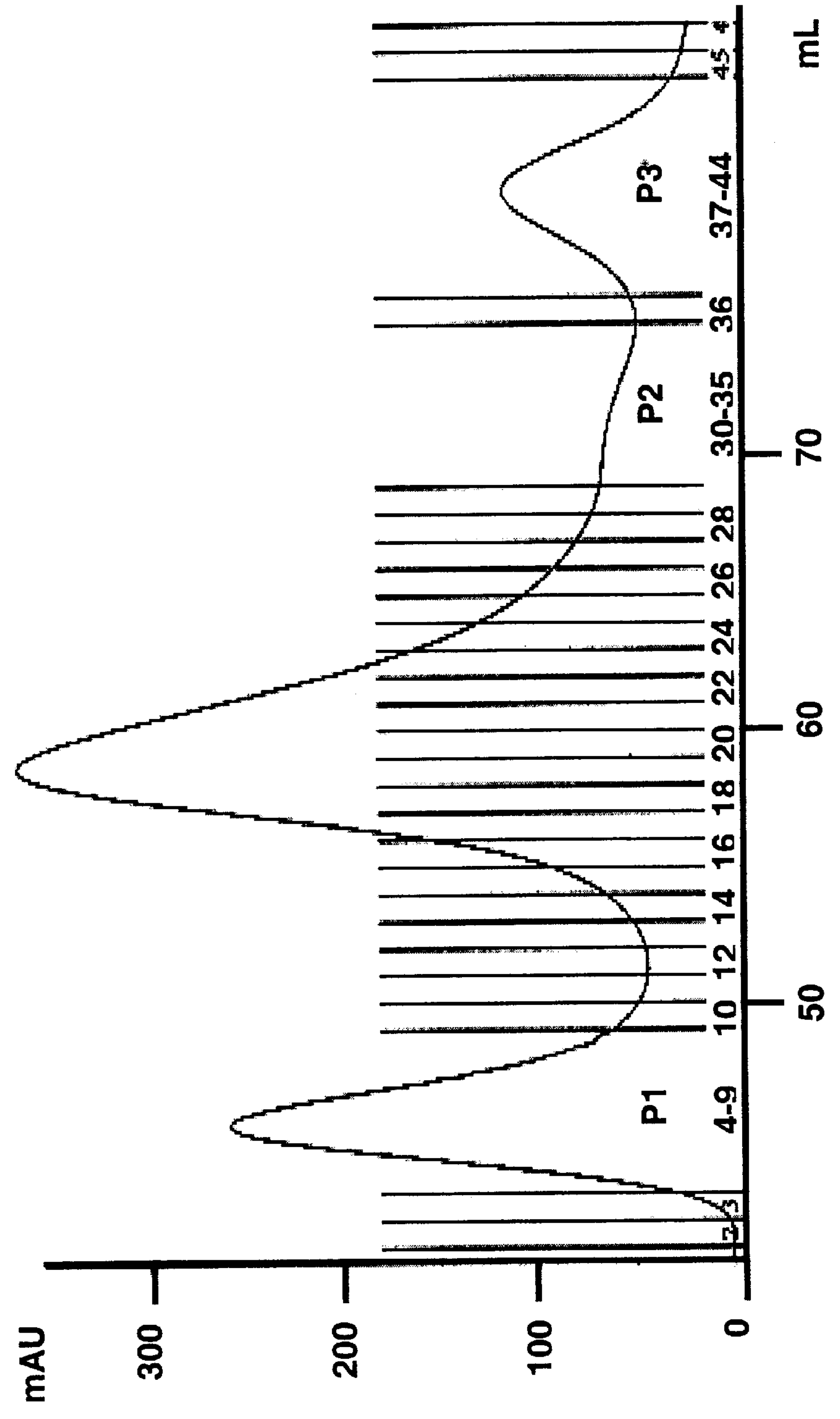
FIG. 37. Elution profile of size exclusion chromatography of IMAC-purified E2-H6 protein expressed from the MFα-E2-H6-expressing *Hansenula polymorpha* (see Example 15). The X-axis indicates the elution volume (in mL). The vertical lines through the elution profile indicate the fractions collected. "P1"=pooled fractions 4 to 9, "P2"=pooled fractions 30 to 35, and "P3"=pooled fractions 37 to 44. The Y-axis indicates absorbance given in mAU (milli absorbance units). The X-axis indicates the elution volume in mL.
Figure 38:
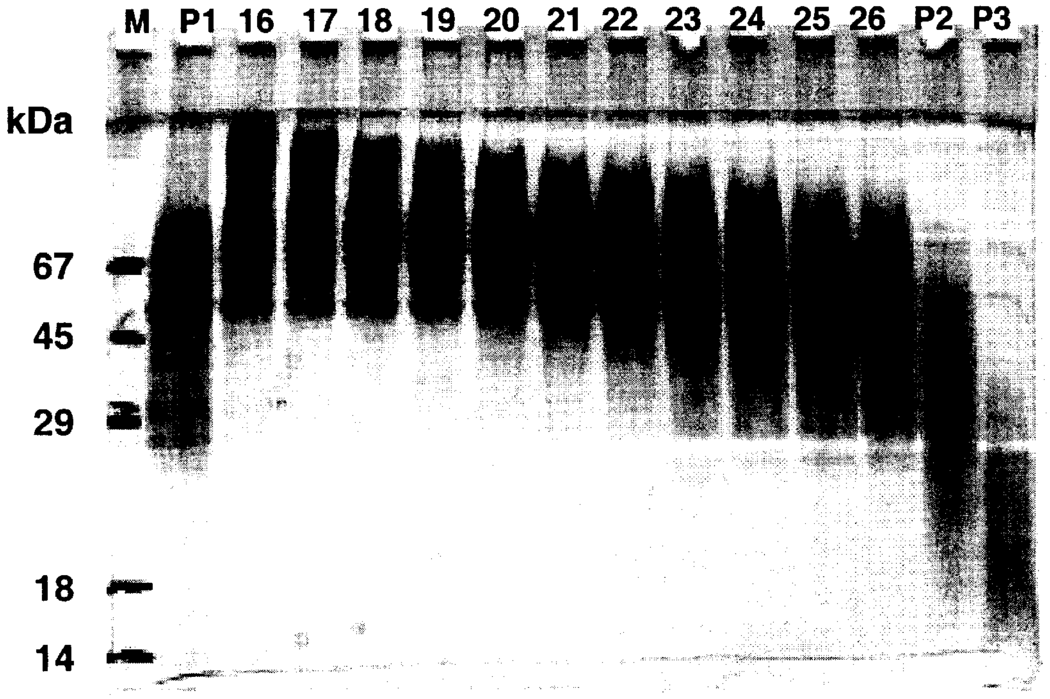
FIG. 38. The different pools and fractions collected after size exclusion chromatography (see FIG. 37) were analyzed by non-reducing SDS-PAGE followed by silver staining of the polyacrylamide gel. The analyzed pools ("P1", "P2", and "P3") and fractions (16 to 26) are indicated on top of the picture of the silver-stained gel. At the left (lane "M") are indicated the sizes of the molecular mass markers.
Figure 39:
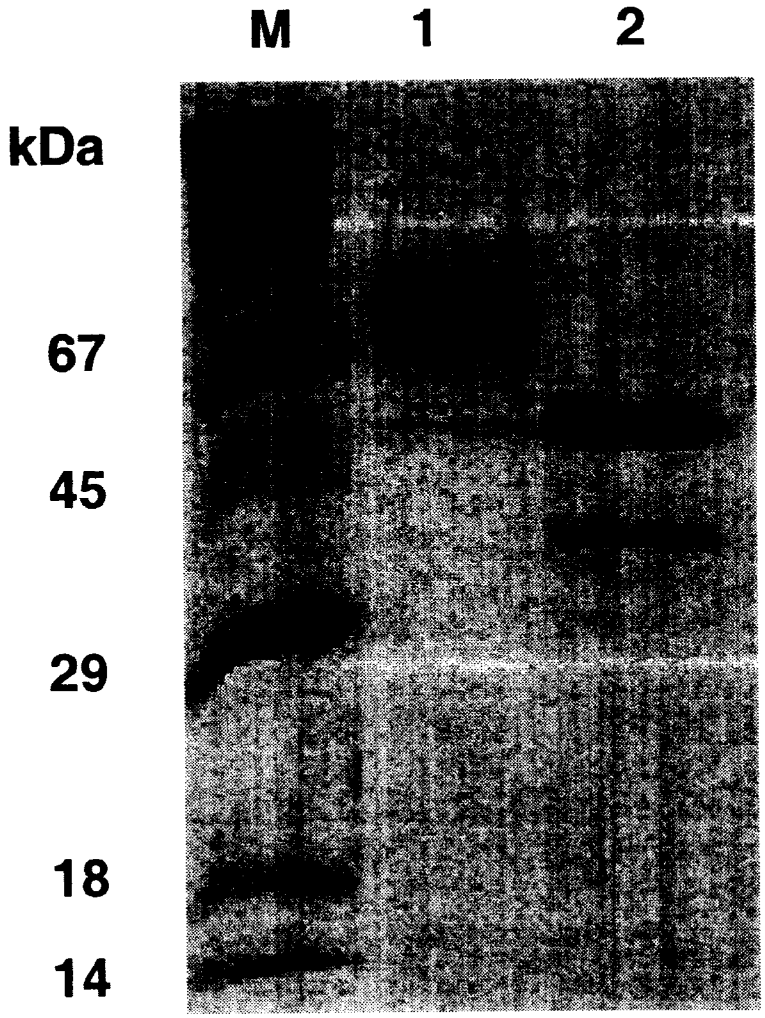
FIG. 39. Fractions 17 to 23 of the size exclusion chromatographic step as shown in FIG. 37 were pooled and alkylated. Thereafter, the protein material was subjected to Endo H treatment for deglycosylation. Untreated material and Endo H-treated material were separated on an SDS-PAGE gel and blotted to a PVDF membrane. The blot was stained with amido black.

Since at this stage, SDS-PAGE revealed already a very complex picture of protein bands for HCV E2, a further fractionation by size exclusion chromatography was performed. The Ni-IDA eluate was concentrated by ultrafiltration (MWCO 10 kDa, centriplus, Amicon, Millipore) and loaded on Superdex G200 (10/30 or 16/60; Pharmacia) in PBS, 1% Empigen or PBS, 3% Empigen. Elution fractions, containing E2 products, with a Mr between ~80 kDa and ~45 kDa, i.e. fractions 17–23 of the elution profile in FIG. 37 based on the migration on SDS-PAGE (FIG. 38), were pooled and alkylated (incubation with 10 mM DTT 3 h at RT followed by incubation with 30 mM iodo-acetamide for 3 hours at RT). Samples for amino-terminal sequencing were treated with Endo H (Roche Biochemicals) or left untreated. The glycosylated and deglycosylated E2 products were blotted on PVDF-membranes for amino-terminal sequencing. An amido-black stained blot of glycosylated and deglycosylated E2 is shown in FIG. 39.

The sequencing of both E1 and E2 purified products lead to the disappointing observation that removal of the signal sequence from the HCV envelope proteins is occurring only partially (see Table 3). In addition, the majority of the side products (degradation products and products still containing the leader sequence or part thereof) are glycosylated. This glycosylation resides even in part on the non-cleaved fragment of the signal sequence which contains also an N-glycosylation site. These sites can be mutated in order to result in less glycosylated side products. However, even more problematic is the finding that some alternatively cleaved products have only 1 to 4 amino acids difference compared to the desired intact envelope protein. Consequently, purification of the correctly processed product is virtually impossible due to the lack of sufficiently discriminating biochemical characteristics between the different expression products. Several of the degradation products may be a result of a Kex-2 like cleavage (e.g. the cleavage observed after aa 196 of E1 which is a cleavage after an arginine), which is also required for the cleavage of the α-mating factor leader and which can thus not be blocked without disturbing this essential process.

Figure 22:
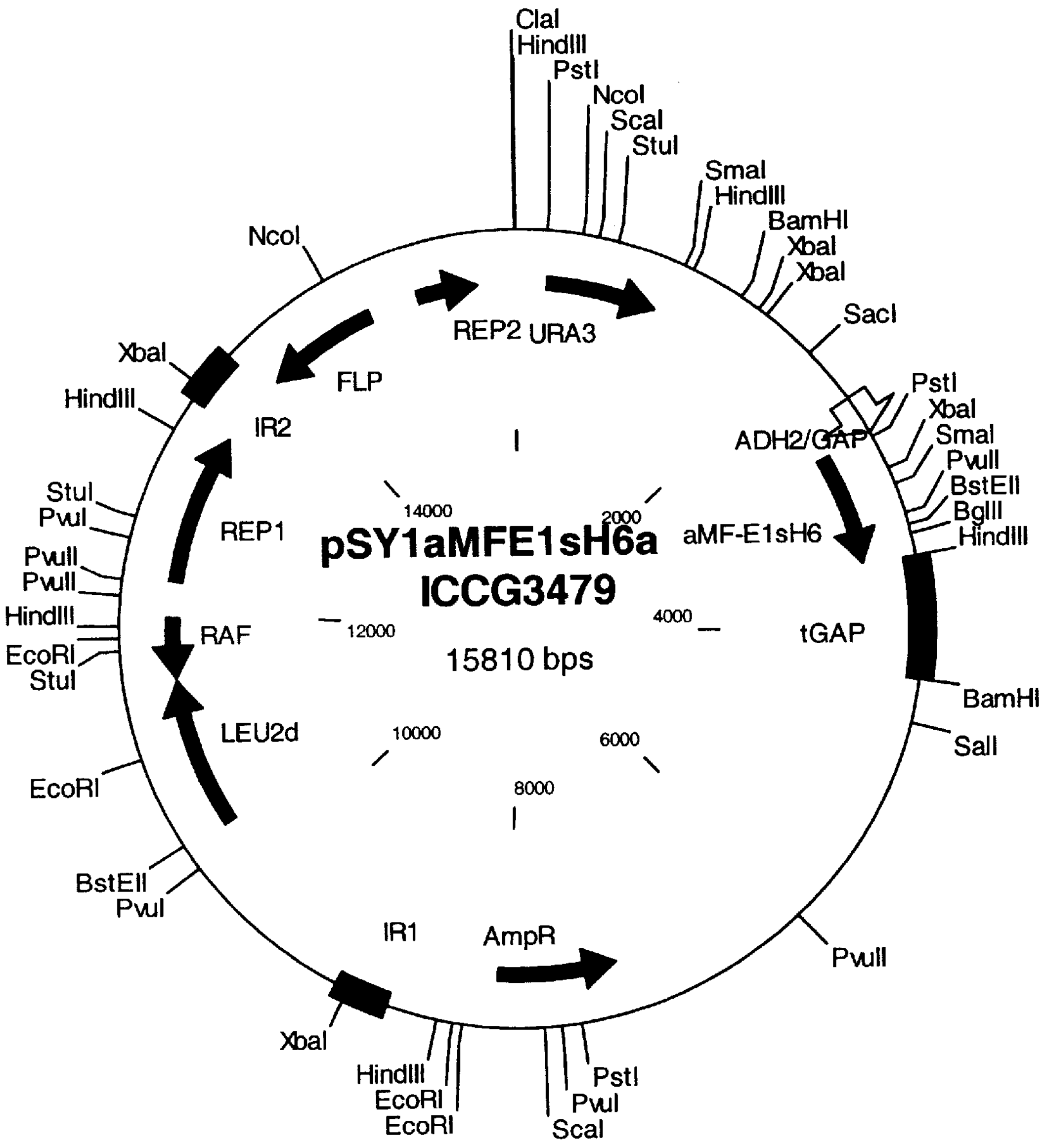
FIG. 22. Schematic map of the vector pSY1aMFE1sH6a which has the sequence as defined in SEQ ID NO:44.
Figure 28:
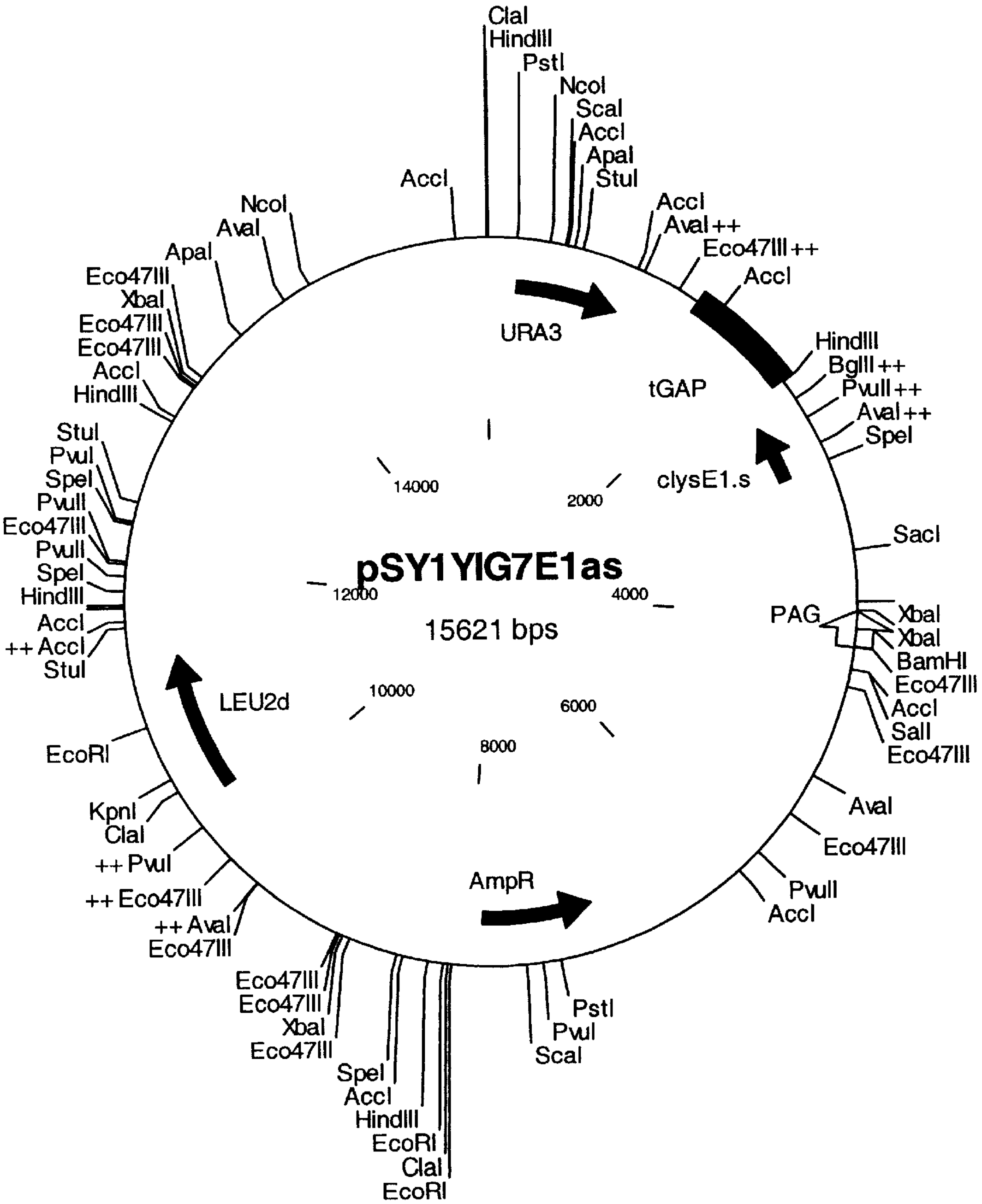
FIG. 28. Schematic map of the vector pSY1YIG7E1 which has the sequence as defined in SEQ ID NO:50.

A high E1 producing clone derived from transformation of *S. cerevisiae* IYCC155 with pSY1YIG7E1s (SEQ ID NO:50; FIG. 28) was compared with a high producing clone derived from transformation of *S. cerevisiae* IYCC155 with pSY1aMFE1sH6YIG1E1s (SEQ ID NO:44; FIG. 22). The intracellular expression of the E1 protein was evaluated after 2 up to 7 days after induction, and this by means of Western-blot using the E1 specific monoclonal antibody (IGH 201). As can be judged from FIG. 40, maximal expression was observed after 2 days for both strains but the expression patterns for both strains are completely different. Expression with the α-mating factor leader results in a very complex pattern of bands, which is a consequence from the fact that the processing of the leader is not efficient. This leads to several expression products with a different aminoterminus and of which some are modified by 1 to 5 N-glycosylations. However, for the E1 expressed with the CL leader a limited number of distinct bands is visible which reflects the high level of correct CL leader removal and the fact that only this correctly processed material may be modified by N-glycosylation (1 to 5 chains), as observed for *Hansenula*-derived E1 expressed with the same CL leader (see Example 16).

The hybridoma cell line producting the monoclonal antibody directed against E1 (IGH201) was deposited on Mar. 12, 1998 under the conditions of the Budapest Treaty at the European Collection of Cell Cultures, Centre for Applied Microbiology & Research, Salisbury, Wiltshire SP4 0JG, UK, and has the accession number ECACC 98031216). The monoclonal antibody directed against E2 (IGH212) has been described as antibody 12D11F2 in Example 7.4 by Maertens et al. in WO96/04385.

TABLE 3

Identification of N-termini of αMF-E1-H6 and αMF-E2-H6 proteins expressed in *S. cerevisiae* or *H. polymorpha*. Based on the N-terminal sequencing the amount of N-termini of the mature E1-H6 and E2-H6 proteins could be estimated ("mature" indicating correct removal of the αMF signal sequence). The total amount of protein products was calculated as of protein based on the intensity of the peaks recovered by pmol Edman degradation. Subsequently, for each specific protein (i.e. for each 'detected N-terminus') the mol % versus the total was estimated.

| Yeast | αMF-E1-H6 | αMF-E2-VIEGR-H6 |
|---|---|---|
| *S. cerevisiae* | Experiment 1:<br>16% of proteins still containing αMF sequences<br>18% of proteins cleaved between aa 195 and 196 of E1<br>66% of proteins with correctly removed αMF | / |
| | Experiment 2<br>18% of proteins still containing αMF sequences<br>33% of proteins cleaved between aa 195 and 196 of E1<br>8% of other proteins other E1 cleavage products<br>44% of proteins with correctly removed αMF | / |

TABLE 3-continued

Identification of N-termini of αMF-E1-H6 and αMF-E2-H6 proteins expressed in *S. cerevisiae* or *H. polymorpha*. Based on the N-terminal sequencing the amount of N-termini of the mature E1-H6 and E2-H6 proteins could be estimated ("mature" indicating correct removal of the αMF signal sequence). The total amount of protein products was calculated as of protein based on the intensity of the peaks recovered by pmol Edman degradation. Subsequently, for each specific protein (i.e. for each 'detected N-terminus') the mol % versus the total was estimated.

| Yeast | αMF-E1-H6 | αMF-E2-VIEGR-H6 |
|---|---|---|
| *H. polymorpha* | 64% of proteins still containing αMF sequences | 75% of proteins still containing αMF sequences |
| | 6% of proteins cleaved between aa 192 and 193 of E1 | 25% of proteins with correctly removed αMF |
| | 30% of proteins with correctly removed αMF | |

Example 16

Expression of an E1 Construct in Yeast Suitable for Large Scale Production and Purification Several other leader sequences were used to replace the *S. cerevisiae* αMF leader peptide including CHH (leader sequence of *Carcinus maenas* hyperglycemic hormone), Amyl (leader sequence of amylase from *S. occidentalis*), Gam1 (leader sequence of glucoamylase from *S. occidentalis*), Phy5 (leader sequence from fungal phytase), phol (leader sequence from acid phosphatase from *Pichia pastoris*) and CL (leader of avian lysozyme C, 1,4-beta-N-acetylmuramidase C) and linked to E1-H6 (i.e. E1 with C-terminal his-tag). All constructs were expressed in *Hansenula polymorpha* and each of the resulting cell lysates was subjected to western blot analysis. This allowed already to conclude that the extent of removal of the leader or signal sequence or peptide was extremely low, except for the construct wherein CL is used as leader peptide. This was confirmed for the CHH-E1-H6 construct by Edman-degradation of Ni-IDA purified material: no correctly cleaved product could be detected although several different sequences were recovered (see Table 4).

TABLE 4

Identification of N-termini of CHH-E1-H6 proteins expressed in *H. polymorpha*, based on N-terminal amino acid sequencing of different protein bands after separation by SDS-PAGE and blotting to a PVDF membrane.

| Molecular size | Identified N-termini |
|---|---|
| 45 kD | starts at amino acid 27 of CHH leader = only pre-sequence cleaved, pro-sequence still attached |
| 26 kD | partially starts at amino acid 1 of CHH leader = no removal of pre-pro-sequence |
| | partially starts at amino acid 9 of CHH leader = product of alternative translation starting at second AUG codon |

TABLE 4-continued

Identification of N-termini of CHH-E1-H6 proteins expressed in *H. polymorpha*, based on N-terminal amino acid sequencing of different protein bands after separation by SDS-PAGE and blotting to a PVDF membrane.

| Molecular size | Identified N-termini |
|---|---|
| 24 kD | partially starts at amino acid 1 of CHH leader = no removal of pre-pro-sequence<br>partially starts at amino acid 9 of CHH leader = product of alternative translation starting at second AUG codon |

As mentioned already, the western-blots of the cell lysates revealed a pattern of E1 specific protein bands, indicative for a higher degree of correct removal of the CL leader peptide. This is surprising since this leader is not derived from a yeast. Amino acid sequencing by Edman degradation of GuHC1 solubilized and Ni-IDA purified material indeed confirmed that 84% of the E1 proteins is correctly cleaved and the material is essentially free of degradation products. Still 16% of non-processed material is present but since this material is non-glycosylated it can be easily removed from the mixture allowing specific enrichment of correctly cleaved and glycosylated E1. Such a method for enrichment may be an affinity chromatography on lectins, other alternatives are also given in Example 19. Alternatively, the higher hydrophobic character of the non-glycosylated material may be used to select and optimize other enrichment procedures. The correct removal of the CL leader peptide from the CL-E1-H6 protein was further confirmed by mass spectrometry which also confirmed that up to 4 out of the 5 N-glycosylation sites of genotype 1b E1s can be occupied, whereby the sequence NNSS (amino acids 233 to 236; SEQ ID NO:65) are considered to be a single N-glycosylation site.

Example 17

Purification and Biochemial Characterization of the HCV E2 Protein Expressed in *Hansenula Polymorpha* from the CL-E2-H6 Encoding Construct The efficiency of removal of the CL leader peptide from CL-E2-VIEGR-H6 (furtheron in this Example denoted as "CL-E2-H6") protein expressed in *Hansenula polymorpha* was analyzed. Since the HCV E2s (aa 383–673) was expressed as a his-tagged protein, a rapid and efficient purification of the expressed protein after GuHCl-solubilization of collected cells was performed on Ni-IDA. In brief, cell pellets were resuspended in 30 mM phosphate, 6 M GuHCl, pH 7.2 (9 mL buffer/g cells). The protein was sulfonated overnight at room temperature in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.). Empigen BB (Albright & Wilson) and imidazole were added to a final concentration of 1% (w/v) and 20 mM, respectively. All further chromatographic steps were executed on an Akta FPLC workstation (Pharmacia). The sample was filtrated through a 0.22 μm pore size membrane (cellulose acetate) and loaded on a Ni-IDA column (Chelating Sepharose FF loaded with $Ni^{2+}$, Pharmacia), which was equilibrated with 50 mM phosphate, 6 M GuHCl, 1% Empigen BB, pH 7.2 (buffer A) supplemented with 20 mM imidazole. The column was washed sequentially with buffer A containing 20 mM and 50 mM imidazole, respectively, till the absorbance at 280 nm reached the baseline level. The his-tagged products were eluted by applying buffer D, 50 mM phosphate, 6 M GuHCl, 0.2% Empigen BB (pH 7.2), 200 mM imidazole. The purified materials were analysed by SDS-PAGE and western-blot using a specific monoclonal antibody directed against E2 (IGH212) (FIG. 41). The IMAC-purified E2-H6 protein was also subjected to N-terminal sequencing by Edman degradation. Thereto proteins were treated with N-glycosidase F (Roche) (0.2 U/μg E2, 1 h incubation at 37° C. in PBS/3% empigen BB) or left untreated. The glycosylated and deglycosylated E2-H6 proteins were subjected to SDS-PAGE and blotted on a PVDF-membrane for amino acid sequencing (analysis was performed on a PROCISE™ 492 protein sequencer, Applied Biosystems). Since at this stage, SDS-PAGE revealed some degradation products, a further fractionation by size exclusion chromatography was performed. Hereto, the Ni-IDA eluate was concentrated by ultrafiltration (MWCO 10 kDa, centriplus, Amicon, Millipore) and loaded on a Superdex G200 (Pharmacia) in PBS, 1% Empigen BB. Elution fractions, containing mainly intact E2s related products with a Mr between ~30 kDa and ~70 kDa based on the migration on SDS-PAGE, were pooled and eventually alkylated (incubation with 5 mM DTT for 30 minutes at 37° C., followed by incubation with 20 mM iodoacetamide for 30 minutes at 37° C.). The possible presence of degradation products after IMAC purification can thus be overcome by a further fractionation of the intact product by means of size exclusion chromatography. An unexpectedly good result was obtained. Based on the N-terminal sequencing the amount of E2 product from which the CL leader peptide is removed could be estimated. The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E2-H6 was detected and other variants of E2-H6 lacking amino acid of the E2 protein or containing N-terminal amino acids not comprised in the E2 protein were absent. In conclusion, the E2-H6 protein expressed by *H. polymorpha* as CL-E2-H6 protein was isolated without any further in vitro processing as a >95% correctly cleaved protein. This is in sharp contrast with the fidelity of leader peptide removal by *H. polymorpha* of the aMF-E2-H6 protein to the E2-H6 protein, which was estimated to occur in 25% of the isolated proteins (see Table 3).

Example 18

Purifictaion and Biochemical Characterization of the HCV E1 Protein Expressed in *Hansenula Polymorpha* from the CL-H6-K-E1 Encodin Construct and In Vitro Processing of H6-Containing Proteins The efficiency of removal of the CL leader peptide from the CL-H6-K-E1 protein expressed in *H. polymorpha* was analyzed, as well as the efficiency of subsequent in vitro processing in order to remove the H6 (his-tag)-adaptor peptide and the Endo Lys-C processing site. Since the HCV E1s (aa 192–326) was expressed as a N-terminal His-K-tagged protein CL-H6-K-E1, a rapid and efficient purification could be performed as described in Example 17. The elution profile of the IMAC-chromatographic purification of H6-K-E1 (and possibly residual CL-H6-K-E1) proteins is shown in FIG. 42. After SDS-PAGE and silver staining of the gel and western-blot analysis using a specific monoclonal antibody directed against E1 (IGH201) (FIG. 43), the elution fractions (63–69) containing the recombinant E1s products were pooled ('IMAC pool') and subjected to an overnight Endoproteinase Lys-C (Roche) treatment (enzyme/substrate ratio of 1/50 (w/w), 37° C.) in order to remove the H6-K-fusion tail. Removal of non-processed fusion product was performed by a negative IMAC chromatography step on a Ni-IDA column whereby Endo-Lys-C-processed proteins are collected in the flow-through fraction. Hereto the Endoproteinase Lys-C digested protein sample was applied on a Ni-IDA column after a 10-fold dilution with 10 mM $NaH_2PO_4$. $3H_2O$, 1% (v/v) Empigen B, pH 7.2 (buffer B) followed by washing with buffer B till the absorbance at 280 nm reached the baseline level. The flow through was collected in different fractions (1–40) that were screened for the presence of E1s-products (FIG. 44). The fractions (7–28), containing intact E1 from which the N-terminal H6-K (and possibly residual CL-H6-K) tail is removed (with a Mr between ~15 kDa and ~30 kDa based on the migration on SDS-PAGE followed by silver staining or western blot analysis using a specific monoclonal antibody directed against E1 (IGH201), were pooled and alkylated (incubation with 5 mM DTT for 30 minutes at 37° C., followed by incubation with 20 mM iodoacetamide for 30 minutes at 37° C.). This material was subjected to N-terminal sequencing (Edman degradation). Hereto, protein samples were treated with N-glycosidase F (Roche) (0.2U/μg E1, 1 h incubation at 37° C. in PBS/3% empigen BB) or left untreated. The glycosylated and deglycosylated E1 proteins were then separated by SDS-PAGE and blotted on a PVDF-membrane for further analysis by Edman degradation (analysis was performed on a PROCISE™ 492 protein sequencer, Applied Biosystems). Based on the N-terminal sequencing the amount of correctly processed E1 product could be estimated (processing includes correct cleavage of the H6-K-sequence). The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E1 was detected and not the N-termini of other processing variants of H6-K-E1. Based thereon, in vitro processing by Endo Lys-C of the H6-K-E1E1 (and possibly residual CL-H6-K-E1) protein to the E1 protein was estimated to occur with a fidelity of more than 95%.

Example 19

Specific Removal of Low-Glycosylated Forms of HCV E1 By Heparin

In order to find specific purification steps for HCV envelope proteins from yeast cells binding with heparin was evaluated. Heparin is known to bind to several viruses and consequently binding to the HCV envelope has already been suggested (Garson, J. A. et al. 1999). In order to analyze this potential binding, heparin was biotinylated and interaction with HCV E1 analyzed in microtiterplates coated with either sulfonated HCV E1 from *H. polymorpha*, alkylated HCV E1 from *H. polymorpha* (both produced as described in Example 16) and alkylated HCV E1 from a culture of mammalian cells transfected with a vaccinia expression vector. Surprisingly, a strong binding could only be observed with sulfonated HCV E1 from *H. polymorpha*, while binding with HCV E1 from mammalian cell culture was completely absent. By means of western-blot we could show that this binding was specific for the lower molecular weight bands of the HCV E1 protein mixture (FIG. 45), corresponding to low-glycosylated mature HCV E1s. FIG. 45 also reveals that sulfonation is not essential for heparin binding since upon removal of this sulfonation binding is still observed for the low molecular weight E1 (lane 4). Alternatively, alkylation is reducing this binding substantially, however, this may be caused by the specific alkylation agent (iodo-acetamide) used in this example. This finding further demonstrated the industrial applicability of the CL-HCV-envelope expression cassettes for yeast since we specifically can enrich HCV E1 preparations towards a preparation with HCV E1 proteins with a higher degree of glycosylation (i.e. more glycosylation sites occupied).

Example 20

Formation and Analysis of Virus-Like Particles (VLPs)

Conversion of the HCV E1 and E2 envelope proteins expressed in *H. polymorpha* (Examples 16 to 18) to VLPs was done essentially as described by Depla et al. in WO99/67285 and by Bosman et al. in WO01/30815. Briefly, after cultivation of the transformed *H. polymorpha* cells during which the HCV envelope proteins were expressed, cells were harvested, lysed in GuHCl and sulphonated as described in Example 17. His-tagged proteins were subsequently purified by IMAC and concentrated by ultrafiltration as described in Example 17.

VLP-formation of HCV Envelope Proteins with Sulphonated Cys-thiol Groups

The concentrated HCV envelope proteins sulphonated during the isolation procedure were not subjected to a reducing treatment and loaded on a size-exclusion chromatograpy column (Superdex G200, Pharmacia) equilibrated with PBS, 1% (v/v) Empigen. The eluted fractions were analyzed by SDS-PAGE and western blotting. The fractions with a relative Mr ~29—~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

VLP-formation of HCV Envelope Proteins with Irreversibly Modified Cys-thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Irreversible Cys-thiol modification was performed by (i) incubation for 30 min in the presence of 20 mM iodoacetamide, or by (ii) incubation for 30 min in the presence of 5 mM N-ethylmaleimide (NEM) and 15 mM biotin-N-ethylmaleimide. The proteins were subsequently loaded on a size-exclusion chromatograpy column (Superdex G200, Pharmacia) equilibrated with PBS, 1% (v/v) Empigen in case of iodoacetamide-blocking, or with PBS, 0.2% CHAPS in case of blocking with NEM and biotin-NEM. The eluted fractions were analyzed by SDS-PAGE and Western blotting. The fractions with a relative Mr ~29-~15 kD (based on SDS-PAGE migration) were pooled, concentrated and, to force virus-like particle formation, loaded on a Superdex G200 column equilibrated with PBS, 3% (w/v) betain. The fractions were pooled, concentrated and desalted to PBS, 0.5% (w/v) betain in case of iodoacetamide-blocking, or with PBS, 0.05% CHAPS in case of blocking with NEM and biotin-NEM.

VLP-formation of HCV Envelope Proteins with Reversibly Modified Cys-thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Reversible Cys-thiol modification was performed by incubation for 30 min in the presence of dithiodipyridine (DTDP), dithiocarbamate (DTC) or cysteine. The proteins were subsequently loaded on a size-exclusion chromatograpy column (Superdex G200, Pharmacia) equilibrated with PBS, 1% (v/v) Empigen. The eluted fractions were analyzed by SDS-PAGE and Western blotting. The fractions with a relative Mr ~29-~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

The elution profiles of size-exclusion chromatography in PBS, 3% (w/v) betain to obtain VLPs of *H. polymorpha*-expressed E2-H6 are shown in FIG. 46 (sulphonated) and FIG. 47 (alkylated with iodoacetamide).

The elution profiles of size-exclusion chromatography in PBS, 3% (w/v) betain to obtain VLPs of *H. polymorpha*-expressed E1 are shown in FIG. 48 (sulphonated) and FIG. 49 (alkylated with iodoacetamide). The resulting VLPs were analyzed by SDS-PAGE and western blotting as shown in FIG. 50.

Size-Analysis of VLPs Formed by *H. polymorpha*-expressed HCV Envelope Proteins

The VLP particle size was determined by Dynamic Light Scattering. For the light-scattering experiments, a particle-size analyzer (Model Zetasizer 1000 HS, Malvern Instruments Ltd., Malvern, Worcester UK) was used which was controlled by photon correlation spectroscopy (PCS) software. Photon correlation spectroscopy or dynamic light scattering (DLS) is an optical method that measures brownian motion and relates this to the size of particles. Light from a continuous, visible laser beam is directed through an ensemble of macromolecules or particles in suspension and moving under brownian motion. Some of the laser light is scattered by the particles and this scattered light is measured by a photomultiplier. Fluctuations in the intensity of scattered light are converted into electrical pulses which are fed into a correlator. This generates the autocorrelation function which is passed to a computer where the appropriate data analysis is performed. The laser used was a 10 mW monochromatic coherent He-Ne laser with a fixed wavelength of 633 nm. For each sample, three to six consecutive measurements were taken.

The results of these experiments are summarized in Table 5.

TABLE 5

Results of dynamic light scattering analysis on the indicated VLP-compositions of HCV envelope proteins expressed by *H. polymorpha*. The VLP particle sizes are given as mean diameter of the particles.

| Cys-thiol modification | E1-H6 | E2-VIEGR-H6 | E1 |
|---|---|---|---|
| sulphonation | 25–45 nm | 20 nm | 20–26 nm |
| alkylation (iodoacetamide) | 23–56 nm | 20–56 nm | 21–25 nm |

The observation that sulphonated HCV E1 derived from *H. polymorpha* still forms particles with a size in the same range as alkylated HCV E1 from *Hansenula* is surprising. Such an effect was not expected since the high (up to 8 Cys-thiol groups can be modified on HCV E1) net increase of negative charges as a consequence of sulphonation should induce an ionic repulsion between the subunits. The other reversible cysteine modifying agents tested also allowed particle formation, the HCV E1 produced in this way, however, proved to be less stable than the sulphonated material, resulting in disulfide-based aggregation of the HCV E1. In order to use these other reversible blockers, further optimization of the conditions is required.

Example 21

Antigenic Equivalence of *Hansenula*-Produced HCV E1-H6 and HCV E1 Produced by Vaccinia-Infected Mammalian Cells The reactivity of *Hansenula*-produced HCV E1-H6 with sera from HCV chronic carriers was compared to the reactivity of HCV E1 produced by HCV-recombinant vaccinia virus-infected mammalian cells as described by Depla et al. in WO 99/67285. Both HCV-E1 preparations tested consisted of VLP's wherein the HCV E1 proteins were alkylated with NEM and biotin-NEM. The reactivities of both HCV E1 VLP-preparations with sera from HCV chronic carriers was determined by ELISA. The results are summarized in Table 6. As can be derived from Table 6, no differences in reactivity were noted between HCV E1 expressed in HCV-recombinant vaccinia virus-infected mammalian cells and HCV E1 expressed in *H. polymorpha*.

TABLE 6

Antigenicity of E1 produced in a mammalian cell culture or produced in *H. polymorpha* were evaluated on a panel of sera from human HCV chronic carriers. For this purpose biotinylated E1 was bound to streptavidin coated ELISA plates. Thereafter human sera were added at a 1/20 dilution and bound immunoglobulins from the sera bound to E1 were detected with a rabbit-anti-human IgG-Fc specific secondary antibody labeled with peroxidase. Results are expressed as OD-values. The average values are the averages of the OD-values of all serum samples tested.

| Serum | Hansenula | mammalian | Serum | Hansenula | mammalian |
|---|---|---|---|---|---|
| 17766 | 1.218 | 1.159 | 55337 | 1.591 | 1.416 |
| 17767 | 1.513 | 1.363 | 55348 | 1.392 | 1.261 |
| 17777 | 0.806 | 0.626 | 55340 | 1.202 | 0.959 |
| 17784 | 1.592 | 1.527 | 55342 | 1.599 | 1.477 |
| 17785 | 1.508 | 1.439 | 55345 | 1.266 | 1.428 |
| 17794 | 1.724 | 1.597 | 55349 | 1.329 | 1.137 |
| 17798 | 1.132 | 0.989 | 55350 | 1.486 | 1.422 |
| 17801 | 1.636 | 1.504 | 55352 | 0.722 | 1.329 |
| 17805 | 1.053 | 0.944 | 55353 | 1.065 | 1.157 |
| 17810 | 1.134 | 0.999 | 55354 | 1.118 | 1.092 |
| 17819 | 1.404 | 1.24 | 55355 | 0.754 | 0.677 |
| 17820 | 1.308 | 1.4 | 55362 | 1.43 | 1.349 |
| 17826 | 1.163 | 1.009 | 55365 | 1.612 | 1.608 |
| 17827 | 1.668 | 1.652 | 55368 | 0.972 | 0.959 |
| 17849 | 1.595 | 1.317 | 55369 | 1.506 | 1.377 |
| 55333 | 1.217 | 1.168 | average | 1.313 | 1.245 |

Example 22

Immunogenic Equivalence of *Hansenula*-Produced HCV E1-H6 and HCV E1 Produced by Vaccina-Infected Mammalian Cells The immunogenecity of *Hansenula*-produced HCV E1-H6 was compared to the immunogenecity of HCV E1 produced by HCV-recombinant vaccinia virus-infected mammalian cells as described by Depla et al. in WO99/67285. Both HCV-E1 preparations tested consisted of VLP's wherein the HCV E1 proteins were alkylated with iodoacetamide. Both VLP preparations were formulated with alum and injected in Balb/c mice (3 intramuscular/subcutaneous injections with a three week interval between each and each consisting of 5 μg E1 in 125 μl containing 0.13% Alhydrogel, Superfos, Denmark). Mice were bled ten days after the third immunization.

Results of this experiment are shown in FIG. 51. For the top part of FIG. 51, antibodies raised following immunization with VLPs of E1 produced in mammalian cells were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein. For the bottom part of FIG. 51, antibodies raised following immunization with VLPs of *Hansenula*-produced E1 were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein.

The antibody titers determined were end point titers. The end point titer is determined as the dilution of serum resulting in an OD (as determined by ELISA) equal to two times the mean of the background of the assay.

FIG. 51 shows that no significant differences were observed between the immunogenic properties of both E1-compositions and that the determined antibody titers are independent of the antigen used in the ELISA to perform the end point titration.

The yeast-derived HCV E1 induced upon vaccination a protective response similar to the protective response obtained upon vaccination with alkylated HCV E1 derived from mammalian cell culture. The latter response was able to prevent chronic evolution of HCV after an acute infection.

Example 23

Antigenic and Immunogenic Profile of *Hansenula*-Produced HCV E1-H6 which is Sulphonated The reactivity of *Hansenula*-produced HCV E1-H6 with sera from HCV chronic carriers was compared to the reactivity of HCV E1 produced by HCV-recombinant vaccinia virus-infected mammalian cells as described by Depla et al. in WO99/67285. Both HCV-E1 preparations tested consisted of VLP's wherein the *Hansenula*-produced HCV E1 proteins were sulphonated and the HCV E1 produced by mammalian cells was alkylated. The results are given in Table 7. Although the overall (average) reactivity was identical, some major differences were noted for individual sera. This implies that the sulphonated material presents at least some of its epitopes in a way different from alkylated HCV E1.

The immunogenecity of *Hansenula*-produced HCV E1-H6 which was sulphonated was compared to the immunogenecity of *Hansenula*-produced HCV E1-H6 which was alkylated. Both HCV-E1 preparations tested consisted of VLP's. Both VLP preparations were formulated with alum and injected in Balb/c mice (3 intramuscular/subcutaneous injections with a three week interval between each and each consisting of 5 μg E1 in 125 μl containing 0.13% Alhydrogel, Superfos, Denmark). Mice were bled ten days after the third immunization.

Antibody titers were determined similarly as described in Example 22. Surprisingly, immunization with sulphonated material resulted in higher antibody titers, regardless of the antigen used in ELISA to assess these titers (FIG. 51; top panel: titration of antibodies raised against alkylated E1; bottom panel: titration of antibodies raised against sulphonated E1; "A": alkylated E1 coated on ELISA plate; "S": sulphonated E1 coated on ELISA plate). However, in this experiment individual titers are different dependent on the antigen used for analysis which confirms the observation noted with sera from HCV patients. Consequently, HCV E1 wherein the cysteine thiol-gorups are modified in a reversible way may be more immunogenic and thus have an increased potency as a vaccine protecting against HCV (chronic infection). In addition thereto, induction of a response to neo-epitopes induced by irrreversible blocking is less likely to occur.

Table 7. Antigenicity of alkylated E1 (produced in mammalian cell culture) or sulphonated E1-E6 (produced in *H. polymorpha*) was evaluated on a panel of sera from human HCV chronic carriers ("patient sera") and a panel of control sera ("blood donor sera"). To this purpose E1 was bound to ELISA plates, after which the plates were further saturated with casein. Human sera were added at a 1/20 dilution and bound immunoglobulins were detected with a rabbit-anti-human IgG-Fc specific secondary antibody labeled with perodidase. Results are expressed as OD-values. The average values are the averages of the OD-values of all serum samples tested.

| patient sera | | | blood donor sera | | |
|---|---|---|---|---|---|
| sernr | Hansenula | mammalian | sernr | Hansenula | mammalian |
| 17766 | 0.646 | 0.333 | F500 | 0.055 | 0.054 |
| 17777 | 0.46 | 0.447 | F504 | 0.05 | 0.05 |
| 17785 | 0.74 | 0.417 | F508 | 0.05 | 0.054 |
| 17794 | 1.446 | 1.487 | F510 | 0.05 | 0.058 |
| 17801 | 0.71 | 0.902 | F511 | 0.05 | 0.051 |
| 17819 | 0.312 | 0.539 | F512 | 0.051 | 0.057 |
| 17827 | 1.596 | 1.576 | F513 | 0.051 | 0.052 |
| 17849 | 0.586 | 0.964 | F527 | 0.057 | 0.054 |
| 55333 | 0.69 | 0.534 | average | 0.052 | 0.054 |
| 55338 | 0.461 | 0.233 | | | |
| 55340 | 0.106 | 0.084 | | | |
| 55345 | 1.474 | 1.258 | | | |
| 55352 | 1.008 | 0.668 | | | |
| 55355 | 0.453 | 0.444 | | | |
| 55362 | 0.362 | 0.717 | | | |
| 55369 | 0.24 | 0.452 | | | |
| average | 0.706 | 0.691 | | | |

Example 24

Identical Antigenic Reactivity of *Hansenula*-Produced HCV E1-H 6 and HCV E1Produced by Vaccinia-Infected Mammalian Cells with Sera from Vaccinated Chimpanzees The reactivities of the E1 produced by HCV-recombinant vaccinia virus-infected mammalian cells and the E1-H6 produced by *Hansenula* (both alkylated) with sera from vaccinated chimpanzees and with monoclonal antibodies were compared. Thereto, said E1 proteins were coated directly to ELISA plates followed by saturation of the plates with casein. The end point titers of antibodies binding the E1 proteins coated to the ELISA plates was determined for chimpanzee sera and for specific murine monoclonal antibodies, all obtained from animals immunized with E1 produced by mammalian cells. End point titer determination was done as described in Example 22. The murine monoclonal antibodies used were IGH201 (see Example 15), IGH198 (IGH198=23C12 in Maertens et al. in WO96/04385), IGH203 (IGH203=15G6 in Maertens et al. in WO96/04385) and IGH202 (IGH202=3F3 in Maertens et al. in WO99/50301).

As can be derived from FIG. 53, the reactivities of 7 different chimpanzee are identical when tested with E1 protein produced by either *Hansenula* or mammalian cells. The reactivities of the monoclonal antibodies against HCV E1 are also almost equal. Two of the chimpanzees (Yoran and Marti) were involved in a prophylactic vaccine study and were able to clear an acute infection upon challenge while a control animal did not clear the infection. The five other chimpanzees (Ton, Phil, Marcel, Peggy, Femma) were involved in therapeutic vaccination studies and showed a reduction in liver damage, as measured by ALT in serum and/or histological activity index on liver biopsy, upon the HCV E1 immunizations.

The results obtained in this experiment are clearly different from the findings of Mustilli and coworkers (Mustilli, A. C. et al. 1999) who expressed the HCV E2 protein both in *Saccharomyces cerevisiae* and *Kluyveromyces lactis*. The purified yeast-produced E2 was, however, different from the HCV E2 produced by mammalian (CHO) cells in that a lower reactivity was observed with sera from chimpanzees immunized with HCV E2 produced by mammalian cells while reactivity with monoclonal antibodies was higher for the yeast-produced HCV E2.

Example 25

Glycoprofiling of HCV E1 By Fluorophore-Assisted Carbohydrate Electrophoresis (FACE)

The glycosylation profiles were compared of *Hansenula*-produced HCV E1 and HCV E1 produced by HCV-recombinant vaccinia virus-infected mammalian cells as described by Depla et al. in WO99/67285. This was done by means of fluorophore-assisted carbohydrate electrophoresis (FACE). Thereto, oligosaccharides were released from E1s produced by mammalian cells or *Hansenula* by peptide-N-glycosidase (PNGase F) and labelled with ANTS (the E1 proteins were alkylated with iodoacetamide prior to PNGase F digestion). ANTS-labeled oligosaccharides were separated by PAGE on a 21% polyacrylamide gel at a current of 15 mA at 4° C. for 2–3 h. From FIG. 54, it was concluded that the oligosaccharides on E1 produced by mammalian cells and E1-H6 produced by *Hansenula* migrate like oligomaltose with a degree of polymerization between 7 and 11 monosaccharides. This indicates that the *Hansenula* expression system surprisingly leads to an E1 protein which is not hyperglycosylated and which has sugar chains with a length similar to the sugar chains added to E1 proteins produced in mammalian cells.

Example 26

Expression of HCV Envelope Proteins in Yeast

In order to produce HCV envelope proteins with a sugar moiety comparable in size with the sugar moiety of HCV envelope proteins expressed in mammalian cell expression systems, several yeast strains were scrutinized.

1.1 Construction of an Expression Vector for HCV E1 in *S. cerevisiae:*

Figure 20:
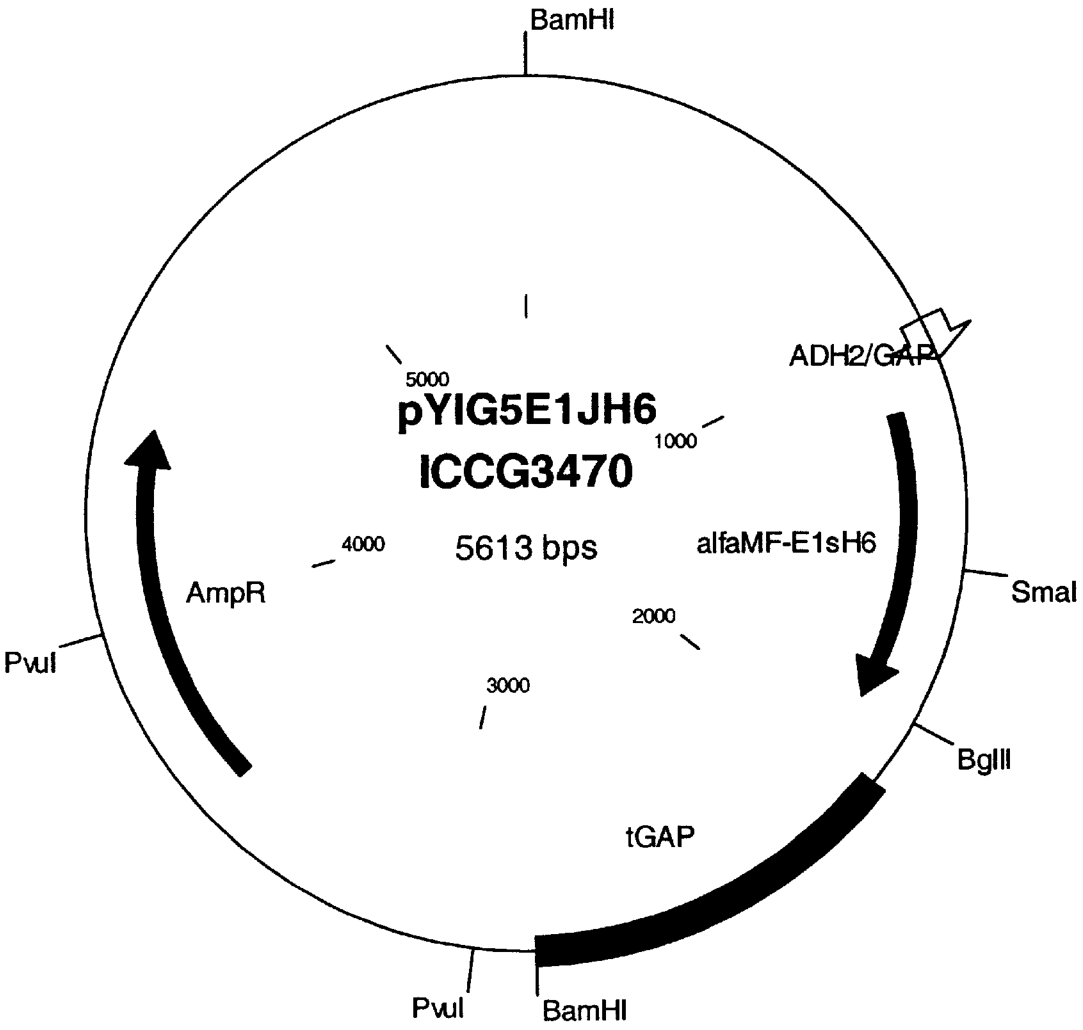
FIG. 20. Schematic map of the vector pYIG5E1H6 which has the sequence as defined in SEQ ID NO:42.

For the construction of an expression vector for HCV E1 in *S. cerevisiae*, a DNA fragment coding for the HCV E1s (aa 192–326; SEQ ID NO 2) ORF was exactly fused to the *S. cerevisiae* α-mating factor preprosequence in vector ICCG No.3470 (FIG. 20). In this vector, the expression of HCV E1, which is fused at its C-terminus to a hexahistidine tag, is under control of the *S. cerevisiae* hybrid ADH/GAPDH promotor (FIG. 20). From this vector, the promotor/gene/terminator-expression cassette was transferred as a BamHI cassette to the BamHII opened *E.coli/S. cerevisiae* shuttlevector pSY1, resulting in vector ICCG No. 3479 (FIG. 22). This shuttlevector was then transformed to the *S. cerevisiae* strain IYCC No. 155 which is a glycosylation deficient strain.

1.2 Construction of an Expression Vector for HCV E2 in *S. cerevisiae:*

Figure 24:
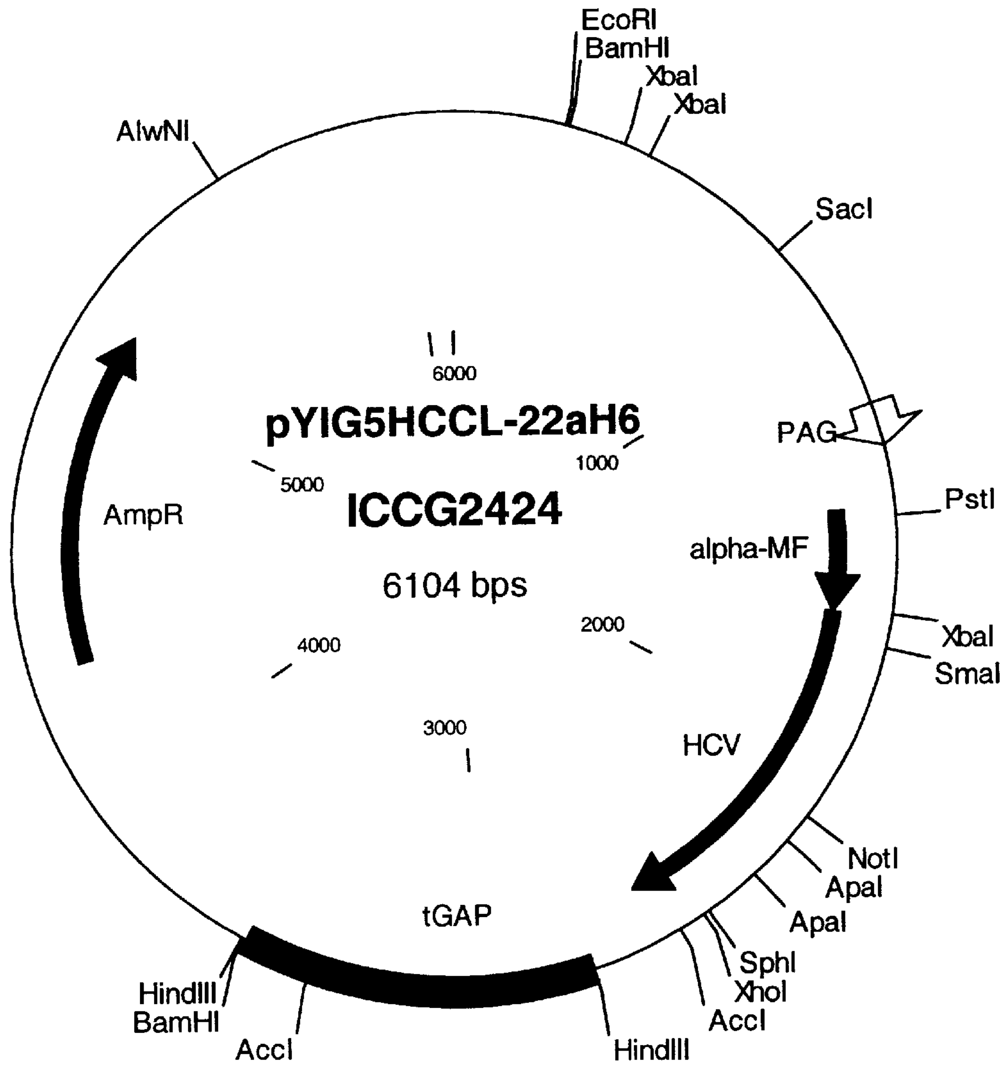
FIG. 24. Schematic map of the vector pYIG5HCCL-22aH6 which has the sequence as defined in SEQ ID NO:46.
Figure 25:
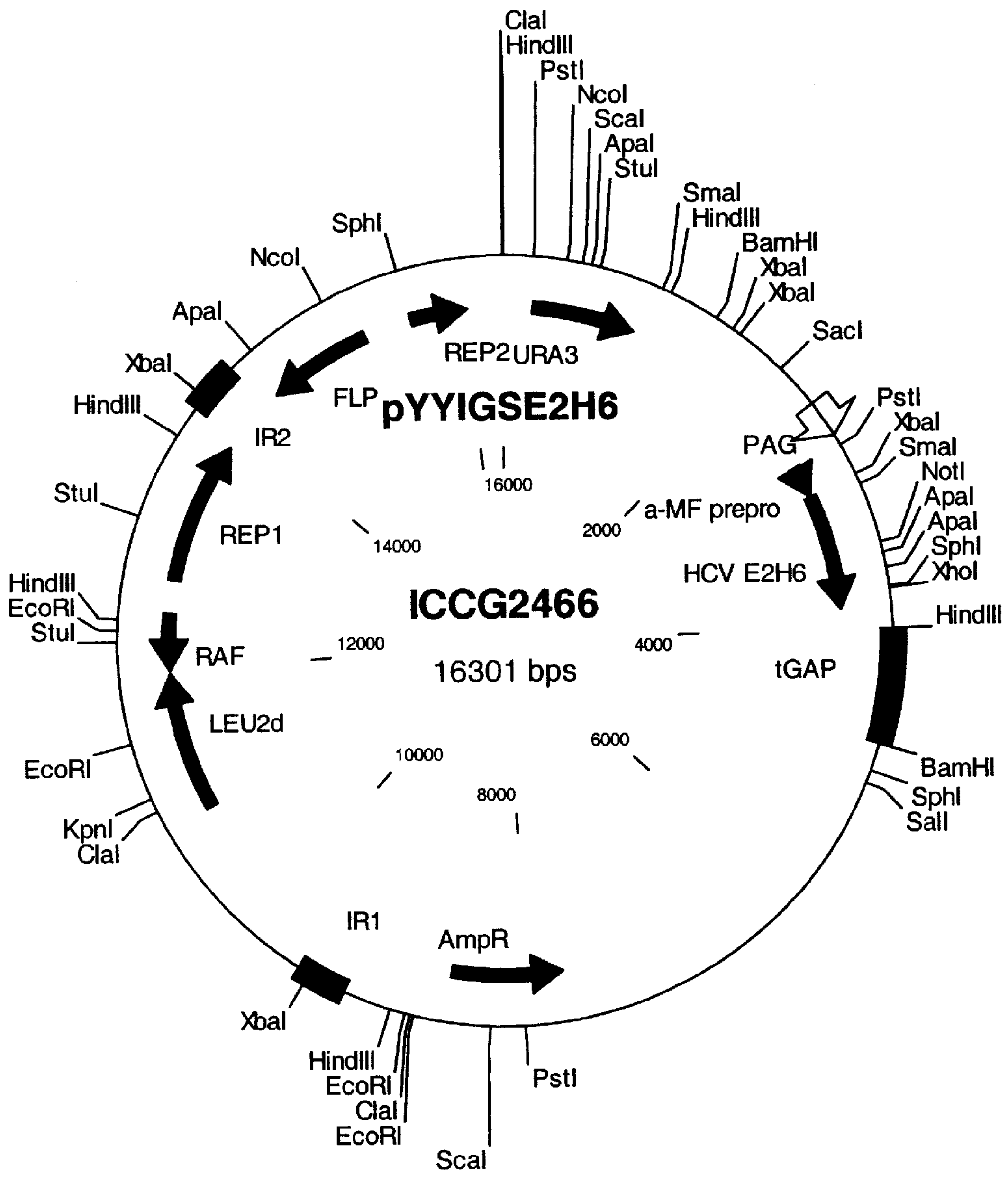
FIG. 25. Schematic map of the vector pYYIGSE2H6 which has the sequence as defined in SEQ ID NO:47.

For the construction of an expression vector for HCV E2 in *S. cerevisiae*, a DNA fragment coding for the HCV E2s (aa384–673; SEQ ID NO 3) ORF was exactly fused to the *S. cerevisiae* α-mating factor preprosequence in vector ICCG No.2424 (FIG. 24). In this vector, the expression of HCV E2, which is fused at its C-terminus to a hexahistidine tag, is under control of the *S. cerevisiae* hybrid ADH/GAPDH promotor. From this vector, the promotor/gene/terminator-expression cassette was transferred as a BamHI cassette to the BamHI opened *E. coli/S. cerevisiae* shuttlevector pSY1, resulting in vector ICCG No. 2466 (FIG. 25). This shuttle vector was then transformed to the *S. cerevisiae* strain IYCC No. 155 which is a glycosylation deficient strain.

1.3 Construction of an Expression Vector for HCV E1 in *H. polymorpha:*

For the construction of an expression vector for HCV E1 in *H. polymorpha*, a DNA coding for HCV E1s (aa 192–326) ORF was exactly fused to the *S. cerevisiae* α-mating factor preprosequence in vector pFPMT-E1-11 (see Gellissen et al., 1992 for description of parent vector; see FIG. 5 for pFPMT-E1-E11). This vector was subsequently transformed into *H. polymorpha* strain RB11 and was, after selection for genomic integration and expression analysis, stored under IYCC No. 205.

1.4 Construction of an Expression Vector for HCV E2 in *H. polymorpha:*

For the construction of an expression vector for HCV E2 in *H. polymorpha*, a DNA coding for HCV E2s (aa384–673) ORF was exactly fused to the *S. cerevisiae* α-mating factor preprosequence in vector pFPMT-E2 (see Gellissen et al., 1992 for description of parent vector). This vector was subsequently transformed into *H. polymorpha* strain RB11 and was, after selection for genomic integration and expression analysis, stored under IYCC No. 168.

1.5 Construction of an Expression Vector for HCV E1 in *P. pastoris:*

For the construction of an expression vector for HCV E1 in *P. pastoris*, a DNA coding for the HCV E1s (aa 192–326) ORF was exactly fused behind the KEX2 or STE13 protease recognition sites in vectors pPICZαD and pPICZαE respectively. These two vectors are modified versions of the pPICZoαA vector (Invitrogen Corp., Carlsbad, Calif., USA), whereby the parent vector was modified in such a way that direct fusion after the KEX2 and STE13 sites became possible. The resulting strains ware named ICCG No. 3694 (FIG. 32) and ICCG No. 3475 (FIG. 33), respectively. Transformation to *P. pastoris* strains, screening for genomic integration and expression analysis was performed according to the manufacturer's instructions.

1.6 Construction of an Expression Vector for HCV E2 in *P. pastoris:*

For the construction of an expression vector for HCV E2 in *P. pastoris*, a DNA coding for the HCV E2s (aa384–673) ORF was exactly fused behind the KEX2 or STE13 protease recognition sites in vectors pPICZαD and pPICZαE respectively. These two vectors are modified versions of the pPICZαA vector (Invitrogen Corp., Carlsbad, Calif., USA), whereby the parent vector was modified in such a way that direct fusion after the KEX2 and STE13 sites became possible. The resulting strains ware named ICCG No. 3692 (FIG. 34) and ICCG No. 3476 (FIG. 35) respectively. Transformation to *P. pastoris* strains, screening for genomic integration and expression analysis was performed according to the manufacturer's instructions.

1.7 Cell Culture Conditions for *Saccharomyces cerevisiae*

Seed cultures of the recombinant *Saccharomyces cerevisiae* strains were grown in YNB (Difco) supplemented with 2% sucrose as carbon source. These seed cultures were started from a cryo-preserved working cell bank vial and grown in 500 ml medium in a 2 l Erlenmeyer shake flasks at 37° C., 200 rpm for 48 h. Fermentations were performed in Biostat C fermentors (B. Braun Int., Melsungen, Germany). The medium contained 1% Yeast Extract, 2% Peptone and 2% sucrose as carbon source; Poly-ethylene glycol was used as anti-foam agent. Temperature was controlled at 37° C., pH at 4.5 and aeration was kept constant at 1.0 vvm. Dissolved oxygen concentration was maintained above 30% air saturation by changing the agitator speed during the growth phase. Throughout the fermentation an overpressure of 0.4 bar was maintained in the vessel. The expression phase was performed under oxygen limiting conditions by implying a fixed agitator rate of is 300 rpm. The fermentation was started by the addition of 10% seed-culture. Upon complete metabolisation of the carbon source supplementary ethanol was added stepwise in order to maintain a concentration of approximately 0.5%. Fermentations were stopped and cells collected when the metabolic activity was strongly reduced, correlated with a steep increase in dissolved oxygen concentration. Cell pellets were stored at −70° C.

1.8 Cell Culture Conditions for *Hansenula polymorpha*

Recombinant *Hansenula polymorpha* seed cultures were grown in rich YPD medium (Difco). These seed cultures were started from a cryo-preserved working cell bank vial and grown in 500 ml medium in a 2 l Erlenmeyer shake flasks at 37° C., 200 rpm for 48 h. Fermentations were performed in Biostat C fermentors (B. Braun Int., Melsungen, Germany). The medium contained 1% Yeast Extract, 2% Peptone and 1% glycerol as carbon source; Polyethylene glycol was used as anti-foam agent. Temperature was controlled at 37° C., pH at 4.8 and aeration was kept constant at 1.5 vvm. Dissolved oxygen concentration was maintained above 30% air saturation by changing the agitator speed throughout the fermentation. The fermentation was started by the addition of 10% seed-culture. During the growth phase the glycerol concentration was monitored off-line and 24 h after complete glycerol consumption 1% methanol was added in order to induce the heterologous protein expression. Cells were collected after 24 h of induction by tangential flow filtration followed by a centrifugation step. Cell pellets were stored at −70° C.

Results:

The expression of proteins in glycosylation mutants of *Saccharomyces cerivisiae* is hampered by the suboptimal growth characteristics of such strains which leads to a lower biomass yield and thus a lower yield of the desired proteins compared to wildtype *Saccharomyces cerivisiae* strains. The yield of the desired proteins was still substantially higher than in mammalian cells. As an alternative for such strains, HCV envelope proteins were expressed in *Pichia pastoris*, a yeast strain well known for the fact that hyperglycosylation is normally absent (Gelissen 2000) and previously used to express dengue virus E protein as GST fusion (Sugrue et al., 1997; 69). Remarkably, this resulted in HCV envelope proteins comparable to what is observed in wild type *Saccharomyces* strains, i.e. carrying hyperglycosylation, and this based on the molecular weight of the expression products detected in western-blots of cell lysates. Surprisingly, *Hansenula polymorpha*, a yeast strain closely related to Pichia pastoris (Gelissen 2000), is able to express HCV proteins essentially without hyperglycosylation and thus with a sugar moiety comparable in size to what mammalian cells express.

In conclusion, of three natural existing yeast strains only *Hansenula polymorpha* was found to be able to produce an HCV envelope protein which is not hyperglycosylated.

Example 27

Biochemical Properties of HCV E1 and E2 Proteins Expressed in Selected Yeast Strains Under the α-Mating Factor Leader Sequence The expression products of HCV E1 and E2 protein constructs with the α-mating factor leader sequence of *Saccharomyces cerevisiae* in *Hansenula polymorpha* or *Saccharomyces cerevisiae* glycosylation minus strain were further analyzed. Since both HCV E1s (aa 192–326) and HCV E2s (aa 383–673) were expressed as C-terminal $(his)_6$-tagged proteins a rapid and efficient purification of the expressed and GuHCl-solubilized products was performed on Ni-IDA. In brief, cell pellets were resuspended in 50 mM phosphate, 6M Gu.HCl, pH 7.4 (9 vol/g cells). Proteins were sulfonated overnight at room temperature (RT) in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.) and Empigen (Albright &Wilson, UK) and imidazole were added to the supernatant to a final concentration of 1% (w/v) and 20 mM respectively. The sample was filtrated and loaded on a Ni-IDA Sepharose FF column, which was equilibrated with 50 mM phosphate, 6M Gu.HCl, 1% Empigen (buffer A) supplemented with 20 mM Imidazole. The column was washed sequentially with buffer A containing 20 mM and 50 mM Imidazole respectively till absorbance at 280 nm reached baseline level. The his-tagged products were eluted by applying buffer A, 200 mM Imidazole or 50 mM phosphate, 6M Gu.HCl, 0.2% (for E1) or 1% (for E2) Empigen, 200 mM Imidazole. The purified materials were analyzed by SDS-PAGE and western-blot using a specific monoclonal antibodies directed against E1 (IGH201, deposited under accession nr 98031216 at ECACC), or E2 (IGH 212). The E1-products were immediately analyzed by Edman degradation.

Since at this stage, SDS-PAGE revealed already a very complex picture of protein bands for HCV E2, a further fractionation by size exclusion chromatography was performed. The Ni-IDA eluate was concentrated by ultrafiltration (MWCO 10 kDa, centriplus, Amicon, Millipore) and loaded on Superdex G200 (10/30 or 16/60; Pharmacia) in PBS, 1% Empigen or PBS, 3% Empigen. Elution fractions, containing E2s related products, with a Mr between ~80 kDa and ~45 kDa based on the migration on SDS-PAGE, were pooled (fractions 17–23, FIGS. 37 and 38) and alkylated (incubation with 10 mM DTT 3 h at RT followed by incubation with 30 mM iodo-acetamide for 3 hours at RT). Samples for amino-terminal sequencing were treated with Endo H (Roche Biochemicals) or left untreated. The glycosylated and deglycosylated E2s products were blotted on PVDF-membranes for amino-terminal sequencing (FIG. 39).

The sequencing of both E1 end E2 purified products leads to the disappointing observation that the HCV envelope proteins are only partially correctly processed (processing includes correct cleavage of the signal sequence) (see Table 3). In addition, the majority of the side products (degradation products and products still containing the leader sequence or part thereof) are glycosylated. This glycosylation resides even in part on the non-cleaved fragment of the signal sequence which contains also an N-glycosylation site. These sites can be mutated in order to result in less glycosylated side products. However, even more problematic is the finding that some alternatively cleaved products have only 1 to 4 amino acids difference compared to the desired intact envelope protein. Consequently, purification of the correctly processed product is virtually impossible due to the lack of sufficiently discriminating biochemical characteristics between the different expression products. Several of the degradation products may be a result of a Kex-2 like cleavage (e.g. the cleavage observed after aa 196 of E1 which is a cleavage after an arginine), which is also required for the cleavage of the α-mating factor leader and which can thus not be blocked without disturbing this essential process.

Example 28

Expression of an E1 Construct in Yeast Suitable for Large Scale Production and Purification Several other leader sequences were used to replace the α-mating factor leader: CHH (leader sequence of Carcinus maenas hyperglycemic hormone), Amyl (leader sequence of amylase from *Saccharomyces occidentalis*), Gam1 (leader sequence of glucoamylase from *Saccharomyces occidentalis*), Phy 5 (leader sequence from fungal phytase), phol (leader sequence from acid phosphatase from *Pichia pastoris*) and CL (lysozyme C, 1,4-beta-N-acetylmuramidase C) and linked to E1s with C-terminal $(his)_6$ tag. All constructs were expressed in *Hansenula polymorpha* and for each of these constructs the western-blot of the cell lysate allowed already to conclude that the degree of processing was extremely low with the exception of the CL construct. For the CHH-E1s-$(his)_6$ construct this was confirmed by Edman-degradation on Ni-IDA purified material. By this method no correctly cleaved product could be detected although several different sequences were recovered (Table 4).

As mentioned already, the western-blots of the cell lysates revealed a pattern of E1 specific protein bands, indicative for a higher degree of correct processing, for the CL construct. This is surprising since this leader is not derived from yeast. Edman degradation on GuHCl solubilized and Ni-IDA purified material indeed confirmed that 84% of the E1 proteins is correctly cleaved and this material is essentially free of degradation products. Still 16% of non-processed material is present but since this material is non-glycosylated it can be easily removed from the mixture allowing specific enrichment of correctly cleaved and glycosylated E1. Such a method for enrichment may be an affinity chromatography on lectins, other alternatives are also given in example 19. Alternatively the higher hydrophobic character of the non-glycosylated material may be used to select and optimize other enrichment procedures. The correct processing (i.e. start of the mature E1 at position 192) of the E1 as produced by the CL derived construct was further confirmed by mass spectrometry which also confirmed that up to 4 out of 5 N-glycosylation sites can be occupied.

Glycoprofiling by means of Fluorophore-assisted carbohydrate electrophoresis allows to conclude that the oligosaccharides of mammalian derived E1 and *Hansenula* derived E1 expressed using the lysozyme leader migrate like oligomaltose with a degree of polymerization between 7 and 11 monosaccharides (FIG. 54). This further confirms the *Hansenula* expression system leads surprisingly to an E1 which is not hyperglycosylated and which has sugar chains with a length similar to mammalian derived E1.

Example 29

Antigenic Equivalence of *Hansenula* Derived HCV E1

The HCV E1 produced in *Hansenula polymorpha* with the CL leader was purified on Ni-IDA and finally eluted in 0.2% (w/v) Empigen BB as described in Example 27. The Empigen was exchanged for 3% betain on size exclusion chromatography. Finally, the HCV E1 was desalted to PBS with 0.5% betain. In brief, the 200 mM imidazole peak was concentrated by ultrafiltration (10 kD MWCO, Centriplus, Amicon, Millipore) and the his-tagged E1s was desulfonated by treatment with 5 mM DTT and the thiol groups were alkylated after 30 min with iodoacetamide (20 mM). The alkylated product was loaded on Superdex G200 (Pharmacia), which was equilibrated with PBS, 1% Empigen. Elution fractions were analyzed by SDS-PAGE and Western blotting. The fractions with a relative Mr ~29-~18 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

Biotinylated his-tagged E1s was obtained by alkylation with 5mM N-ethylmaleimide (NEM)/15 mM NEM.bio after reduction with DTT. The gelfiltration chromatographies (SEC) in the presence Empigen, the VLP formation step and desalting step were performed as described for acetamidated E1s, except that the 3% and 0.5% betain in the buffer was replaced by 0.2 (w/v) and 0.05% (w/v) CHAPS respectively.

Similar to HCV E1 derived from mammalian cell culture, the yeast derived protein forms particles with a size between 25 and 45 nm as determined by Dynamic Light Scattering. For the light-scattering experiments, a particle-size analyzer (Model Zetasizer 1000 HS, Malvern Instruments Ltd., Malvern, Worcester UK) was used which was controlled by photon correlation spectroscopy (PCS) software. Photon correlation spectroscopy or dynamic light scattering (DLS) is an optical method that measures brownian motion and relates this to the size of particles. Light from a continuous, visible laser beam is directed through an ensemble of macromolecules or particles in suspension and moving under brownian motion. Some of the laser light is scattered by the particles and this scattered light is measured by a photomultiplier. Fluctuations in the intensity of scattered light are converted into electrical pulses which are fed into a correlator. This generates the autocorrelation function which is passed to a computer where the appropriate data analysis is performed. The laser used was a 10 mW monochromatic coherent He-Ne laser with a fixed wavelength of 633 nm. For each sample, six consecutive measurements were taken.

The reactivity of this HCV E1 with sera from HCV chronic carriers was determined in ELISA and compared to the reactivity with HCV E1 from mammalian cell culture which was prepared as described in WO 99/67285. As can be judged from Table 6 no differences were noted between HCV E1 expressed in mammalian cells and HCV E1 expressed in *Hansenula polymorpha.*

Example 30

Immunogenic Equivalence of *Hansenula* Derived HCV E1

HCV E1 from *Hansenula* expressed with the CL leader and alkylated with iodo-acetamide or HCV E1 derived from mammalian cell culture similarly alkylated as described in PCT/EP99/04342 was formulated with alum and injected in Balb/c mice (3 intramuscular/subcutaneous injections with a three week interval and consisting of 5 μg E1 in 125 μl containing 0.13% Alhydrogel, Superfos, Denmark). Mice were bled ten days after the third immunization. The end point titers of the induced antibodies were determined for each series of mice both on mammalian and *Hansenula* derived E1. FIG. 51 shows that no differences were observed and that the obtained titers are also independent of the antigen used in ELISA to perform titration.

Similar to the alkylated HCV E1 derived from mammalian cell culture, which was able to prevent chronic evolution of HCV after an acute infection, the yeast derived HCV E1 induced a similar protective response upon vaccination.

Example 31

Production of Reversible Cysteine Blocked HCV E1: Antigenic and Immunogenic Profile In Example 30, the immunogenicity of alkylated HCV E1 from yeast and mammalian cell culture was compared. Alkylation is, however, an irreversible modification. Therefore, we also tried reversible modifications of the cysteines by dithiodipyridine (DTDP), dithiocarbamate (DTC), cysteine and sulfonation. *H. polymorpha* cell pellets homogenization, cell lysis, protein sulfonation and chromatography on IDA-Sepharose were performed for his-tagged HCV E1s as described in Example 27. The sulfonated product was loaded without any reduction treatment on SEC in the presence of 1% Empigen, and VLP formation was forced by SEC in 3% (w/v) betain. The eluate was concentrated and desalted to 0.5% betain. Alternatively, sulfonated HCV E1s was treated with 5 mM DTT in PBS and DTDP, DTC or cysteine were added after 30 min at RT till a final concentration of 20 mM. The SEC in 1% Empigen, the VLP formation step on SEC in 3% betain and the desalting step were performed as described for the acetamide modified his-tagged HCV E1s in Example 4.

The HCV E1s.his containing fractions were stored at −70° C. after addition of the respective reversible blocking agent (2 mM final concentration) in order to prevent disulfide exchanges and aggregation.

To our surprise we observed that sulfonated HCV E1 derived from *Hansenula polymorpha* still can form particles with a size in the same range as alkylated HCV E1 from Hansenula. This was not expected since the high (up to 8 sulfon groups can be induced on HCV E1 which contains 8 cysteines) net increase of negative charges as a consequence of sulfonation should induce an ionic repulsion between the subunits. Also the other reversible cysteine modifying agents tested still allowed particle formation, however the HCV E1 produced in this way proved to be less stable, compared to the sulfonated material. This finally resulted in disulfide based aggregation of the HCV E1. In order to use these other reversible blockers, further optimization of the conditions is required. Such optimizations may include the addition of anti-oxidants and/or storing the material at a pH different than 7 to 8, which is in the art. The sulfonated material was used already for evaluation.

Example 32

Antigenic and Immunogenic Profile of Sulfonated HCV E1

In Table 7, the reactivity with human sera of sulfonated HCV E1s(his)$_6$ derived from *Hansenula* (CL leader, extracted with GuHCl, purified with Ni-IDA and finally formulated in 0.5% betain as a particle) was compared with alkylated HCV E1s derived from mammalian cell culture. Although the overall (average) reactivity was identical, some major difference were noted for individual sera. This implies that the sulfonated material presents at least some of its epitopes in a different way compared to alkylated HCV E1. Alkylated or sulfonated HCV E1 from *Hansenula* (CL leader, extracted with GuHCl, purified with Ni-IDA and finally formulated in 0.5% betain as a particle) was formulated with alum and injected in 6 Balb/c mice (3 intramuscular/subcutaneous injections with a three week interval and consisting of 5 μg E1 in 125 μl containing 0.13% Alhydrogel, Superfos, Denmark). Mice were bled 10 days after the third immunization. To our surprise, we found that immunization with sulfonated material resulted in higher antibody titers, regardless of the antigen used in ELISA to assess these titers (FIG. 52). However, also in this experiment individual titers are different dependent on the antigen used for analysis which confirms the observation noted with sera from HCV patients. Consequently, HCV E1 with cysteines which are modified in a reversible way may be more immunogenic and thus have an increased potency as a vaccine protecting against HCV (chronic infection). In addition the induction of a response to neo-epitopes induced by irrreversible blocking is less likely to occur.

Example 33

Specific Removal of Non-processed HCV E1 by Heparin

In order to find specific purification steps for HCV envelope proteins from yeast cells binding with heparin was evaluated. Heparin is known to bind to several viruses and consequently binding to the HCV envelope has already been suggested (Garson et al., 1999). In order to analyze this potential binding, heparin was biotinylated and interaction with HCV E1 analyzed in microtiterplates coated with either sulfonated HCV E1 from *Hansenula*, alkylated HCV E1 from *Hansenula* and alkylated HCV E1 from mammalian cell culture. Surprisingly, a strong binding could only be observed with sulfonated HCV E1 from Hansenula, while binding with HCV E1 from mammalian cell culture was completely absent. By means of western-blot we could show that this binding was specific for the lowest molecular weight bands of the HCV E1 protein mixture (FIG. 45). This is in case of HCV E1 produced in yeast using the CL leader essentially identical to non-glycosylated mature HCV E1s and non-glycosylated HCV E1s still containing the CL leader. FIG. 45 also reveals that sulfonation is not essential for heparin binding since upon removal of this sulfonation binding is still observed for the low molecular weight E1 (lane 4). Alternatively, alkylation is reducing this binding substantially, however, this may be caused by the specific alkylation agent (iodo-acetamide) used in this example. This finding further demonstrated the industrial applicability of the CL-HCV-envelope expression cassettes for yeast since we specifically can enrich HCV E1 preparations for correctly processed and at least partially glycosylated material.

Example 34

Identical Reactivity of Vaccinees with Mammalian or Yeast Derived HCV E1

Mustilli and coworkers described in 1999 the expression of HCV E2 in *Saccharomyces cerevisiae* and *Kluyveromyces lactis*. The purified product was however, clearly different from the HCV E2 derived from mammalian cells (CHO), since a lower reactivity was observed with sera from chimpanzees immunized with mammalian derived HCV E2 while reactivity with monoclonal antibodies was higher for the yeast derived HCV E2.

Such a difference in reactivity was not noted between the HCV E1 produced by mammalian cells or by yeast by the methods described here as shown in FIG. 53. The reactivity of 7 different chimpanzee sera obtained after immunization with mammalian derived HCV E1 is identical for when tested with *Hansenula* or mammalian derived HCV E1 while the monoclonal antibody against HCV E1 shows also an almost equal reactivity. Two of the chimpanzees (Yoran and Marti) were involved in a prophylactic vaccine study and were able to clear an acute infection upon challenge while a control animal did not clear the infection. The other five chimpanzees (Ton, Phil, Marcel, Peggy, Femma) were involved in therapeutic vaccination studies and showed a reduction in liver damage, as measured by ALT in serum and/or histological activity index on liver biopsy, upon the HCV E1 immunizations.

LIST OF REFERENCES

Ballou L, Hitzeman R A, Lewis M S and Ballou C E. Vanadate-resistant yeast mutants are defective in protein glycosylation. PNAS 1991; 88; 3209–3212.

Beekman, N., Schaaper, W., Tesser, G., Dalsgaard, K., Kamstrup, S., Langeveld, J., Boshuizen, R. & Meloen, R., Synthetic peptide vaccines: palmitoylation of peptide antigens by a thioester bond increases immunogenicity. J. Peptide Res., 50, 357–364,1997.

Burns, J., Butler, J. & Whitesides, G., Selective reduction of disulfides by tris(2-carboxyethyl)phosphine. J. Org. Chem. 56, 2648–2650 (1991).

Darbre, A., Practical protein Chemistry: A handbook. A Whiley-interscience publication. Ed. J. Whiley & Sons Ltd., 1986.

Doms et al. (1993) Virology 193: 545–562.

Elble, R. (1992) A simple and efficient procedure for transformation of yeasts. Biotechniques 13:18–20.

Gailit, J. Restoring free sulfydryl groups in synthetic peptides. Anal. Biochem., 214,334–335 (1993).

Garson J A, Lubach D, Passas J, Whitby K, Grant P R. Suramin blocks hepatitis C binding to human hepatoma cells in vitro. J. Med. Virol. 1999; 57; 238–42.

Gellissen G, Weydemann U, Strasse A, Piontek M, Janowicz Z & Hollenberg C. Progress in developing methylotrophic yeasts as expression systems. TIBTECH 1992; 10; 413–417.

Gelissen G Heterologous production in methylotrophic yeasts. Appl Microbiol Biotechnol 2000; 54; 714–750.

Grakoui et al. (1993) Journal of Virology 67:1385–1395.

Heile J M, Fong Y L, Rosa D, Berger K, Saletti G, Campagnoli S, Bensi G, Capo S, Coates S, Crawford K, Dong C, Wininger M, Baker G, Cousens L, Chien D, Ng P, Archangel P, Grandi G, Houghton M, Abrignani S. Evaluation of hepatitis C virus glycoprotein E2 for vaccine design: an endoplasmic reticulum-retained recombinant protein is superior to secreted recombinant protein and DNA-based vaccine candidates. J. Virol. 2000; 74; 6885–6892.

Helenius (1994) Mol. Biol. Cell. 5: 253–265.

Hermanson, G. T. in Bioconjugate Techniques (1996) Part I section 1.43 and section 2.2.1, Academic Press San Diego Calif., USA.

Herscovics A and Orlean(1993) P Glycoprotein biosynthesis in yeast. FASEB 7; 540–550.

Hijikata, M., Kato, N., Ootsuyama, Y., Nakagawa, M. & Shimotohno, K. (1991) Proc. Natl. Acad. Sci. U.S.A. 88(13): 5547–51.

Holmgren, A., Thioredoxin catalyzes the reduction of insulin disulfides bydithiothreitol and dihydrolipoamide. J. Biol. Chem., 254, 9627–9632 (1979).

Houghton M. Immunity to HCV: The case for vaccine development. 4th International meeting on hepatitis C Virus and related viruses. Sattelite Symposium: New appraoch to prevention and therapy of HCV infection. Mar. 7 1997, Kyoto, Japan.

Jayasbaskaran, J., Davison, P. & Paulus, H., Facile preparation and some applications of an affinity matrix with a cleavable connector arm containing a disulfide bond. Prep. Biochem., 17,121–141 (1987).

Kalef, E, Walfish, P. & Gitler C., Arsenical based affinity chromatography of vicinal dithiol-containing proteins: Purification of L1210 Leukemia cytoplasmatic proteins and the recombinant rat c-erb $Au_1$ $T_3$ receptor. Anal. Biochem., 212, 325–334(1993).

Kato, N., Oostuyama, Y., Tanaka, T., Nakagawa, M., Muraiso, K., Ohkoshi, S., Hijikata, M., Shimitohno, K. (1992) Virus Res. 22:107–123.

Klebe, R. J., Harriss, J. V., Sharp, Z. D., and Douglas, M. G. (1983) A general method for polyethylene-glycol-induced genetic transformation of bacteria and yeast. Gene 25:333–341.

Kumar, N, Kella, D & Kinsella, J., Anomalous effect of denaturants on sulfitolysis of protein disulfide bonds. Int. J. Peptide Protein Res., 28, 586–592, (1986).

Kumar, N, Kella, D. & Kinsella, J., A method for the controlled cleavage of disulfide bonds in proteins in the absence of denaturants. J. Biochem. Biophys. Meth., 11, 253–261,1985.

Maertens G. and Stuyver L. Genotypes and genetic variation of hepatitis C virus. In: The molecular medicine of viral hepatitis. Ed: Harrison T. J. and Zuckerman A. J. 1997.

Major M. E. and Feinstone S. M. The molecular virology of hepatitis C. Hepatology 1997: 25:1527–1538.

Mustilli A C, Izzo E, Houghton M, Galeotti C L. Comparison of secretion of a hepatitis C virus glycoprotein in *Saccharomyces cerevisiae* and *Kluyveromyces lactis*. Res. Microbiol. 1999; 150; 179–187.

Padgett, K. A. and Sorge, J. A. (1996) Creating seamless junctions independent of restriction sites in PCR cloning. Gene 168:31–35.

Pomroy, N & Deber, C., Solubilisation of hydrophobic peptides by reversible cysteine PEGylation. Biochem. & Biophys. Res. Commun., 245, 618–621 (1998).

Roggenkamp, R., Hansen, H., Eckart, M., Janowicz, Z., and Hollenberg, C. P. (1986) Transformation of the methylotrophic yeast *Hansenula polymorpha* by autonomous replication and integration vectors. Mol Gen Genet 202:302–308.

Rose et al. (1988) Annu. Rev. Biol. 4: 257–288.

Singh, R. & Kats, L., Catalysis of reduction of disulfide by selenol. Anal. Biochem., 232,86–91 (1995).

Sugrue R J, Cui T, Xu Q, Fu J, Chan Y C The production of recombinant dengeu virus E protein using *Escherichia coli* and *Pichia pastoris*. J. Virol. Meth. 1997; 69; 159–169.

Thakur, M., Defulvio, J., Richard, M & Park, C., Technetium-99m labelled monoclonal antibodies: evaluation of reducing agents. Nuc. Med. Biol., 18, 227–2333(1991)

Rein, A., Ott, D., Mirro, J., Arthur, L, Rice, W. & Henderson, L., Inactivation of Murine leukemia virus by compounds that react with the Zn-finger in viral nucleocapsid protein. J. Virol., 70, 4966–4972, 1996.

Rosa D, Campagnoli S, Moretto C, Guenzi E, Cousens L, Chin M, Dong C, Weiner A J, Lau J Y N, Choo Q L, Chien D, Pileri P, Houghton M, Abrignani S. A quantitative test to estimate neutralizing antibodies to the hepatitis C virus: cytofluorimetric assessment of envelope glycoprotein 2 binding to target cells. PNAS 1996; 93; 1759–1763.

Sambrook, J., Fritsch, E. F. and Maniatis, T. (1989) Molecular Cloning, a laboratory manual, second edition. Cold Spring Harbor University Press, Cold Spring Harbor, N.Y. USA.

Stuyver, L., Van Arnhem, W., Wyseur, A., Hernandez, F., Delaporte, E., Maertens, G. (1994), Proc. Natl. Acad. Sci. USA 91:10134–10138.

Vingerhoeds, M., Haisma, H., Belliot, S., Smit, R., Crommelin, D. & Storm, G, Immunoliposomes as enzyme-carriers (immunoenzyzomes) for antibody-directed enzyme prodrug therapy (ADEPT): optimization of prodrug activating capacity. Pharm. Res., 13,603–610 (1996).

Zauberman, A., Nussbaum, O., Ilan, E., Eren, R., Ben-Moshe, O., Arazi, Y., Berre, S., Lubin, I., Shouval, D., Galun, E., Reisner, Y. and Dagan, S. The trimera mouse system: a mouse model for hepatitis C infection and evaluation of therapeutic agents. Jun. 6–9, 1999; Oral 4.3. In: 6th International Symposium on Hepatitis C & Related Viruses. Bethesda USA

The invention claimed is:

1. A HCV virus-like particle formed of an HCV envelope protein or a part thereof wherein the cysteines are chemically modified and wherein said modification is reversible.

2. The HCV virus-like particle according to claim 1 wherein said chemical modification is sulphonation.

3. The HCV virus-like particle according to claim 1 wherein said chemical is dithiodipyridine, dithiocarbamate or cysteine.

4. The HCV virus-like particle according to claim 1 wherein said HCV envelope protein or part thereof is an E1s envelope protein or a part thereof and/or an E2s envelope protein or a part thereof.

5. The HCV virus-like particle according to claim 4 wherein said HCV envelope protein or part thereof is chosen from SEQ ID NOs: 2–4.

6. The HCV virus-like particle according to claim 1 wherein said HCV envelope protein or part thereof is the product of expression in a eukaryotic cell.

7. The HCV virus-like particle according to claim 6 wherein said eukaryotic cell is a fungal cell or a yeast cell.

8. The HCV virus-like particle according to claim 7 wherein said yeast cell is a *Hansenula cell.*

9. The HCV virus-like particle according to claim 7 wherein said HCV envelope protein or part thereof is expressed from a gene encoding a protein containing a signal sequence and said HCV envelope protein or part thereof.

10. The HCV virus-like particle according to claim 9 wherein the signal sequence is a CL leader peptide.

11. HCV virus-like particle according to any of claims 1 to 3 or 4 to 7 or 8 or 9 or 10 wherein said HCV envelope protein or part thereof is core-glycosylated.

12. A medicament comprising the HCV virus-like particle according to claim 11.

13. A medicament comprising the HCV virus-like particle according to any of claims 1 to 3 or 4 to 7 or 8 or 9 or 10.

14. A composition comprising the HCV virus-like particle according to any of claims 1 to 3 or 4 to 7 or 8 or 9 or 10.

15. A composition comprising the HCV virus-like particle according to claim 11.

16. A method for the detection of the presence of anti-HCV antibodies in a sample suspected to comprise anti-HCV antibodies, said method comprising:

(i) contacting a HCV virus-like particle according to any of claims 1 to 3 or 4 to 7 or 8 or 9 or 10 with said sample under conditions allowing complexation of said HCV virus-like particle with said anti-HCV antibodies, (ii) detecting the complex formed in (i), and (iii) inferring from (ii) the presence of said anti-HCV antibodies in said sample.

17. The method according to claim 16 wherein said contacting in step (i) is occurring under competitive conditions.

18. The method according to claim 16 wherein said HCV virus-like particle is attached to a solid support.

19. A diagnostic kit for the detection of the presence of anti-HCV antibodies in a sample suspected to comprise anti-HCV antibodies, said kit comprising a HCV virus-like particle according to any of claims 1 to 3 or 4 to 7 or 8 or 9 or 10.

20. The diagnostic kit according to claim 19 wherein said HCV virus-like particle is attached to a solid support.

21. A method for forming a HCV virus-like particle according to any of claims 1 to 3 or 4 to 7 or 8 or 9 or 10 comprising growing of an eukaryotic cell transformed with a gene encoding a protein containing a signal seauence and said HCV envelope protein or part thereof in a suitable culture medium to produce said HCV envelope protein or part thereof, treating said HCV envelope protein or part thereof to chemically modify cys-amino acids of said protein or part thereof, said chemical modification being reversible, and isolating said protein or part thereof under conditions to form virus-like particles.

22. The method according to claim 21 wherein said isolating comprises lysing said eukaryotic cell with a chaotropic agent.

23. The method according to claim 22 wherein said isolating further comprises hepari n chromatography.

24. The method according to claim 21 wherein said isolating further comprises heparin chromatography.

25. The method of claim 21 wherein said eukaryotic cell is a *Hansenula* or *Saceharomyces* glycosylation minus strain.

26. A method of making the HCV virus-like particle according to claim 1, said method comprises growing a *Hansenula* or *Saccharomyces* glycosylation minus strain transformed with a gene encoding said for HCV envelope protein, or said part thereof, characterized in that said HCV E1 and/or HCV envelope protein or said part thereof are core-glycosylated; chemically modifying cysteines of said protein or said part thereof in a manner which is reversible, and isolating said protein or part thereof under conditions to form virus-like particles.

27. A method for purifying core-glycosylated hepatitis C virus (HCV) envelope protein virus-like particles containing reversibly modified cysteines, which method comprising:

-i- growing *Hansenula* or *Saccharomyces* glycosylation minus strains transformed with an envelope gene encoding an HCV E1 and/or HCV E2 protein, or a particle-forming part thereof, in a suitable culture medium, in which said HCV E1 and/or HCV E2 protein, or part thereof, comprises at least two Cys-amino acids, -ii- expressing said HCV E1 and/or HCV E2 gene, or aiIy part thereof; and -iii- purifying from said culture said core-glycosylated HCV E1 and/or HCV E2 protein, or part thereof, under conditions in which said Cys-amino acids are reversibly protected by chemical and/or enzymatic means, and virus-like particles are formed.

28. The method of claim 27 wherein said expressing further comprises intracellular expression of core- glycosylated HCV E1 and/or HCV E2 protein, or part thereof, and said purifying further comprises lysing said strains to obtaing said protein or any part thereof under conditions wherein Cys-amino acids are reversibly protected by chemical and/or enzymatic means.

29. The method of claim 27 or 28 wherein said purifying further comprises heparin affinity chromatography.

30. The method of claim 27 or 28 wherein said chemical means is sulfonation.

31. The method of claim 27 or 28, further comprising exchanging said reversibly protected Cys-amino acid with an irreversible protection by chemical and/or enzymatic means.

32. The method according to claim 31, in which said irreversible protection by chemical means comprises treatment with iodo-acetamide.

33. The method according to claim 31, in which said irreversible protection by chemical means comprises treatment with NEM or Biotin-NEM or a mixture thereof.

34. Immunoassay for detecting HCV antibody in a biological sample, which immunoassay comprises:

providing the HCV virus-like particle of claim 1;

incubating said biological sample under conditions that allow formation of an immuno-complex between said antibody and said virus-like particle; and determining whether said immune-complex is formed.

* * * * *

SEQUENCE LISTING

```
<160> NUMBER OF SEQ ID NOS: 65
<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Avian
      lysozyme signal peptide
<220> FEATURE:
```

-continued

<221> NAME/KEY: MOD_RES
<222> LOCATION: (6)
<223> OTHER INFORMATION: Ile or Val

<400> SEQUENCE: 1

Met Arg Ser Leu Leu Xaa Leu Val Leu Cys Phe Leu Pro Leu Ala Ala
1               5                   10                  15

Leu Gly

<210> SEQ ID NO 2
<211> LENGTH: 135
<212> TYPE: PRT
<213> ORGANISM: Hepatitis C virus

<400> SEQUENCE: 2

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp
    130                 135

<210> SEQ ID NO 3
<211> LENGTH: 290
<212> TYPE: PRT
<213> ORGANISM: Hepatitis C virus

<400> SEQUENCE: 3

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Phe Gly Val Pro Thr Tyr

-continued

```
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln
    290


<210> SEQ ID NO 4
<211> LENGTH: 141
<212> TYPE: PRT
<213> ORGANISM: Hepatitis C virus

<400> SEQUENCE: 4

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp His His His His His His
    130                 135                 140


<210> SEQ ID NO 5
<211> LENGTH: 301
<212> TYPE: PRT
<213> ORGANISM: Hepatitis C virus

<400> SEQUENCE: 5

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
```

-continued

```
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln Val Ile Glu Gly Arg His His His His His His
    290                 295                 300


<210> SEQ ID NO 6
<211> LENGTH: 3448
<212> TYPE: DNA
<213> ORGANISM: Artificial Sequence
<220> FEATURE:
<223> OTHER INFORMATION: Description of Artificial Sequence: Vector
      pGEMTE1sH6 sequence

<400> SEQUENCE: 6

aatcactagt gcggccgcct gcaggtcgac catatgggag agctcccaac gcgttggatg     60

catagcttga gtattctata gtgtcaccta aatagcttgg cgtaatcatg gtcatagctg    120

tttcctgtgt gaaattgtta tccgctcaca attccacaca acatacgagc cggaagcata    180

aagtgtaaag cctggggtgc ctaatgagtg agctaactca cattaattgc gttgcgctca    240

ctgcccgctt tccagtcggg aaacctgtcg tgccagctgc attaatgaat cggccaacgc    300

gcggggagag gcggtttgcg tattgggcgc tcttccgctt cctcgctcac tgactcgctg    360

cgctcggtcg ttcggctgcg gcgagcggta tcagctcact caaaggcggt aatacggtta    420

tccacagaat caggggataa cgcaggaaag aacatgtgag caaaaggcca gcaaaaggcc    480
```

-continued

```
aggaaccgta aaaaggccgc gttgctggcg tttttcgata ggctccgccc ccctgacgag    540
catcacaaaa atcgacgctc aagtcagagg tggcgaaacc cgacaggact ataaagatac    600
caggcgtttc cccctggaag ctccctcgtg cgctctcctg ttccgaccct gccgcttacc    660
ggatacctgt ccgcctttct cccttcggga agcgtggcgc tttctcatag ctcacgctgt    720
aggtatctca gttcggtgta ggtcgttcgc tccaagctgg gctgtgtgca cgaacccccc    780
gttcagcccg accgctgcgc cttatccggt aactatcgtc ttgagtccaa cccggtaaga    840
cacgacttat cgccactggc agcagccact ggtaacagga ttagcagagc gaggtatgta    900
ggcggtgcta cagagttctt gaagtggtgg cctaactacg gctacactag aaggacagta    960
tttggtatct gcgctctgct gaagccagtt accttcggaa aaagagttgg tagctcttga   1020
tccggcaaac aaaccaccgc tggtagcggt ggtttttttg tttgcaagca gcagattacg   1080
cgcagaaaaa aaggatctca agaagatcct ttgatctttt ctacggggtc tgacgctcag   1140
tggaacgaaa actcacgtta agggattttg gtcatgagat tatcaaaaag gatcttcacc   1200
tagatccttt taaattaaaa atgaagtttt aaatcaatct aaagtatata tgagtaaact   1260
tggtctgaca gttaccaatg cttaatcagt gaggcaccta tctcagcgat ctgtctattt   1320
cgttcatcca tagttgcctg actccccgtc gtgtagataa ctacgatacg ggagggctta   1380
ccatctggcc ccagtgctgc aatgataccg cgagacccac gctcaccggc tccagattta   1440
tcagcaataa accagccagc cggaagggcc gagcgcagaa gtggtcctgc aactttatcc   1500
gcctccatcc agtctattaa ttgttgccgg gaagctagag taagtagttc gccagttaat   1560
agtttgcgca acgttgttgg cattgctaca ggcatcgtgg tgtcacgctc gtcgtttggt   1620
atggcttcat tcagctccgg ttcccaacga tcaaggcgag ttacatgatc ccccatgttg   1680
tgcaaaaaag cggttagctc cttcggtcct ccgatcgttg tcagaagtaa gttggccgca   1740
gtgttatcac tcatggttat ggcagcactg cataattctc ttactgtcat gccatccgta   1800
agatgctttt ctgtgactgg tgagtactca accaagtcat tctgagaata ccgcgcccgg   1860
cgaccgagtt gctcttgccc ggcgtcaata cgggataata gtgtatgaca tagcagaact   1920
ttaaaagtgc tcatcattgg aaaacgttct tcggggcgaa aactctcaag gatcttaccg   1980
ctgttgagat ccagttcgat gtaacccact cgtgcaccca actgatcttc agcatctttt   2040
actttcacca gcgtttctgg gtgagcaaaa acaggaaggc aaaatgccgc aaaaaaggga   2100
ataagggcga cacggaaatg ttgaatactc atactcttcc tttttcaata ttattgaagc   2160
atttatcagg gttattgtct catgagcgga tacatatttg aatgtattta gaaaaataaa   2220
caaatagggg ttccgcgcac atttccccga aaagtgccac ctgtatgcgg tgtgaaatac   2280
cgcacagatg cgtaaggaga aaataccgca tcaggcgaaa ttgtaaacgt taatattttg   2340
ttaaaattcg cgttaaatat ttgttaaatc agctcatttt ttaaccaata ggccgaaatc   2400
ggcaaaatcc cttataaatc aaaagaatag accgagatag ggttgagtgt tgttccagtt   2460
tggaacaaga gtccactatt aaagaacgtg gactccaacg tcaaagggcg aaaaaccgtc   2520
tatcagggcg atggcccact acgtgaacca tcacccaaat caagtttttt gcggtcgagg   2580
tgccgtaaag ctctaaatcg gaaccctaaa gggagccccc gatttagagc ttgacgggga   2640
aagccggcga acgtggcgag aaaggaaggg aagaaagcga aaggagcggg cgctagggcg   2700
ctggcaagtg tagcggtcac gctgcgcgta accaccacac ccgccgcgct taatgcgccg   2760
ctacagggcg cgtccattcg ccattcaggc tgcgcaactg ttgggaaggg cgatcggtgc   2820
```

-continued

```
gggcctcttc gctattacgc cagctggcga aagggggatg tgctgcaagg cgattaagtt   2880

gggtaacgcc agggttttcc cagtcacgac gttgtaaaac gacggccagt gaattgtaat   2940

acgactcact atagggcgaa ttgggcccga cgtcgcatgc tcccggccgc catggccgcg   3000

ggattccaat gcatatgagg tgcgcaacgt gtccgggatg taccatgtca cgaacgactg   3060

ctccaactca agcattgtgt atgaggcagc ggacatgatc atgcacaccc ccgggtgcgt   3120

gccctgcgtt cgggagaaca actcttcccg ctgctgggta gcgctcaccc ccacgctcgc   3180

agctaggaac gccagcgtcc ccactacgac aatacgacgc cacgtcgatt tgctcgttgg   3240

ggcggctgct ttctgttccg ctatgtacgt gggggatctc tgcggatctg tcttcctcgt   3300

ctcccagctg ttcaccatct cgcctcgccg gcatgagacg gtgcaggact gcaattgctc   3360

aatctatccc ggccacataa caggtcaccg tatggcttgg gatatgatga tgaactggca   3420

ccaccaccat caccattaag gatccaag                                      3448


<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      CHHE1-F sequence

<400> SEQUENCE: 7

agttactctt caaggtatga ggtgcgcaac gtgtccg                              37


<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      CHHE1-R sequence

<400> SEQUENCE: 8

agttactctt cacagggatc ctccttaatg gtgatggtgg tggtgcc                   47


<210> SEQ ID NO 9
<211> LENGTH: 3067
<212> TYPE: DNA
<213> ORGANISM: Artificial Sequence
<220> FEATURE:
<223> OTHER INFORMATION: Description of Artificial Sequence: Vector
      pCHH-Hir sequence

<400> SEQUENCE: 9

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagcttgc    240

atgcctgcag gtcgacccta gatctctatt actgcaggta ttcttccggg atttcttcga    300

agtcgccgtc gttgtgagac tgcggacgcg ggtaccttc gccagtaacg cactggttac    360

gttcgccttt agagcccagg atgcatttgt tgccctggcc gcaaacgtta gagccttcgc    420

acaggcacag gttctgaccg gattcagtgc agtcagtgta aacaaccctc ttttccaacg    480

ggtgtgtagt tccattctcc accgctaggg ctgcgctggg ctccattggc gaggttttca    540

aggccgctag gatgcgatcc atgcgtccgt agccttgcgt ggagcgtgcg tgtgcgtgcg    600
```

-continued

```
ggagtgcgca taggtaggct acggtgatga ttgctagcat ggcgggaata gttttgctat    660
acatgaattc actggccgtc gttttacaac gtcgtgactg ggaaaaccct ggcgttaccc    720
aacttaatcg ccttgcagca catccccctt tcgccagctg gcgtaatagc gaagaggccc    780
gcaccgatcg cccttcccaa cagttgcgca gcctgaatgg cgaatggcgc ctgatgcggt    840
attttctcct tacgcatctg tgcggtattt cacaccgcat atggtgcact ctcagtacaa    900
tctgctctga tgccgcatag ttaagccagc cccgacaccc gccaacaccc gctgacgcgc    960
cctgacgggc ttgtctgctc ccggcatccg cttacagaca agctgtgacc gtctccggga   1020
gctgcatgtg tcagaggttt tcaccgtcat caccgaaacg cgcgagacga aagggcctcg   1080
tgatacgcct atttttatag gttaatgtca tgataataat ggtttcttag acgtcaggtg   1140
gcacttttcg gggaaatgtg cgcggaaccc ctatttgttt atttttctaa atacattcaa   1200
atatgtatcc gctcatgaga caataaccct gataaatgct tcaataatat tgaaaaagga   1260
agagtatgag tattcaacat ttccgtgtcg cccttattcc cttttttgcg gcattttgcc   1320
ttcctgtttt tgctcaccca gaaacgctgg tgaaagtaaa agatgctgaa gatcagttgg   1380
gtgcacgagt gggttacatc gaactggatc tcaacagcgg taagatcctt gagagttttc   1440
gccccgaaga acgttttcca atgatgagca cttttaaagt tctgctatgt ggcgcggtat   1500
tatcccgtat tgacgccggg caagagcaac tcggtcgccg catacactat tctcagaatg   1560
acttggttga gtactcacca gtcacagaaa agcatcttac ggatggcatg acagtaagag   1620
aattatgcag tgctgccata accatgagtg ataacactgc ggccaactta cttctgacaa   1680
cgatcggagg accgaaggag ctaaccgctt ttttgcacaa catgggggat catgtaactc   1740
gccttgatcg ttgggaaccg gagctgaatg aagccatacc aaacgacgag cgtgacacca   1800
cgatgcctgt agcaatggca acaacgttgc gcaaactatt aactggcgaa ctacttactc   1860
tagcttcccg gcaacaatta atagactgga tggaggcgga taaagttgca ggaccacttc   1920
tgcgctcggc ccttccggct ggctggttta ttgctgataa atctggagcc ggtgagcgtg   1980
ggtctcgcgg tatcattgca gcactggggc cagatggtaa gccctcccgt atcgtagtta   2040
tctacacgac ggggagtcag gcaactatgg atgaacgaaa tagacagatc gctgagatag   2100
gtgcctcact gattaagcat tggtaactgt cagaccaagt ttactcatat atactttaga   2160
ttgatttaaa acttcatttt taatttaaaa ggatctaggt gaagatcctt tttgataatc   2220
tcatgaccaa aatcccttaa cgtgagtttt cgttccactg agcgtcagac cccgtagaaa   2280
agatcaaagg atcttcttga gatccttttt ttctgcgcgt aatctgctgc ttgcaaacaa   2340
aaaaaccacc gctaccagcg gtggtttgtt tgccggatca agagctacca actctttttc   2400
cgaaggtaac tggcttcagc agagcgcaga taccaaatac tgtccttcta gtgtagccgt   2460
agttaggcca ccacttcaag aactctgtag caccgcctac atacctcgct ctgctaatcc   2520
tgttaccagt ggctgctgcc agtggcgata agtcgtgtct taccgggttg gactcaagac   2580
gatagttacc ggataaggcg cagcggtcgg gctgaacggg gggttcgtgc acacagccca   2640
gcttggagcg aacgacctac accgaactga gatacctaca gcgtgagcta tgagaaagcg   2700
ccacgcttcc cgaagggaga aaggcggaca ggtatccggt aagcggcagg gtcggaacag   2760
gagagcgcac gagggagctt ccagggggaa acgcctggta tctttatagt cctgtcgggt   2820
ttcgccacct ctgacttgag cgtcgatttt tgtgatgctc gtcagggggg cggagcctat   2880
ggaaaaacgc cagcaacgcg gcctttttac ggttcctggc cttttgctgg ccttttgctc   2940
acatgttctt tcctgcgtta tcccctgatt ctgtggataa ccgtattacc gcctttgagt   3000
```

-continued

```
gagctgatac cgctcgccgc agccgaacga ccgagcgcag cgagtcagtg agcgaggaag   3060

cggaaga                                                             3067


<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      probe or primer

<400> SEQUENCE: 10

agttactctt cacctctttt ccaacgggtg tgtag                                35


<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      probe or primer

<400> SEQUENCE: 11

agtcactctt cactgcaggc atgcaagctt ggcg                                 34


<210> SEQ ID NO 12
<211> LENGTH: 6973
<212> TYPE: DNA
<213> ORGANISM: Artificial Sequence
<220> FEATURE:
<223> OTHER INFORMATION: Description of Artificial Sequence: Vector
      pFPMT121 sequence

<400> SEQUENCE: 12

ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccagatc tgaattcccg    360

atgaagcaga gagcgcagga ggcggtattt atagtgccat tcccctctct gagagacccg    420

gatggtagtc gagtgtatcg gagacagctt gatgtagact ccgtgcctgc cggctcctct    480

tattggcgga caccagtgag acaccccgga acttgctgtt tttctgcaaa atccggggtg    540

accagtggga gcctatttgc acacacgagc gggacacccc actctggtga agagtgccaa    600

agtcattctt tttcccgttg cggggcagcc gattgcatgt tttaggaaaa tattaccttt    660

gctacaccct gtcagattta ccctccacac atatatattc cgtcacctcc agggactatt    720

attcgtcgtt gcgccgccag cggaagatat ccagaagctg ttttccgaga gactcggttg    780

gcgcctggta tatttgatgg atgtcgcgct gcctcacgtc ccggtaccca ggaacgcggt    840

gggatctcgg gcccatcgaa gactgtgctc cagactgctc gcccagcagg tgtttcttga    900

tcgccgcctc taaattgtcc gcgcatcgcc ggtaacattt ttccagctcg gagtttgcgt    960

ttagatacag tttctgcgat gccaaaggag cctgcagatt ataacctcgg atgctgtcat   1020

tcagcgcttt taatttgacc tccagatagt tgctgtattt ctgttcccat tggctgctgc   1080

gcagcttcgt ataactcgag ttattgttgc gctctgcctc ggcgtactgg ctcatgatct   1140
```

-continued

```
ggatcttgtc cgtgtcgctt ttcttcgagt gtttctcgca aacgatgtgc acggcctgca   1200
gtgtccaatc ggagtcgagc tggcgccgaa actggcggat ctgagcctcc acactgccct   1260
gtttctctat ccacggcgga accgcctcct gccgtttcag aatgttgttc aagtggtact   1320
ctgtgcggtc aatgaaggcg ttattgccgg tgaaatcttt gggaagcggt tttcctcggg   1380
gaagattacg aaattccccg cgtcgttgcg cttcctggat ctcgaggaga tcgttctccg   1440
cgtcgaggag atcgttctcc gcgtcgacac cattccttgc ggcggcggtg ctcaacggcc   1500
tcaacctact actgggctgc ttcctaatgc aggagtcgca taagggagag cgtcgacaaa   1560
cccgcgtttg agaacttgct caagcttctg gtaaacgttg tagtactctg aaacaaggcc   1620
ctagcactct gatctgtttc tcttgggtag cggtgagtgg tttattggag ttcactggtt   1680
tcagcacatc tgtcatctag acaatattgt tactaaattt ttttgaacta caattgttcg   1740
taattcatct attattatac atcctcgtca gcaatttctg gcagacggag tttactaacg   1800
tcttgagtat gaggccgaga atccagctct gtggccatac tcagtcttga cagcctgctg   1860
atgtggctgc gttcaacgca ataagcgtgt cctccgactc cgagttgtgc tcgttatcgt   1920
cgttctcatc ctcggaaaaa tcacacgaaa gaacatactc accagtaggc tttctggtcc   1980
ctggggcacg gctgtttctg acgtattccg gcgttgataa tagctcgaaa gtgaacgccg   2040
agtcgcggga gtcgaccgat gcccttgaga gccttcaacc cagtcagctc cttccggtgg   2100
gcgcggggca tgactatcgt cgccgcactt atgactgtct tctttatcat gcaactcgta   2160
ggacaggtgc cggcagcgct ctgggtcatt ttcggcgagg accgctttcg ctggagcgcg   2220
acgatgatcg gcctgtcgct tgcggtattc ggaatcttgc acgccctcgc tcaagccttc   2280
gtcactggtc ccgccaccaa acgtttcggc gagaagcagg ccattatcgc cggcatggcg   2340
gccgacgcgc tgggctacgt cttgctggcg ttcgcgacgc gaggctggat ggccttcccc   2400
attatgattc ttctcgcttc cggcggcatc gggatgcccg cgttgcaggc catgctgtcc   2460
aggcaggtag atgacgacca tcagggacag cttcaaggat cgctcgcggc tcttaccagc   2520
ctaacttcga tcactggacc gctgatcgtc acggcgattt atgccgcctc ggcgagcaca   2580
tggaacgggt tggcatggat tgtaggcgcc gccctatacc ttgtctgcct ccccgcgttg   2640
cgtcgcggtg catggagccg ggccacctcg acctgaatgg aagccggcgg cacctcgcta   2700
acggattcac cactccaaga attggagcca atcaattctt gcggagaact gtgaatgcgc   2760
aaaccaaccc ttggcagaac atatccatcg cgtccgccat ctccagcagc cgcacgcggc   2820
gcatcggggg gggggggggg gggggggggc aaacaattca tcattttttt tttattcttt   2880
tttttgattt cggtttcttt gaaatttttt tgattcggta atctccgaac agaaggaaga   2940
acgaaggaag gagcacagac ttagattggt atatatacgc atatgtagtg ttgaagaaac   3000
atgaaattgc ccagtattct taacccaact gcacagaaca aaaacctgca ggaaacgaag   3060
ataaatcatg tcgaaagcta catataagga acgtgctgct actcatccta gtcctgttgc   3120
tgccaagcta tttaatatca tgcacgaaaa gcaaacaaac ttgtgtgctt cattggatgt   3180
tcgtaccacc aaggaattac tggagttagt tgaagcatta ggtcccaaaa tttgtttact   3240
aaaaacacat gtggatatct tgactgattt ttccatggag ggcacagtta agccgctaaa   3300
ggcattatcc gccaagtaca atttttttact cttcgaagac agaaaatttg ctgacattgg   3360
taatacagtc aaattgcagt actctgcggg tgtatacaga atagcagaat gggcagacat   3420
tacgaatgca cacggtgtgg tgggcccagg tattgttagc ggtttgaagc aggcggcaga   3480
```

-continued

```
agaagtaaca aaggaaccta gaggcctttt gatgttagca gaattgtcat gcaagggctc   3540
cctatctact ggagaatata ctaagggtac tgttgacatt gcgaagagcg acaaagattt   3600
tgttatcggc tttattgctc aaagagacat gggtggaaga gatgaaggtt acgattggtt   3660
gattatgaca cccggtgtgg gtttagatga caagggagac gcattgggtc aacagtatag   3720
aaccgtggat gatgtggtct ctacaggatc tgacattatt attgttggaa gaggactatt   3780
tgcaaaggga agggatgcta aggtagaggg tgaacgttac agaaaagcag gctgggaagc   3840
atatttgaga agatgcggcc agcaaaacta aaaaactgta ttataagtaa atgcatgtat   3900
actaaactca caaattagag cttcaattta attatatcag ttattacccg ggaatctcgg   3960
tcgtaatgat tttataatg acgaaaaaaa aaaaattgga aagaaaagcc cccccccccc   4020
cccccccccc cccccccccc ccgcagcgtt gggtcctggc cacgggtgcg catgatcgtg   4080
ctcctgtcgt tgaggacccg gctaggctgg cggggttgcc ttactggtta gcagaatgaa   4140
tcaccgatac gcgagcgaac gtgaagcgac tgctgctgca aaacgtctgc gacctgagca   4200
acaacatgaa tggtcttcgg tttccgtgtt tcgtaaagtc tggaaacgcg gaagtcagcg   4260
ccctgcacca ttatgttccg gatctgcatc gcaggatgct gctggctacc ctgtggaaca   4320
cctacatctg tattaacgaa gcgctggcat tgaccctgag tgatttttct ctggtcccgc   4380
cgcatccata ccgccagttg tttaccctca caacgttcca gtaaccgggc atgttcatca   4440
tcagtaaccc gtatcgtgag catcctctct cgtttcatcg gtatcattac ccccatgaac   4500
agaaattccc ccttacacgg aggcatcaag tgaccaaaca ggaaaaaacc gcccttaaca   4560
tggcccgctt tatcagaagc cagacattaa cgcttctgga gaaactcaac gagctggacg   4620
cggatgaaca ggcagacatc tgtgaatcgc ttcacgacca cgctgatgag ctttaccgca   4680
gctgcctcgc gcgtttcggt gatgacggtg aaaacctctg acacatgcag ctcccggaga   4740
cggtcacagc ttgtctgtaa gcggatgccg ggagcagaca agcccgtcag ggcgcgtcag   4800
cgggtgttgg cgggtgtcgg ggcgcagcca tgacccagtc acgtagcgat agcggagtgt   4860
atactggctt aactatgcgg catcagagca gattgtactg agagtgcacc atatgcggtg   4920
tgaaataccg cacagatgcg taaggagaaa ataccgcatc aggcgctctt ccgcttcctc   4980
gctcactgac tcgctgcgct cggtcgttcg gctgcggcga gcggtatcag ctcactcaaa   5040
ggcggtaata cggttatcca cagaatcagg ggataacgca ggaaagaaca tgtgagcaaa   5100
aggccagcaa aaggccagga accgtaaaaa ggccgcgttg ctggcgtttt tccataggct   5160
ccgcccccct gacgagcatc acaaaaatcg acgctcaagt cagaggtggc gaaacccgac   5220
aggactataa agataccagg cgtttccccc tggaagctcc ctcgtgcgct ctcctgttcc   5280
gaccctgccg cttaccggat acctgtccgc ctttctccct tcgggaagcg tggcgctttc   5340
tcatagctca cgctgtaggt atctcagttc ggtgtaggtc gttcgctcca agctgggctg   5400
tgtgcacgaa ccccccgttc agcccgaccg ctgcgcctta tccggtaact atcgtcttga   5460
gtccaacccg gtaagacacg acttatcgcc actggcagca gccactggta acaggattag   5520
cagagcgagg tatgtaggcg gtgctacaga gttcttgaag tggtggccta actacggcta   5580
cactagaagg acagtatttg gtatctgcgc tctgctgaag ccagttacct tcggaaaaag   5640
agttggtagc tcttgatccg gcaaacaaac caccgctggt agcggtggtt tttttgtttg   5700
caagcagcag attacgcgca gaaaaaaagg atctcaagaa gatcctttga tcttttctac   5760
ggggtctgac gctcagtgga acgaaaactc acgttaaggg attttggtca tgagattatc   5820
aaaaaggatc ttcacctaga tccttttaaa ttaaaaatga agttttaaat caatctaaag   5880
```

-continued tatatatgag taaacttggt ctgacagtta ccaatgctta atcagtgagg cacctatctc 5940
agcgatctgt ctatttcgtt catccatagt tgcctgactc cccgtcgtgt agataactac 6000
gatacgggag ggcttaccat ctggccccag tgctgcaatg ataccgcgag acccacgctc 6060
accggctcca gatttatcag caataaacca gccagccgga agggccgagc gcagaagtgg 6120
tcctgcaact ttatccgcct ccatccagtc tattaattgt tgccgggaag ctagagtaag 6180
tagttcgcca gttaatagtt tgcgcaacgt tgttgccatt gctgcaggca tcgtggtgtc 6240
acgctcgtcg tttggtatgg cttcattcag ctccggttcc caacgatcaa ggcgagttac 6300
atgatccccc atgttgtgca aaaaagcggt tagctccttc ggtcctccga tcgttgtcag 6360
aagtaagttg gccgcagtgt tatcactcat ggttatggca gcactgcata attctcttac 6420
tgtcatgcca tccgtaagat gcttttctgt gactggtgag tactcaacca agtcattctg 6480
agaatagtgt atgcggcgac cgagttgctc ttgcccggcg tcaacacggg ataataccgc 6540
gccacatagc agaactttaa aagtgctcat cattggaaaa cgttcttcgg ggcgaaaact 6600
ctcaaggatc ttaccgctgt tgagatccag ttcgatgtaa cccactcgtg cacccaactg 6660
atcttcagca tcttttactt tcaccagcgt ttctgggtga gcaaaaacag gaaggcaaaa 6720
tgccgcaaaa aagggaataa gggcgacacg gaaatgttga atactcatac tcttcctttt 6780
tcaatattat tgaagcattt atcagggtta ttgtctcatg agcggataca tatttgaatg 6840
tatttagaaa aataaacaaa taggggttcc gcgcacattt ccccgaaaag tgccacctga 6900
cgtctaagaa accattatta tcatgacatt aacctataaa aataggcgta tcacgaggcc 6960
ctttcgtctt caa 6973

<210> SEQ ID NO 13
<211> LENGTH: 7591
<212> TYPE: DNA
<213> ORGANISM: Artificial Sequence
<220> FEATURE:
<223> OTHER INFORMATION: Description of Artificial Sequence: Vector
pFPMT-CHH-E1H6 sequence

<400> SEQUENCE: 13
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccttaat ggtgatggtg 360
gtggtgccag ttcatcatca tatcccaagc catacggtga cctgttatgt ggccgggata 420
gattgagcaa ttgcagtcct gcaccgtctc atgccggcga ggcgagatgg tgaacagctg 480
ggagacgagg aagacagatc cgcagagatc ccccacgtac atagcggaac agaaagcagc 540
cgccccaacc agcaaatcga cgtggcgtcg tattgtcgta gtggggacgc tggcgttcct 600
agctgcgagc gtgggggtga gcgctaccca gcagcgggaa gagttgttct cccgaacgca 660
gggcacgcac ccgggggtgt gcatgatcat gtccgctgcc tcatacacaa tgcttgagtt 720
ggagcagtcg ttcgtgacat ggtacatccc ggacacgttg cgcacctcat acctcttttc 780
caacgggtgt gtagttccat tctccaccgc tagggctgcg ctgggctcca ttggcgaggt 840
tttcaaggcc gctaggatgc gatccatgcg tccgtagcct tgcgtggagc gtgcgtgtgc 900

-continued

```
gtgcgggagt gcgcataggt aggctacggt gatgattgct agcatggcgg gaatagtttt    960
gctatacatg aattcccgat gaagcagaga gcgcaggagg cggtatttat agtgccattc   1020
ccctctctga gagacccgga tggtagtcga gtgtatcgga gacagcttga tgtagactcc   1080
gtgcctgccg gctcctctta ttggcggaca ccagtgagac accccggaac ttgctgtttt   1140
tctgcaaaat ccggggtgac cagtgggagc ctatttgcac acacgagcgg gacaccccac   1200
tctggtgaag agtgccaaag tcattctttt tcccgttgcg gggcagccga ttgcatgttt   1260
taggaaaata ttacctttgc tacaccctgt cagatttacc ctccacacat atatattccg   1320
tcacctccag ggactattat tcgtcgttgc gccgccagcg gaagatatcc agaagctgtt   1380
ttccgagaga ctcggttggc gcctggtata tttgatggat gtcgcgctgc ctcacgtccc   1440
ggtacccagg aacgcggtgg gatctcgggc ccatcgaaga ctgtgctcca gactgctcgc   1500
ccagcaggtg tttcttgatc gccgcctcta aattgtccgc gcatcgccgg taacattttt   1560
ccagctcgga gtttgcgttt agatacagtt tctgcgatgc caaaggagcc tgcagattat   1620
aacctcggat gctgtcattc agcgctttta atttgacctc cagatagttg ctgtatttct   1680
gttcccattg gctgctgcgc agcttcgtat aactcgagtt attgttgcgc tctgcctcgg   1740
cgtactggct catgatctgg atcttgtccg tgtcgctttt cttcgagtgt ttctcgcaaa   1800
cgatgtgcac ggcctgcagt gtccaatcgg agtcgagctg gcgccgaaac tggcggatct   1860
gagcctccac actgccctgt ttctctatcc acggcggaac cgcctcctgc cgtttcagaa   1920
tgttgttcaa gtggtactct gtgcggtcaa tgaaggcgtt attgccggtg aaatctttgg   1980
gaagcggttt tcctcgggga agattacgaa attccccgcg tcgttgcgct tcctggatct   2040
cgaggagatc gttctccgcg tcgaggagat cgttctccgc gtcgacacca ttccttgcgg   2100
cggcggtgct caacggcctc aacctactac tgggctgctt cctaatgcag gagtcgcata   2160
agggagagcg tcgacaaacc cgcgtttgag aacttgctca agcttctggt aaacgttgta   2220
gtactctgaa acaaggccct agcactctga tctgtttctc ttgggtagcg gtgagtggtt   2280
tattggagtt cactggtttc agcacatctg tcatctagac aatattgtta ctaaattttt   2340
ttgaactaca attgttcgta attcatctat tattatacat cctcgtcagc aatttctggc   2400
agacggagtt tactaacgtc ttgagtatga ggccgagaat ccagctctgt ggccatactc   2460
agtcttgaca gcctgctgat gtggctgcgt tcaacgcaat aagcgtgtcc tccgactccg   2520
agttgtgctc gttatcgtcg ttctcatcct cggaaaaatc acacgaaaga acatactcac   2580
cagtaggctt tctggtccct ggggcacggc tgtttctgac gtattccggc gttgataata   2640
gctcgaaagt gaacgccgag tcgcgggagt cgaccgatgc ccttgagagc cttcaaccca   2700
gtcagctcct tccggtgggc gcggggcatg actatcgtcg ccgcacttat gactgtcttc   2760
tttatcatgc aactcgtagg acaggtgccg gcagcgctct gggtcatttt cggcgaggac   2820
cgctttcgct ggagcgcgac gatgatcggc ctgtcgcttg cggtattcgg aatcttgcac   2880
gccctcgctc aagccttcgt cactggtccc gccaccaaac gtttcggcga gaagcaggcc   2940
attatcgccg gcatggcggc cgacgcgctg ggctacgtct tgctggcgtt cgcgacgcga   3000
ggctggatgg ccttccccat tatgattctt ctcgcttccg gcggcatcgg gatgcccgcg   3060
ttgcaggcca tgctgtccag gcaggtagat gacgaccatc agggacagct tcaaggatcg   3120
ctcgcggctc ttaccagcct aacttcgatc actggaccgc tgatcgtcac ggcgatttat   3180
gccgcctcgg cgagcacatg gaacgggttg gcatggattg taggcgccgc cctatacctt   3240
```

-continued

```
gtctgcctcc ccgcgttgcg tcgcggtgca tggagccggg ccacctcgac ctgaatggaa   3300
gccggcggca cctcgctaac ggattcacca ctccaagaat tggagccaat caattcttgc   3360
ggagaactgt gaatgcgcaa accaaccctt ggcagaacat atccatcgcg tccgccatct   3420
ccagcagccg cacgcggcgc atcggggggg gggggggggg gggggggcaa acaattcatc   3480
attttttttt tattcttttt tttgatttcg gtttctttga aatttttttg attcggtaat   3540
ctccgaacag aaggaagaac gaaggaagga gcacagactt agattggtat atatacgcat   3600
atgtagtgtt gaagaaacat gaaattgccc agtattctta acccaactgc acagaacaaa   3660
aacctgcagg aaacgaagat aaatcatgtc gaaagctaca tataaggaac gtgctgctac   3720
tcatcctagt cctgttgctg ccaagctatt taatatcatg cacgaaaagc aaacaaactt   3780
gtgtgcttca ttggatgttc gtaccaccaa ggaattactg gagttagttg aagcattagg   3840
tcccaaaatt tgtttactaa aaacacatgt ggatatcttg actgattttt ccatggaggg   3900
cacagttaag ccgctaaagg cattatccgc caagtacaat tttttactct tcgaagacag   3960
aaaatttgct gacattggta atacagtcaa attgcagtac tctgcgggtg tatacagaat   4020
agcagaatgg gcagacatta cgaatgcaca cggtgtggtg ggcccaggta ttgttagcgg   4080
tttgaagcag gcggcagaag aagtaacaaa ggaacctaga ggccttttga tgttagcaga   4140
attgtcatgc aagggctccc tatctactgg agaatatact aagggtactg ttgacattgc   4200
gaagagcgac aaagattttg ttatcggctt tattgctcaa agagacatgg gtggaagaga   4260
tgaaggttac gattggttga ttatgacacc cggtgtgggt ttagatgaca agggagacgc   4320
attgggtcaa cagtatagaa ccgtggatga tgtggtctct acaggatctg acattattat   4380
tgttggaaga ggactatttg caaagggaag ggatgctaag gtagagggtg aacgttacag   4440
aaaagcaggc tgggaagcat atttgagaag atgcggccag caaaactaaa aaactgtatt   4500
ataagtaaat gcatgtatac taaactcaca aattagagct tcaatttaat tatatcagtt   4560
attacccggg aatctcggtc gtaatgattt ttataatgac gaaaaaaaaa aaattggaaa   4620
gaaaagcccc cccccccccc cccccccccc cccccccccc gcagcgttgg gtcctggcca   4680
cgggtgcgca tgatcgtgct cctgtcgttg aggacccggc taggctggcg gggttgcctt   4740
actggttagc agaatgaatc accgatacgc gagcgaacgt gaagcgactg ctgctgcaaa   4800
acgtctgcga cctgagcaac aacatgaatg gtcttcggtt tccgtgtttc gtaaagtctg   4860
gaaacgcgga agtcagcgcc ctgcaccatt atgttccgga tctgcatcgc aggatgctgc   4920
tggctaccct gtggaacacc tacatctgta ttaacgaagc gctggcattg accctgagtg   4980
atttttctct ggtcccgccg catccatacc gccagttgtt taccctcaca acgttccagt   5040
aaccgggcat gttcatcatc agtaacccgt atcgtgagca tcctctctcg tttcatcggt   5100
atcattaccc ccatgaacag aaattccccc ttacacggag gcatcaagtg accaaacagg   5160
aaaaaaccgc ccttaacatg gcccgcttta tcagaagcca gacattaacg cttctggaga   5220
aactcaacga gctggacgcg gatgaacagg cagacatctg tgaatcgctt cacgaccacg   5280
ctgatgagct ttaccgcagc tgcctcgcgc gtttcggtga tgacggtgaa aacctctgac   5340
acatgcagct cccggagacg gtcacagctt gtctgtaagc ggatgccggg agcagacaag   5400
cccgtcaggg cgcgtcagcg ggtgttggcg ggtgtcgggg cgcagccatg acccagtcac   5460
gtagcgatag cggagtgtat actggcttaa ctatgcggca tcagagcaga ttgtactgag   5520
agtgcaccat atgcggtgtg aaataccgca cagatgcgta aggagaaaat accgcatcag   5580
gcgctcttcc gcttcctcgc tcactgactc gctgcgctcg gtcgttcggc tgcggcgagc   5640
```

-continued ggtatcagct cactcaaagg cggtaatacg gttatccaca gaatcagggg ataacgcagg 5700
aaagaacatg tgagcaaaag gccagcaaaa ggccaggaac cgtaaaaagg ccgcgttgct 5760
ggcgtttttc cataggctcc gcccccctga cgagcatcac aaaaatcgac gctcaagtca 5820
gaggtggcga aacccgacag gactataaag ataccaggcg tttccccctg gaagctccct 5880
cgtgcgctct cctgttccga ccctgccgct taccggatac ctgtccgcct ttctcccttc 5940
gggaagcgtg gcgctttctc atagctcacg ctgtaggtat ctcagttcgg tgtaggtcgt 6000
tcgctccaag ctgggctgtg tgcacgaacc ccccgttcag cccgaccgct gcgccttatc 6060
cggtaactat cgtcttgagt ccaacccggt aagacacgac ttatcgccac tggcagcagc 6120
cactggtaac aggattagca gagcgaggta tgtaggcggt gctacagagt tcttgaagtg 6180
gtggcctaac tacggctaca ctagaaggac agtatttggt atctgcgctc tgctgaagcc 6240
agttaccttc ggaaaaagag ttggtagctc ttgatccggc aaacaaacca ccgctggtag 6300
cggtggtttt tttgtttgca agcagcagat tacgcgcaga aaaaaaggat ctcaagaaga 6360
tcctttgatc ttttctacgg ggtctgacgc tcagtggaac gaaaactcac gttaagggat 6420
tttggtcatg agattatcaa aaaggatctt cacctagatc cttttaaatt aaaaatgaag 6480
ttttaaatca atctaaagta tatatgagta aacttggtct gacagttacc aatgcttaat 6540
cagtgaggca cctatctcag cgatctgtct atttcgttca tccatagttg cctgactccc 6600
cgtcgtgtag ataactacga tacgggaggg cttaccatct ggccccagtg ctgcaatgat 6660
accgcgagac ccacgctcac cggctccaga tttatcagca ataaaccagc cagccggaag 6720
ggccgagcgc agaagtggtc ctgcaacttt atccgcctcc atccagtcta ttaattgttg 6780
ccgggaagct agagtaagta gttcgccagt taatagtttg cgcaacgttg ttgccattgc 6840
tgcaggcatc gtggtgtcac gctcgtcgtt tggtatggct tcattcagct ccggttccca 6900
acgatcaagg cgagttacat gatcccccat gttgtgcaaa aaagcggtta gctccttcgg 6960
tcctccgatc gttgtcagaa gtaagttggc cgcagtgtta tcactcatgg ttatggcagc 7020
actgcataat tctcttactg tcatgccatc cgtaagatgc ttttctgtga ctggtgagta 7080
ctcaaccaag tcattctgag aatagtgtat gcggcgaccg agttgctctt gcccggcgtc 7140
aacacgggat aataccgcgc cacatagcag aactttaaaa gtgctcatca ttggaaaacg 7200
ttcttcgggg cgaaaactct caaggatctt accgctgttg agatccagtt cgatgtaacc 7260
cactcgtgca cccaactgat cttcagcatc ttttactttc accagcgttt ctgggtgagc 7320
aaaaacagga aggcaaaatg ccgcaaaaaa gggaataagg gcgacacgga aatgttgaat 7380
actcatactc ttcctttttc aatattattg aagcatttat cagggttatt gtctcatgag 7440
cggatacata tttgaatgta tttagaaaaa taaacaaata ggggttccgc gcacatttcc 7500
ccgaaaagtg ccacctgacg tctaagaaac cattattatc atgacattaa cctataaaaa 7560
taggcgtatc acgaggccct ttcgtcttca a 7591

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
probe or primer

<400> SEQUENCE: 14
aggggtaagc ttggataaaa ggtatgaggt gcgcaacgtg tccgggatgt 50

-continued

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 15
agttacggat ccttaatggt gatggtggtg gtgccagttc at 42

<210> SEQ ID NO 16
<211> LENGTH: 7648
<212> TYPE: DNA
<213> ORGANISM: Artificial Sequence
<220> FEATURE:
<223> OTHER INFORMATION: Description of Artificial Sequence: Vector pFPMT-Mfalfa-E1-H6 sequence

<400> SEQUENCE: 16
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccttaat ggtgatggtg 360
gtggtgccag ttcatcatca tatcccaagc catacggtga cctgttatgt ggccgggata 420
gattgagcaa ttgcagtcct gcaccgtctc atgccggcga ggcgagatgg tgaacagctg 480
ggagacgagg aagacagatc cgcagagatc ccccacgtac atagcggaac agaaagcagc 540
cgccccaacg agcaaatcga cgtggcgtcg tattgtcgta gtggggacgc tggcgttcct 600
agctgcgagc gtgggggtga gcgctaccca gcagcgggaa gagttgttct cccgaacgca 660
gggcacgcac ccgggggtgt gcatgatcat gtccgctgcc tcatacacaa tgcttgagtt 720
ggagcagtcg ttcgtgacat ggtacatccc ggacacgttg cgcacctcat accttttatc 780
caagcttacc ccttcttctt tagcagcaat gctggcaata gtagtattta taaacaataa 840
cccgttattt gtgctgttgg aaaatggcaa aacagcaaca tcgaaatccc cttctaaatc 900
tgagtaaccg atgacagctt cagccggaat ttgtgccgtt tcatcttctg ttgtagtgtt 960
gactggagca gctaatgcgg aggatgctgc gaataaaact gcagtaaaaa ttgaaggaaa 1020
tctcatgaat tcccgatgaa gcagagagcg caggaggcgg tatttatagt gccattcccc 1080
tctctgagag acccggatgg tagtcgagtg tatcggagac agcttgatgt agactccgtg 1140
cctgccggct cctcttattg gcggacacca gtgagacacc ccggaacttg ctgtttttct 1200
gcaaaatccg gggtgaccag tgggagccta tttgcacaca cgagcgggac accccactct 1260
ggtgaagagt gccaaagtca ttctttttcc cgttgcgggg cagccgattg catgttttag 1320
gaaaatatta cctttgctac accctgtcag atttaccctc cacacatata tattccgtca 1380
cctccaggga ctattattcg tcgttgcgcc gccagcggaa gatatccaga agctgttttc 1440
cgagagactc ggttggcgcc tggtatattt gatggatgtc gcgctgcctc acgtcccggt 1500
acccaggaac gcggtgggat ctcgggccca tcgaagactg tgctccagac tgctcgccca 1560
gcaggtgttt cttgatcgcc gcctctaaat tgtccgcgca tcgccggtaa catttttcca 1620

-continued

```
gctcggagtt tgcgtttaga tacagtttct gcgatgccaa aggagcctgc agattataac   1680
ctcggatgct gtcattcagc gcttttaatt tgacctccag atagttgctg tatttctgtt   1740
cccattggct gctgcgcagc ttcgtataac tcgagttatt gttgcgctct gcctcggcgt   1800
actggctcat gatctggatc ttgtccgtgt cgcttttctt cgagtgtttc tcgcaaacga   1860
tgtgcacggc ctgcagtgtc caatcggagt cgagctggcg ccgaaactgg cggatctgag   1920
cctccacact gccctgtttc tctatccacg gcggaaccgc ctcctgccgt ttcagaatgt   1980
tgttcaagtg gtactctgtg cggtcaatga aggcgttatt gccggtgaaa tctttgggaa   2040
gcggttttcc tcggggaaga ttacgaaatt ccccgcgtcg ttgcgcttcc tggatctcga   2100
ggagatcgtt ctccgcgtcg aggagatcgt tctccgcgtc gacaccattc cttgcggcgg   2160
cggtgctcaa cggcctcaac ctactactgg gctgcttcct aatgcaggag tcgcataagg   2220
gagagcgtcg acaaacccgc gtttgagaac ttgctcaagc ttctggtaaa cgttgtagta   2280
ctctgaaaca aggccctagc actctgatct gtttctcttg ggtagcggtg agtggtttat   2340
tggagttcac tggtttcagc acatctgtca tctagacaat attgttacta aatttttttg   2400
aactacaatt gttcgtaatt catctattat tatacatcct cgtcagcaat ttctggcaga   2460
cggagtttac taacgtcttg agtatgaggc cgagaatcca gctctgtggc catactcagt   2520
cttgacagcc tgctgatgtg gctgcgttca acgcaataag cgtgtcctcc gactccgagt   2580
tgtgctcgtt atcgtcgttc tcatcctcgg aaaaatcaca cgaaagaaca tactcaccag   2640
taggctttct ggtccctggg gcacggctgt ttctgacgta ttccggcgtt gataatagct   2700
cgaaagtgaa cgccgagtcg cgggagtcga ccgatgccct tgagagcctt caacccagtc   2760
agctccttcc ggtgggcgcg gggcatgact atcgtcgccg cacttatgac tgtcttcttt   2820
atcatgcaac tcgtaggaca ggtgccggca gcgctctggg tcattttcgg cgaggaccgc   2880
tttcgctgga gcgcgacgat gatcggcctg tcgcttgcgg tattcggaat cttgcacgcc   2940
ctcgctcaag ccttcgtcac tggtcccgcc accaaacgtt tcggcgagaa gcaggccatt   3000
atcgccggca tggcggccga cgcgctgggc tacgtcttgc tggcgttcgc gacgcgaggc   3060
tggatggcct tccccattat gattcttctc gcttccggcg gcatcgggat gcccgcgttg   3120
caggccatgc tgtccaggca ggtagatgac gaccatcagg gacagcttca aggatcgctc   3180
gcggctctta ccagcctaac ttcgatcact ggaccgctga tcgtcacggc gatttatgcc   3240
gcctcggcga gcacatggaa cgggttggca tggattgtag gcgccgccct ataccttgtc   3300
tgcctccccg cgttgcgtcg cggtgcatgg agccgggcca cctcgacctg aatggaagcc   3360
ggcggcacct cgctaacgga ttcaccactc caagaattgg agccaatcaa ttcttgcgga   3420
gaactgtgaa tgcgcaaacc aacccttggc agaacatatc catcgcgtcc gccatctcca   3480
gcagccgcac gcggcgcatc gggggggggg gggggggggg ggggcaaaca attcatcatt   3540
tttttttat tcttttttt gatttcggtt tctttgaaat tttttgatt cggtaatctc   3600
cgaacagaag gaagaacgaa ggaaggagca cagacttaga ttggtatata tacgcatatg   3660
tagtgttgaa gaaacatgaa attgcccagt attcttaacc caactgcaca gaacaaaaac   3720
ctgcaggaaa cgaagataaa tcatgtcgaa agctacatat aaggaacgtg ctgctactca   3780
tcctagtcct gttgctgcca agctatttaa tatcatgcac gaaaagcaaa caaacttgtg   3840
tgcttcattg gatgttcgta ccaccaagga attactggag ttagttgaag cattaggtcc   3900
caaaatttgt ttactaaaaa cacatgtgga tatcttgact gatttttcca tggagggcac   3960
agttaagccg ctaaaggcat tatccgccaa gtacaatttt ttactcttcg aagacagaaa   4020
```

-continued atttgctgac attggtaata cagtcaaatt gcagtactct gcgggtgtat acagaatagc 4080
agaatgggca gacattacga atgcacacgg tgtggtgggc ccaggtattg ttagcggttt 4140
gaagcaggcg gcagaagaag taacaaagga acctagaggc cttttgatgt tagcagaatt 4200
gtcatgcaag ggctccctat ctactggaga atatactaag ggtactgttg acattgcgaa 4260
gagcgacaaa gattttgtta tcggctttat tgctcaaaga gacatgggtg gaagagatga 4320
aggttacgat tggttgatta tgacacccgg tgtgggttta gatgacaagg gagacgcatt 4380
gggtcaacag tatagaaccg tggatgatgt ggtctctaca ggatctgaca ttattattgt 4440
tggaagagga ctatttgcaa agggaaggga tgctaaggta gagggtgaac gttacagaaa 4500
agcaggctgg gaagcatatt tgagaagatg cggccagcaa aactaaaaaa ctgtattata 4560
agtaaatgca tgtatactaa actcacaaat tagagcttca atttaattat atcagttatt 4620
acccgggaat ctcggtcgta atgattttta taatgacgaa aaaaaaaaaa ttggaaagaa 4680
aagccccccc cccccccccc cccccccccc cccccccgca gcgttgggtc ctggccacgg 4740
gtgcgcatga tcgtgctcct gtcgttgagg acccggctag gctggcgggg ttgccttact 4800
ggttagcaga atgaatcacc gatacgcgag cgaacgtgaa gcgactgctg ctgcaaaacg 4860
tctgcgacct gagcaacaac atgaatggtc ttcggtttcc gtgtttcgta aagtctggaa 4920
acgcggaagt cagcgccctg caccattatg ttccggatct gcatcgcagg atgctgctgg 4980
ctaccctgtg gaacacctac atctgtatta acgaagcgct ggcattgacc ctgagtgatt 5040
tttctctggt cccgccgcat ccataccgcc agttgtttac cctcacaacg ttccagtaac 5100
cgggcatgtt catcatcagt aacccgtatc gtgagcatcc tctctcgttt catcggtatc 5160
attaccccca tgaacagaaa ttccccctta cacggaggca tcaagtgacc aaacaggaaa 5220
aaaccgccct taacatggcc cgctttatca gaagccagac attaacgctt ctggagaaac 5280
tcaacgagct ggacgcggat gaacaggcag acatctgtga atcgcttcac gaccacgctg 5340
atgagcttta ccgcagctgc ctcgcgcgtt tcggtgatga cggtgaaaac ctctgacaca 5400
tgcagctccc ggagacggtc acagcttgtc tgtaagcgga tgccgggagc agacaagccc 5460
gtcagggcgc gtcagcgggt gttggcgggt gtcggggcgc agccatgacc cagtcacgta 5520
gcgatagcgg agtgtatact ggcttaacta tgcggcatca gagcagattg tactgagagt 5580
gcaccatatg cggtgtgaaa taccgcacag atgcgtaagg agaaaatacc gcatcaggcg 5640
ctcttccgct tcctcgctca ctgactcgct gcgctcggtc gttcggctgc ggcgagcggt 5700
atcagctcac tcaaaggcgg taatacggtt atccacagaa tcaggggata acgcaggaaa 5760
gaacatgtga gcaaaaggcc agcaaaaggc caggaaccgt aaaaaggccg cgttgctggc 5820
gtttttccat aggctccgcc cccctgacga gcatcacaaa aatcgacgct caagtcagag 5880
gtggcgaaac ccgacaggac tataaagata ccaggcgttt ccccctggaa gctccctcgt 5940
gcgctctcct gttccgaccc tgccgcttac cggatacctg tccgcctttc tcccttcggg 6000
aagcgtggcg ctttctcata gctcacgctg taggtatctc agttcggtgt aggtcgttcg 6060
ctccaagctg ggctgtgtgc acgaaccccc cgttcagccc gaccgctgcg ccttatccgg 6120
taactatcgt cttgagtcca acccggtaag acacgactta tcgccactgg cagcagccac 6180
tggtaacagg attagcagag cgaggtatgt aggcggtgct acagagttct tgaagtggtg 6240
gcctaactac ggctacacta gaaggacagt atttggtatc tgcgctctgc tgaagccagt 6300
taccttcgga aaaagagttg gtagctcttg atccggcaaa caaaccaccg ctggtagcgg 6360

-continued

```
tggttttttt gtttgcaagc agcagattac gcgcagaaaa aaaggatctc aagaagatcc   6420

tttgatcttt tctacggggt ctgacgctca gtggaacgaa aactcacgtt aagggatttt   6480

ggtcatgaga ttatcaaaaa ggatcttcac ctagatcctt ttaaattaaa aatgaagttt   6540

taaatcaatc taaagtatat atgagtaaac ttggtctgac agttaccaat gcttaatcag   6600

tgaggcacct atctcagcga tctgtctatt tcgttcatcc atagttgcct gactccccgt   6660

cgtgtagata actacgatac gggagggctt accatctggc cccagtgctg caatgatacc   6720

gcgagaccca cgctcaccgg ctccagattt atcagcaata aaccagccag ccggaagggc   6780

cgagcgcaga agtggtcctg caactttatc cgcctccatc cagtctatta attgttgccg   6840

ggaagctaga gtaagtagtt cgccagttaa tagtttgcgc aacgttgttg ccattgctgc   6900

aggcatcgtg gtgtcacgct cgtcgtttgg tatggcttca ttcagctccg gttcccaacg   6960

atcaaggcga gttacatgat cccccatgtt gtgcaaaaaa gcggttagct ccttcggtcc   7020

tccgatcgtt gtcagaagta agttggccgc agtgttatca ctcatggtta tggcagcact   7080

gcataattct cttactgtca tgccatccgt aagatgcttt tctgtgactg gtgagtactc   7140

aaccaagtca ttctgagaat agtgtatgcg gcgaccgagt tgctcttgcc cggcgtcaac   7200

acgggataat accgcgccac atagcagaac tttaaaagtg ctcatcattg gaaaacgttc   7260

ttcggggcga aaactctcaa ggatcttacc gctgttgaga tccagttcga tgtaacccac   7320

tcgtgcaccc aactgatctt cagcatcttt tactttcacc agcgtttctg ggtgagcaaa   7380

aacaggaagg caaaatgccg caaaaaaggg aataagggcg acacggaaat gttgaatact   7440

catactcttc ctttttcaat attattgaag catttatcag ggttattgtc tcatgagcgg   7500

atacatattt gaatgtattt agaaaaataa acaaataggg gttccgcgca catttccccg   7560

aaaagtgcca cctgacgtct aagaaaccat tattatcatg acattaacct ataaaaatag   7620

gcgtatcacg aggccctttc gtcttcaa                                      7648
```

<210> SEQ ID NO 17
<211> LENGTH: 4453
<212> TYPE: DNA
<213> ORGANISM: Artificial Sequence
<220> FEATURE:
<223> OTHER INFORMATION: Description of Artificial Sequence: Vector pUC18-FMD-MFalfa-E1-H6 sequence
<220> FEATURE:
<221> NAME/KEY: modified_base
<222> LOCATION: (1207)..(1208)
<223> OTHER INFORMATION: Any nucleotide
<220> FEATURE:
<221> NAME/KEY: modified_base
<222> LOCATION: (1386)..(1387)
<223> OTHER INFORMATION: Any nucleotide

<400> SEQUENCE: 17

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtacccgg ggatccttaa tggtgatggt ggtggtgcca gttcatcatc atatcccaag    300

ccatacggtg acctgttatg tggccgggat agattgagca attgcagtcc tgcaccgtct    360

catgccggcg aggcgagatg gtgaacagct gggagacgag gaagacagat ccgcagagat    420

cccccacgta catagcggaa cagaaagcag ccgccccaac gagcaaatcg acgtggcgtc    480
```

-continued

```
gtattgtcgt agtggggacg ctggcgttcc tagctgcgag cgtgggggtg agcgctaccc    540
agcagcggga agagttgttc tcccgaacgc agggcacgca cccgggggtg tgcatgatca    600
tgtccgctgc ctcatacaca atgcttgagt tggagcagtc gttcgtgaca tggtacatcc    660
cggacacgtt gcgcacctca taccttttat ccaagcttac cccttcttct ttagcagcaa    720
tgctggcaat agtagtattt ataaacaata acccgttatt tgtgctgttg gaaaatggca    780
aaacagcaac atcgaaatcc ccttctaaat ctgagtaacc gatgacagct tcagccggaa    840
tttgtgccgt ttcatcttct gttgtagtgt tgactggagc agctaatgcg gaggatgctg    900
cgaataaaac tgcagtaaaa attgaaggaa atctcatgaa ttcccgatga aggcagagag    960
cgcaaggagg cggtatttat agtgccattc ccctctctga gagacccgga tggtagtcga   1020
gtgttatcgg agacagcttg atgtagactc cgtgcctgcc ggtcctctta ttggcggaca   1080
ccagtgagac accccggaac ttgctgtttt tctgcaaaat ccggggtgac cagtgggagc   1140
ctatttgcac acacgagcgg gacaccccac tctggtgaag agtgccaaag tcattctttt   1200
tcccgtnncg gggcagccga ttgcatgttt taggaaaata ttacctttgc tacaccctgt   1260
cagatttacc ctccacacat atatattccg tcacctccag ggactattct tggctcgttg   1320
cgccgccgcg gaagatatcc agaagctgtg ttttccgaga gactcggttg gcgcctggta   1380
tatttnnagg atgtcgcgct gcctcacgtc ccggtaccca ggaacgcggt gggatctcgg   1440
gcccatcgaa gactgtgctc cagactgctc gcccagcagg tgtttcttga ttgccgcctc   1500
taaatagtcc gcgcatcgcc ggtaacattt ttccagctcg gagtttgcgt ttagatacat   1560
ttctgcgatg ccaaaggagc ctgcagatta taacctcgga tgctgtcatt cagcgctttt   1620
aatttgacct ccagatagtt gctgtatttc tgttccattg gctgctggac gttcgtataa   1680
ctcgagttat tgttgcgctc tgcctcggcg tactggctca tgactgactg cggtcgcttc   1740
tcgagtgttc tcgcaacagg acgcctgcag gtcatcgagt cgagctggcg ccgaaactgg   1800
cggatctgac ctccacactg ccctgtatct ctatccaccg ggaaccgcct cctgccgttc   1860
cagaatgttg ttcaagtggt agctctgtgc ggtcaatgaa ggcgttattg ccggtgaaat   1920
ctttgggaag cggtttatcc tcggggaaga ttacgaaatt cccgcgcgtc gttgcgcttc   1980
ctggatctcg aggaagatcg ttctccgcgt cgaggagatc gttctccgcg tcgacctgca   2040
ggcatgcaag cttggcactg gccgtcgttt tacaacgtcg tgactgggaa aaccctggcg   2100
ttacccaact taatcgcctt gcagcacatc ccccctttcgc cagctggcgt aatagcgaag   2160
aggcccgcac cgatcgccct tcccaacagt tgcgcagcct gaatggcgaa tggcgcctga   2220
tgcggtattt tctccttacg catctgtgcg gtatttcaca ccgcatatgg tgcactctca   2280
gtacaatctg ctctgatgcc gcatagttaa gccagccccg acacccgcca acacccgctg   2340
acgcgccctg acgggcttgt ctgctcccgg catccgctta cagacaagct gtgaccgtct   2400
ccgggagctg catgtgtcag aggttttcac cgtcatcacc gaaacgcgcg agacgaaagg   2460
gcctcgtgat acgcctattt ttataggtta atgtcatgat aataatggtt tcttagacgt   2520
caggtggcac ttttcgggga aatgtgcgcg gaacccctat ttgtttattt ttctaaatac   2580
attcaaatat gtatccgctc atgagacaat aaccctgata aatgcttcaa taatattgaa   2640
aaaggaagag tatgagtatt caacatttcc gtgtcgccct tattcccttt tttgcggcat   2700
tttgccttcc tgtttttgct cacccagaaa cgctggtgaa agtaaaagat gctgaagatc   2760
agttgggtgc acgagtgggt tacatcgaac tggatctcaa cagcggtaag atccttgaga   2820
gttttcgccc cgaagaacgt tttccaatga tgagcacttt taaagttctg ctatgtggcg   2880
```

-continued

```
cggtattatc ccgtattgac gccgggcaag agcaactcgg tcgccgcata cactattctc   2940

agaatgactt ggttgagtac tcaccagtca cagaaaagca tcttacggat ggcatgacag   3000

taagagaatt atgcagtgct gccataacca tgagtgataa cactgcggcc aacttacttc   3060

tgacaacgat cggaggaccg aaggagctaa ccgctttttt gcacaacatg ggggatcatg   3120

taactcgcct tgatcgttgg gaaccggagc tgaatgaagc cataccaaac gacgagcgtg   3180

acaccacgat gcctgtagca atggcaacaa cgttgcgcaa actattaact ggcgaactac   3240

ttactctagc ttcccggcaa caattaatag actggatgga ggcggataaa gttgcaggac   3300

cacttctgcg ctcggccctt ccggctggct ggtttattgc tgataaatct ggagccggtg   3360

agcgtgggtc tcgcggtatc attgcagcac tggggccaga tggtaagccc tcccgtatcg   3420

tagttatcta cacgacgggg agtcaggcaa ctatggatga acgaaataga cagatcgctg   3480

agataggtgc ctcactgatt aagcattggt aactgtcaga ccaagtttac tcatatatac   3540

tttagattga tttaaaactt catttttaat ttaaaaggat ctaggtgaag atcctttttg   3600

ataatctcat gaccaaaatc ccttaacgtg agttttcgtt ccactgagcg tcagaccccg   3660

tagaaaagat caaaggatct tcttgagatc cttttttct gcgcgtaatc tgctgcttgc   3720

aaacaaaaaa accaccgcta ccagcggtgg tttgtttgcc ggatcaagag ctaccaactc   3780

tttttccgaa ggtaactggc ttcagcagag cgcagatacc aaatactgtc cttctagtgt   3840

agccgtagtt aggccaccac ttcaagaact ctgtagcacc gcctacatac ctcgctctgc   3900

taatcctgtt accagtggct gctgccagtg gcgataagtc gtgtcttacc gggttggact   3960

caagacgata gttaccggat aaggcgcagc ggtcgggctg aacggggggt tcgtgcacac   4020

agcccagctt ggagcgaacg acctacaccg aactgagata cctacagcgt gagctatgag   4080

aaagcgccac gcttcccgaa gggagaaagg cggacaggta tccggtaagc ggcagggtcg   4140

gaacaggaga gcgcacgagg gagcttccag ggggaaacgc ctggtatctt tatagtcctg   4200

tcgggtttcg ccacctctga cttgagcgtc gatttttgtg atgctcgtca ggggggcgga   4260

gcctatggaa aaacgccagc aacgcggcct ttttacggtt cctggccttt tgctggcctt   4320

ttgctcacat gttctttcct gcgttatccc ctgattctgt ggataaccgt attaccgcct   4380

ttgagtgagc tgataccgct cgccgcagcc gaacgaccga gcgcagcgag tcagtgagcg   4440

aggaagcgga aga                                                      4453
```

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 18

```
tgcttcctac cactagcagc actaggatat gaggtgcgca acgtgtccgg g              51
```

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 19

-continued tagtactagt attagtaggc ttcgcatgaa ttcccgatga aggcagagag cg 52

<210> SEQ ID NO 20
<211> LENGTH: 4252
<212> TYPE: DNA
<213> ORGANISM: Artificial Sequence
<220> FEATURE:
<223> OTHER INFORMATION: Description of Artificial Sequence: Vector
pUC18-FMD-CL-E1-H6 sequence
<220> FEATURE:
<221> NAME/KEY: modified_base
<222> LOCATION: (1006)..(1007)
<223> OTHER INFORMATION: Any nucleotide
<220> FEATURE:
<221> NAME/KEY: modified_base
<222> LOCATION: (1185)..(1186)
<223> OTHER INFORMATION: Any nucleotide

<400> SEQUENCE: 20
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtacccgg ggatccttaa tggtgatggt ggtggtgcca gttcatcatc atatcccaag 300
ccatacggtg acctgttatg tggccgggat agattgagca attgcagtcc tgcaccgtct 360
catgccggcg aggcgagatg gtgaacagct gggagacgag gaagacagat ccgcagagat 420
cccccacgta catagcggaa cagaaagcag ccgccccaac gagcaaatcg acgtggcgtc 480
gtattgtcgt agtggggacg ctggcgttcc tagctgcgag cgtgggggtg agcgctaccc 540
agcagcggga agagttgttc tcccgaacgc agggcacgca cccgggggtg tgcatgatca 600
tgtccgctgc ctcatacaca atgcttgagt tggagcagtc gttcgtgaca tggtacatcc 660
cggacacgtt gcgcacctca tatcctagtg ctgctagtgg taggaagcat agtactagta 720
ttagtaggct tcgcatgaat tcccgatgaa ggcagagagc gcaaggaggc ggtatttata 780
gtgccattcc cctctctgag agacccggat ggtagtcgag tgttatcgga gacagcttga 840
tgtagactcc gtgcctgccg gtcctcttat tggcggacac cagtgagaca ccccggaact 900
tgctgttttt ctgcaaaatc cggggtgacc agtgggagcc tatttgcaca cacgagcggg 960
acaccccact ctggtgaaga gtgccaaagt cattcttttt cccgtnncgg ggcagccgat 1020
tgcatgtttt aggaaaatat tacctttgct acaccctgtc agatttaccc tccacacata 1080
tatattccgt cacctccagg gactattctt ggctcgttgc gccgccgcgg aagatatcca 1140
gaagctgtgt tttccgagag actcggttgg cgcctggtat atttnnagga tgtcgcgctg 1200
cctcacgtcc cggtacccag gaacgcggtg ggatctcggg cccatcgaag actgtgctcc 1260
agactgctcg cccagcaggt gtttcttgat tgccgcctct aaatagtccg cgcatcgccg 1320
gtaacatttt tccagctcgg agtttgcgtt tagatacatt tctgcgatgc caaaggagcc 1380
tgcagattat aacctcggat gctgtcattc agcgctttta atttgacctc cagatagttg 1440
ctgtatttct gttccattgg ctgctggacg ttcgtataac tcgagttatt gttgcgctct 1500
gcctcggcgt actggctcat gactgactgc ggtcgcttct cgagtgttct cgcaacagga 1560
cgcctgcagg tcatcgagtc gagctggcgc cgaaactggc ggatctgacc tccacactgc 1620
cctgtatctc tatccaccgg gaaccgcctc ctgccgttcc agaatgttgt tcaagtggta 1680
gctctgtgcg gtcaatgaag gcgttattgc cggtgaaatc tttgggaagc ggtttatcct 1740

-continued cggggaagat tacgaaattc ccgcgcgtcg ttgcgcttcc tggatctcga ggaagatcgt 1800
tctccgcgtc gaggagatcg ttctccgcgt cgacctgcag gcatgcaagc ttggcactgg 1860
ccgtcgtttt acaacgtcgt gactgggaaa accctggcgt tacccaactt aatcgccttg 1920
cagcacatcc ccctttcgcc agctggcgta atagcgaaga ggcccgcacc gatcgccctt 1980
cccaacagtt gcgcagcctg aatggcgaat ggcgcctgat gcggtatttt ctccttacgc 2040
atctgtgcgg tatttcacac cgcatatggt gcactctcag tacaatctgc tctgatgccg 2100
catagttaag ccagccccga cacccgccaa cacccgctga cgcgccctga cgggcttgtc 2160
tgctcccggc atccgcttac agacaagctg tgaccgtctc cgggagctgc atgtgtcaga 2220
ggttttcacc gtcatcaccg aaacgcgcga gacgaaaggg cctcgtgata cgcctatttt 2280
tataggttaa tgtcatgata ataatggttt cttagacgtc aggtggcact tttcggggaa 2340
atgtgcgcgg aacccctatt tgtttatttt tctaaataca ttcaaatatg tatccgctca 2400
tgagacaata accctgataa atgcttcaat aatattgaaa aaggaagagt atgagtattc 2460
aacatttccg tgtcgccctt attccctttt ttgcggcatt ttgccttcct gtttttgctc 2520
acccagaaac gctggtgaaa gtaaaagatg ctgaagatca gttgggtgca cgagtgggtt 2580
acatcgaact ggatctcaac agcggtaaga tccttgagag ttttcgcccc gaagaacgtt 2640
ttccaatgat gagcactttt aaagttctgc tatgtggcgc ggtattatcc cgtattgacg 2700
ccgggcaaga gcaactcggt cgccgcatac actattctca gaatgacttg gttgagtact 2760
caccagtcac agaaaagcat cttacggatg gcatgacagt aagagaatta tgcagtgctg 2820
ccataaccat gagtgataac actgcggcca acttacttct gacaacgatc ggaggaccga 2880
aggagctaac cgcttttttg cacaacatgg gggatcatgt aactcgcctt gatcgttggg 2940
aaccggagct gaatgaagcc ataccaaacg acgagcgtga caccacgatg cctgtagcaa 3000
tggcaacaac gttgcgcaaa ctattaactg gcgaactact tactctagct tcccggcaac 3060
aattaataga ctggatggag gcggataaag ttgcaggacc acttctgcgc tcggcccttc 3120
cggctggctg gtttattgct gataaatctg gagccggtga gcgtgggtct cgcggtatca 3180
ttgcagcact ggggccagat ggtaagccct cccgtatcgt agttatctac acgacgggga 3240
gtcaggcaac tatggatgaa cgaaatagac agatcgctga gataggtgcc tcactgatta 3300
agcattggta actgtcagac caagtttact catatatact ttagattgat ttaaaacttc 3360
atttttaatt taaaaggatc taggtgaaga tcctttttga taatctcatg accaaaatcc 3420
cttaacgtga gttttcgttc cactgagcgt cagaccccgt agaaaagatc aaaggatctt 3480
cttgagatcc tttttttctg cgcgtaatct gctgcttgca aacaaaaaaa ccaccgctac 3540
cagcggtggt ttgtttgccg gatcaagagc taccaactct ttttccgaag gtaactggct 3600
tcagcagagc gcagatacca aatactgtcc ttctagtgta gccgtagtta ggccaccact 3660
tcaagaactc tgtagcaccg cctacatacc tcgctctgct aatcctgtta ccagtggctg 3720
ctgccagtgg cgataagtcg tgtcttaccg ggttggactc aagacgatag ttaccggata 3780
aggcgcagcg gtcgggctga acggggggtt cgtgcacaca gcccagcttg gagcgaacga 3840
cctacaccga actgagatac ctacagcgtg agctatgaga aagcgccacg cttcccgaag 3900
ggagaaaggc ggacaggtat ccggtaagcg gcagggtcgg aacaggagag cgcacgaggg 3960
agcttccagg gggaaacgcc tggtatcttt atagtcctgt cgggtttcgc cacctctgac 4020
ttgagcgtcg atttttgtga tgctcgtcag gggggcggag cctatggaaa aacgccagca 4080
acgcggcctt tttacggttc ctggcctttt gctggccttt tgctcacatg ttctttcctg 4140

-continued cgttatcccc tgattctgtg gataaccgta ttaccgcctt tgagtgagct gataccgctc 4200
gccgcagccg aacgaccgag cgcagcgagt cagtgagcga ggaagcggaa ga 4252

<210> SEQ ID NO 21
<211> LENGTH: 7447
<212> TYPE: DNA
<213> ORGANISM: Artificial Sequence
<220> FEATURE:
<223> OTHER INFORMATION: Description of Artificial Sequence: Vector
pFPMT-CL-E1-H6 sequence

<400> SEQUENCE: 21
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccttaat ggtgatggtg 360
gtggtgccag ttcatcatca tatcccaagc catacggtga cctgttatgt ggccgggata 420
gattgagcaa ttgcagtcct gcaccgtctc atgccggcga ggcgagatgg tgaacagctg 480
ggagacgagg aagacagatc cgcagagatc ccccacgtac atagcggaac agaaagcagc 540
cgccccaacg agcaaatcga cgtggcgtcg tattgtcgta gtggggacgc tggcgttcct 600
agctgcgagc gtgggggtga gcgctaccca gcagcgggaa gagttgttct cccgaacgca 660
gggcacgcac ccgggggtgt gcatgatcat gtccgctgcc tcatacacaa tgcttgagtt 720
ggagcagtcg ttcgtgacat ggtacatccc ggacacgttg cgcacctcat atcctagtgc 780
tgctagtggt aggaagcata gtactagtat tagtaggctt cgcatgaatt cccgatgaag 840
cagagagcgc aggaggcggt atttatagtg ccattcccct ctctgagaga cccggatggt 900
agtcgagtgt atcggagaca gcttgatgta gactccgtgc ctgccggctc ctcttattgg 960
cggacaccag tgagacaccc cggaacttgc tgtttttctg caaaatccgg ggtgaccagt 1020
gggagcctat ttgcacacac gagcgggaca ccccactctg gtgaagagtg ccaaagtcat 1080
tctttttccc gttgcggggc agccgattgc atgttttagg aaaatattac ctttgctaca 1140
ccctgtcaga tttaccctcc acacatatat attccgtcac ctccagggac tattattcgt 1200
cgttgcgccg ccagcggaag atatccagaa gctgttttcc gagagactcg gttggcgcct 1260
ggtatatttg atggatgtcg cgctgcctca cgtcccggta cccaggaacg cggtgggatc 1320
tcgggcccat cgaagactgt gctccagact gctcgcccag caggtgtttc ttgatcgccg 1380
cctctaaatt gtccgcgcat cgccggtaac atttttccag ctcggagttt gcgtttagat 1440
acagtttctg cgatgccaaa ggagcctgca gattataacc tcggatgctg tcattcagcg 1500
cttttaattt gacctccaga tagttgctgt atttctgttc ccattggctg ctgcgcagct 1560
tcgtataact cgagttattg ttgcgctctg cctcggcgta ctggctcatg atctggatct 1620
tgtccgtgtc gcttttcttc gagtgtttct cgcaaacgat gtgcacggcc tgcagtgtcc 1680
aatcggagtc gagctggcgc cgaaactggc ggatctgagc ctccacactg ccctgtttct 1740
ctatccacgg cggaaccgcc tcctgccgtt tcagaatgtt gttcaagtgg tactctgtgc 1800
ggtcaatgaa ggcgttattg ccggtgaaat ctttgggaag cggttttcct cggggaagat 1860
tacgaaattc cccgcgtcgt tgcgcttcct ggatctcgag gagatcgttc tccgcgtcga 1920

-continued

```
ggagatcgtt ctccgcgtcg acaccattcc ttgcggcggc ggtgctcaac ggcctcaacc   1980
tactactggg ctgcttccta atgcaggagt cgcataaggg agagcgtcga caaacccgcg   2040
tttgagaact tgctcaagct tctggtaaac gttgtagtac tctgaaacaa ggccctagca   2100
ctctgatctg tttctcttgg gtagcggtga gtggtttatt ggagttcact ggtttcagca   2160
catctgtcat ctagacaata ttgttactaa attttttga actacaattg ttcgtaattc    2220
atctattatt atacatcctc gtcagcaatt tctggcagac ggagtttact aacgtcttga   2280
gtatgaggcc gagaatccag ctctgtggcc atactcagtc ttgacagcct gctgatgtgg   2340
ctgcgttcaa cgcaataagc gtgtcctccg actccgagtt gtgctcgtta tcgtcgttct   2400
catcctcgga aaaatcacac gaaagaacat actcaccagt aggctttctg gtccctgggg   2460
cacggctgtt tctgacgtat tccggcgttg ataatagctc gaaagtgaac gccgagtcgc   2520
gggagtcgac cgatgccctt gagagccttc aacccagtca gctccttccg gtgggcgcgg   2580
ggcatgacta tcgtcgccgc acttatgact gtcttcttta tcatgcaact cgtaggacag   2640
gtgccggcag cgctctgggt cattttcggc gaggaccgct ttcgctggag cgcgacgatg   2700
atcggcctgt cgcttgcggt attcggaatc ttgcacgccc tcgctcaagc cttcgtcact   2760
ggtcccgcca ccaaacgttt cggcgagaag caggccatta tcgccggcat ggcggccgac   2820
gcgctgggct acgtcttgct ggcgttcgcg acgcgaggct ggatggcctt ccccattatg   2880
attcttctcg cttccggcgg catcgggatg cccgcgttgc aggccatgct gtccaggcag   2940
gtagatgacg accatcaggg acagcttcaa ggatcgctcg cggctcttac cagcctaact   3000
tcgatcactg gaccgctgat cgtcacggcg atttatgccg cctcggcgag cacatggaac   3060
gggttggcat ggattgtagg cgccgcccta taccttgtct gcctccccgc gttgcgtcgc   3120
ggtgcatgga gccgggccac ctcgacctga atggaagccg gcggcacctc gctaacggat   3180
tcaccactcc aagaattgga gccaatcaat tcttgcggag aactgtgaat gcgcaaacca   3240
acccttggca gaacatatcc atcgcgtccg ccatctccag cagccgcacg cggcgcatcg   3300
gggggggggg gggggggggg gggcaaacaa ttcatcattt tttttttatt cttttttttg   3360
atttcggttt ctttgaaatt tttttgattc ggtaatctcc gaacagaagg aagaacgaag   3420
gaaggagcac agacttagat tggtatatat acgcatatgt agtgttgaag aaacatgaaa   3480
ttgcccagta ttcttaaccc aactgcacag aacaaaaacc tgcaggaaac gaagataaat   3540
catgtcgaaa gctacatata aggaacgtgc tgctactcat cctagtcctg ttgctgccaa   3600
gctatttaat atcatgcacg aaaagcaaac aaacttgtgt gcttcattgg atgttcgtac   3660
caccaaggaa ttactggagt tagttgaagc attaggtccc aaaatttgtt tactaaaaac   3720
acatgtggat atcttgactg atttttccat ggagggcaca gttaagccgc taaaggcatt   3780
atccgccaag tacaattttt tactcttcga agacagaaaa tttgctgaca ttggtaatac   3840
agtcaaattg cagtactctg cgggtgtata cagaatagca gaatgggcag acattacgaa   3900
tgcacacggt gtggtgggcc caggtattgt tagcggtttg aagcaggcgg cagaagaagt   3960
aacaaaggaa cctagaggcc ttttgatgtt agcagaattg tcatgcaagg gctccctatc   4020
tactggagaa tatactaagg gtactgttga cattgcgaag agcgacaaag attttgttat   4080
cggctttatt gctcaaagag acatgggtgg aagagatgaa ggttacgatt ggttgattat   4140
gacacccggt gtgggtttag atgacaaggg agacgcattg ggtcaacagt atagaaccgt   4200
ggatgatgtg gtctctacag gatctgacat tattattgtt ggaagaggac tatttgcaaa   4260
```

-continued

```
gggaagggat gctaaggtag agggtgaacg ttacagaaaa gcaggctggg aagcatattt   4320
gagaagatgc ggccagcaaa actaaaaaac tgtattataa gtaaatgcat gtatactaaa   4380
ctcacaaatt agagcttcaa tttaattata tcagttatta cccgggaatc tcggtcgtaa   4440
tgatttttat aatgacgaaa aaaaaaaaat tggaaagaaa agcccccccc cccccccccc   4500
cccccccccc ccccccgcag cgttgggtcc tggccacggg tgcgcatgat cgtgctcctg   4560
tcgttgagga cccggctagg ctggcggggt tgccttactg gttagcagaa tgaatcaccg   4620
atacgcgagc gaacgtgaag cgactgctgc tgcaaaacgt ctgcgacctg agcaacaaca   4680
tgaatggtct tcggtttccg tgtttcgtaa agtctggaaa cgcggaagtc agcgccctgc   4740
accattatgt tccggatctg catcgcagga tgctgctggc taccctgtgg aacacctaca   4800
tctgtattaa cgaagcgctg gcattgaccc tgagtgattt ttctctggtc ccgccgcatc   4860
cataccgcca gttgtttacc ctcacaacgt tccagtaacc gggcatgttc atcatcagta   4920
acccgtatcg tgagcatcct ctctcgtttc atcggtatca ttacccccat gaacagaaat   4980
tccccttac acggaggcat caagtgacca aacaggaaaa aaccgccctt aacatggccc   5040
gctttatcag aagccagaca ttaacgcttc tggagaaact caacgagctg gacgcggatg   5100
aacaggcaga catctgtgaa tcgcttcacg accacgctga tgagctttac cgcagctgcc   5160
tcgcgcgttt cggtgatgac ggtgaaaacc tctgacacat gcagctcccg gagacggtca   5220
cagcttgtct gtaagcggat gccgggagca gacaagcccg tcagggcgcg tcagcgggtg   5280
ttggcgggtg tcggggcgca gccatgaccc agtcacgtag cgatagcgga gtgtatactg   5340
gcttaactat gcggcatcag agcagattgt actgagagtg caccatatgc ggtgtgaaat   5400
accgcacaga tgcgtaagga gaaaataccg catcaggcgc tcttccgctt cctcgctcac   5460
tgactcgctg cgctcggtcg ttcggctgcg gcgagcggta tcagctcact caaaggcggt   5520
aatacggtta tccacagaat caggggataa cgcaggaaag aacatgtgag caaaaggcca   5580
gcaaaaggcc aggaaccgta aaaaggccgc gttgctggcg tttttccata ggctccgccc   5640
ccctgacgag catcacaaaa atcgacgctc aagtcagagg tggcgaaacc cgacaggact   5700
ataaagatac caggcgtttc cccctggaag ctccctcgtg cgctctcctg ttccgaccct   5760
gccgcttacc ggatacctgt ccgcctttct cccttcggga agcgtggcgc tttctcatag   5820
ctcacgctgt aggtatctca gttcggtgta ggtcgttcgc tccaagctgg gctgtgtgca   5880
cgaacccccc gttcagcccg accgctgcgc cttatccggt aactatcgtc ttgagtccaa   5940
cccggtaaga cacgacttat cgccactggc agcagccact ggtaacagga ttagcagagc   6000
gaggtatgta ggcggtgcta cagagttctt gaagtggtgg cctaactacg gctacactag   6060
aaggacagta tttggtatct gcgctctgct gaagccagtt accttcggaa aaagagttgg   6120
tagctcttga tccggcaaac aaaccaccgc tggtagcggt ggtttttttg tttgcaagca   6180
gcagattacg cgcagaaaaa aaggatctca agaagatcct ttgatctttt ctacggggtc   6240
tgacgctcag tggaacgaaa actcacgtta agggattttg gtcatgagat tatcaaaaag   6300
gatcttcacc tagatccttt taaattaaaa atgaagtttt aaatcaatct aaagtatata   6360
tgagtaaact tggtctgaca gttaccaatg cttaatcagt gaggcaccta tctcagcgat   6420
ctgtctattt cgttcatcca tagttgcctg actccccgtc gtgtagataa ctacgatacg   6480
ggagggctta ccatctggcc ccagtgctgc aatgataccg cgagacccac gctcaccggc   6540
tccagattta tcagcaataa accagccagc cggaagggcc gagcgcagaa gtggtcctgc   6600
aactttatcc gcctccatcc agtctattaa ttgttgccgg gaagctagag taagtagttc   6660
```

-continued gccagttaat agtttgcgca acgttgttgc cattgctgca ggcatcgtgg tgtcacgctc 6720
gtcgtttggt atggcttcat tcagctccgg ttcccaacga tcaaggcgag ttacatgatc 6780
ccccatgttg tgcaaaaaag cggttagctc cttcggtcct ccgatcgttg tcagaagtaa 6840
gttggccgca gtgttatcac tcatggttat ggcagcactg cataattctc ttactgtcat 6900
gccatccgta agatgctttt ctgtgactgg tgagtactca accaagtcat tctgagaata 6960
gtgtatgcgg cgaccgagtt gctcttgccc ggcgtcaaca cgggataata ccgcgccaca 7020
tagcagaact ttaaaagtgc tcatcattgg aaaacgttct tcggggcgaa aactctcaag 7080
gatcttaccg ctgttgagat ccagttcgat gtaacccact cgtgcaccca actgatcttc 7140
agcatctttt actttcacca gcgtttctgg gtgagcaaaa acaggaaggc aaaatgccgc 7200
aaaaaaggga ataagggcga cacggaaatg ttgaatactc atactcttcc tttttcaata 7260
ttattgaagc atttatcagg gttattgtct catgagcgga tacatatttg aatgtattta 7320
gaaaaataaa caaatagggg ttccgcgcac atttccccga aaagtgccac ctgacgtcta 7380
agaaaccatt attatcatga cattaaccta taaaaatagg cgtatcacga ggccctttcg 7440
tcttcaa 7447

<210> SEQ ID NO 22
<211> LENGTH: 3730
<212> TYPE: DNA
<213> ORGANISM: Artificial Sequence
<220> FEATURE:
<223> OTHER INFORMATION: Description of Artificial Sequence: Vector
pSP72E2H6 sequence

<400> SEQUENCE: 22
gaactcgagc agctgaagct tgaattcatg agatttcctt caatttttac tgcagtttta 60
ttcgcagcat cctccgcatt agctgctcca gtcaacacta caacagaaga tgaaacggca 120
caaattccgg ctgaagctgt catcggttac tcagatttag aaggggattt cgatgttgct 180
gttttgccat tttccaacag cacaaataac gggttattgt ttataaatac tactattgcc 240
agcattgctg ctaaagaaga aggggtatct ctagataaaa ggcatacccg cgtgtcagga 300
ggggcagcag cctccgatac caggggcctt gtgtccctct ttagccccgg gtcggctcag 360
aaaatccagc tcgtaaacac caacggcagt tggcacatca acaggactgc cctgaactgc 420
aacgactccc tccaaacagg gttctttgcc gcactattct acaaacacaa attcaactcg 480
tctggatgcc cagagcgctt ggccagctgt cgctccatcg acaagttcgc tcaggggtgg 540
ggtcccctca cttacactga gcctaacagc tcggaccaga ggccctactg ctggcactac 600
gcgcctcgac cgtgtggtat tgtacccgcg tctcaggtgt gcggtccagt gtattgcttc 660
accccgagcc ctgttgtggt ggggacgacc gatcggtttg gtgtccccac gtataactgg 720
ggggcgaacg actcggatgt gctgattctc aacaacacgc ggccgccgcg aggcaactgg 780
ttcggctgta catggatgaa tggcactggg ttcaccaaga cgtgtggggg ccccccgtgc 840
aacatcgggg gggccggcaa caacaccttg acctgcccca ctgactgttt tcggaagcac 900
cccgaggcca cttacgccag atgcggttct gggccctggc tgacacctag gtgtatggtt 960
cattacccat ataggctctg gcactacccc tgcactgtca acttcaccat cttcaaggtt 1020
aggatgtacg tgggggggcgt ggagcacagg ttcgaagccg catgcaattg gactcgagga 1080
gagcgttgtg acttggagga cagggataga tcagagctta gctcgctgct gctgtctaca 1140
acagagtggc aggtgatcga gggcagacac catcaccacc atcactaata gttaattaac 1200

-continued

```
gatctcgact tggttgaaca cgttgccaag gcttaagtga atttacttta aagtcttgca   1260
tttaaataaa ttttcttttt atagctttat gacttagttt caatttatat actattttaa   1320
tgacattttc gattcattga ttgaaagcta tcagatctgc cggtctccct atagtgagtc   1380
gtattaattt cgataagcca ggttaacctg cattaatgaa tcggccaacg cgcgggggaga  1440
ggcggtttgc gtattgggcg ctcttccgct tcctcgctca ctgactcgct gcgctcggtc   1500
gttcggctgc ggcgagcggt atcagctcac tcaaaggcgg taatacggtt atccacagaa   1560
tcaggggata acgcaggaaa gaacatgtga gcaaaaggcc agcaaaaggc caggaaccgt   1620
aaaaaggccg cgttgctggc gtttttccat aggctccgcc cccctgacga gcatcacaaa   1680
aatcgacgct caagtcagag gtggcgaaac ccgacaggac tataaagata ccaggcgttt   1740
ccccctggaa gctccctcgt gcgctctcct gttccgaccc tgccgcttac cggatacctg   1800
tccgcctttc tcccttcggg aagcgtggcg ctttctcaat gctcacgctg taggtatctc   1860
agttcggtgt aggtcgttcg ctccaagctg ggctgtgtgc acgaaccccc cgttcagccc   1920
gaccgctgcg ccttatccgg taactatcgt cttgagtcca acccggtaag acacgactta   1980
tcgccactgg cagcagccac tggtaacagg attagcagag cgaggtatgt aggcggtgct   2040
acagagttct tgaagtggtg gcctaactac ggctacacta gaaggacagt atttggtatc   2100
tgcgctctgc tgaagccagt taccttcgga aaaagagttg gtagctcttg atccggcaaa   2160
caaaccaccg ctggtagcgg tggttttttt gtttgcaagc agcagattac gcgcagaaaa   2220
aaaggatctc aagaagatcc tttgatcttt tctacggggt ctgacgctca gtggaacgaa   2280
aactcacgtt aagggatttt ggtcatgaga ttatcaaaaa ggatcttcac ctagatcctt   2340
ttaaattaaa aatgaagttt taaatcaatc taaagtatat atgagtaaac ttggtctgac   2400
agttaccaat gcttaatcag tgaggcacct atctcagcga tctgtctatt tcgttcatcc   2460
atagttgcct gactccccgt cgtgtagata actacgatac gggagggctt accatctggc   2520
cccagtgctg caatgatacc gcgagaccca cgctcaccgg ctccagattt atcagcaata   2580
aaccagccag ccggaagggc cgagcgcaga agtggtcctg caactttatc cgcctccatc   2640
cagtctatta attgttgccg ggaagctaga gtaagtagtt cgccagttaa tagtttgcgc   2700
aacgttgttg ccattgctac aggcatcgtg gtgtcacgct cgtcgtttgg tatggcttca   2760
ttcagctccg gttcccaacg atcaaggcga gttacatgat cccccatgtt gtgcaaaaaa   2820
gcggttagct ccttcggtcc tccgatcgtt gtcagaagta agttggccgc agtgttatca   2880
ctcatggtta tggcagcact gcataattct cttactgtca tgccatccgt aagatgcttt   2940
tctgtgactg gtgagtactc aaccaagtca ttctgagaat agtgtatgcg gcgaccgagt   3000
tgctcttgcc cggcgtcaat acgggataat accgcgccac atagcagaac tttaaaagtg   3060
ctcatcattg gaaaacgttc ttcggggcga aaactctcaa ggatcttacc gctgttgaga   3120
tccagttcga tgtaacccac tcgtgcaccc aactgatctt cagcatcttt tactttcacc   3180
agcgtttctg ggtgagcaaa aacaggaagg caaaatgccg caaaaaaggg aataagggcg   3240
acacggaaat gttgaatact catactcttc ctttttcaat attattgaag catttatcag   3300
ggttattgtc tcatgagcgg atacatattt gaatgtattt agaaaaataa acaaataggg   3360
gttccgcgca catttccccg aaaagtgcca cctgacgtct aagaaaccat tattatcatg   3420
acattaacct ataaaaatag gcgtatcacg aggccctttc gtctcgcgcg tttcggtgat   3480
gacggtgaaa acctctgaca catgcagctc ccggagacgg tcacagcttg tctgtaagcg   3540
```

-continued

```
gatgccggga gcagacaagc ccgtcagggc gcgtcagcgg gtgttggcgg gtgtcggggc   3600

tggcttaact atgcggcatc agagcagatt gtactgagag tgcaccatat ggacatattg   3660

tcgttagaac gcggctacaa ttaatacata accttatgta tcatacacat acgatttagg   3720

tgacactata                                                           3730
```

<210> SEQ ID NO 23
<211> LENGTH: 7370
<212> TYPE: DNA
<213> ORGANISM: Artificial Sequence
<220> FEATURE:
<223> OTHER INFORMATION: Description of Artificial Sequence: Vector pMPT121 sequence
<220> FEATURE:
<221> NAME/KEY: modified_base
<222> LOCATION: (778)
<223> OTHER INFORMATION: Any nucleotide

<400> SEQUENCE: 23

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccagatc tgaattcgtt    360

tttgtacttt agattgatgt caccaccgtg cactggcagc agtatttata gatggaccgt    420

gtggggacgg ttgggtacac ttagcggcag cgctgacccc atctgtgatc aagtagggca    480

aaaactgggg atgtcggagt cgctgcacgg tagcataaga atttactttc tggccggttc    540

acccgcattt gcactgtgga gaaacagcct gtccgacacc ccaccagttg ccacatcggc    600

cctctgctgc tctggtgatt ttctggtagc aggcacagac agcagtgggt agcgccgtcc    660

ggttaggcaa ggtcacgttg taggctaccc cagcaaacag agcctcacat gacaccatcc    720

agctgcgtcc tcgaagcgaa aagttcggtt gcggctgcag aaccccctca gttgccanat    780

tcacaagttt tacgcgacgg ctaaagcgag tgggttttaa aaacttgcgg tgcaaggatg    840

catgcggcaa caattaattg gtgcatccag cacagcaagc ccagtctcga gatgtccagt    900

cgctacagag tggagtacgc actcaaggaa caccgtcgag atggcctcat agaatggatc    960

aagggcctgc tggccacgcc gttcgtcctg tacgcggtga agagcaacgg catctctgca   1020

gtggacgacc tcatggtaaa ctctgaggca aaacgccgct acgcggaaat cttccacgac   1080

ctcgaactcc tcatcgacga caacattgaa atgaccaaag ccggcacccc cgaattgtct   1140

cggctcgtgc agctggttcc gagcgttggc agcttcttca cgagactgcc tctggaaaag   1200

gccttctaca tcgaggacga gcgccgcgcc atcagcaaac gccggcttgt ggccccctcg   1260

ttcaacgacg tccggctcat tctcaacacg gcccagctgt tggagatgtc gcggttcttc   1320

cattccaaaa ccatccgaga tcgcaagctg cagctcatta cattcgatgg tgacatcaca   1380

ctgtacgacg acggcaaaaa tttcgatgcc gagtcgccca tcctgcccca cctcatcaaa   1440

ctaatggcca aggacctcta tgtgggtatc gtcaccgcgg ccggctacag cgacggaaca   1500

agtactacga gcgcctcaag ggcctcatcg acgccgtcca gacgtccccg ctgctcacag   1560

gccaccagaa agagaacctg ttcattatgg gcggcgaggc aaactacctc ttccggtaca   1620

gtaacgagga gcagagatta cgcttctact ccaaagacag atggctgctc gagaacatgc   1680
```

-continued

```
tgaattggtc cgaggaggac attcatctga cactggactt tgcgcaggac gttctaaacg   1740
acctcgttca caaactgggc tcgccagcca ccgtggtccg caaggagcgt cgcgtcggcc   1800
tggttccatt accgggccac aagctgatcc gcgagcagct cgaggagatc gttctccgcg   1860
tcgacaccat tccttgcggc ggcggtgctc aacggcctca acctactact gggctgcttc   1920
ctaatgcagg agtcgcataa gggagagcgt cgactcccgc gactcggcgt tcactttcga   1980
gctattatca acgccggaat acgtcagaaa cagccgtgcc ccagggacca gaaagcctac   2040
tggtgagtat gttctttcgt gtgatttttc cgaggatgag aacgacgata acgagcacaa   2100
ctcggagtcg gaggacacgc ttattgcgtt gaacgcagcc acatcagcag gctgtcaaga   2160
ctgagtatgg ccacagagct ggattctcgg cctcatactc aagacgttag taaactccgt   2220
ctgccagaaa ttgctgacga ggatgtataa taatagatga attacgaaca attgtagttc   2280
aaaaaaattt agtaacaata ttgtctagat gacagatgtg ctgaaaccag tgaactccaa   2340
taaaccactc accgctaccc aagagaaaca gatcagagtg ctagggcctt gtttcagagt   2400
actacaacgt ttaccagaag cttgagcaag ttctcaaacg cgggtttgtc gaccgatgcc   2460
cttgagagcc ttcaacccag tcagctcctt ccggtgggcg cggggcatga ctatcgtcgc   2520
cgcacttatg actgtcttct ttatcatgca actcgtagga caggtgccgg cagcgctctg   2580
ggtcattttc ggcgaggacc gctttcgctg gagcgcgacg atgatcggcc tgtcgcttgc   2640
ggtattcgga atcttgcacg ccctcgctca agccttcgtc actggtcccg ccaccaaacg   2700
tttcggcgag aagcaggcca ttatcgccgg catggcggcc gacgcgctgg gctacgtctt   2760
gctggcgttc gcgacgcgag gctggatggc cttccccatt atgattcttc tcgcttccgg   2820
cggcatcggg atgcccgcgt tgcaggccat gctgtccagg caggtagatg acgaccatca   2880
gggacagctt caaggatcgc tcgcggctct taccagccta acttcgatca ctggaccgct   2940
gatcgtcacg gcgatttatg ccgcctcggc gagcacatgg aacgggttgg catggattgt   3000
aggcgccgcc ctataccttg tctgcctccc cgcgttgcgt cgcggtgcat ggagccgggc   3060
cacctcgacc tgaatggaag ccggcggcac ctcgctaacg gattcaccac tccaagaatt   3120
ggagccaatc aattcttgcg gagaactgtg aatgcgcaaa ccaacccttg gcagaacata   3180
tccatcgcgt ccgccatctc cagcagccgc acgcggcgca tcgggggggg gggggggggg   3240
ggggggcaaa caattcatca tttttttttt attctttttt ttgatttcgg tttctttgaa   3300
atttttttga ttcggtaatc tccgaacaga aggaagaacg aaggaaggag cacagactta   3360
gattggtata tatacgcata tgtagtgttg aagaaacatg aaattgccca gtattcttaa   3420
cccaactgca cagaacaaaa acctgcagga aacgaagata aatcatgtcg aaagctacat   3480
ataaggaacg tgctgctact catcctagtc ctgttgctgc caagctattt aatatcatgc   3540
acgaaaagca aacaaacttg tgtgcttcat tggatgttcg taccaccaag gaattactgg   3600
agttagttga agcattaggt cccaaaattt gtttactaaa aacacatgtg gatatcttga   3660
ctgatttttc catggagggc acagttaagc cgctaaaggc attatccgcc aagtacaatt   3720
ttttactctt cgaagacaga aaatttgctg acattggtaa tacagtcaaa ttgcagtact   3780
ctgcgggtgt atacagaata gcagaatggg cagacattac gaatgcacac ggtgtggtgg   3840
gcccaggtat tgttagcggt ttgaagcagg cggcagaaga agtaacaaag gaacctagag   3900
gcctttttgat gttagcagaa ttgtcatgca agggctccct atctactgga gaatatacta   3960
agggtactgt tgacattgcg aagagcgaca aagattttgt tatcggcttt attgctcaaa   4020
gagacatggg tggaagagat gaaggttacg attggttgat tatgacaccc ggtgtgggtt   4080
```

-continued

```
tagatgacaa gggagacgca ttgggtcaac agtatagaac cgtggatgat gtggtctcta   4140
caggatctga cattattatt gttggaagag gactatttgc aaagggaagg gatgctaagg   4200
tagagggtga acgttacaga aaagcaggct gggaagcata tttgagaaga tgcggccagc   4260
aaaactaaaa aactgtatta taagtaaatg catgtatact aaactcacaa attagagctt   4320
caatttaatt atatcagtta ttacccggga atctcggtcg taatgatttt tataatgacg   4380
aaaaaaaaaa aattggaaag aaaagccccc cccccccccc cccccccccc cccccccccg   4440
cagcgttggg tcctggccac gggtgcgcat gatcgtgctc ctgtcgttga ggacccggct   4500
aggctggcgg ggttgcctta ctggttagca gaatgaatca ccgatacgcg agcgaacgtg   4560
aagcgactgc tgctgcaaaa cgtctgcgac ctgagcaaca acatgaatgg tcttcggttt   4620
ccgtgtttcg taaagtctgg aaacgcggaa gtcagcgccc tgcaccatta tgttccggat   4680
ctgcatcgca ggatgctgct ggctaccctg tggaacacct acatctgtat taacgaagcg   4740
ctggcattga ccctgagtga tttttctctg gtcccgccgc atccataccg ccagttgttt   4800
accctcacaa cgttccagta accgggcatg ttcatcatca gtaacccgta tcgtgagcat   4860
cctctctcgt ttcatcggta tcattacccc catgaacaga aattccccct tacacggagg   4920
catcaagtga ccaaacagga aaaaaccgcc cttaacatgg cccgctttat cagaagccag   4980
acattaacgc ttctggagaa actcaacgag ctggacgcgg atgaacaggc agacatctgt   5040
gaatcgcttc acgaccacgc tgatgagctt taccgcagct gcctcgcgcg tttcggtgat   5100
gacggtgaaa acctctgaca catgcagctc ccggagacgg tcacagcttg tctgtaagcg   5160
gatgccggga gcagacaagc ccgtcagggc gcgtcagcgg gtgttggcgg gtgtcggggc   5220
gcagccatga cccagtcacg tagcgatagc ggagtgtata ctggcttaac tatgcggcat   5280
cagagcagat tgtactgaga gtgcaccata tgcggtgtga aataccgcac agatgcgtaa   5340
ggagaaaata ccgcatcagg cgctcttccg cttcctcgct cactgactcg ctgcgctcgg   5400
tcgttcggct gcggcgagcg gtatcagctc actcaaaggc ggtaatacgg ttatccacag   5460
aatcagggga taacgcagga aagaacatgt gagcaaaagg ccagcaaaag gccaggaacc   5520
gtaaaaaggc cgcgttgctg gcgtttttcc ataggctccg cccccctgac gagcatcaca   5580
aaaatcgacg ctcaagtcag aggtggcgaa acccgacagg actataaaga taccaggcgt   5640
ttccccctgg aagctccctc gtgcgctctc ctgttccgac cctgccgctt accggatacc   5700
tgtccgcctt tctcccttcg ggaagcgtgg cgctttctca tagctcacgc tgtaggtatc   5760
tcagttcggt gtaggtcgtt cgctccaagc tgggctgtgt gcacgaaccc cccgttcagc   5820
ccgaccgctg cgccttatcc ggtaactatc gtcttgagtc caacccggta agacacgact   5880
tatcgccact ggcagcagcc actggtaaca ggattagcag agcgaggtat gtaggcggtg   5940
ctacagagtt cttgaagtgg tggcctaact acggctacac tagaaggaca gtatttggta   6000
tctgcgctct gctgaagcca gttaccttcg gaaaaagagt tggtagctct tgatccggca   6060
aacaaaccac cgctggtagc ggtggttttt ttgtttgcaa gcagcagatt acgcgcagaa   6120
aaaaaggatc tcaagaagat cctttgatct tttctacggg gtctgacgct cagtggaacg   6180
aaaactcacg ttaagggatt ttggtcatga gattatcaaa aaggatcttc acctagatcc   6240
ttttaaatta aaaatgaagt tttaaatcaa tctaaagtat atatgagtaa acttggtctg   6300
acagttacca atgcttaatc agtgaggcac ctatctcagc gatctgtcta tttcgttcat   6360
ccatagttgc ctgactcccc gtcgtgtaga taactacgat acgggagggc ttaccatctg   6420
```

-continued

```
gccccagtgc tgcaatgata ccgcgagacc cacgctcacc ggctccagat ttatcagcaa   6480

taaaccagcc agccggaagg gccgagcgca gaagtggtcc tgcaacttta tccgcctcca   6540

tccagtctat taattgttgc cgggaagcta gagtaagtag ttcgccagtt aatagtttgc   6600

gcaacgttgt tgccattgct gcaggcatcg tggtgtcacg ctcgtcgttt ggtatggctt   6660

cattcagctc cggttcccaa cgatcaaggc gagttacatg atcccccatg ttgtgcaaaa   6720

aagcggttag ctccttcggt cctccgatcg ttgtcagaag taagttggcc gcagtgttat   6780

cactcatggt tatggcagca ctgcataatt ctcttactgt catgccatcc gtaagatgct   6840

tttctgtgac tggtgagtac tcaaccaagt cattctgaga atagtgtatg cggcgaccga   6900

gttgctcttg cccggcgtca acacgggata ataccgcgcc acatagcaga actttaaaag   6960

tgctcatcat tggaaaacgt tcttcggggc gaaaactctc aaggatctta ccgctgttga   7020

gatccagttc gatgtaaccc actcgtgcac ccaactgatc ttcagcatct tttactttca   7080

ccagcgtttc tgggtgagca aaaacaggaa ggcaaaatgc cgcaaaaaag ggaataaggg   7140

cgacacggaa atgttgaata ctcatactct tcctttttca atattattga agcatttatc   7200

agggttattg tctcatgagc ggatacatat ttgaatgtat ttagaaaaat aaacaaatag   7260

gggttccgcg cacatttccc cgaaaagtgc cacctgacgt ctaagaaacc attattatca   7320

tgacattaac ctataaaaat aggcgtatca cgaggccctt tcgtcttcaa              7370
```

<210> SEQ ID NO 24
<211> LENGTH: 8298
<212> TYPE: DNA
<213> ORGANISM: Artificial Sequence
<220> FEATURE:
<223> OTHER INFORMATION: Description of Artificial Sequence: Vector
      pFMPT-MFalfa-E2-H6 sequence

<400> SEQUENCE: 24

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccagatc tgatagcttt    360

caatcaatga atcgaaaatg tcattaaaat agtatataaa ttgaaactaa gtcataaagc    420

tataaaaaga aaatttattt aaatgcaaga ctttaaagta aattcactta agccttggca    480

acgtgttcaa ccaagtcgag atcgttaatt aactattagt gatggtggtg atggtgtctg    540

ccctcgatca cctgccactc tgttgtagac agcagcagcg agctaagctc tgatctatcc    600

ctgtcctcca agtcacaacg ctctcctcga gtccaattgc atgcggcttc gaacctgtgc    660

tccacgcccc ccacgtacat cctaaccttg aagatggtga agttgacagt gcaggggtag    720

tgccagagcc tatatgggta atgaaccata cacctaggtg tcagccaggg cccagaaccg    780

catctggcgt aagtggcctc ggggtgcttc cgaaaacagt cagtggggca ggtcaaggtg    840

ttgttgccgg cccccccgat gttgcacggg gggcccccac acgtcttggt gaacccagtg    900

ccattcatcc atgtacagcc gaaccagttg cctcgcggcg gccgcgtgtt gttgagaatc    960

agcacatccg agtcgttcgc cccccagtta tacgtgggga caccaaaccg atcggtcgtc   1020

cccaccacaa cagggctcgg ggtgaagcaa tacactggac cgcacacctg agacgcgggt   1080
```

-continued

```
acaataccac acggtcgagg cgcgtagtgc cagcagtagg gcctctggtc cgagctgtta   1140
ggctcagtgt aagtgagggg accccacccc tgagcgaact tgtcgatgga gcgacagctg   1200
gccaagcgct ctgggcatcc agacgagttg aatttgtgtt tgtagaatag tgcggcaaag   1260
aaccctgttt ggagggagtc gttgcagttc agggcagtcc tgttgatgtg ccaactgccg   1320
ttggtgttta cgagctggat tttctgagcc gacccggggc taaagaggga cacaaggccc   1380
ctggtatcgg aggctgctgc ccctcctgac acgcgggtat gccttttatc tagagatacc   1440
ccttcttctt tagcagcaat gctggcaata gtagtattta taaacaataa cccgttattt   1500
gtgctgttgg aaaatggcaa aacagcaaca tcgaaatccc cttctaaatc tgagtaaccg   1560
atgacagctt cagccggaat ttgtgccgtt tcatcttctg ttgtagtgtt gactggagca   1620
gctaatgcgg aggatgctgc gaataaaact gcagtaaaaa ttgaaggaaa tctcatgaat   1680
tcccgatgaa gcagagagcg caggaggcgg tatttatagt gccattcccc tctctgagag   1740
acccggatgg tagtcgagtg tatcggagac agcttgatgt agactccgtg cctgccggct   1800
cctcttattg gcggacacca gtgagacacc ccggaacttg ctgtttttct gcaaaatccg   1860
gggtgaccag tgggagccta tttgcacaca cgagcgggac accccactct ggtgaagagt   1920
gccaaagtca ttctttttcc cgttgcgggg cagccgattg catgttttag gaaaatatta   1980
cctttgctac accctgtcag atttaccctc cacacatata tattccgtca cctccaggga   2040
ctattattcg tcgttgcgcc gccagcggaa gatatccaga agctgttttc cgagagactc   2100
ggttggcgcc tggtatattt gatggatgtc gcgctgcctc acgtcccggt acccaggaac   2160
gcggtgggat ctcgggccca tcgaagactg tgctccagac tgctcgccca gcaggtgttt   2220
cttgatcgcc gcctctaaat tgtccgcgca tcgccggtaa catttttcca gctcggagtt   2280
tgcgtttaga tacagtttct gcgatgccaa aggagcctgc agattataac ctcggatgct   2340
gtcattcagc gcttttaatt tgacctccag atagttgctg tatttctgtt cccattggct   2400
gctgcgcagc ttcgtataac tcgagttatt gttgcgctct gcctcggcgt actggctcat   2460
gatctggatc ttgtccgtgt cgcttttctt cgagtgtttc tcgcaaacga tgtgcacggc   2520
ctgcagtgtc caatcggagt cgagctggcg ccgaaactgg cggatctgag cctccacact   2580
gccctgtttc tctatccacg gcggaaccgc ctcctgccgt ttcagaatgt tgttcaagtg   2640
gtactctgtg cggtcaatga aggcgttatt gccggtgaaa tctttgggaa gcggttttcc   2700
tcggggaaga ttacgaaatt ccccgcgtcg ttgcgcttcc tggatctcga ggagatcgtt   2760
ctccgcgtcg aggagatcgt tctccgcgtc gacaccattc cttgcggcgg cggtgctcaa   2820
cggcctcaac ctactactgg gctgcttcct aatgcaggag tcgcataagg gagagcgtcg   2880
acaaacccgc gtttgagaac ttgctcaagc ttctggtaaa cgttgtagta ctctgaaaca   2940
aggccctagc actctgatct gtttctcttg ggtagcggtg agtggtttat tggagttcac   3000
tggtttcagc acatctgtca tctagacaat attgttacta aattttttttg aactacaatt   3060
gttcgtaatt catctattat tatacatcct cgtcagcaat ttctggcaga cggagtttac   3120
taacgtcttg agtatgaggc cgagaatcca gctctgtggc catactcagt cttgacagcc   3180
tgctgatgtg gctgcgttca acgcaataag cgtgtcctcc gactccgagt tgtgctcgtt   3240
atcgtcgttc tcatcctcgg aaaaatcaca cgaaagaaca tactcaccag taggctttct   3300
ggtccctggg gcacggctgt ttctgacgta ttccggcgtt gataatagct cgaaagtgaa   3360
cgccgagtcg cgggagtcga ccgatgccct tgagagcctt caacccagtc agctccttcc   3420
ggtgggcgcg gggcatgact atcgtcgccg cacttatgac tgtcttcttt atcatgcaac   3480
```

-continued

```
tcgtaggaca ggtgccggca gcgctctggg tcattttcgg cgaggaccgc tttcgctgga   3540
gcgcgacgat gatcggcctg tcgcttgcgg tattcggaat cttgcacgcc ctcgctcaag   3600
ccttcgtcac tggtcccgcc accaaacgtt tcggcgagaa gcaggccatt atcgccggca   3660
tggcggccga cgcgctgggc tacgtcttgc tggcgttcgc gacgcgaggc tggatggcct   3720
tccccattat gattcttctc gcttccggcg gcatcgggat gcccgcgttg caggccatgc   3780
tgtccaggca ggtagatgac gaccatcagg gacagcttca aggatcgctc gcggctctta   3840
ccagcctaac ttcgatcact ggaccgctga tcgtcacggc gatttatgcc gcctcggcga   3900
gcacatggaa cgggttggca tggattgtag gcgccgccct ataccttgtc tgcctccccg   3960
cgttgcgtcg cggtgcatgg agccgggcca cctcgacctg aatggaagcc ggcggcacct   4020
cgctaacgga ttcaccactc caagaattgg agccaatcaa ttcttgcgga gaactgtgaa   4080
tgcgcaaacc aacccttggc agaacatatc catcgcgtcc gccatctcca gcagccgcac   4140
gcggcgcatc gggggggggg gggggggggg ggggcaaaca attcatcatt ttttttttat   4200
tctttttttt gatttcggtt tctttgaaat ttttttgatt cggtaatctc cgaacagaag   4260
gaagaacgaa ggaaggagca cagacttaga ttggtatata tacgcatatg tagtgttgaa   4320
gaaacatgaa attgcccagt attcttaacc caactgcaca gaacaaaaac ctgcaggaaa   4380
cgaagataaa tcatgtcgaa agctacatat aaggaacgtg ctgctactca tcctagtcct   4440
gttgctgcca agctatttaa tatcatgcac gaaaagcaaa caaacttgtg tgcttcattg   4500
gatgttcgta ccaccaagga attactggag ttagttgaag cattaggtcc caaaatttgt   4560
ttactaaaaa cacatgtgga tatcttgact gatttttcca tggagggcac agttaagccg   4620
ctaaaggcat tatccgccaa gtacaatttt ttactcttcg aagacagaaa atttgctgac   4680
attggtaata cagtcaaatt gcagtactct gcgggtgtat acagaatagc agaatgggca   4740
gacattacga atgcacacgg tgtggtgggc ccaggtattg ttagcggttt gaagcaggcg   4800
gcagaagaag taacaaagga acctagaggc cttttgatgt tagcagaatt gtcatgcaag   4860
ggctccctat ctactggaga atatactaag ggtactgttg acattgcgaa gagcgacaaa   4920
gattttgtta tcggctttat tgctcaaaga gacatgggtg gaagagatga aggttacgat   4980
tggttgatta tgacacccgg tgtgggttta gatgacaagg gagacgcatt gggtcaacag   5040
tatagaaccg tggatgatgt ggtctctaca ggatctgaca ttattattgt tggaagagga   5100
ctatttgcaa agggaaggga tgctaaggta gagggtgaac gttacagaaa agcaggctgg   5160
gaagcatatt tgagaagatg cggccagcaa aactaaaaaa ctgtattata agtaaatgca   5220
tgtatactaa actcacaaat tagagcttca atttaattat atcagttatt acccgggaat   5280
ctcggtcgta atgattttta taatgacgaa aaaaaaaaaa ttggaaagaa aagccccccc   5340
cccccccccc cccccccccc cccccccgca gcgttgggtc ctggccacgg gtgcgcatga   5400
tcgtgctcct gtcgttgagg acccggctag gctggcgggg ttgccttact ggttagcaga   5460
atgaatcacc gatacgcgag cgaacgtgaa gcgactgctg ctgcaaaacg tctgcgacct   5520
gagcaacaac atgaatggtc ttcggtttcc gtgtttcgta aagtctggaa acgcggaagt   5580
cagcgccctg caccattatg ttccggatct gcatcgcagg atgctgctgg ctaccctgtg   5640
gaacacctac atctgtatta acgaagcgct ggcattgacc ctgagtgatt tttctctggt   5700
cccgccgcat ccataccgcc agttgtttac cctcacaacg ttccagtaac cgggcatgtt   5760
catcatcagt aacccgtatc gtgagcatcc tctctcgttt catcggtatc attaccccca   5820
```

-continued tgaacagaaa ttcccctta cacggaggca tcaagtgacc aaacaggaaa aaaccgccct 5880
taacatggcc cgctttatca gaagccagac attaacgctt ctggagaaac tcaacgagct 5940
ggacgcggat gaacaggcag acatctgtga atcgcttcac gaccacgctg atgagcttta 6000
ccgcagctgc ctcgcgcgtt tcggtgatga cggtgaaaac ctctgacaca tgcagctccc 6060
ggagacggtc acagcttgtc tgtaagcgga tgccgggagc agacaagccc gtcagggcgc 6120
gtcagcgggt gttggcgggt gtcggggcgc agccatgacc cagtcacgta gcgatagcgg 6180
agtgtatact ggcttaacta tgcggcatca gagcagattg tactgagagt gcaccatatg 6240
cggtgtgaaa taccgcacag atgcgtaagg agaaaatacc gcatcaggcg ctcttccgct 6300
tcctcgctca ctgactcgct gcgctcggtc gttcggctgc ggcgagcggt atcagctcac 6360
tcaaaggcgg taatacggtt atccacagaa tcaggggata acgcaggaaa gaacatgtga 6420
gcaaaaggcc agcaaaaggc caggaaccgt aaaaaggccg cgttgctggc gtttttccat 6480
aggctccgcc cccctgacga gcatcacaaa aatcgacgct caagtcagag gtggcgaaac 6540
ccgacaggac tataaagata ccaggcgttt ccccctggaa gctccctcgt gcgctctcct 6600
gttccgaccc tgccgcttac cggatacctg tccgcctttc tcccttcggg aagcgtggcg 6660
ctttctcata gctcacgctg taggtatctc agttcggtgt aggtcgttcg ctccaagctg 6720
ggctgtgtgc acgaaccccc cgttcagccc gaccgctgcg ccttatccgg taactatcgt 6780
cttgagtcca acccggtaag acacgactta tcgccactgg cagcagccac tggtaacagg 6840
attagcagag cgaggtatgt aggcggtgct acagagttct tgaagtggtg gcctaactac 6900
ggctacacta gaaggacagt atttggtatc tgcgctctgc tgaagccagt taccttcgga 6960
aaaagagttg gtagctcttg atccggcaaa caaaccaccg ctggtagcgg tggttttttt 7020
gtttgcaagc agcagattac gcgcagaaaa aaaggatctc aagaagatcc tttgatcttt 7080
tctacggggt ctgacgctca gtggaacgaa aactcacgtt aagggatttt ggtcatgaga 7140
ttatcaaaaa ggatcttcac ctagatcctt ttaaattaaa aatgaagttt taaatcaatc 7200
taaagtatat atgagtaaac ttggtctgac agttaccaat gcttaatcag tgaggcacct 7260
atctcagcga tctgtctatt tcgttcatcc atagttgcct gactccccgt cgtgtagata 7320
actacgatac gggagggctt accatctggc cccagtgctg caatgatacc gcgagaccca 7380
cgctcaccgg ctccagattt atcagcaata aaccagccag ccggaagggc cgagcgcaga 7440
agtggtcctg caactttatc cgcctccatc cagtctatta attgttgccg ggaagctaga 7500
gtaagtagtt cgccagttaa tagtttgcgc aacgttgttg ccattgctgc aggcatcgtg 7560
gtgtcacgct cgtcgtttgg tatggcttca ttcagctccg gttcccaacg atcaaggcga 7620
gttacatgat cccccatgtt gtgcaaaaaa gcggttagct ccttcggtcc tccgatcgtt 7680
gtcagaagta agttggccgc agtgttatca ctcatggtta tggcagcact gcataattct 7740
cttactgtca tgccatccgt aagatgcttt tctgtgactg gtgagtactc aaccaagtca 7800
ttctgagaat agtgtatgcg gcgaccgagt tgctcttgcc cggcgtcaac acgggataat 7860
accgcgccac atagcagaac tttaaaagtg ctcatcattg gaaaacgttc ttcggggcga 7920
aaactctcaa ggatcttacc gctgttgaga tccagttcga tgtaacccac tcgtgcaccc 7980
aactgatctt cagcatcttt tactttcacc agcgtttctg ggtgagcaaa aacaggaagg 8040
caaaatgccg caaaaaaggg aataagggcg acacggaaat gttgaatact catactcttc 8100
ctttttcaat attattgaag catttatcag ggttattgtc tcatgagcgg atacatattt 8160
gaatgtattt agaaaaataa acaaataggg gttccgcgca catttccccg aaaagtgcca 8220

```
cctgacgtct aagaaaccat tattatcatg acattaacct ataaaaatag gcgtatcacg   8280

aggccctttc gtcttcaa                                                 8298
```

<210> SEQ ID NO 25
<211> LENGTH: 8695
<212> TYPE: DNA
<213> ORGANISM: Artificial Sequence
<220> FEATURE:
<223> OTHER INFORMATION: Description of Artificial Sequence: Vector pMPT-Mfalfa-E2-H6 sequence
<220> FEATURE:
<221> NAME/KEY: modified_base
<222> LOCATION: (2103)
<223> OTHER INFORMATION: Any nucleotide

<400> SEQUENCE: 25

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccagatc tgatagcttt    360

caatcaatga atcgaaaatg tcattaaaat agtatataaa ttgaaactaa gtcataaagc    420

tataaaaaga aaatttattt aaatgcaaga ctttaaagta aattcactta agccttggca    480

acgtgttcaa ccaagtcgag atcgttaatt aactattagt gatggtggtg atggtgtctg    540

ccctcgatca cctgccactc tgttgtagac agcagcagcg agctaagctc tgatctatcc    600

ctgtcctcca agtcacaacg ctctcctcga gtccaattgc atgcggcttc gaacctgtgc    660

tccacgcccc ccacgtacat cctaaccttg aagatggtga agttgacagt gcaggggtag    720

tgccagagcc tatatgggta atgaaccata cacctaggtg tcagccaggg cccagaaccg    780

catctggcgt aagtggcctc ggggtgcttc cgaaaacagt cagtggggca ggtcaaggtg    840

ttgttgccgg cccccccgat gttgcacggg gggcccccac acgtcttggt gaacccagtg    900

ccattcatcc atgtacagcc gaaccagttg cctcgcggcg gccgcgtgtt gttgagaatc    960

agcacatccg agtcgttcgc cccccagtta tacgtgggga caccaaaccg atcggtcgtc   1020

cccaccacaa cagggctcgg ggtgaagcaa tacactggac cgcacacctg agacgcgggt   1080

acaataccac acggtcgagg cgcgtagtgc cagcagtagg gcctctggtc cgagctgtta   1140

ggctcagtgt aagtgagggg accccacccc tgagcgaact tgtcgatgga gcgacagctg   1200

gccaagcgct ctgggcatcc agacgagttg aatttgtgtt tgtagaatag tgcggcaaag   1260

aaccctgttt ggagggagtc gttgcagttc agggcagtcc tgttgatgtg ccaactgccg   1320

ttggtgttta cgagctggat ttctgagccc gacccggggc taaagaggga cacaaggccc   1380

ctggtatcgg aggctgctgc ccctcctgac acgcgggtat gccttttatc tagagatacc   1440

ccttcttctt tagcagcaat gctggcaata gtagtattta taaacaataa cccgttattt   1500

gtgctgttgg aaaatggcaa aacagcaaca tcgaaatccc cttctaaatc tgagtaaccg   1560

atgacagctt cagccggaat ttgtgccgtt tcatcttctg ttgtagtgtt gactggagca   1620

gctaatgcgg aggatgctgc gaataaaact gcagtaaaaa ttgaaggaaa tctcatgaat   1680

tcgtttttgt actttagatt gatgtcacca ccgtgcactg gcagcagtat ttatagatgg   1740

accgtgtggg gacggttggg tacacttagc ggcagcgctg accccatctg tgatcaagta   1800
```

-continued gggcaaaaac tggggatgtc ggagtcgctg cacggtagca taagaattta ctttctggcc 1860
ggttcacccg catttgcact gtggagaaac agcctgtccg acaccccacc agttgccaca 1920
tcggccctct gctgctctgg tgattttctg gtagcaggca cagacagcag tgggtagcgc 1980
cgtccggtta ggcaaggtca cgttgtaggc taccccagca aacagagcct cacatgacac 2040
catccagctg cgtcctcgaa gcgaaaagtt cggttgcggc tgcagaaccc cctcagttgc 2100
canattcaca agttttacgc gacggctaaa gcgagtgggt tttaaaaact tgcggtgcaa 2160
ggatgcatgc ggcaacaatt aattggtgca tccagcacag caagcccagt ctcgagatgt 2220
ccagtcgcta cagagtggag tacgcactca aggaacaccg tcgagatggc ctcatagaat 2280
ggatcaaggg cctgctggcc acgccgttcg tcctgtacgc ggtgaagagc aacggcatct 2340
ctgcagtgga cgacctcatg gtaaactctg aggcaaaacg ccgctacgcg gaaatcttcc 2400
acgacctcga actcctcatc gacgacaaca ttgaaatgac caaagccggc acccccgaat 2460
tgtctcggct cgtgcagctg gttccgagcg ttggcagctt cttcacgaga ctgcctctgg 2520
aaaaggcctt ctacatcgag gacgagcgcc gcgccatcag caaacgccgg cttgtggccc 2580
cctcgttcaa cgacgtccgg ctcattctca acacggccca gctgttggag atgtcgcggt 2640
tcttccattc caaaaccatc cgagatcgca agctgcagct cattacattc gatggtgaca 2700
tcacactgta cgacgacggc aaaaatttcg atgccgagtc gcccatcctg ccccacctca 2760
tcaaactaat ggccaaggac ctctatgtgg gtatcgtcac cgcggccggc tacagcgacg 2820
gaacaagtac tacgagcgcc tcaagggcct catcgacgcc gtccagacgt ccccgctgct 2880
cacaggccac cagaaagaga acctgttcat tatgggcggc gaggcaaact acctcttccg 2940
gtacagtaac gaggagcaga gattacgctt ctactccaaa gacagatggc tgctcgagaa 3000
catgctgaat tggtccgagg aggacattca tctgacactg gactttgcgc aggacgttct 3060
aaacgacctc gttcacaaac tgggctcgcc agccaccgtg gtccgcaagg agcgtcgcgt 3120
cggcctggtt ccattaccgg gccacaagct gatccgcgag cagctcgagg agatcgttct 3180
ccgcgtcgac accattcctt gcggcggcgg tgctcaacgg cctcaaccta ctactgggct 3240
gcttcctaat gcaggagtcg cataagggag agcgtcgact cccgcgactc ggcgttcact 3300
ttcgagctat tatcaacgcc ggaatacgtc agaaacagcc gtgccccagg gaccagaaag 3360
cctactggtg agtatgttct ttcgtgtgat ttttccgagg atgagaacga cgataacgag 3420
cacaactcgg agtcggagga cacgcttatt gcgttgaacg cagccacatc agcaggctgt 3480
caagactgag tatggccaca gagctggatt ctcggcctca tactcaagac gttagtaaac 3540
tccgtctgcc agaaattgct gacgaggatg tataataata gatgaattac gaacaattgt 3600
agttcaaaaa aatttagtaa caatattgtc tagatgacag atgtgctgaa accagtgaac 3660
tccaataaac cactcaccgc tacccaagag aaacagatca gagtgctagg gccttgtttc 3720
agagtactac aacgtttacc agaagcttga gcaagttctc aaacgcgggt ttgtcgaccg 3780
atgcccttga gagccttcaa cccagtcagc tccttccggt gggcgcgggg catgactatc 3840
gtcgccgcac ttatgactgt cttctttatc atgcaactcg taggacaggt gccggcagcg 3900
ctctgggtca ttttcggcga ggaccgcttt cgctggagcg cgacgatgat cggcctgtcg 3960
cttgcggtat tcggaatctt gcacgccctc gctcaagcct tcgtcactgg tcccgccacc 4020
aaacgtttcg gcgagaagca ggccattatc gccggcatgg cggccgacgc gctgggctac 4080
gtcttgctgg cgttcgcgac gcgaggctgg atggccttcc ccattatgat tcttctcgct 4140

-continued tccggcggca tcgggatgcc cgcgttgcag gccatgctgt ccaggcaggt agatgacgac 4200
catcagggac agcttcaagg atcgctcgcg gctcttacca gcctaacttc gatcactgga 4260
ccgctgatcg tcacggcgat ttatgccgcc tcggcgagca catggaacgg gttggcatgg 4320
attgtaggcg ccgccctata ccttgtctgc ctccccgcgt tgcgtcgcgg tgcatggagc 4380
cgggccacct cgacctgaat ggaagccggc ggcacctcgc taacggattc accactccaa 4440
gaattggagc caatcaattc ttgcggagaa ctgtgaatgc gcaaaccaac ccttggcaga 4500
acatatccat cgcgtccgcc atctccagca gccgcacgcg gcgcatcggg gggggggggg 4560
gggggggggg gcaaacaatt catcattttt tttttattct tttttttgat ttcggtttct 4620
ttgaaatttt tttgattcgg taatctccga acagaaggaa gaacgaagga aggagcacag 4680
acttagattg gtatatatac gcatatgtag tgttgaagaa acatgaaatt gcccagtatt 4740
cttaacccaa ctgcacagaa caaaaacctg caggaaacga agataaatca tgtcgaaagc 4800
tacatataag gaacgtgctg ctactcatcc tagtcctgtt gctgccaagc tatttaatat 4860
catgcacgaa aagcaaacaa acttgtgtgc ttcattggat gttcgtacca ccaaggaatt 4920
actggagtta gttgaagcat taggtcccaa aatttgttta ctaaaaacac atgtggatat 4980
cttgactgat tttuccatgg agggcacagt taagccgcta aaggcattat ccgccaagta 5040
caatttttta ctcttcgaag acagaaaatt tgctgacatt ggtaatacag tcaaattgca 5100
gtactctgcg ggtgtataca gaatagcaga atgggcagac attacgaatg cacacggtgt 5160
ggtgggccca ggtattgtta gcggtttgaa gcaggcggca gaagaagtaa caaaggaacc 5220
tagaggcctt ttgatgttag cagaattgtc atgcaagggc tccctatcta ctggagaata 5280
tactaagggt actgttgaca ttgcgaagag cgacaaagat tttgttatcg gctttattgc 5340
tcaaagagac atgggtggaa gagatgaagg ttacgattgg ttgattatga cacccggtgt 5400
gggtttagat gacaagggag acgcattggg tcaacagtat agaaccgtgg atgatgtggt 5460
ctctacagga tctgacatta ttattgttgg aagaggacta tttgcaaagg gaagggatgc 5520
taaggtagag ggtgaacgtt acagaaaagc aggctgggaa gcatatttga gaagatgcgg 5580
ccagcaaaac taaaaaactg tattataagt aaatgcatgt atactaaact cacaaattag 5640
agcttcaatt taattatatc agttattacc cgggaatctc ggtcgtaatg atttttataa 5700
tgacgaaaaa aaaaaaattg gaaagaaaag cccccccccc cccccccccc cccccccccc 5760
ccccgcagcg ttgggtcctg gccacgggtg cgcatgatcg tgctcctgtc gttgaggacc 5820
cggctaggct ggcggggttg ccttactggt tagcagaatg aatcaccgat acgcgagcga 5880
acgtgaagcg actgctgctg caaaacgtct gcgacctgag caacaacatg aatggtcttc 5940
ggtttccgtg tttcgtaaag tctggaaacg cggaagtcag cgccctgcac cattatgttc 6000
cggatctgca tcgcaggatg ctgctggcta ccctgtggaa cacctacatc tgtattaacg 6060
aagcgctggc attgaccctg agtgattttt ctctggtccc gccgcatcca taccgccagt 6120
tgtttaccct cacaacgttc cagtaaccgg gcatgttcat catcagtaac ccgtatcgtg 6180
agcatcctct ctcgtttcat cggtatcatt acccccatga acagaaattc ccccttacac 6240
ggaggcatca agtgaccaaa caggaaaaaa ccgcccttaa catggcccgc tttatcagaa 6300
gccagacatt aacgcttctg gagaaactca acgagctgga cgcggatgaa caggcagaca 6360
tctgtgaatc gcttcacgac cacgctgatg agctttaccg cagctgcctc gcgcgtttcg 6420
gtgatgacgg tgaaaacctc tgacacatgc agctcccgga gacggtcaca gcttgtctgt 6480
aagcggatgc cgggagcaga caagcccgtc agggcgcgtc agcgggtgtt ggcgggtgtc 6540

-continued

```
ggggcgcagc catgacccag tcacgtagcg atagcggagt gtatactggc ttaactatgc   6600
ggcatcagag cagattgtac tgagagtgca ccatatgcgg tgtgaaatac cgcacagatg   6660
cgtaaggaga aaataccgca tcaggcgctc ttccgcttcc tcgctcactg actcgctgcg   6720
ctcggtcgtt cggctgcggc gagcggtatc agctcactca aaggcggtaa tacggttatc   6780
cacagaatca ggggataacg caggaaagaa catgtgagca aaaggccagc aaaaggccag   6840
gaaccgtaaa aaggccgcgt tgctggcgtt tttccatagg ctccgccccc ctgacgagca   6900
tcacaaaaat cgacgctcaa gtcagaggtg gcgaaacccg acaggactat aaagatacca   6960
ggcgtttccc cctggaagct ccctcgtgcg ctctcctgtt ccgaccctgc cgcttaccgg   7020
atacctgtcc gcctttctcc cttcgggaag cgtggcgctt tctcatagct cacgctgtag   7080
gtatctcagt tcggtgtagg tcgttcgctc caagctgggc tgtgtgcacg aaccccccgt   7140
tcagcccgac cgctgcgcct tatccggtaa ctatcgtctt gagtccaacc cggtaagaca   7200
cgacttatcg ccactggcag cagccactgg taacaggatt agcagagcga ggtatgtagg   7260
cggtgctaca gagttcttga agtggtggcc taactacggc tacactagaa ggacagtatt   7320
tggtatctgc gctctgctga agccagttac cttcggaaaa agagttggta gctcttgatc   7380
cggcaaacaa accaccgctg gtagcggtgg tttttttgtt tgcaagcagc agattacgcg   7440
cagaaaaaaa ggatctcaag aagatccttt gatcttttct acggggtctg acgctcagtg   7500
gaacgaaaac tcacgttaag ggattttggt catgagatta tcaaaaagga tcttcaccta   7560
gatcctttta aattaaaaat gaagttttaa atcaatctaa agtatatatg agtaaacttg   7620
gtctgacagt taccaatgct taatcagtga ggcacctatc tcagcgatct gtctatttcg   7680
ttcatccata gttgcctgac tccccgtcgt gtagataact acgatacggg agggcttacc   7740
atctggcccc agtgctgcaa tgataccgcg agacccacgc tcaccggctc cagatttatc   7800
agcaataaac cagccagccg gaagggccga gcgcagaagt ggtcctgcaa ctttatccgc   7860
ctccatccag tctattaatt gttgccggga agctagagta agtagttcgc cagttaatag   7920
tttgcgcaac gttgttgcca ttgctgcagg catcgtggtg tcacgctcgt cgtttggtat   7980
ggcttcattc agctccggtt cccaacgatc aaggcgagtt acatgatccc ccatgttgtg   8040
caaaaaagcg gttagctcct tcggtcctcc gatcgttgtc agaagtaagt tggccgcagt   8100
gttatcactc atggttatgg cagcactgca taattctctt actgtcatgc catccgtaag   8160
atgcttttct gtgactggtg agtactcaac caagtcattc tgagaatagt gtatgcggcg   8220
accgagttgc tcttgcccgg cgtcaacacg ggataatacc gcgccacata gcagaacttt   8280
aaaagtgctc atcattggaa aacgttcttc ggggcgaaaa ctctcaagga tcttaccgct   8340
gttgagatcc agttcgatgt aacccactcg tgcacccaac tgatcttcag catcttttac   8400
tttcaccagc gtttctgggt gagcaaaaac aggaaggcaa aatgccgcaa aaaagggaat   8460
aagggcgaca cggaaatgtt gaatactcat actcttcctt tttcaatatt attgaagcat   8520
ttatcagggt tattgtctca tgagcggata catatttgaa tgtatttaga aaaataaaca   8580
aataggggtt ccgcgcacat ttccccgaaa agtgccacct gacgtctaag aaaccattat   8640
tatcatgaca ttaacctata aaaataggcg tatcacgagg ccctttcgtc ttcaa        8695
```

<210> SEQ ID NO 26
<211> LENGTH: 36
<212> TYPE: DNA
<213> ORGANISM: Artificial Sequence
<220> FEATURE:

-continued

<223> OTHER INFORMATION: Description of Artificial Sequence: Synthetic probe or primer

<400> SEQUENCE: 26
agtcactctt caaggcatac ccgcgtgtca ggaggg 36

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 27
agtcactctt cacagggatc cttagtgatg gtggtgatg 39

<210> SEQ ID NO 28
<211> LENGTH: 4190
<212> TYPE: DNA
<213> ORGANISM: Artificial Sequence
<220> FEATURE:
<223> OTHER INFORMATION: Description of Artificial Sequence: Vector pMF30 sequence

<400> SEQUENCE: 28
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag ttgattgcag atgccagatc ccgaaagaac agaggacgga gcgtaaactt 300
gtggcattcc accagaaatt gatacagata agcttccgga gtcaccagct aaaacggaat 360
tgcaagaaat aatatcgata actttatcac cactagaata gccggtgttg ctgacagtaa 420
tatcctgtga cccgtttgaa cctaaattat taaaaatgga aatcaattga ttagcatcgc 480
tacccttcct agtggctata tagtggtctg aagaagaaac aactgaggat ttgtaagttg 540
aataggcaga atccttctta atagcttgat ttcttatttg atttagttta ctgattagct 600
cgtagtattc tgaatcggta ttatatccac ttaaccataa agcttctcta ttggcaggat 660
cggaaccacc attgagacct tgttcttggc cataataaat aattgggata ccatcaccca 720
aaattataaa agccatgtca ttcttaatca aggatgtgtc tgaggtaact gatggaaatc 780
taacttggtc atggttttca ataaagtttc ccaacaaaga gacgtccgaa caagatgact 840
gtaacgtgga gatcattgaa gttaactcac tggaagtcgc cgaagtatca ctgaagaatc 900
tatatactgg atagtataat ggatagttgg taactccttt catataattc tgatatggac 960
aagtataagt tggatctcct tgataaactt cacctaagtt ataaacacca gaagcgtcct 1020
caaacttcgt taatgaagcg gtatctacgt gctttgcact atcaattctt aaaccatcga 1080
ttgaatagtt ttgaacaaaa tctgacaccc aagtttgaaa tactcctata acttcattat 1140
cctcggtact taaatctgga agggagactt cagtatcacc ttcccaacaa tcttcaacat 1200
tggtttgatc attataattt gtaatcaaac aataatcgtg gaagtaagat tgttgattga 1260
atggagtgaa actagaataa tctacgcttg aaccatctcc gttccaagca taatggttgt 1320
aaacaacgtc gaccatcaat aacatgcttc tggaatgcaa ttcgctagct aattgtttca 1380
attcatcagc ggtaccaaaa ttagtgttca attcatcaat atttttcatc caataaccat 1440

-continued

```
ggtaagcata accataagca gtattgtcag gaatttgctc aacaactggg gagatccaga   1500
tcgcagtgaa acccatacct tgaatataat ccaacttgtc gataatccct ttataagatc   1560
caccacagta cttgcgatca ctcactaaac agtcagctgt ggtcgagcca tcagatctgg   1620
caaacctatc agtaacgatt tgataaatcg attggtcttt ccatttatca gctgacgagc   1680
taacatccct cttgtcaaaa ataatcggtt gagcagatac caatcttgag aatgctaaaa   1740
ttgctgcaac aactttactt gtaaatcctt cagttgaaaa tctcattgaa ttcactggcc   1800
gtcgttttac aacgtcgtga ctgggaaaac cctggcgtta cccaacttaa tcgccttgca   1860
gcacatcccc ctttcgccag ctggcgtaat agcgaagagg cccgcaccga tcgcccttcc   1920
caacagttgc gcagcctgaa tggcgaatgg cgcctgatgc ggtattttct ccttacgcat   1980
ctgtgcggta tttcacaccg catatggtgc actctcagta caatctgctc tgatgccgca   2040
tagttaagcc agccccgaca cccgccaaca cccgctgacg cgccctgacg ggcttgtctg   2100
ctcccggcat ccgcttacag acaagctgtg accgtctccg ggagctgcat gtgtcagagg   2160
ttttcaccgt catcaccgaa acgcgcgaga cgaaagggcc tcgtgatacg cctattttta   2220
taggttaatg tcatgataat aatggtttct tagacgtcag gtggcacttt tcggggaaat   2280
gtgcgcggaa cccctatttg tttatttttc taaatacatt caaatatgta tccgctcatg   2340
agacaataac cctgataaat gcttcaataa tattgaaaaa ggaagagtat gagtattcaa   2400
catttccgtg tcgcccttat tccctttttt gcggcatttt gccttcctgt ttttgctcac   2460
ccagaaacgc tggtgaaagt aaaagatgct gaagatcagt tgggtgcacg agtgggttac   2520
atcgaactgg atctcaacag cggtaagatc cttgagagtt ttcgccccga agaacgtttt   2580
ccaatgatga gcacttttaa agttctgcta tgtggcgcgg tattatcccg tattgacgcc   2640
gggcaagagc aactcggtcg ccgcatacac tattctcaga atgacttggt tgagtactca   2700
ccagtcacag aaaagcatct tacggatggc atgacagtaa gagaattatg cagtgctgcc   2760
ataaccatga gtgataacac tgcggccaac ttacttctga caacgatcgg aggaccgaag   2820
gagctaaccg cttttttgca caacatgggg gatcatgtaa ctcgccttga tcgttgggaa   2880
ccggagctga atgaagccat accaaacgac gagcgtgaca ccacgatgcc tgtagcaatg   2940
gcaacaacgt tgcgcaaact attaactggc gaactactta ctctagcttc ccggcaacaa   3000
ttaatagact ggatggaggc ggataaagtt gcaggaccac ttctgcgctc ggcccttccg   3060
gctggctggt ttattgctga taaatctgga gccggtgagc gtgggtctcg cggtatcatt   3120
gcagcactgg ggccagatgg taagccctcc cgtatcgtag ttatctacac gacggggagt   3180
caggcaacta tggatgaacg aaatagacag atcgctgaga taggtgcctc actgattaag   3240
cattggtaac tgtcagacca agtttactca tatatacttt agattgattt aaaacttcat   3300
ttttaattta aaaggatcta ggtgaagatc ctttttgata atctcatgac caaaatccct   3360
taacgtgagt tttcgttcca ctgagcgtca gaccccgtag aaaagatcaa aggatcttct   3420
tgagatcctt tttttctgcg cgtaatctgc tgcttgcaaa caaaaaaacc accgctacca   3480
gcggtggttt gtttgccgga tcaagagcta ccaactcttt ttccgaaggt aactggcttc   3540
agcagagcgc agataccaaa tactgtcctt ctagtgtagc cgtagttagg ccaccacttc   3600
aagaactctg tagcaccgcc tacatacctc gctctgctaa tcctgttacc agtggctgct   3660
gccagtggcg ataagtcgtg tcttaccggg ttggactcaa gacgatagtt accggataag   3720
gcgcagcggt cgggctgaac ggggggttcg tgcacacagc ccagcttgga gcgaacgacc   3780
tacaccgaac tgagatacct acagcgtgag ctatgagaaa gcgccacgct tcccgaaggg   3840
```

-continued agaaaggcgg acaggtatcc ggtaagcggc agggtcggaa caggagagcg cacgagggag 3900
cttccagggg gaaacgcctg gtatctttat agtcctgtcg ggtttcgcca cctctgactt 3960
gagcgtcgat ttttgtgatg ctcgtcaggg gggcggagcc tatggaaaaa cgccagcaac 4020
gcggcctttt tacggttcct ggccttttgc tggccttttg ctcacatgtt ctttcctgcg 4080
ttatcccctg attctgtgga taaccgtatt accgcctttg agtgagctga taccgctcgc 4140
cgcagccgaa cgaccgagcg cagcgagtca gtgagcgagg aagcggaaga 4190

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
primer MF30-Links

<400> SEQUENCE: 29
agtcactctt cacctcttgt caaaaataat cggttgag 38

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
primer CL2 hin

<400> SEQUENCE: 30
tgcttcctac cactagcagc actaggacat acccgcgtgt caggaggggc ag 52

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic
probe or primer

<400> SEQUENCE: 31
tagtactagt attagtaggc ttcgcatgga attcactggc cgtcgtttta caacgtc 57

<210> SEQ ID NO 32
<211> LENGTH: 7927
<212> TYPE: DNA
<213> ORGANISM: Artificial Sequence
<220> FEATURE:
<223> OTHER INFORMATION: Description of Artificial Sequence: Vector
pFMPT-CL-E2-H6 sequence

<400> SEQUENCE: 32
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccttagt gatggtggtg 360
atggtgtctg ccctcgatca cctgccactc tgttgtagac agcagcagcg agctaagctc 420
tgatctatcc ctgtcctcca agtcacaacg ctctcctcga gtccaattgc atgcggcttc 480

-continued

```
gaacctgtgc tccacgcccc ccacgtacat cctaaccttg aagatggtga agttgacagt    540
gcaggggtag tgccagagcc tatatgggta atgaaccata cacctaggtg tcagccaggg    600
cccagaaccg catctggcgt aagtggcctc ggggtgcttc cgaaaacagt cagtggggca    660
ggtcaaggtg ttgttgccgg ccccccccgat gttgcacggg gggcccccac acgtcttggt    720
gaacccagtg ccattcatcc atgtacagcc gaaccagttg cctcgcggcg gccgcgtgtt    780
gttgagaatc agcacatccg agtcgttcgc cccccagtta tacgtgggga caccaaaccg    840
atcggtcgtc cccaccacaa cagggctcgg ggtgaagcaa tacactggac cgcacacctg    900
agacgcgggt acaataccac acggtcgagg cgcgtagtgc cagcagtagg gcctctggtc    960
cgagctgtta ggctcagtgt aagtgagggg accccacccc tgagcgaact tgtcgatgga   1020
gcgacagctg gccaagcgct ctgggcatcc agacgagttg aatttgtgtt tgtagaatag   1080
tgcggcaaag aaccctgttt ggagggagtc gttgcagttc agggcagtcc tgttgatgtg   1140
ccaactgccg ttggtgttta cgagctggat tttctgagcc gacccggggc taaagaggga   1200
cacaaggccc ctggtatcgg aggctgctgc ccctcctgac acgcgggtat gtcctagtgc   1260
tgctagtggt aggaagcata gtactagtat tagtaggctg cgcatgaatt cccgatgaag   1320
cagagagcgc aggaggcggt atttatagtg ccattcccct ctctgagaga cccggatggt   1380
agtcgagtgt atcggagaca gcttgatgta gactccgtgc ctgccggctc ctcttattgg   1440
cggacaccag tgagacaccc cggaacttgc tgtttttctg caaaatccgg ggtgaccagt   1500
gggagcctat ttgcacacac gagcgggaca ccccactctg gtgaagagtg ccaaagtcat   1560
tctttttccc gttgcggggc agccgattgc atgttttagg aaaatattac ctttgctaca   1620
ccctgtcaga tttaccctcc acacatatat attccgtcac ctccagggac tattattcgt   1680
cgttgcgccg ccagcggaag atatccagaa gctgttttcc gagagactcg gttggcgcct   1740
ggtatatttg atggatgtcg cgctgcctca cgtcccggta cccaggaacg cggtgggatc   1800
tcgggcccat cgaagactgt gctccagact gctcgcccag caggtgtttc ttgatcgccg   1860
cctctaaatt gtccgcgcat cgccggtaac atttttccag ctcggagttt gcgtttagat   1920
acagtttctg cgatgccaaa ggagcctgca gattataacc tcggatgctg tcattcagcg   1980
cttttaattt gacctccaga tagttgctgt atttctgttc ccattggctg ctgcgcagct   2040
tcgtataact cgagttattg ttgcgctctg cctcggcgta ctggctcatg atctggatct   2100
tgtccgtgtc gcttttcttc gagtgtttct cgcaaacgat gtgcacggcc tgcagtgtcc   2160
aatcggagtc gagctggcgc cgaaactggc ggatctgagc ctccacactg ccctgtttct   2220
ctatccacgg cggaaccgcc tcctgccgtt tcagaatgtt gttcaagtgg tactctgtgc   2280
ggtcaatgaa ggcgttattg ccggtgaaat ctttgggaag cggttttcct cggggaagat   2340
tacgaaattc cccgcgtcgt tgcgcttcct ggatctcgag gagatcgttc tccgcgtcga   2400
ggagatcgtt ctccgcgtcg acaccattcc ttgcggcggc ggtgctcaac ggcctcaacc   2460
tactactggg ctgcttccta atgcaggagt cgcataaggg agagcgtcga caaacccgcg   2520
tttgagaact tgctcaagct tctggtaaac gttgtagtac tctgaaacaa ggccctagca   2580
ctctgatctg tttctcttgg gtagcggtga gtggtttatt ggagttcact ggtttcagca   2640
catctgtcat ctagacaata ttgttactaa attttttga actacaattg ttcgtaattc    2700
atctattatt atacatcctc gtcagcaatt tctggcagac ggagtttact aacgtcttga   2760
gtatgaggcc gagaatccag ctctgtggcc atactcagtc ttgacagcct gctgatgtgg   2820
ctgcgttcaa cgcaataagc gtgtcctccg actccgagtt gtgctcgtta tcgtcgttct   2880
```

-continued

```
catcctcgga aaaatcacac gaaagaacat actcaccagt aggctttctg gtccctgggg   2940
cacggctgtt tctgacgtat tccggcgttg ataatagctc gaaagtgaac gccgagtcgc   3000
gggagtcgac cgatgccctt gagagccttc aacccagtca gctccttccg gtgggcgcgg   3060
ggcatgacta tcgtcgccgc acttatgact gtcttcttta tcatgcaact cgtaggacag   3120
gtgccggcag cgctctgggt cattttcggc gaggaccgct ttcgctggag cgcgacgatg   3180
atcggcctgt cgcttgcggt attcggaatc ttgcacgccc tcgctcaagc cttcgtcact   3240
ggtcccgcca ccaaacgttt cggcgagaag caggccatta tcgccggcat ggcggccgac   3300
gcgctgggct acgtcttgct ggcgttcgcg acgcgaggct ggatggcctt ccccattatg   3360
attcttctcg cttccggcgg catcgggatg cccgcgttgc aggccatgct gtccaggcag   3420
gtagatgacg accatcaggg acagcttcaa ggatcgctcg cggctcttac cagcctaact   3480
tcgatcactg gaccgctgat cgtcacggcg atttatgccg cctcggcgag cacatggaac   3540
gggttggcat ggattgtagg cgccgcccta taccttgtct gcctccccgc gttgcgtcgc   3600
ggtgcatgga gccgggccac ctcgacctga atggaagccg gcggcacctc gctaacggat   3660
tcaccactcc aagaattgga gccaatcaat tcttgcggag aactgtgaat gcgcaaacca   3720
acccttggca gaacatatcc atcgcgtccg ccatctccag cagccgcacg cggcgcatcg   3780
gggggggggg gggggggggg gggcaaacaa ttcatcattt tttttttatt cttttttttg   3840
atttcggttt ctttgaaatt tttttgattc ggtaatctcc gaacagaagg aagaacgaag   3900
gaaggagcac agacttagat tggtatatat acgcatatgt agtgttgaag aaacatgaaa   3960
ttgcccagta ttcttaaccc aactgcacag aacaaaaacc tgcaggaaac gaagataaat   4020
catgtcgaaa gctacatata aggaacgtgc tgctactcat cctagtcctg ttgctgccaa   4080
gctatttaat atcatgcacg aaaagcaaac aaacttgtgt gcttcattgg atgttcgtac   4140
caccaaggaa ttactggagt tagttgaagc attaggtccc aaaatttgtt tactaaaaac   4200
acatgtggat atcttgactg atttttccat ggagggcaca gttaagccgc taaaggcatt   4260
atccgccaag tacaattttt tactcttcga agacagaaaa tttgctgaca ttggtaatac   4320
agtcaaattg cagtactctg cgggtgtata cagaatagca gaatgggcag acattacgaa   4380
tgcacacggt gtggtgggcc caggtattgt tagcggtttg aagcaggcgg cagaagaagt   4440
aacaaaggaa cctagaggcc ttttgatgtt agcagaattg tcatgcaagg gctccctatc   4500
tactggagaa tatactaagg gtactgttga cattgcgaag agcgacaaag attttgttat   4560
cggctttatt gctcaaagag acatgggtgg aagagatgaa ggttacgatt ggttgattat   4620
gacacccggt gtgggtttag atgacaaggg agacgcattg ggtcaacagt atagaaccgt   4680
ggatgatgtg gtctctacag gatctgacat tattattgtt ggaagaggac tatttgcaaa   4740
gggaagggat gctaaggtag agggtgaacg ttacagaaaa gcaggctggg aagcatattt   4800
gagaagatgc ggccagcaaa actaaaaaac tgtattataa gtaaatgcat gtatactaaa   4860
ctcacaaatt agagcttcaa tttaattata tcagttatta cccgggaatc tcggtcgtaa   4920
tgatttttat aatgacgaaa aaaaaaaaat tggaaagaaa agcccccccc cccccccccc   4980
cccccccccc ccccccgcag cgttgggtcc tggccacggg tgcgcatgat cgtgctcctg   5040
tcgttgagga cccggctagg ctggcggggt tgccttactg gttagcagaa tgaatcaccg   5100
atacgcgagc gaacgtgaag cgactgctgc tgcaaaacgt ctgcgacctg agcaacaaca   5160
tgaatggtct tcggtttccg tgtttcgtaa agtctggaaa cgcggaagtc agcgccctgc   5220
```

-continued

```
accattatgt tccggatctg catcgcagga tgctgctggc taccctgtgg aacacctaca   5280
tctgtattaa cgaagcgctg gcattgaccc tgagtgattt ttctctggtc ccgccgcatc   5340
cataccgcca gttgtttacc ctcacaacgt tccagtaacc gggcatgttc atcatcagta   5400
acccgtatcg tgagcatcct ctctcgtttc atcggtatca ttacccccat gaacagaaat   5460
tcccccttac acggaggcat caagtgacca aacaggaaaa aaccgccctt aacatggccc   5520
gctttatcag aagccagaca ttaacgcttc tggagaaact caacgagctg gacgcggatg   5580
aacaggcaga catctgtgaa tcgcttcacg accacgctga tgagctttac cgcagctgcc   5640
tcgcgcgttt cggtgatgac ggtgaaaacc tctgacacat gcagctcccg gagacggtca   5700
cagcttgtct gtaagcggat gccgggagca gacaagcccg tcagggcgcg tcagcgggtg   5760
ttggcgggtg tcggggcgca gccatgaccc agtcacgtag cgatagcgga gtgtatactg   5820
gcttaactat gcggcatcag agcagattgt actgagagtg caccatatgc ggtgtgaaat   5880
accgcacaga tgcgtaagga gaaaataccg catcaggcgc tcttccgctt cctcgctcac   5940
tgactcgctg cgctcggtcg ttcggctgcg gcgagcggta tcagctcact caaaggcggt   6000
aatacggtta tccacagaat caggggataa cgcaggaaag aacatgtgag caaaaggcca   6060
gcaaaaggcc aggaaccgta aaaaggccgc gttgctggcg tttttccata ggctccgccc   6120
ccctgacgag catcacaaaa atcgacgctc aagtcagagg tggcgaaacc cgacaggact   6180
ataaagatac caggcgtttc cccctggaag ctccctcgtg cgctctcctg ttccgaccct   6240
gccgcttacc ggatacctgt ccgcctttct cccttcggga agcgtggcgc tttctcatag   6300
ctcacgctgt aggtatctca gttcggtgta ggtcgttcgc tccaagctgg gctgtgtgca   6360
cgaacccccc gttcagcccg accgctgcgc cttatccggt aactatcgtc ttgagtccaa   6420
cccggtaaga cacgacttat cgccactggc agcagccact ggtaacagga ttagcagagc   6480
gaggtatgta ggcggtgcta cagagttctt gaagtggtgg cctaactacg gctacactag   6540
aaggacagta tttggtatct gcgctctgct gaagccagtt accttcggaa aaagagttgg   6600
tagctcttga tccggcaaac aaaccaccgc tggtagcggt ggtttttttg tttgcaagca   6660
gcagattacg cgcagaaaaa aaggatctca agaagatcct ttgatctttt ctacggggtc   6720
tgacgctcag tggaacgaaa actcacgtta agggattttg gtcatgagat tatcaaaaag   6780
gatcttcacc tagatccttt taaattaaaa atgaagtttt aaatcaatct aaagtatata   6840
tgagtaaact tggtctgaca gttaccaatg cttaatcagt gaggcaccta tctcagcgat   6900
ctgtctattt cgttcatcca tagttgcctg actccccgtc gtgtagataa ctacgatacg   6960
ggagggctta ccatctggcc ccagtgctgc aatgataccg cgagacccac gctcaccggc   7020
tccagattta tcagcaataa accagccagc cggaagggcc gagcgcagaa gtggtcctgc   7080
aactttatcc gcctccatcc agtctattaa ttgttgccgg gaagctagag taagtagttc   7140
gccagttaat agtttgcgca acgttgttgc cattgctgca ggcatcgtgg tgtcacgctc   7200
gtcgtttggt atggcttcat tcagctccgg ttcccaacga tcaaggcgag ttacatgatc   7260
ccccatgttg tgcaaaaaag cggttagctc cttcggtcct ccgatcgttg tcagaagtaa   7320
gttggccgca gtgttatcac tcatggttat ggcagcactg cataattctc ttactgtcat   7380
gccatccgta agatgctttt ctgtgactgg tgagtactca accaagtcat tctgagaata   7440
gtgtatgcgg cgaccgagtt gctcttgccc ggcgtcaaca cgggataata ccgcgccaca   7500
tagcagaact ttaaaagtgc tcatcattgg aaaacgttct tcggggcgaa aactctcaag   7560
gatcttaccg ctgttgagat ccagttcgat gtaacccact cgtgcaccca actgatcttc   7620
```

-continued

```
agcatctttt actttcacca gcgtttctgg gtgagcaaaa acaggaaggc aaaatgccgc   7680

aaaaaaggga ataagggcga cacggaaatg ttgaatactc atactcttcc tttttcaata   7740

ttattgaagc atttatcagg gttattgtct catgagcgga tacatatttg aatgtattta   7800

gaaaaataaa caaatagggg ttccgcgcac atttccccga aaagtgccac ctgacgtcta   7860

agaaaccatt attatcatga cattaaccta taaaaatagg cgtatcacga ggccctttcg   7920

tcttcaa                                                             7927
```

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 33

```
taaggatccc cgggtaccga gctc                                            24
```

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 34

```
ccagttcatc atcatatccc aagcc                                           25
```

<210> SEQ ID NO 35
<211> LENGTH: 4234
<212> TYPE: DNA
<213> ORGANISM: Artificial Sequence
<220> FEATURE:
<223> OTHER INFORMATION: Description of Artificial Sequence: Vector pUC18-FMD-CL-E1 sequence
<220> FEATURE:
<221> NAME/KEY: modified_base
<222> LOCATION: (988)..(989)
<223> OTHER INFORMATION: Any nucleotide
<220> FEATURE:
<221> NAME/KEY: modified_base
<222> LOCATION: (1167)..(1168)
<223> OTHER INFORMATION: Any nucleotide

<400> SEQUENCE: 35

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtacccgg ggatccttac cagttcatca tcatatccca agccatacgg tgacctgtta    300

tgtggccggg atagattgag caattgcagt cctgcaccgt ctcatgccgg cgaggcgaga    360

tggtgaacag ctgggagacg aggaagacag atccgcagag atcccccacg tacatagcgg    420

aacagaaagc agccgcccca acgagcaaat cgacgtggcg tcgtattgtc gtagtgggga    480

cgctggcgtt cctagctgcg agcgtggggg tgagcgctac ccagcagcgg gaagagttgt    540

tctcccgaac gcagggcacg cacccggggg tgtgcatgat catgtccgct gcctcataca    600

caatgcttga gttggagcag tcgttcgtga catggtacat cccggacacg ttgcgcacct    660
```

-continued catatcctag tgctgctagt ggtaggaagc atagtactag tattagtagg cttcgcatga 720
attcccgatg aaggcagaga gcgcaaggag gcggtattta tagtgccatt cccctctctg 780
agagacccgg atggtagtcg agtgttatcg gagacagctt gatgtagact ccgtgcctgc 840
cggtcctctt attggcggac accagtgaga caccccggaa cttgctgttt ttctgcaaaa 900
tccggggtga ccagtgggag cctatttgca cacacgagcg ggacacccca ctctggtgaa 960
gagtgccaaa gtcattcttt ttcccgtnnc ggggcagccg attgcatgtt ttaggaaaat 1020
attacctttg ctacaccctg tcagatttac cctccacaca tatatattcc gtcacctcca 1080
gggactattc ttggctcgtt gcgccgccgc ggaagatatc cagaagctgt gttttccgag 1140
agactcggtt ggcgcctggt atatttnnag gatgtcgcgc tgcctcacgt cccggtaccc 1200
aggaacgcgg tgggatctcg ggcccatcga agactgtgct ccagactgct cgcccagcag 1260
gtgtttcttg attgccgcct ctaaatagtc cgcgcatcgc cggtaacatt tttccagctc 1320
ggagtttgcg tttagataca tttctgcgat gccaaaggag cctgcagatt ataacctcgg 1380
atgctgtcat tcagcgcttt taatttgacc tccagatagt tgctgtattt ctgttccatt 1440
ggctgctgga cgttcgtata actcgagtta ttgttgcgct ctgcctcggc gtactggctc 1500
atgactgact gcggtcgctt ctcgagtgtt ctcgcaacag gacgcctgca ggtcatcgag 1560
tcgagctggc gccgaaactg gcggatctga cctccacact gccctgtatc tctatccacc 1620
gggaaccgcc tcctgccgtt ccagaatgtt gttcaagtgg tagctctgtg cggtcaatga 1680
aggcgttatt gccggtgaaa tctttgggaa gcggtttatc ctcggggaag attacgaaat 1740
tcccgcgcgt cgttgcgctt cctggatctc gaggaagatc gttctccgcg tcgaggagat 1800
cgttctccgc gtcgacctgc aggcatgcaa gcttggcact ggccgtcgtt ttacaacgtc 1860
gtgactggga aaaccctggc gttacccaac ttaatcgcct tgcagcacat ccccctttcg 1920
ccagctggcg taatagcgaa gaggcccgca ccgatcgccc ttcccaacag ttgcgcagcc 1980
tgaatggcga atggcgcctg atgcggtatt ttctccttac gcatctgtgc ggtatttcac 2040
accgcatatg gtgcactctc agtacaatct gctctgatgc cgcatagtta agccagcccc 2100
gacacccgcc aacacccgct gacgcgccct gacgggcttg tctgctcccg gcatccgctt 2160
acagacaagc tgtgaccgtc tccgggagct gcatgtgtca gaggttttca ccgtcatcac 2220
cgaaacgcgc gagacgaaag ggcctcgtga tacgcctatt tttataggtt aatgtcatga 2280
taataatggt ttcttagacg tcaggtggca cttttcgggg aaatgtgcgc ggaaccccta 2340
tttgtttatt tttctaaata cattcaaata tgtatccgct catgagacaa taaccctgat 2400
aaatgcttca ataatattga aaaaggaaga gtatgagtat tcaacatttc cgtgtcgccc 2460
ttattccctt ttttgcggca ttttgccttc ctgtttttgc tcacccagaa acgctggtga 2520
aagtaaaaga tgctgaagat cagttgggtg cacgagtggg ttacatcgaa ctggatctca 2580
acagcggtaa gatccttgag agttttcgcc ccgaagaacg ttttccaatg atgagcactt 2640
ttaaagttct gctatgtggc gcggtattat cccgtattga cgccgggcaa gagcaactcg 2700
gtcgccgcat acactattct cagaatgact tggttgagta ctcaccagtc acagaaaagc 2760
atcttacgga tggcatgaca gtaagagaat tatgcagtgc tgccataacc atgagtgata 2820
acactgcggc caacttactt ctgacaacga tcggaggacc gaaggagcta accgcttttt 2880
tgcacaacat gggggatcat gtaactcgcc ttgatcgttg ggaaccggag ctgaatgaag 2940
ccataccaaa cgacgagcgt gacaccacga tgcctgtagc aatggcaaca acgttgcgca 3000

-continued

```
aactattaac tggcgaacta cttactctag cttcccggca acaattaata gactggatgg   3060
aggcggataa agttgcagga ccacttctgc gctcggccct tccggctggc tggtttattg   3120
ctgataaatc tggagccggt gagcgtgggt ctcgcggtat cattgcagca ctggggccag   3180
atggtaagcc ctcccgtatc gtagttatct acacgacggg gagtcaggca actatggatg   3240
aacgaaatag acagatcgct gagataggtg cctcactgat taagcattgg taactgtcag   3300
accaagttta ctcatatata ctttagattg atttaaaact tcatttttaa tttaaaagga   3360
tctaggtgaa gatccttttt gataatctca tgaccaaaat cccttaacgt gagttttcgt   3420
tccactgagc gtcagacccc gtagaaaaga tcaaaggatc ttcttgagat cctttttttc   3480
tgcgcgtaat ctgctgcttg caaacaaaaa aaccaccgct accagcggtg gtttgtttgc   3540
cggatcaaga gctaccaact ctttttccga aggtaactgg cttcagcaga gcgcagatac   3600
caaatactgt ccttctagtg tagccgtagt taggccacca cttcaagaac tctgtagcac   3660
cgcctacata cctcgctctg ctaatcctgt taccagtggc tgctgccagt ggcgataagt   3720
cgtgtcttac cgggttggac tcaagacgat agttaccgga taaggcgcag cggtcgggct   3780
gaacgggggg ttcgtgcaca cagcccagct tggagcgaac gacctacacc gaactgagat   3840
acctacagcg tgagctatga gaaagcgcca cgcttcccga agggagaaag gcggacaggt   3900
atccggtaag cggcagggtc ggaacaggag agcgcacgag ggagcttcca gggggaaacg   3960
cctggtatct ttatagtcct gtcgggtttc gccacctctg acttgagcgt cgatttttgt   4020
gatgctcgtc aggggggcgg agcctatgga aaaacgccag caacgcggcc tttttacggt   4080
tcctggcctt ttgctggcct tttgctcaca tgttctttcc tgcgttatcc cctgattctg   4140
tggataaccg tattaccgcc tttgagtgag ctgataccgc tcgccgcagc cgaacgaccg   4200
agcgcagcga gtcagtgagc gaggaagcgg aaga                               4234
```

<210> SEQ ID NO 36
<211> LENGTH: 7429
<212> TYPE: DNA
<213> ORGANISM: Artificial Sequence
<220> FEATURE:
<223> OTHER INFORMATION: Description of Artificial Sequence: Vector pFPMT-CL-E1 sequence

<400> SEQUENCE: 36

```
ggtaccctgc tcaatctccg gaatggtgat ctgatcgttc ctgaaaacct cgacattggc     60
tccctcctga cacaggtact cgtacaggtt ccaggtaaac gagtcgtagt tgtcgatcat    120
gacaacgttc ttagaagcgg ccggcatttt gaaggtgact aatagcctaa gaaaatattt    180
aatttaattt tcattaaatt ttcctatact cgctatttca gcttttcatc tcatcacttc    240
ataaacgata taaaccagaa aaagaactat tttcaaacac gcttctcaaa agcggtatgt    300
ccttccacgt ctccttagaa tctggcaagt ccgcgagggg gatccttacc agttcatcat    360
catatcccaa gccatacggt gacctgttat gtggccggga tagattgagc aattgcagtc    420
ctgcaccgtc tcatgccggc gaggcgagat ggtgaacagc tgggagacga ggaagacaga    480
tccgcagaga tcccccacgt acatagcgga acagaaagca gccgccccaa cgagcaaatc    540
gacgtggcgt cgtattgtcg tagtggggac gctggcgttc ctagctgcga gcgtgggggt    600
gagcgctacc cagcagcggg aagagttgtt ctcccgaacg cagggcacgc acccgggggt    660
gtgcatgatc atgtccgctg cctcatacac aatgcttgag ttggagcagt cgttcgtgac    720
atggtacatc ccggacacgt tgcgcacctc atatcctagt gctgctagtg gtaggaagca    780
```

-continued

```
tagtactagt attagtaggc ttcgcatgaa ttcccgatga agcagagagc gcaggaggcg     840
gtatttatag tgccattccc ctctctgaga gacccggatg gtagtcgagt gtatcggaga     900
cagcttgatg tagactccgt gcctgccggc tcctcttatt ggcggacacc agtgagacac     960
cccggaactt gctgtttttc tgcaaaatcc ggggtgacca gtgggagcct atttgcacac    1020
acgagcggga caccccactc tggtgaagag tgccaaagtc attctttttc ccgttgcggg    1080
gcagccgatt gcatgtttta ggaaaatatt acctttgcta caccctgtca gatttaccct    1140
ccacacatat atattccgtc acctccaggg actattattc gtcgttgcgc cgccagcgga    1200
agatatccag aagctgtttt ccgagagact cggttggcgc ctggtatatt tgatggatgt    1260
cgcgctgcct cacgtcccgg tacccaggaa cgcggtggga tctcgggccc atcgaagact    1320
gtgctccaga ctgctcgccc agcaggtgtt tcttgatcgc cgcctctaaa ttgtccgcgc    1380
atcgccggta acatttttcc agctcggagt ttgcgtttag atacagtttc tgcgatgcca    1440
aaggagcctg cagattataa cctcggatgc tgtcattcag cgcttttaat ttgacctcca    1500
gatagttgct gtatttctgt tcccattggc tgctgcgcag cttcgtataa ctcgagttat    1560
tgttgcgctc tgcctcggcg tactggctca tgatctggat cttgtccgtg tcgcttttct    1620
tcgagtgttt ctcgcaaacg atgtgcacgg cctgcagtgt ccaatcggag tcgagctggc    1680
gccgaaactg gcggatctga gcctccacac tgccctgttt ctctatccac ggcggaaccg    1740
cctcctgccg tttcagaatg ttgttcaagt ggtactctgt gcggtcaatg aaggcgttat    1800
tgccggtgaa atctttggga agcggttttc ctcggggaag attacgaaat tccccgcgtc    1860
gttgcgcttc ctggatctcg aggagatcgt tctccgcgtc gaggagatcg ttctccgcgt    1920
cgacaccatt ccttgcggcg gcggtgctca acggcctcaa cctactactg ggctgcttcc    1980
taatgcagga gtcgcataag ggagagcgtc gacaaacccg cgtttgagaa cttgctcaag    2040
cttctggtaa acgttgtagt actctgaaac aaggccctag cactctgatc tgtttctctt    2100
gggtagcggt gagtggttta ttggagttca ctggtttcag cacatctgtc atctagacaa    2160
tattgttact aaattttttt gaactacaat tgttcgtaat tcatctatta ttatacatcc    2220
tcgtcagcaa tttctggcag acggagttta ctaacgtctt gagtatgagg ccgagaatcc    2280
agctctgtgg ccatactcag tcttgacagc ctgctgatgt ggctgcgttc aacgcaataa    2340
gcgtgtcctc cgactccgag ttgtgctcgt tatcgtcgtt ctcatcctcg gaaaaatcac    2400
acgaaagaac atactcacca gtaggctttc tggtccctgg ggcacggctg tttctgacgt    2460
attccggcgt tgataatagc tcgaaagtga acgccgagtc gcgggagtcg accgatgccc    2520
ttgagagcct tcaacccagt cagctccttc cggtgggcgc ggggcatgac tatcgtcgcc    2580
gcacttatga ctgtcttctt tatcatgcaa ctcgtaggac aggtgccggc agcgctctgg    2640
gtcattttcg gcgaggaccg ctttcgctgg agcgcgacga tgatcggcct gtcgcttgcg    2700
gtattcggaa tcttgcacgc cctcgctcaa gccttcgtca ctggtcccgc caccaaacgt    2760
ttcggcgaga agcaggccat tatcgccggc atggcggccg acgcgctggg ctacgtcttg    2820
ctggcgttcg cgacgcgagg ctggatggcc ttccccatta tgattcttct cgcttccggc    2880
ggcatcggga tgcccgcgtt gcaggccatg ctgtccaggc aggtagatga cgaccatcag    2940
ggacagcttc aaggatcgct cgcggctctt accagcctaa cttcgatcac tggaccgctg    3000
atcgtcacgg cgatttatgc cgcctcggcg agcacatgga acgggttggc atggattgta    3060
ggcgccgccc tataccttgt ctgcctcccc gcgttgcgtc gcggtgcatg gagccgggcc    3120
acctcgacct gaatggaagc cggcggcacc tcgctaacgg attcaccact ccaagaattg    3180
```

-continued

```
gagccaatca attcttgcgg agaactgtga atgcgcaaac caacccttgg cagaacatat   3240
ccatcgcgtc cgccatctcc agcagccgca cgcggcgcat cggggggggg gggggggggg   3300
gggggcaaac aattcatcat ttttttttta ttcttttttt tgatttcggt ttctttgaaa   3360
tttttttgat tcggtaatct ccgaacagaa ggaagaacga aggaaggagc acagacttag   3420
attggtatat atacgcatat gtagtgttga agaaacatga aattgcccag tattcttaac   3480
ccaactgcac agaacaaaaa cctgcaggaa acgaagataa atcatgtcga aagctacata   3540
taaggaacgt gctgctactc atcctagtcc tgttgctgcc aagctattta atatcatgca   3600
cgaaaagcaa acaaacttgt gtgcttcatt ggatgttcgt accaccaagg aattactgga   3660
gttagttgaa gcattaggtc ccaaaatttg tttactaaaa acacatgtgg atatcttgac   3720
tgatttttcc atggagggca cagttaagcc gctaaaggca ttatccgcca agtacaattt   3780
tttactcttc gaagacagaa aatttgctga cattggtaat acagtcaaat tgcagtactc   3840
tgcgggtgta tacagaatag cagaatgggc agacattacg aatgcacacg gtgtggtggg   3900
cccaggtatt gttagcggtt tgaagcaggc ggcagaagaa gtaacaaagg aacctagagg   3960
ccttttgatg ttagcagaat tgtcatgcaa gggctcccta tctactggag aatatactaa   4020
gggtactgtt gacattgcga agagcgacaa agattttgtt atcggcttta ttgctcaaag   4080
agacatgggt ggaagagatg aaggttacga ttggttgatt atgacacccg gtgtgggttt   4140
agatgacaag ggagacgcat tgggtcaaca gtatagaacc gtggatgatg tggtctctac   4200
aggatctgac attattattg ttggaagagg actatttgca aagggaaggg atgctaaggt   4260
agagggtgaa cgttacagaa aagcaggctg ggaagcatat ttgagaagat gcggccagca   4320
aaactaaaaa actgtattat aagtaaatgc atgtatacta aactcacaaa ttagagcttc   4380
aatttaatta tatcagttat tacccgggaa tctcggtcgt aatgattttt ataatgacga   4440
aaaaaaaaaa attggaaaga aaagcccccc cccccccccc cccccccccc cccccccgc   4500
agcgttgggt cctggccacg ggtgcgcatg atcgtgctcc tgtcgttgag gacccggcta   4560
ggctggcggg gttgccttac tggttagcag aatgaatcac cgatacgcga gcgaacgtga   4620
agcgactgct gctgcaaaac gtctgcgacc tgagcaacaa catgaatggt cttcggtttc   4680
cgtgtttcgt aaagtctgga aacgcggaag tcagcgccct gcaccattat gttccggatc   4740
tgcatcgcag gatgctgctg gctaccctgt ggaacaccta catctgtatt aacgaagcgc   4800
tggcattgac cctgagtgat ttttctctgg tcccgccgca tccataccgc cagttgttta   4860
ccctcacaac gttccagtaa ccgggcatgt tcatcatcag taacccgtat cgtgagcatc   4920
ctctctcgtt tcatcggtat cattaccccc atgaacagaa attcccctt acacggaggc   4980
atcaagtgac caaacaggaa aaaaccgccc ttaacatggc ccgctttatc agaagccaga   5040
cattaacgct tctggagaaa ctcaacgagc tggacgcgga tgaacaggca gacatctgtg   5100
aatcgcttca cgaccacgct gatgagcttt accgcagctg cctcgcgcgt ttcggtgatg   5160
acggtgaaaa cctctgacac atgcagctcc cggagacggt cacagcttgt ctgtaagcgg   5220
atgccgggag cagacaagcc cgtcagggcg cgtcagcggg tgttggcggg tgtcggggcg   5280
cagccatgac ccagtcacgt agcgatagcg gagtgtatac tggcttaact atgcggcatc   5340
agagcagatt gtactgagag tgcaccatat gcggtgtgaa ataccgcaca gatgcgtaag   5400
gagaaaatac cgcatcaggc gctcttccgc ttcctcgctc actgactcgc tgcgctcggt   5460
cgttcggctg cggcgagcgg tatcagctca ctcaaaggcg gtaatacggt tatccacaga   5520
```

-continued

```
atcaggggat aacgcaggaa agaacatgtg agcaaaaggc cagcaaaagg ccaggaaccg   5580

taaaaaggcc gcgttgctgg cgtttttcca taggctccgc ccccctgacg agcatcacaa   5640

aaatcgacgc tcaagtcaga ggtggcgaaa cccgacagga ctataaagat accaggcgtt   5700

tccccctgga agctccctcg tgcgctctcc tgttccgacc ctgccgctta ccggatacct   5760

gtccgccttt ctcccttcgg gaagcgtggc gctttctcat agctcacgct gtaggtatct   5820

cagttcggtg taggtcgttc gctccaagct gggctgtgtg cacgaacccc ccgttcagcc   5880

cgaccgctgc gccttatccg gtaactatcg tcttgagtcc aacccggtaa gacacgactt   5940

atcgccactg gcagcagcca ctggtaacag gattagcaga gcgaggtatg taggcggtgc   6000

tacagagttc ttgaagtggt ggcctaacta cggctacact agaaggacag tatttggtat   6060

ctgcgctctg ctgaagccag ttaccttcgg aaaaagagtt ggtagctctt gatccggcaa   6120

acaaaccacc gctggtagcg gtggtttttt tgtttgcaag cagcagatta cgcgcagaaa   6180

aaaaggatct caagaagatc ctttgatctt ttctacgggg tctgacgctc agtggaacga   6240

aaactcacgt taagggattt tggtcatgag attatcaaaa aggatcttca cctagatcct   6300

tttaaattaa aaatgaagtt ttaaatcaat ctaaagtata tatgagtaaa cttggtctga   6360

cagttaccaa tgcttaatca gtgaggcacc tatctcagcg atctgtctat ttcgttcatc   6420

catagttgcc tgactccccg tcgtgtagat aactacgata cgggagggct taccatctgg   6480

ccccagtgct gcaatgatac cgcgagaccc acgctcaccg gctccagatt tatcagcaat   6540

aaaccagcca gccggaaggg ccgagcgcag aagtggtcct gcaactttat ccgcctccat   6600

ccagtctatt aattgttgcc gggaagctag agtaagtagt tcgccagtta atagtttgcg   6660

caacgttgtt gccattgctg caggcatcgt ggtgtcacgc tcgtcgtttg gtatggcttc   6720

attcagctcc ggttcccaac gatcaaggcg agttacatga tcccccatgt tgtgcaaaaa   6780

agcggttagc tccttcggtc ctccgatcgt tgtcagaagt aagttggccg cagtgttatc   6840

actcatggtt atggcagcac tgcataattc tcttactgtc atgccatccg taagatgctt   6900

ttctgtgact ggtgagtact caaccaagtc attctgagaa tagtgtatgc ggcgaccgag   6960

ttgctcttgc ccggcgtcaa cacgggataa taccgcgcca catagcagaa ctttaaaagt   7020

gctcatcatt ggaaaacgtt cttcggggcg aaaactctca aggatcttac cgctgttgag   7080

atccagttcg atgtaaccca ctcgtgcacc caactgatct tcagcatctt ttactttcac   7140

cagcgtttct gggtgagcaa aaacaggaag gcaaaatgcc gcaaaaaagg gaataagggc   7200

gacacggaaa tgttgaatac tcatactctt cctttttcaa tattattgaa gcatttatca   7260

gggttattgt ctcatgagcg gatacatatt tgaatgtatt tagaaaaata aacaaatagg   7320

ggttccgcgc acatttcccc gaaaagtgcc acctgacgtc taagaaacca ttattatcat   7380

gacattaacc tataaaaata ggcgtatcac gaggcccttt cgtcttcaa              7429
```

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
probe or primer

<400> SEQUENCE: 37

```
catcacaaat atgaggtgcg caacgtgtcc gggatgtac                            39
```

<210> SEQ ID NO 38

-continued

<211> LENGTH: 42
<212> TYPE: DNA
<213> ORGANISM: Artificial Sequence
<220> FEATURE:
<223> OTHER INFORMATION: Description of Artificial Sequence: Synthetic
probe or primer

<400> SEQUENCE: 38
gtgatggtgg tgtcctagtg ctgctagtgg taggaagcat ag 42

<210> SEQ ID NO 39
<211> LENGTH: 4273
<212> TYPE: DNA
<213> ORGANISM: Artificial Sequence
<220> FEATURE:
<223> OTHER INFORMATION: Description of Artificial Sequence: Vector
pUC18-FMD-CL-E1-H-K6 sequence
<220> FEATURE:
<221> NAME/KEY: modified_base
<222> LOCATION: (1027)..(1028)
<223> OTHER INFORMATION: Any nucleotide
<220> FEATURE:
<221> NAME/KEY: modified_base
<222> LOCATION: (1206)..(1207)
<223> OTHER INFORMATION: Any nucleotide

<400> SEQUENCE: 39
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtacccgg ggatccttaa tggtgatggt ggtggtgcca gttcatcatc atatcccaag 300
ccatacggtg acctgttatg tggccgggat agattgagca attgcagtcc tgcaccgtct 360
catgccggcg aggcgagatg gtgaacagct gggagacgag gaagacagat ccgcagagat 420
cccccacgta catagcggaa cagaaagcag ccgccccaac gagcaaatcg acgtggcgtc 480
gtattgtcgt agtggggacg ctggcgttcc tagctgcgag cgtgggggtg agcgctaccc 540
agcagcggga agagttgttc tcccgaacgc agggcacgca cccgggggtg tgcatgatca 600
tgtccgctgc ctcatacaca atgcttgagt tggagcagtc gttcgtgaca tggtacatcc 660
cggacacgtt gcgcacctca tatttgtgat ggtgatggtg gtgtcctagt gctgctagtg 720
gtaggaagca tagtactagt attagtaggc ttcgcatgaa ttcccgatga aggcagagag 780
cgcaaggagg cggtatttat agtgccattc ccctctctga gagacccgga tggtagtcga 840
gtgttatcgg agacagcttg atgtagactc cgtgcctgcc ggtcctctta ttggcggaca 900
ccagtgagac accccggaac ttgctgtttt tctgcaaaat ccggggtgac cagtgggagc 960
ctatttgcac acacgagcgg gacaccccac tctggtgaag agtgccaaag tcattctttt 1020
tcccgtnncg gggcagccga ttgcatgttt taggaaaata ttacctttgc tacaccctgt 1080
cagatttacc ctccacacat atatattccg tcacctccag ggactattct tggctcgttg 1140
cgccgccgcg gaagatatcc agaagctgtg ttttccgaga gactcggttg gcgcctggta 1200
tatttnnagg atgtcgcgct gcctcacgtc ccggtaccca ggaacgcggt gggatctcgg 1260
gcccatcgaa gactgtgctc cagactgctc gcccagcagg tgtttcttga ttgccgcctc 1320
taaatagtcc gcgcatcgcc ggtaacattt ttccagctcg gagtttgcgt ttagatacat 1380
ttctgcgatg ccaaaggagc ctgcagatta taacctcgga tgctgtcatt cagcgctttt 1440
aatttgacct ccagatagtt gctgtatttc tgttccattg gctgctggac gttcgtataa 1500

-continued

```
ctcgagttat tgttgcgctc tgcctcggcg tactggctca tgactgactg cggtcgcttc   1560
tcgagtgttc tcgcaacagg acgcctgcag gtcatcgagt cgagctggcg ccgaaactgg   1620
cggatctgac ctccacactg ccctgtatct ctatccaccg ggaaccgcct cctgccgttc   1680
cagaatgttg ttcaagtggt agctctgtgc ggtcaatgaa ggcgttattg ccggtgaaat   1740
ctttgggaag cggtttatcc tcggggaaga ttacgaaatt cccgcgcgtc gttgcgcttc   1800
ctggatctcg aggaagatcg ttctccgcgt cgaggagatc gttctccgcg tcgacctgca   1860
ggcatgcaag cttggcactg gccgtcgttt tacaacgtcg tgactgggaa aaccctggcg   1920
ttacccaact taatcgcctt gcagcacatc ccccttcgc cagctggcgt aatagcgaag   1980
aggcccgcac cgatcgccct tcccaacagt tgcgcagcct gaatggcgaa tggcgcctga   2040
tgcggtattt tctccttacg catctgtgcg gtatttcaca ccgcatatgg tgcactctca   2100
gtacaatctg ctctgatgcc gcatagttaa gccagccccg acacccgcca acacccgctg   2160
acgcgccctg acgggcttgt ctgctcccgg catccgctta cagacaagct gtgaccgtct   2220
ccgggagctg catgtgtcag aggttttcac cgtcatcacc gaaacgcgcg agacgaaagg   2280
gcctcgtgat acgcctattt ttataggtta atgtcatgat aataatggtt tcttagacgt   2340
caggtggcac ttttcgggga aatgtgcgcg gaacccctat ttgtttattt ttctaaatac   2400
attcaaatat gtatccgctc atgagacaat aaccctgata aatgcttcaa taatattgaa   2460
aaaggaagag tatgagtatt caacatttcc gtgtcgccct tattcccttt tttgcggcat   2520
tttgccttcc tgtttttgct cacccagaaa cgctggtgaa agtaaaagat gctgaagatc   2580
agttgggtgc acgagtgggt tacatcgaac tggatctcaa cagcggtaag atccttgaga   2640
gttttcgccc cgaagaacgt tttccaatga tgagcacttt taaagttctg ctatgtggcg   2700
cggtattatc ccgtattgac gccgggcaag agcaactcgg tcgccgcata cactattctc   2760
agaatgactt ggttgagtac tcaccagtca cagaaaagca tcttacggat ggcatgacag   2820
taagagaatt atgcagtgct gccataacca tgagtgataa cactgcggcc aacttacttc   2880
tgacaacgat cggaggaccg aaggagctaa ccgctttttt gcacaacatg ggggatcatg   2940
taactcgcct tgatcgttgg gaaccggagc tgaatgaagc cataccaaac gacgagcgtg   3000
acaccacgat gcctgtagca atggcaacaa cgttgcgcaa actattaact ggcgaactac   3060
ttactctagc ttcccggcaa caattaatag actggatgga ggcggataaa gttgcaggac   3120
cacttctgcg ctcggccctt ccggctggct ggtttattgc tgataaatct ggagccggtg   3180
agcgtgggtc tcgcggtatc attgcagcac tggggccaga tggtaagccc tcccgtatcg   3240
tagttatcta cacgacgggg agtcaggcaa ctatggatga acgaaataga cagatcgctg   3300
agataggtgc ctcactgatt aagcattggt aactgtcaga ccaagtttac tcatatatac   3360
tttagattga tttaaaactt catttttaat ttaaaaggat ctaggtgaag atcctttttg   3420
ataatctcat gaccaaaatc ccttaacgtg agttttcgtt ccactgagcg tcagaccccg   3480
tagaaaagat caaaggatct tcttgagatc ctttttttct gcgcgtaatc tgctgcttgc   3540
aaacaaaaaa accaccgcta ccagcggtgg tttgtttgcc ggatcaagag ctaccaactc   3600
tttttccgaa ggtaactggc ttcagcagag cgcagatacc aaatactgtc cttctagtgt   3660
agccgtagtt aggccaccac ttcaagaact ctgtagcacc gcctacatac ctcgctctgc   3720
taatcctgtt accagtggct gctgccagtg gcgataagtc gtgtcttacc gggttggact   3780
caagacgata gttaccggat aaggcgcagc ggtcgggctg aacggggggt tcgtgcacac   3840
```

-continued

```
agcccagctt ggagcgaacg acctacaccg aactgagata cctacagcgt gagctatgag   3900

aaagcgccac gcttcccgaa gggagaaagg cggacaggta tccggtaagc ggcagggtcg   3960

gaacaggaga gcgcacgagg gagcttccag ggggaaacgc ctggtatctt tatagtcctg   4020

tcgggtttcg ccacctctga cttgagcgtc gatttttgtg atgctcgtca ggggggcgga   4080

gcctatggaa aaacgccagc aacgcggcct ttttacggtt cctggccttt tgctggcctt   4140

ttgctcacat gttctttcct gcgttatccc ctgattctgt ggataaccgt attaccgcct   4200

ttgagtgagc tgataccgct cgccgcagcc gaacgaccga gcgcagcgag tcagtgagcg   4260

aggaagcgga aga                                                      4273
```

<210> SEQ ID NO 40
<211> LENGTH: 7330
<212> TYPE: DNA
<213> ORGANISM: Artificial Sequence
<220> FEATURE:
<223> OTHER INFORMATION: Description of Artificial Sequence: Vector
pFPMT-CL-H6-K-E1 sequence
<220> FEATURE:
<221> NAME/KEY: modified_base
<222> LOCATION: (1098)..(1099)
<223> OTHER INFORMATION: Any nucleotide
<220> FEATURE:
<221> NAME/KEY: modified_base
<222> LOCATION: (1277)..(1278)
<223> OTHER INFORMATION: Any nucleotide

<400> SEQUENCE: 40

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccttacc agttcatcat    360

catatcccaa gccatacggt gacctgttat gtggccggga tagattgagc aattgcagtc    420

ctgcaccgtc tcatgccggc gaggcgagat ggtgaacagc tgggagacga ggaagacaga    480

tccgcagaga tcccccacgt acatagcgga acagaaagca gccgccccaa cgagcaaatc    540

gacgtggcgt cgtattgtcg tagtggggac gctggcgttc ctagctgcga gcgtgggggt    600

gagcgctacc cagcagcggg aagagttgtt ctcccgaacg cagggcacgc acccgggggt    660

gtgcatgatc atgtccgctg cctcatacac aatgcttgag ttggagcagt cgttcgtgac    720

atggtacatc ccggacacgt tgcgcacctc atatttgtga tggtgatggt ggtgtcctag    780

tgctgctagt ggtaggaagc atagtactag tattagtagg cttcgcatga attcccgatg    840

aaggcagaga gcgcaaggag gcggtattta tagtgccatt cccctctctg agagacccgg    900

atggtagtcg agtgttatcg gagacagctt gatgtagact ccgtgcctgc cggtcctctt    960

attggcggac accagtgaga caccccggaa cttgctgttt ttctgcaaaa tccggggtga   1020

ccagtgggag cctatttgca cacacgagcg ggacacccca ctctggtgaa gagtgccaaa   1080

gtcattcttt ttcccgtnnc ggggcagccg attgcatgtt ttaggaaaat attacctttg   1140

ctacaccctg tcagatttac cctccacaca tatatattcc gtcacctcca gggactattc   1200

ttggctcgtt gcgccgccgc ggaagatatc cagaagctgt gttttccgag agactcggtt   1260

ggcgcctggt atatttnnag gatgtcgcgc tgcctcacgt cccggtaccc aggaacgcgg   1320
```

-continued

```
tgggatctcg ggcccatcga agactgtgct ccagactgct cgcccagcag gtgtttcttg   1380
attgccgcct ctaaatagtc cgcgcatcgc cggtaacatt tttccagctc ggagtttgcg   1440
tttagataca tttctgcgat gccaaaggag cctgcagatt ataacctcgg atgctgtcat   1500
tcagcgcttt taatttgacc tccagatagt tgctgtattt ctgttccatt ggctgctgga   1560
cgttcgtata actcgagtta ttgttgcgct ctgcctcggc gtactggctc atgactgact   1620
gcggtcgctt ctcgagtgtt ctcgcaacag gacgcctgca ggtcatcgag tcgagctggc   1680
gccgaaactg gcggatctga cctccacact gccctgtatc tctatccacc gggaaccgcc   1740
tcctgccgtt ccagaatgtt gttcaagtgg tagctctgtg cggtcaatga aggcgttatt   1800
gccggtgaaa tctttgggaa gcggtttatc ctcggggaag attacgaaat tcccgcgcgt   1860
cgttgcgctt cctggatctc gaggaagatc gttctccgcg tcgaggagat cgttctccgc   1920
gtcgacctgc aggcatgcaa gcttctggta aacgttgtag tactctgaaa caaggcccta   1980
gcactctgat ctgtttctct tgggtagcgg tgagtggttt attggagttc actggtttca   2040
gcacatctgt catctagaca atattgttac taaatttttt tgaactacaa ttgttcgtaa   2100
ttcatctatt attatacatc ctcgtcagca atttctggca gacggagttt actaacgtct   2160
tgagtatgag gccgagaatc cagctctgtg gccatactca gtcttgacag cctgctgatg   2220
tggctgcgtt caacgcaata agcgtgtcct ccgactccga gttgtgctcg ttatcgtcgt   2280
tctcatcctc ggaaaaatca cacgaaagaa catactcacc agtaggcttt ctggtccctg   2340
gggcacggct gtttctgacg tattccggcg ttgataatag ctcgaaagtg aacgccgagt   2400
cgcgggagtc gaccgatgcc cttgagagcc ttcaacccag tcagctcctt ccggtgggcg   2460
cggggcatga ctatcgtcgc cgcacttatg actgtcttct ttatcatgca actcgtagga   2520
caggtgccgg cagcgctctg ggtcattttc ggcgaggacc gctttcgctg gagcgcgacg   2580
atgatcggcc tgtcgcttgc ggtattcgga atcttgcacg ccctcgctca agccttcgtc   2640
actggtcccg ccaccaaacg tttcggcgag aagcaggcca ttatcgccgg catggcggcc   2700
gacgcgctgg gctacgtctt gctggcgttc gcgacgcgag gctggatggc cttccccatt   2760
atgattcttc tcgcttccgg cggcatcggg atgcccgcgt tgcaggccat gctgtccagg   2820
caggtagatg acgaccatca gggacagctt caaggatcgc tcgcggctct taccagccta   2880
acttcgatca ctggaccgct gatcgtcacg gcgatttatg ccgcctcggc gagcacatgg   2940
aacgggttgg catggattgt aggcgccgcc ctataccttg tctgcctccc cgcgttgcgt   3000
cgcggtgcat ggagccgggc cacctcgacc tgaatggaag ccggcggcac ctcgctaacg   3060
gattcaccac tccaagaatt ggagccaatc aattcttgcg gagaactgtg aatgcgcaaa   3120
ccaacccttg gcagaacata tccatcgcgt ccgccatctc cagcagccgc acgcggcgca   3180
tcgggggggg gggggggggg ggggggcaaa caattcatca tttttttttt attctttttt   3240
ttgatttcgg tttctttgaa attttttttga ttcggtaatc tccgaacaga aggaagaacg   3300
aaggaaggag cacagactta gattggtata tatacgcata tgtagtgttg aagaaacatg   3360
aaattgccca gtattcttaa cccaactgca cagaacaaaa acctgcagga aacgaagata   3420
aatcatgtcg aaagctacat ataaggaacg tgctgctact catcctagtc ctgttgctgc   3480
caagctattt aatatcatgc acgaaaagca aacaaacttg tgtgcttcat tggatgttcg   3540
taccaccaag gaattactgg agttagttga agcattaggt cccaaaattt gtttactaaa   3600
aacacatgtg gatatcttga ctgatttttc catggagggc acagttaagc cgctaaaggc   3660
attatccgcc aagtacaatt ttttactctt cgaagacaga aaatttgctg acattggtaa   3720
```

-continued

```
tacagtcaaa ttgcagtact ctgcgggtgt atacagaata gcagaatggg cagacattac   3780
gaatgcacac ggtgtggtgg gcccaggtat tgttagcggt ttgaagcagg cggcagaaga   3840
agtaacaaag gaacctagag gccttttgat gttagcagaa ttgtcatgca agggctccct   3900
atctactgga gaatatacta agggtactgt tgacattgcg aagagcgaca aagattttgt   3960
tatcggcttt attgctcaaa gagacatggg tggaagagat gaaggttacg attggttgat   4020
tatgacaccc ggtgtgggtt tagatgacaa gggagacgca ttgggtcaac agtatagaac   4080
cgtggatgat gtggtctcta caggatctga cattattatt gttggaagag gactatttgc   4140
aaagggaagg gatgctaagg tagagggtga acgttacaga aaagcaggct gggaagcata   4200
tttgagaaga tgcggccagc aaaactaaaa aactgtatta taagtaaatg catgtatact   4260
aaactcacaa attagagctt caatttaatt atatcagtta ttacccggga atctcggtcg   4320
taatgatttt tataatgacg aaaaaaaaaa aattggaaag aaaagccccc cccccccccc   4380
cccccccccc cccccccccg cagcgttggg tcctggccac gggtgcgcat gatcgtgctc   4440
ctgtcgttga ggacccggct aggctggcgg ggttgcctta ctggttagca gaatgaatca   4500
ccgatacgcg agcgaacgtg aagcgactgc tgctgcaaaa cgtctgcgac ctgagcaaca   4560
acatgaatgg tcttcggttt ccgtgtttcg taaagtctgg aaacgcggaa gtcagcgccc   4620
tgcaccatta tgttccggat ctgcatcgca ggatgctgct ggctaccctg tggaacacct   4680
acatctgtat taacgaagcg ctggcattga ccctgagtga tttttctctg gtcccgccgc   4740
atccataccg ccagttgttt accctcacaa cgttccagta accgggcatg ttcatcatca   4800
gtaacccgta tcgtgagcat cctctctcgt ttcatcggta tcattacccc catgaacaga   4860
aattccccct tacacggagg catcaagtga ccaaacagga aaaaaccgcc cttaacatgg   4920
cccgctttat cagaagccag acattaacgc ttctggagaa actcaacgag ctggacgcgg   4980
atgaacaggc agacatctgt gaatcgcttc acgaccacgc tgatgagctt taccgcagct   5040
gcctcgcgcg tttcggtgat gacggtgaaa acctctgaca catgcagctc ccggagacgg   5100
tcacagcttg tctgtaagcg gatgccggga gcagacaagc ccgtcagggc gcgtcagcgg   5160
gtgttggcgg gtgtcggggc gcagccatga cccagtcacg tagcgatagc ggagtgtata   5220
ctggcttaac tatgcggcat cagagcagat tgtactgaga gtgcaccata tgcggtgtga   5280
aataccgcac agatgcgtaa ggagaaaata ccgcatcagg cgctcttccg cttcctcgct   5340
cactgactcg ctgcgctcgg tcgttcggct gcggcgagcg gtatcagctc actcaaaggc   5400
ggtaatacgg ttatccacag aatcagggga taacgcagga aagaacatgt gagcaaaagg   5460
ccagcaaaag gccaggaacc gtaaaaaggc cgcgttgctg gcgtttttcc ataggctccg   5520
cccccctgac gagcatcaca aaaatcgacg ctcaagtcag aggtggcgaa acccgacagg   5580
actataaaga taccaggcgt ttccccctgg aagctccctc gtgcgctctc ctgttccgac   5640
cctgccgctt accggatacc tgtccgcctt tctcccttcg ggaagcgtgg cgctttctca   5700
tagctcacgc tgtaggtatc tcagttcggt gtaggtcgtt cgctccaagc tgggctgtgt   5760
gcacgaaccc cccgttcagc ccgaccgctg cgccttatcc ggtaactatc gtcttgagtc   5820
caacccggta agacacgact tatcgccact ggcagcagcc actggtaaca ggattagcag   5880
agcgaggtat gtaggcggtg ctacagagtt cttgaagtgg tggcctaact acggctacac   5940
tagaaggaca gtatttggta tctgcgctct gctgaagcca gttaccttcg gaaaaagagt   6000
tggtagctct tgatccggca aacaaaccac cgctggtagc ggtggttttt ttgtttgcaa   6060
```

-continued

```
gcagcagatt acgcgcagaa aaaaaggatc tcaagaagat cctttgatct tttctacggg   6120

gtctgacgct cagtggaacg aaaactcacg ttaagggatt ttggtcatga gattatcaaa   6180

aaggatcttc acctagatcc ttttaaatta aaaatgaagt tttaaatcaa tctaaagtat   6240

atatgagtaa acttggtctg acagttacca atgcttaatc agtgaggcac ctatctcagc   6300

gatctgtcta tttcgttcat ccatagttgc ctgactcccc gtcgtgtaga taactacgat   6360

acgggagggc ttaccatctg gccccagtgc tgcaatgata ccgcgagacc cacgctcacc   6420

ggctccagat ttatcagcaa taaaccagcc agccggaagg gccgagcgca gaagtggtcc   6480

tgcaacttta tccgcctcca tccagtctat taattgttgc cgggaagcta gagtaagtag   6540

ttcgccagtt aatagtttgc gcaacgttgt tgccattgct gcaggcatcg tggtgtcacg   6600

ctcgtcgttt ggtatggctt cattcagctc cggttcccaa cgatcaaggc gagttacatg   6660

atcccccatg ttgtgcaaaa aagcggttag ctccttcggt cctccgatcg ttgtcagaag   6720

taagttggcc gcagtgttat cactcatggt tatggcagca ctgcataatt ctcttactgt   6780

catgccatcc gtaagatgct tttctgtgac tggtgagtac tcaaccaagt cattctgaga   6840

atagtgtatg cggcgaccga gttgctcttg cccggcgtca acacgggata ataccgcgcc   6900

acatagcaga actttaaaag tgctcatcat tggaaaacgt tcttcggggc gaaaactctc   6960

aaggatctta ccgctgttga gatccagttc gatgtaaccc actcgtgcac ccaactgatc   7020

ttcagcatct tttactttca ccagcgtttc tgggtgagca aaaacaggaa ggcaaaatgc   7080

cgcaaaaaag ggaataaggg cgacacggaa atgttgaata ctcatactct tcctttttca   7140

atattattga agcatttatc agggttattg tctcatgagc ggatacatat ttgaatgtat   7200

ttagaaaaat aaacaaatag gggttccgcg cacatttccc cgaaaagtgc cacctgacgt   7260

ctaagaaacc attattatca tgacattaac ctataaaaat aggcgtatca cgaggccctt   7320

tcgtcttcaa                                                          7330
```

<210> SEQ ID NO 41
<211> LENGTH: 5202
<212> TYPE: DNA
<213> ORGANISM: Artificial Sequence
<220> FEATURE:
<223> OTHER INFORMATION: Description of Artificial Sequence: Vector
pYIG5 sequence

<400> SEQUENCE: 41

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gaatttaata    240

cgactcacta tagggaattc gaggatcctt caatatgcgc acatacgctg ttatgttcaa    300

ggtcccttcg tttaagaacg aaagcggtct tccttttgag ggatgtttca agttgttcaa    360

atctatcaaa tttgcaaatc cccagtctgt atctagagcg ttgaatcggt gatgcgattt    420

gttaattaaa ttgatggtgt caccattacc aggtctagat ataccaatgg caaactgagc    480

acaacaatac cagtccggat caactggcac catctctccc gtagtctcat ctaatttttc    540

ttccggatga ggttccagat ataccgcaac acctttatta tggtttccct gagggaataa    600

tagaatgtcc cattcgaaat caccaattct aaacctgggc gaattgtatt tcgggtttgt    660

taactcgttc cagtcaggaa tgttccacgt gaagctatct tccagcaaag tctccacttc    720
```

-continued

```
ttcatcaaat tgtggagaat actcccaatg ctcttatcta tgggacttcc gggaaacaca    780

gtaccgatac ttcccaattc gtcttcagag ctcattgttt gtttgaagag actaatcaaa    840

gaatcgtttt ctcaaaaaaa ttaatatctt aactgatagt ttgatcaaag gggcaaaacg    900

taggggcaaa caaacggaaa aatcgtttct caaattttct gatgccaaga actctaacca    960

gtcttatcta aaaattgcct tatgatccgt ctctccggtt acagcctgtg taactgatta   1020

atcctgcctt tctaatcacc attctaatgt tttaattaag ggattttgtc ttcattaacg   1080

gctttcgctc ataaaaatgt tatgacgttt tgcccgcagg cgggaaacca tccacttcac   1140

gagactgatc tcctctgccg gaacaccggg catctccaac ttataagttg gagaaataag   1200

agaatttcag attgagagaa tgaaaaaaaa aaaccctgaa aaaaaggtt gaaaccagtt   1260

ccctgaaatt attcccctac ttgactaata agtatataaa gacggtaggt attgattgta   1320

attctgtaaa tctatttctt aaacttctta aattctactt ttatagttag tctttttttt   1380

agttttaaaa caccaagaac ttagtttcga ataaacacac ataaacaaac accatgagat   1440

ttccttcaat ttttactgca gttttattcg cagcatcctc cgcattagct gctccagtca   1500

acactacaac agaagatgaa acggcacaaa ttccggctga agctgtcatc ggttactcag   1560

atttagaagg ggatttcgat gttgctgttt tgccattttc caacagcaca aataacgggt   1620

tattgtttat aaatactact attgccagca ttgctgctaa agaagaaggg gtatctctag   1680

ataaaaggcc tgtcgacggt accagatctc gacttggttg aacacgttgc caaggcttaa   1740

gtgaatttac tttaaagtct tgcatttaaa taaattttct ttttatagct ttatgactta   1800

gtttcaattt atatactatt ttaatgacat tttcgattca ttgattgaaa gctttgtgtt   1860

ttttcttgat gcgctattgc attgttcttg tctttttcgc cacatgtaat atctgtagta   1920

gatacctgat acattgtgga tgctgagtga aattttagtt aataatggag gcgctcttaa   1980

taattttggg gatattggct tttttttta aagtttacaa atgaattttt tccgccagga   2040

taacgattct gaagttactc ttagcgttcc tatcggtaca gccatcaaat catgcctata   2100

aatcatgcct atatttgcgt gcagtcagta tcatctacat gaaaaaaact cccgcaattt   2160

cttatagaat acgttgaaaa ttaaatgtac gcgccaagat aagataacat atatctagct   2220

agatgcagta atatacacag attcccgcgg acgtgggaag gaaaaaatta gataacaaaa   2280

tctgagtgat atggaaattc cgctgtatag ctcatatctt tcccttcaac accagaaatg   2340

taaaaatctt gttacgaagg atctttttgc taatgtttct cgctcaatcc tcatttcttc   2400

cctacgaaga gtcaaatcta cttgttttct gccggtatca agatccatat cttctagttt   2460

caccatcaaa gtccaatttc tagtatacag tttatgtccc aacgtaacag acaatcaaaa   2520

ttggaaagga taagtatcct tcaaagaatg attctgcgct ggctcctgaa ccgcctaatg   2580

ggaacagaga agtccaaaac gatgctataa gaaccagaaa taaaacgata aaaccatacc   2640

aggatccaag cttggcactg gccgtcgttt tacaacgtcg tgactgggaa aaccctggcg   2700

ttacccaact taatcgcctt gcagcacatc ccccttttcgc cagctggcgt aatagcgaag   2760

aggcccgcac cgatcgccct tcccaacagt tgcgcagcct gaatggcgaa tgggaaattg   2820

taaacgttaa tattttgtta aaattcgcgt taaatttttg ttaaatcagc tcatttttta   2880

accaataggc cgaaatcggc aaaatccctt ataaatcaaa agaatagacc gagatagggt   2940

tgagtgttgt tccagtttgg aacaagagtc cactattaaa gaacgtggac tccaacgtca   3000

aagggcgaaa aaccgtctat cagggcgatg gcccactacg tgaaccatca ccctaatcaa   3060

gtttttttggg gtcgaggtgc cgtaaagcac taaatcggaa ccctaaaggg agcccccgat   3120
```

-continued

```
ttagagcttg acggggaaag ccggcgaacg tggcgagaaa ggaagggaag aaagcgaaag   3180
gagcgggcgc tagggcgctg gcaagtgtag cggtcacgct gcgcgtaacc accacacccg   3240
ccgcgcttaa tgcgccgcta cagggcgcgt caggtggcac ttttcgggga aatgtgcgcg   3300
gaacccctat ttgtttattt ttctaaatac attcaaatat gtatccgctc atgagacaat   3360
aaccctgata aatgcttcaa taatattgaa aaaggaagag tatgagtatt caacatttcc   3420
gtgtcgccct tattcccttt tttgcggcat tttgccttcc tgtttttgct cacccagaaa   3480
cgctggtgaa agtaaaagat gctgaagatc agttgggtgc acgagtgggt tacatcgaac   3540
tggatctcaa cagcggtaag atccttgaga gttttcgccc cgaagaacgt tttccaatga   3600
tgagcacttt taaagttctg ctatgtggcg cggtattatc ccgtattgac gccgggcaag   3660
agcaactcgg tcgccgcata cactattctc agaatgactt ggttgagtac tcaccagtca   3720
cagaaaagca tcttacggat ggcatgacag taagagaatt atgcagtgct gccataacca   3780
tgagtgataa cactgcggcc aacttacttc tgacaacgat cggaggaccg aaggagctaa   3840
ccgctttttt gcacaacatg ggggatcatg taactcgcct tgatcgttgg gaaccggagc   3900
tgaatgaagc cataccaaac gacgagcgtg acaccacgat gcctgtagca atggcaacaa   3960
cgttgcgcaa actattaact ggcgaactac ttactctagc ttcccggcaa caattaatag   4020
actggatgga ggcggataaa gttgcaggac cacttctgcg ctcggccctt ccggctggct   4080
ggtttattgc tgataaatct ggagccggtg agcgtgggtc tcgcggtatc attgcagcac   4140
tggggccaga tggtaagccc tcccgtatcg tagttatcta cacgacgggg agtcaggcaa   4200
ctatggatga acgaaataga cagatcgctg agataggtgc ctcactgatt aagcattggt   4260
aactgtcaga ccaagtttac tcatatatac tttagattga tttaaaactt catttttaat   4320
ttaaaaggat ctaggtgaag atcctttttg ataatctcat gaccaaaatc ccttaacgtg   4380
agttttcgtt ccactgagcg tcagaccccg tagaaaagat caaaggatct tcttgagatc   4440
cttttttctt gcgcgtaatc tgctgcttgc aaacaaaaaa accaccgcta ccagcggtgg   4500
tttgtttgcc ggatcaagag ctaccaactc tttttccgaa ggtaactggc ttcagcagag   4560
cgcagatacc aaatactgtc cttctagtgt agccgtagtt aggccaccac ttcaagaact   4620
ctgtagcacc gcctacatac ctcgctctgc taatcctgtt accagtggct gctgccagtg   4680
gcgataagtc gtgtcttacc gggttggact caagacgata gttaccggat aaggcgcagc   4740
ggtcgggctg aacggggggt tcgtgcacac agcccagctt ggagcgaacg acctacaccg   4800
aactgagata cctacagcgt gagcattgag aaagcgccac gcttcccgaa gggagaaagg   4860
cggacaggta tccggtaagc ggcagggtcg gaacaggaga gcgcacgagg gagcttccag   4920
ggggaaacgc ctggtatctt tatagtcctg tcgggtttcg ccacctctga cttgagcgtc   4980
gatttttgtg atgctcgtca ggggggcgga gcctatggaa aaacgccagc aacgcggcct   5040
ttttacggtt cctggccttt tgctggcctt ttgctcacat gttctttcct gcgttatccc   5100
ctgattctgt ggataaccgt attaccgcct ttgagtgagc tgataccgct cgccgcagcc   5160
gaacgaccga gcgcagcgag tcagtgagcg aggaagcgga ag                      5202
```

<210> SEQ ID NO 42
<211> LENGTH: 5613
<212> TYPE: DNA
<213> ORGANISM: Artificial Sequence
<220> FEATURE:
<223> OTHER INFORMATION: Description of Artificial Sequence: Vector
pYIG5E1H6 sequence -continued

<400> SEQUENCE: 42

```
ggatccttca atatgcgcac atacgctgtt atgttcaagg tcccttcgtt taagaacgaa      60
agcggtcttc cttttgaggg atgtttcaag ttgttcaaat ctatcaaatt tgcaaatccc     120
cagtctgtat ctagagcgtt gaatcggtga tgcgatttgt taattaaatt gatggtgtca     180
ccattaccag gtctagatat accaatggca aactgagcac aacaatacca gtccggatca     240
actggcacca tctctcccgt agtctcatct aatttttctt ccggatgagg ttccagatat     300
accgcaacac ctttattatg gtttccctga gggaataata gaatgtccca ttcgaaatca     360
ccaattctaa acctgggcga attgtatttc gggtttgtta actcgttcca gtcaggaatg     420
ttccacgtga agctatcttc cagcaaagtc tccacttctt catcaaattg tggagaatac     480
tcccaatgct cttatctatg ggacttccgg gaaacacagt accgatactt cccaattcgt     540
cttcagagct cattgtttgt ttgaagagac taatcaaaga atcgttttct caaaaaaatt     600
aatatcttaa ctgatagttt gatcaaaggg gcaaaacgta ggggcaaaca aacggaaaaa     660
tcgtttctca aattttctga tgccaagaac tctaaccagt cttatctaaa aattgcctta     720
tgatccgtct ctccggttac agcctgtgta actgattaat cctgcctttc taatcaccat     780
tctaatgttt taattaaggg attttgtctt cattaacggc tttcgctcat aaaaatgtta     840
tgacgttttg cccgcaggcg ggaaaccatc cacttcacga gactgatctc ctctgccgga     900
acaccgggca tctccaactt ataagttgga gaaataagag aatttcagat tgagagaatg     960
aaaaaaaaaa accctgaaaa aaaaggttga aaccagttcc ctgaaattat tcccctactt    1020
gactaataag tatataaaga cggtaggtat tgattgtaat tctgtaaatc tatttcttaa    1080
acttcttaaa ttctactttt atagttagtc ttttttttag ttttaaaaca ccaagaactt    1140
agtttcgaat aaacacacat aaacaaacac catgagattt ccttcaattt ttactgcagt    1200
tttattcgca gcatcctccg cattagctgc tccagtcaac actacaacag aagatgaaac    1260
ggcacaaatt ccggctgaag ctgtcatcgg ttacttagat ttagaagggg atttcgatgt    1320
tgctgttttg ccattttcca acagcacaaa taacgggtta ttgtttataa atactactat    1380
tgccagcatt gctgctaaag aagaaggggt atctctagat aaaaggtatg aggtgcgcaa    1440
cgtgtccggg atgtaccatg tcacgaacga ctgctccaac tcaagcattg tgtatgaggc    1500
agcggacatg atcatgcaca cccccgggtg cgtgccctgc gttcgggaga acaactcttc    1560
ccgctgctgg gtagcgctca cccccacgct cgcagctagg aacgccagcg tccccactac    1620
gacaatacga cgccacgtcg atttgctcgt tggggcggct gctttctgtt ccgctatgta    1680
cgtgggggat ctctgcggat ctgtcttcct cgtctcccag ctgttcacca tctcgcctcg    1740
ccggcatgag acggtgcagg actgcaattg ctcaatctat cccggccaca taacaggtca    1800
ccgtatggct tgggatatga tgatgaactg gcaccaccac catcaccatt aaagatctcg    1860
acttggttga acacgttgcc aaggcttaag tgaatttact ttaaagtctt gcatttaaat    1920
aaattttctt tttatagctt tatgacttag tttcaattta tatactattt taatgacatt    1980
ttcgattcat tgattgaaag ctttgtgttt tttcttgatg cgctattgca ttgttcttgt    2040
ctttttcgcc acatgtaata tctgtagtag atacctgata cattgtggat gctgagtgaa    2100
attttagtta ataatggagg cgctcttaat aattttgggg atattggctt ttttttttaa    2160
agtttacaaa tgaatttttt ccgccaggat aacgattctg aagttactct tagcgttcct    2220
atcggtacag ccatcaaatc atgcctataa atcatgccta tatttgcgtg cagtcagtat    2280
```

-continued

```
catctacatg aaaaaaactc ccgcaatttc ttatagaata cgttgaaaat taaatgtacg   2340
cgccaagata agataacata tatctagcta gatgcagtaa tatacacaga ttcccgcgga   2400
cgtgggaagg aaaaaattag ataacaaaat ctgagtgata tggaaattcc gctgtatagc   2460
tcatatcttt cccttcaaca ccagaaatgt aaaaatcttg ttacgaagga tctttttgct   2520
aatgtttctc gctcaatcct catttcttcc ctacgaagag tcaaatctac ttgttttctg   2580
ccggtatcaa gatccatatc ttctagtttc accatcaaag tccaatttct agtatacagt   2640
ttatgtccca acgtaacaga caatcaaaat tggaaaggat aagtatcctt caaagaatga   2700
ttctgcgctg gctcctgaac cgcctaatgg gaacagagaa gtccaaaacg atgctataag   2760
aaccagaaat aaaacgataa aaccatacca ggatccaagc ttggcactgg ccgtcgtttt   2820
acaacgtcgt gactgggaaa accctggcgt tacccaactt aatcgccttg cagcacatcc   2880
ccctttcgcc agctggcgta atagcgaaga ggcccgcacc gatcgccctt cccaacagtt   2940
gcgcagcctg aatggcgaat gggaaattgt aaacgttaat attttgttaa aattcgcgtt   3000
aaatttttgt taaatcagct cattttttaa ccaataggcc gaaatcggca aaatccctta   3060
taaatcaaaa gaatagaccg agatagggtt gagtgttgtt ccagtttgga acaagagtcc   3120
actattaaag aacgtggact ccaacgtcaa agggcgaaaa accgtctatc agggcgatgg   3180
cccactacgt gaaccatcac cctaatcaag ttttttgggg tcgaggtgcc gtaaagcact   3240
aaatcggaac cctaaaggga gcccccgatt tagagcttga cggggaaagc cggcgaacgt   3300
ggcgagaaag gaagggaaga aagcgaaagg agcgggcgct agggcgctgg caagtgtagc   3360
ggtcacgctg cgcgtaacca ccacacccgc cgcgcttaat gcgccgctac agggcgcgtc   3420
aggtggcact tttcggggaa atgtgcgcgg aacccctatt tgtttatttt tctaaataca   3480
ttcaaatatg tatccgctca tgagacaata accctgataa atgcttcaat aatattgaaa   3540
aaggaagagt atgagtattc aacatttccg tgtcgccctt attccctttt ttgcggcatt   3600
ttgccttcct gtttttgctc acccagaaac gctggtgaaa gtaaaagatg ctgaagatca   3660
gttgggtgca cgagtgggtt acatcgaact ggatctcaac agcggtaaga tccttgagag   3720
ttttcgcccc gaagaacgtt ttccaatgat gagcactttt aaagttctgc tatgtggcgc   3780
ggtattatcc cgtattgacg ccgggcaaga gcaactcggt cgccgcatac actattctca   3840
gaatgacttg gttgagtact caccagtcac agaaaagcat cttacggatg gcatgacagt   3900
aagagaatta tgcagtgctg ccataaccat gagtgataac actgcggcca acttacttct   3960
gacaacgatc ggaggaccga aggagctaac cgcttttttg cacaacatgg gggatcatgt   4020
aactcgcctt gatcgttggg aaccggagct gaatgaagcc ataccaaacg acgagcgtga   4080
caccacgatg cctgtagcaa tggcaacaac gttgcgcaaa ctattaactg gcgaactact   4140
tactctagct tcccggcaac aattaataga ctggatggag gcggataaag ttgcaggacc   4200
acttctgcgc tcggcccttc cggctggctg gtttattgct gataaatctg gagccggtga   4260
gcgtgggtct cgcggtatca ttgcagcact ggggccagat ggtaagccct cccgtatcgt   4320
agttatctac acgacgggga gtcaggcaac tatggatgaa cgaaatagac agatcgctga   4380
gataggtgcc tcactgatta agcattggta actgtcagac caagtttact catatatact   4440
ttagattgat ttaaaacttc atttttaatt taaaaggatc taggtgaaga tcctttttga   4500
taatctcatg accaaaatcc cttaacgtga gttttcgttc cactgagcgt cagaccccgt   4560
agaaaagatc aaaggatctt cttgagatcc tttttttctg cgcgtaatct gctgcttgca   4620
aacaaaaaaa ccaccgctac cagcggtggt ttgtttgccg gatcaagagc taccaactct   4680
```

-continued

```
ttttccgaag gtaactggct tcagcagagc gcagatacca aatactgtcc ttctagtgta   4740

gccgtagtta ggccaccact tcaagaactc tgtagcaccg cctacatacc tcgctctgct   4800

aatcctgtta ccagtggctg ctgccagtgg cgataagtcg tgtcttaccg ggttggactc   4860

aagacgatag ttaccggata aggcgcagcg gtcgggctga acggggggtt cgtgcacaca   4920

gcccagcttg gagcgaacga cctacaccga actgagatac ctacagcgtg agcattgaga   4980

aagcgccacg cttcccgaag ggagaaaggc ggacaggtat ccggtaagcg gcagggtcgg   5040

aacaggagag cgcacgaggg agcttccagg gggaaacgcc tggtatcttt atagtcctgt   5100

cgggtttcgc cacctctgac ttgagcgtcg atttttgtga tgctcgtcag gggggcggag   5160

cctatggaaa aacgccagca acgcggcctt tttacggttc ctggcctttt gctggccttt   5220

tgctcacatg ttctttcctg cgttatcccc tgattctgtg gataaccgta ttaccgcctt   5280

tgagtgagct gataccgctc gccgcagccg aacgaccgag cgcagcgagt cagtgagcga   5340

ggaagcggaa gagcgcccaa tacgcaaacc gcctctcccc gcgcgttggc cgattcatta   5400

atgcagctgg cacgacaggt ttcccgactg gaaagcgggc agtgagcgca acgcaattaa   5460

tgtgagttag ctcactcatt aggcacccca ggctttacac tttatgcttc cggctcgtat   5520

gttgtgtgga attgtgagcg gataacaatt tcacacagga aacagctatg accatgatta   5580

cgaatttaat acgactcact atagggaatt cga                                5613
```

<210> SEQ ID NO 43
<211> LENGTH: 13020
<212> TYPE: DNA
<213> ORGANISM: Artificial Sequence
<220> FEATURE:
<223> OTHER INFORMATION: Description of Artificial Sequence: Vector pSY1 sequence

<400> SEQUENCE: 43

```
atcgataagc ttttcaattc aattcatcat tttttttta ttcttttttt tgatttcggt     60

ttctttgaaa ttttttgat tcggtaatct ccgaacagaa ggaagaacga aggaaggagc    120

acagacttag attggtatat atacgcatat gtagtgttga agaaacatga aattgcccag    180

tattcttaac ccaactgcac agaacaaaaa cctgcaggaa acgaagataa atcatgtcga    240

aagctacata taaggaacgt gctgctactc atcctagtcc tgttgctgcc aagctattta    300

atatcatgca cgaaaagcaa acaaacttgt gtgcttcatt ggatgttcgt accaccaagg    360

aattactgga gttagttgaa gcattaggtc ccaaaatttg tttactaaaa acacatgtgg    420

atatcttgac tgatttttcc atggagggca cagttaagcc gctaaaggca ttatccgcca    480

agtacaattt tttactcttc gaagacagaa aatttgctga cattggtaat acagtcaaat    540

tgcagtactc tgcgggtgta tacagaatag cagaatgggc agacattacg aatgcacacg    600

gtgtggtggg cccaggtatt gttagcggtt tgaagcaggc ggcagaagaa gtaacaaagg    660

aacctagagg ccttttgatg ttagcagaat tgtcatgcaa gggctcccta tctactggag    720

aatatactaa gggtactgtt gacattgcga agagcgacaa agattttgtt atcggcttta    780

ttgctcaaag agacatgggt ggaagagatg aaggttacga ttggttgatt atgacacccg    840

gtgtgggttt agatgacaag ggagacgcat tgggtcaaca gtatagaacc gtggatgatg    900

tggtctctac aggatctgac attattattg ttggaagagg actatttgca aagggaaggg    960

atgctaaggt agagggtgaa cgttacagaa aagcaggctg ggaagcatat ttgagaagat   1020

gcggccagca aaactaaaaa actgtattat aagtaaatgc atgtatacta aactcacaaa   1080
```

-continued ttagagcttc aatttaatta tatcagttat tacccgggaa tctcggtcgt aatgattttt 1140
ataatgacga aaaaaaaaaa attggaaaga aaaagcttta atgcggtagt ttatcacagt 1200
taaattgcta acgcagtcag gcaccgtgta tgaaatctaa caatgcgctc atcgtcatcc 1260
tcggcaccgt caccctggat gctgtaggca taggcttggt tatgccggta ctgccgggcc 1320
tcttgcggga tatcgtccat tccgacagca tcgccagtca ctatggcgtg ctgctagcgc 1380
tatatgcgtt gatgcaattt ctatgcgcac ccgttctcgg agcactgtcc gaccgctttg 1440
gccgccgccc agtcctgctc gcttcgctac ttggagccac tatcgactac gcgatcatgg 1500
cgaccacacc cgtcctgtgg atcctctacg ccggacgcat cgtggccggc atcaccggcg 1560
ccacaggtgc ggttgctggc ccctatatcg ccgacatcac cgatggggaa gatcgggctc 1620
gccacttcgg gctcatgagc gcttgtttcg gcgtgggtat ggtggcaggc cccgtggccg 1680
ggggactgtt gggcgccatc tccttgcatg caccattcct tgcggcggcg gtgctcaacg 1740
gcctcaacct actactgggc tgcttcctaa tgcaggagtc gcataaggga gagcgtcgac 1800
cgatgccctt gagagccttc aacccagtca gctccttccg gtgggcgcgg ggcatgacta 1860
tcgtcgccgc acttatgact gtcttcttta tcatgcaact cgtaggacag gtgccggcag 1920
cgctctgggt cattttcggc gaggaccgct ttcgctggag cgcgacgatg atcggcctgt 1980
cgcttgcggt attcggaatc ttgcacgccc tcgctcaagc cttcgtcact ggtcccgcca 2040
ccaaacgttt cggcgagaag caggccatta tcgccggcat ggcggccgac gcgctgggct 2100
acgtcttgct ggcgttcgcg acgcgaggct ggatggcctt ccccattatg attcttctcg 2160
cttccggcgg catcgggatg cccgcgttgc aggccatgct gtccaggcag gtagatgacg 2220
accatcaggg acagcttcaa ggatcgctcg cggctcttac cagcctaact tcgatcactg 2280
gaccgctgat cgtcacggcg atttatgccg cctcggcgag cacatggaac gggttggcat 2340
ggattgtagg cgccgcccta taccttgtct gcctccccgc gttgcgtcgc ggtgcatgga 2400
gccgggccac ctcgacctga atggaagccg gcggcacctc gctaacggat tcaccactcc 2460
aagaattgga gccaatcaat tcttgcggag aactgtgaat gcgcaaacca acccttggca 2520
gaacatatcc atcgcgtccg ccatctccag cagccgcacg cggcgcatct cgggcagcgt 2580
tgggtcctgg ccacgggtgc gcatgatcgt gctcctgtcg ttgaggaccc ggctaggctg 2640
gcggggttgc cttactggtt agcagaatga atcaccgata cgcgagcgaa cgtgaagcga 2700
ctgctgctgc aaaacgtctg cgacctgagc aacaacatga atggtcttcg gtttccgtgt 2760
ttcgtaaagt ctggaaacgc ggaagtcagc gccctgcacc attatgttcc ggatctgcat 2820
cgcaggatgc tgctggctac cctgtggaac acctacatct gtattaacga agcgctggca 2880
ttgaccctga gtgatttttc tctggtcccg ccgcatccat accgccagtt gtttaccctc 2940
acaacgttcc agtaaccggg catgttcatc atcagtaacc cgtatcgtga gcatcctctc 3000
tcgtttcatc ggtatcatta cccccatgaa cagaaattcc cccttacacg gaggcatcaa 3060
gtgaccaaac aggaaaaaac cgcccttaac atggcccgct ttatcagaag ccagacatta 3120
acgcttctgg agaaactcaa cgagctggac gcggatgaac aggcagacat ctgtgaatcg 3180
cttcacgacc acgctgatga gctttaccgc agctgcctcg cgcgtttcgg tgatgacggt 3240
gaaaacctct gacacatgca gctcccggag acggtcacag cttgtctgta agcggtgccg 3300
ggagcagaca agcccgtcag ggcgcgtcag cgggtgttgg cgggtgtcgg ggcgcagcca 3360
tgacccagtc acgtagcgat agcggagtgt atactggctt aactatgcgg catcagagca 3420

-continued gattgtactg agagtgcacc atatgcggtg tgaaataccg cacagatgcg taaggagaaa 3480
ataccgcatc aggcgctctt ccgcttcctc gctcactgac tcgctgcgct cggtcgttcg 3540
gctgcggcga gcggtatcag ctcactcaaa ggcggtaata cggttatcca cagaatcagg 3600
ggataacgca ggaaagaaca tgtgagcaaa aggccagcaa aaggccagga accgtaaaaa 3660
ggccgcgttg ctggcgtttt tccataggct ccgcccccct gacgagcatc acaaaaatcg 3720
acgctcaagt cagaggtggc gaaacccgac aggactataa agataccagg cgtttccccc 3780
tggaagctcc ctcgtgcgct ctcctgttcc gaccctgccg cttaccggat acctgtccgc 3840
ctttctccct tcgggaagcg tggcgctttc tcatagctca cgctgtaggt atctcagttc 3900
ggtgtaggtc gttcgctcca agctgggctg tgtgcacgaa ccccccgttc agcccgaccg 3960
ctgcgcctta tccggtaact atcgtcttga gtccaacccg gtaagacacg acttatcgcc 4020
actggcagca gccactggta acaggattag cagagcgagg tatgtaggcg gtgctacaga 4080
gttcttgaag tggtggccta actacggcta cactagaagg acagtatttg gtatctgcgc 4140
tctgctgaag ccagttacct tcggaaaaag agttggtagc tcttgatccg gcaaacaaac 4200
caccgctggt agcggtggtt tttttgtttg caagcagcag attacgcgca gaaaaaaagg 4260
atctcaagaa gatcctttga tcttttctac ggggtctgac gctcagtgga acgaaaactc 4320
acgttaaggg attttggtca tgagattatc aaaaaggatc ttcacctaga tccttttaaa 4380
ttaaaaatga agttttaaat caatctaaag tatatatgag taaacttggt ctgacagtta 4440
ccaatgctta atcagtgagg cacctatctc agcgatctgt ctatttcgtt catccatagt 4500
tgcctgactc cccgtcgtgt agataactac gatacgggag ggcttaccat ctggccccag 4560
tgctgcaatg ataccgcgag acccacgctc accggctcca gatttatcag caataaacca 4620
gccagccgga agggccgagc gcagaagtgg tcctgcaact ttatccgcct ccatccagtc 4680
tattaattgt tgccgggaag ctagagtaag tagttcgcca gttaatagtt tgcgcaacgt 4740
tgttgccatt gctgcaggca tcgtggtgtc acgctcgtcg tttggtatgg cttcattcag 4800
ctccggttcc caacgatcaa ggcgagttac atgatccccc atgttgtgca aaaaagcggt 4860
tagctccttc ggtcctccga tcgttgtcag aagtaagttg gccgcagtgt tatcactcat 4920
ggttatggca gcactgcata attctcttac tgtcatgcca tccgtaagat gcttttctgt 4980
gactggtgag tactcaacca agtcattctg agaatagtgt atgcggcgac cgagttgctc 5040
ttgcccggcg tcaacacggg ataataccgc gccacatagc agaactttaa aagtgctcat 5100
cattggaaaa cgttcttcgg ggcgaaaact ctcaaggatc ttaccgctgt tgagatccag 5160
ttcgatgtaa cccactcgtg cacccaactg atcttcagca tcttttactt tcaccagcgt 5220
ttctgggtga gcaaaaacag gaaggcaaaa tgccgcaaaa aagggaataa gggcgacacg 5280
gaaatgttga atactcatac tcttcctttt tcaatattat tgaagcattt atcagggtta 5340
ttgtctcatg agcggataca tatttgaatg tatttagaaa aataaacaaa taggggttcc 5400
gcgcacattt ccccgaaaag tgccacctga cgtctaagaa accattatta tcatgacatt 5460
aacctataaa aataggcgt atcacgaggc cctttcgtct tcaagaattc tcatgtttga 5520
cagcttatca tcgatccact tgtatatttg gatgaatttt tgaggaattc tgaaccagtc 5580
ctaaaacgag taaataggac cggcaattct tcaagcaata aacaggaata ccaattatta 5640
aaagataact tagtcagatc gtacaataaa gctttgaaga aaaatgcgcc ttattcaatc 5700
tttgcataaa aaaatggccc aaaatctcac attggaagac atttgatgac ctcatttctt 5760
tcaatgaagg gcctaacgga gttgactaat gttgtgggaa attggaccga taagcgtgct 5820

-continued

```
tctgccgtgg ccaggacaac gtatactcat cagataacag caatacctga tcactacttc   5880
gcactagttt ctcggtacta tgcatatgat ccaatatcaa aggaaatgat agcattgaag   5940
gatgagacta atccaattga ggagtggcag catatagaac agctaaaggg tagtgctgaa   6000
ggaagcatac gataccccgc atggaatggg ataatatcac aggaggtact agactacctt   6060
tcatcctaca taaatagacg catataagta cgcatttaag cataaacacg cactatgccg   6120
ttcttctcat gtatatatat atacaggcaa cacgcagata taggtgcgac gtgaacagtg   6180
agctgtatgt gcgcagctcg cgttgcattt tcggaagcgc tcgttttcgg aaacgctttg   6240
aagttcctat tccgaagttc ctattctcta gaaagtatag gaacttcaga gcgcttttga   6300
aaaccaaaag cgctctgaag acgcactttc aaaaaaccaa aaacgcaccg gactgtaacg   6360
agctactaaa atattgcgaa taccgcttcc acaaacattg ctcaaaagta tctctttgct   6420
atatatctct gtgctatatc cctatataac catcccatcc acctttcgct ccttgaactt   6480
gcatctaaac tcgacctcta cattttttat gtttatctct agtattacct cttagacaaa   6540
aaaattgtag taagaactat tcatagagtt aatcgaaaac aatacgaaaa tgtaaacatt   6600
tcctatacgt agtatataga gacaaaatag aagaaaccgt tcataatttt ctgaccaatg   6660
aagaatcatc aacgctatca ctttctgttc acaaagtatg cgcaatccac atcggtatag   6720
aatataatcg ggatgcctt tatcttgaaa aaatgcaccc gcagcttcgc tagtaatcag    6780
taaacgcggg aagtggagtc aggcttttt tatggaagag aaaatagaca ccaaagtagc    6840
cttcttctaa ccttaacgga cctacagtgc aaaaagttat caagagactg cattatagag   6900
cgcacaaagg agaaaaaaag taatctaaga tgctttgtta gaaaaatagc gctctcggga   6960
tgcatttttg tagaacaaaa aagaagtata gattcttgtt ggtaaaatag cgctctcgcg   7020
ttgcatttct gttctgtaaa aatgcagctc agattctttg tttgaaaaat tagcgctctc   7080
gcgttgcatt tttgttttac aaaaatgaag cacagattct tcgttggtaa aatagcgctt   7140
tcgcgttgca tttctgttct gtaaaaatgc agctcagatt ctttgtttga aaaattagcg   7200
ctctcgcgtt gcatttttgt tctacaaaat gaagcacaga tgcttcgtta acaaagatat   7260
gctattgaag tgcaagatgg aaacgcagaa aatgaaccgg ggatgcgacg tgcaagatta   7320
cctatgcaat agatgcaata gtttctccag gaaccgaaat acatacattg tcttccgtaa   7380
agcgctagac tatatattat tatacaggtt caaatatact atctgtttca gggaaaactc   7440
ccaggttcgg atgttcaaaa ttcaatgatg ggtaacaagt acgatcgtaa atctgtaaaa   7500
cagtttgtcg gatattaggc tgtatctcct caaagcgtat tcgaatatca ttgagaagct   7560
gcattttttt tttttttttt tttttttttt tttttatata tatttcaagg atataccatt   7620
gtaatgtctg cccctaagaa gatcgtcgtt ttgccaggtg accacgttgg tcaagaaatc   7680
acagccgaag ccattaaggt tcttaaagct atttctgatg ttcgttccaa tgtcaagttc   7740
gatttcgaaa atcatttaat tggtggtgct gctatcgatg ctacaggtgt cccacttcca   7800
gatgaggcgc tggaagcctc caagaaggtt gatgccgttt tgttaggtgc tgtgggtggt   7860
cctaaatggg gtaccggtag tgttagacct gaacaaggtt tactaaaaat ccgtaaagaa   7920
cttcaattgt acgccaactt aagaccatgt aactttgcat ccgactctct tttagactta   7980
tctccaatca agccacaatt tgctaaaggt actgacttcg ttgttgtcag agaattagtg   8040
ggaggtattt actttggtaa gagaaaggaa gacgatggtg atggtgtcgc ttgggatagt   8100
gaacaataca ccgttccaga agtgcaaaga atcacaagaa tggccgcttt catggcccta   8160
```

-continued

```
caacatgagc caccattgcc tatttggtcc ttggataaag ctaatgtttt ggcctcttca   8220
agattatgga gaaaaactgt ggaggaaacc atcaagaacg aattccctac attgaaggtt   8280
caacatcaat tgattgattc tgccgccatg atcctagtta agaacccaac ccacctaaat   8340
ggtattataa tcaccagcaa catgtttggt gatatcatct ccgatgaagc ctccgttatc   8400
ccaggttcct tgggtttgtt gccatctgcg tccttggcct ctttgccaga caagaacacc   8460
gcatttggtt tgtacgaacc atgccacggt tctgctccag atttgccaaa gaataaggtt   8520
gaccctatcg ccactatctt gtctgctgca atgatgttga aattgtcatt gaacttgcct   8580
gaagaaggta aggccattga agatgcagtt aaaaaggttt tggatgcagg tatcagaact   8640
ggtgatttag gtggttccaa cagtaccacc gaagtcggtg atgctgtcgc cgaagaagtt   8700
aagaaaatcc ttgcttaaaa agattctctt tttttatgat atttgtacaa aaaaaaaaaa   8760
aaaaaaaaaa aaaaaaaaaa aaaaaaaaaa aaaatgcagc gtcacatcgg ataataatga   8820
tggcagccat tgtagaagtg ccttttgcat ttctagtctc tttctcggtc tagctagttt   8880
tactacatcg cgaagataga atcttagatc acactgcctt tgctgagctg gatcatatga   8940
gtaacaaaag agtggtaagg cctcgttaaa ggacaaggac ctgagcggaa gtgtatcgta   9000
aagtagacgg agtatactag tatagtctat agtccgtgga attctaagtg ccagctttat   9060
aatgtcattc tccttactac agacccgcct gaaagtagac acatcatcat cagtaagctt   9120
tgacaaaaag cattgagtag ctaactcttc tatgcaatct atagctgttt tataaggcat   9180
tcaatggaca gattgaggtt tttgaaacat actagtgaaa ttagccttaa tcccttctcg   9240
aagttaatca tgcattatgg tgtaaaaaat gcaactcgcg ttgctctact tttcccgaa    9300
tttccaaata cgcagctggg gtgattgctc gatttcgtaa cgaaagtttt gtttataaaa   9360
accgcgaaaa ccttctgtaa cagatagatt tttacagcgc tgatatacaa tgacatcagc   9420
tgtaatggaa aataactgaa atatgaatgg cgagagactg cttgcttgta ttaagcaatg   9480
tattatgcag cacttccaac ctatggtgta cgatgaaagt aggtgtgtaa tcgagacgac   9540
aagggggact tttccagttc ctgatcatta taagaaatac aaaacgttag catttgcatt   9600
tgttggacat gtactgaata cagacgacac accggtaatt gaaaaagaac tggattggcc   9660
tgatcctgca ctagtgtaca atacaattgt cgatcgaatc ataaatcacc cagaattatc   9720
acagtttata tcggttgcat ttattagtca gttaaaggcc accatcggag agggtttaga   9780
tattaatgta aaaggcacgc taaaccgcag gggaaagggt atcagaaggc ctaaaggcgt   9840
attttttaga tacatggaat ctccatttgt caatacaaag gtcactgcat tcttctctta   9900
tcttcgagat tataataaaa ttgcctcaga atatcacaat aatactaaat tcattctcac   9960
gttttcatgt caagcatatt gggcatctgg cccaaacttc tccgccttga agaatgttat  10020
ttggtgctcc ataattcatg aatacatttc taagtttgtg gaaagagaac aggataaagg  10080
tcatatagga gatcaggagc taccgcctga agaggaccct tctcgtgaac taaacaatgt  10140
acaacatgaa gtcaatagtt taacggaaca agatgcggag gcggatgaag gattgtgggg  10200
tgaaatagat tcattatgtg aaaaatggca gtctgaagcg gagagtcaaa ctgaggcgga  10260
gataatagcc gacaggataa ttggaaatag ccagaggatg gcgaacctca aaattcgtcg  10320
tacaaagttc aaaagtgtct tgtatcatat actaaaggaa ctaattcaat ctcagggaac  10380
cgtaaaggtt tatcgcggta gtagtttttc acacgattcg ataaagataa gcttacatta  10440
tgaagagcag catattacag ccgtatgggt ctacttgata gtaaaatttg aagagcattg  10500
gaagcctgtt gatgtagagg tcgagtttag atgcaagttc aaggagcgaa aggtggatgg  10560
```

-continued

```
gtaggttata tagggatata gcacagagat atatagcaaa gagatacttt tgaggcaatg  10620
tttgtggaag cggtattcgc aatattttag tagctcgtta cagtccggtg cgtttttggt  10680
tttttgaaag tgcgtcttca gagcgctttt ggttttcaaa agcgctctga agttcctata  10740
ctttctagag aataggaact tcggaatagg aacttcaaag cgtttccgaa aacgagcgct  10800
tccgaaaatg caacgcgagc tgcgcacata cagctcactg ttcacgtcgc acctatatct  10860
gcgtgttgcc tgtatatata tatacatgag aagaacggca tagtgcgtgt ttatgcttaa  10920
atgcgtactt atatgcgtct atttatgtag gatgaaaggt agtctagtac ctcctgtgat  10980
attatcccat tccatgcggg gtatcgtatg cttccttcag cactaccctt tagctgttct  11040
atatgctgcc actcctcaat tggattagtc tcatccttca atgcattcat ttcctttgat  11100
attggatcat accctagaag tattacgtga ttttctgccc cttaccctcg ttgctactct  11160
ccttttttc gtgggaaccg ctttagggcc ctcagtgatg gtgttttgta atttatatgc  11220
tcctcttgca tttgtgtctc tacttcttgt tcgcctggag ggaacttctt catttgtatt  11280
agcatggttc acttcagtcc ttccttccaa ctcactcttt ttttgctgta aacgattctc  11340
tgccgccagt tcattgaaac tattgaatat atcctttaga gattccggga tgaataaatc  11400
acctattaaa gcagcttgac gatctggtgg aactaaagta agcaattggg taacgacgct  11460
tacgagcttc ataacatctt cttccgttgg agctggtggg actaataact gtgtacaatc  11520
catttttctc atgagcattt cggtagctct cttcttgtct ttctcgggca atcttcctat  11580
tattatagca atagatttgt atagttgctt tctattgtct aacagcttgt tattctgtag  11640
catcaaatct atggcagcct gacttgcttc ttgtgaagag agcataccat ttccaatcga  11700
agatacgctg gaatcttctg cgctagaatc aagaccatac ggcctaccgg ttgtgagaga  11760
ttccatgggc cttatgacat atcctggaaa gagtagctca tcagacttac gtttactctc  11820
tatatcaata tctacatcag gagcaatcat ttcaataaac agccgacata catcccagac  11880
gctataagct gtacgtgctt ttaccgtcag attcttggct gtttcaatgt cgtccatttt  11940
ggttttcttt taccagtatt gttcgtttga taatgtattc ttgcttatta cattataaaa  12000
tctgtgcaga tcacatgtca aaacaacttt ttatcacaag atagtaccgc aaaacgaacc  12060
tgcgggccgt ctaaaaatta aggaaaagca gcaaaggtgc atttttaaaa tatgaaatga  12120
agataccgca gtaccaatta ttttcgcagt acaaataatg cgcggccggt gcatttttcg  12180
aaagaacgcg agacaaacag gacaattaaa gttagttttt cgagttagcg tgtttgaata  12240
ctgcaagata caagataaat agagtagttg aaactagata tcaattgcac acaagatcgg  12300
cgctaagcat gccacaattt ggtatattat gtaaaacacc acctaaggtg cttgttcgtc  12360
agtttgtgga aaggtttgaa agaccttcag gtgagaaaat agcattatgt gctgctgaac  12420
taacctattt atgttggatg attacacata acggaacagc aatcaagaga gccacattca  12480
tgagctataa tactatcata agcaattcgc tgagtttcga tattgtcaat aaatcactcc  12540
agtttaaata caagacgcaa aaagcaacaa ttctggaagc ctcattaaag aaattgattc  12600
ctgcttggga atttacaatt attccttact atggacaaaa acatcaatct gatatcactg  12660
atattgtaag tagtttgcaa ttacagttcg aatcatcgga agaagcagat aagggaaata  12720
gccacagtaa aaaaatgcta aagcacttct aagtgagggt gaaagcatct gggagatcac  12780
tgagaaaata ctaaattcgt ttgagtatac ttcgagattt acaaaaacaa aaactttata  12840
ccaattcctc ttcctagcta ctttcatcaa ttgtggaaga ttcagcgata ttaagaacgt  12900
```

-continued tgatccgaaa tcatttaaat tagtccaaaa taagtatctg ggagtaataa tccagtgttt 12960
agtgacagag acaaagacaa gcgttagtag gcacatatac ttctttagcg caaggggtag 13020

<210> SEQ ID NO 44
<211> LENGTH: 15810
<212> TYPE: DNA
<213> ORGANISM: Artificial Sequence
<220> FEATURE:
<223> OTHER INFORMATION: Description of Artificial Sequence: Vector
pSY1aMFE1sH6a sequence

<400> SEQUENCE: 44
atcgataagc ttttcaattc aattcatcat ttttttttta ttcttttttt tgatttcggt 60
ttctttgaaa tttttttgat tcggtaatct ccgaacagaa ggaagaacga aggaaggagc 120
acagacttag attggtatat atacgcatat gtagtgttga agaaacatga aattgcccag 180
tattcttaac ccaactgcac agaacaaaaa cctgcaggaa acgaagataa atcatgtcga 240
aagctacata taaggaacgt gctgctactc atcctagtcc tgttgctgcc aagctattta 300
atatcatgca cgaaaagcaa acaaacttgt gtgcttcatt ggatgttcgt accaccaagg 360
aattactgga gttagttgaa gcattaggtc ccaaaatttg tttactaaaa acacatgtgg 420
atatcttgac tgatttttcc atggagggca cagttaagcc gctaaaggca ttatccgcca 480
agtacaattt tttactcttc gaagacagaa aatttgctga cattggtaat acagtcaaat 540
tgcagtactc tgcgggtgta tacagaatag cagaatgggc agacattacg aatgcacacg 600
gtgtggtggg cccaggtatt gttagcggtt tgaagcaggc ggcagaagaa gtaacaaagg 660
aacctagagg ccttttgatg ttagcagaat tgtcatgcaa gggctcccta tctactggag 720
aatatactaa gggtactgtt gacattgcga agagcgacaa agattttgtt atcggcttta 780
ttgctcaaag agacatgggt ggaagagatg aaggttacga ttggttgatt atgacacccg 840
gtgtgggttt agatgacaag ggagacgcat tgggtcaaca gtatagaacc gtggatgatg 900
tggtctctac aggatctgac attattattg ttggaagagg actatttgca aagggaaggg 960
atgctaaggt agagggtgaa cgttacagaa aagcaggctg ggaagcatat ttgagaagat 1020
gcggccagca aaactaaaaa actgtattat aagtaaatgc atgtatacta aactcacaaa 1080
ttagagcttc aatttaatta tatcagttat tacccgggaa tctcggtcgt aatgattttt 1140
ataatgacga aaaaaaaaaa attggaaaga aaaagcttta atgcggtagt ttatcacagt 1200
taaattgcta acgcagtcag gcaccgtgta tgaaatctaa caatgcgctc atcgtcatcc 1260
tcggcaccgt caccctggat gctgtaggca taggcttggt tatgccggta ctgccgggcc 1320
tcttgcggga tatcgtccat tccgacagca tcgccagtca ctatggcgtg ctgctagcgc 1380
tatatgcgtt gatgcaattt ctatgcgcac ccgttctcgg agcactgtcc gaccgctttg 1440
gccgccgccc agtcctgctc gcttcgctac ttggagccac tatcgactac gcgatcatgg 1500
cgaccacacc cgtcctgtgg atccttcaat atgcgcacat acgctgttat gttcaaggtc 1560
ccttcgttta agaacgaaag cggtcttcct tttgagggat gtttcaagtt gttcaaatct 1620
atcaaatttg caaatcccca gtctgtatct agagcgttga atcggtgatg cgatttgtta 1680
attaaattga tggtgtcacc attaccaggt ctagatatac caatggcaaa ctgagcacaa 1740
caataccagt ccggatcaac tggcaccatc tctcccgtag tctcatctaa tttttcttcc 1800
ggatgaggtt ccagatatac cgcaacacct ttattatggt ttccctgagg gaataataga 1860
atgtcccatt cgaaatcacc aattctaaac ctgggcgaat tgtatttcgg gtttgttaac 1920

-continued

```
tcgttccagt caggaatgtt ccacgtgaag ctatcttcca gcaaagtctc cacttcttca   1980
tcaaattgtg gagaatactc ccaatgctct tatctatggg acttccggga aacacagtac   2040
cgatacttcc caattcgtct tcagagctca ttgtttgttt gaagagacta atcaaagaat   2100
cgttttctca aaaaaattaa tatcttaact gatagtttga tcaaaggggc aaaacgtagg   2160
ggcaaacaaa cggaaaaatc gtttctcaaa ttttctgatg ccaagaactc taaccagtct   2220
tatctaaaaa ttgccttatg atccgtctct ccggttacag cctgtgtaac tgattaatcc   2280
tgcctttcta atcaccattc taatgtttta attaagggat tttgtcttca ttaacggctt   2340
tcgctcataa aaatgttatg acgttttgcc cgcaggcggg aaaccatcca cttcacgaga   2400
ctgatctcct ctgccggaac accgggcatc tccaacttat aagttggaga aataagagaa   2460
tttcagattg agagaatgaa aaaaaaaaac cctgaaaaaa aaggttgaaa ccagttccct   2520
gaaattattc ccctacttga ctaataagta tataaagacg gtaggtattg attgtaattc   2580
tgtaaatcta tttcttaaac ttcttaaatt ctacttttat agttagtctt ttttttagtt   2640
ttaaaacacc aagaacttag tttcgaataa acacacataa acaaacacca tgagatttcc   2700
ttcaattttt actgcagttt tattcgcagc atcctccgca ttagctgctc cagtcaacac   2760
tacaacagaa gatgaaacgg cacaaattcc ggctgaagct gtcatcggtt actcagattt   2820
agaaggggat ttcgatgttg ctgttttgcc attttccaac agcacaaata acgggttatt   2880
gtttataaat actactattg ccagcattgc tgctaaagaa gaaggggtat ctctagataa   2940
aaggtatgag gtgcgcaacg tgtccgggat gtaccatgtc acgaacgact gctccaactc   3000
aagcattgtg tatgaggcag cggacatgat catgcacacc cccgggtgcg tgccctgcgt   3060
tcgggagaac aactcttccc gctgctgggt agcgctcacc cccacgctcg cagctaggaa   3120
cgccagcgtc cccactacga caatacgacg ccacgtcgat ttgctcgttg ggcggctgc    3180
tttctgttcc gctatgtacg tgggggatct ctgcggatct gtcttcctcg tctcccagct   3240
gttcaccatc tcgcctcgcc ggcatgagac ggtgcaggac tgcaattgct caatctatcc   3300
cggccacata acgggtcacc gtatggcttg ggatatgatg atgaactggc accaccacca   3360
tcaccattaa agatctcgac ttggttgaac acgttgccaa ggcttaagtg aatttacttt   3420
aaagtcttgc atttaaataa attttctttt tatagcttta tgacttagtt tcaatttata   3480
tactatttta atgacatttt cgattcattg attgaaagct ttgtgttttt tcttgatgcg   3540
ctattgcatt gttcttgtct ttttcgccac atgtaatatc tgtagtagat acctgataca   3600
ttgtggatgc tgagtgaaat tttagttaat aatggaggcg ctcttaataa ttttggggat   3660
attggctttt tttttaaag tttacaaatg aatttttttcc gccaggataa cgattctgaa   3720
gttactctta gcgttcctat cggtacagcc atcaaatcat gcctataaat catgcctata   3780
tttgcgtgca gtcagtatca tctacatgaa aaaaactccc gcaatttctt atagaatacg   3840
ttgaaaatta aatgtacgcg ccaagataag ataacatata tctagctaga tgcagtaata   3900
tacacagatt cccgcggacg tgggaaggaa aaaattagat aacaaaatct gagtgatatg   3960
gaaattccgc tgtatagctc atatctttcc cttcaacacc agaaatgtaa aaatcttgtt   4020
acgaaggatc tttttgctaa tgtttctcgc tcaatcctca tttcttccct acgaagagtc   4080
aaatctactt gttttctgcc ggtatcaaga tccatatctt ctagtttcac catcaaagtc   4140
caatttctag tatacagttt atgtcccaac gtaacagaca atcaaaattg gaaaggataa   4200
gtatccttca aagaatgatt ctgcgctggc tcctgaaccg cctaatggga acagagaagt   4260
ccaaaacgat gctataagaa ccagaaataa aacgataaaa ccataccagg atcctctacg   4320
```

-continued ccggacgcat cgtggccggc atcaccggcg ccacaggtgc ggttgctggc ccctatatcg 4380
ccgacatcac cgatggggaa gatcgggctc gccacttcgg gctcatgagc gcttgtttcg 4440
gcgtgggtat ggtggcaggc cccgtggccg ggggactgtt gggcgccatc tccttgcatg 4500
caccattcct tgcggcggcg gtgctcaacg gcctcaacct actactgggc tgcttcctaa 4560
tgcaggagtc gcataaggga gagcgtcgac cgatgccctt gagagccttc aacccagtca 4620
gctccttccg gtgggcgcgg ggcatgacta tcgtcgccgc acttatgact gtcttcttta 4680
tcatgcaact cgtaggacag gtgccggcag cgctctgggt cattttcggc gaggaccgct 4740
ttcgctggag cgcgacgatg atcggcctgt cgcttgcggt attcggaatc ttgcacgccc 4800
tcgctcaagc cttcgtcact ggtcccgcca ccaaacgttt cggcgagaag caggccatta 4860
tcgccggcat ggcggccgac gcgctgggct acgtcttgct ggcgttcgcg acgcgaggct 4920
ggatggcctt ccccattatg attcttctcg cttccggcgg catcgggatg cccgcgttgc 4980
aggccatgct gtccaggcag gtagatgacg accatcaggg acagcttcaa ggatcgctcg 5040
cggctcttac cagcctaact tcgatcactg gaccgctgat cgtcacggcg atttatgccg 5100
cctcggcgag cacatggaac gggttggcat ggattgtagg cgccgcccta taccttgtct 5160
gcctccccgc gttgcgtcgc ggtgcatgga gccgggccac ctcgacctga atggaagccg 5220
gcggcacctc gctaacggat tcaccactcc aagaattgga gccaatcaat tcttgcggag 5280
aactgtgaat gcgcaaacca acccttggca gaacatatcc atcgcgtccg ccatctccag 5340
cagccgcacg cggcgcatct cgggcagcgt tgggtcctgg ccacgggtgc gcatgatcgt 5400
gctcctgtcg ttgaggaccc ggctaggctg gcggggttgc cttactggtt agcagaatga 5460
atcaccgata cgcgagcgaa cgtgaagcga ctgctgctgc aaaacgtctg cgacctgagc 5520
aacaacatga atggtcttcg gtttccgtgt ttcgtaaagt ctggaaacgc ggaagtcagc 5580
gccctgcacc attatgttcc ggatctgcat cgcaggatgc tgctggctac cctgtggaac 5640
acctacatct gtattaacga agcgctggca ttgaccctga gtgatttttc tctggtcccg 5700
ccgcatccat accgccagtt gtttaccctc acaacgttcc agtaaccggg catgttcatc 5760
atcagtaacc cgtatcgtga gcatcctctc tcgtttcatc ggtatcatta cccccatgaa 5820
cagaaattcc cccttacacg gaggcatcaa gtgaccaaac aggaaaaaac cgcccttaac 5880
atggcccgct ttatcagaag ccagacatta acgcttctgg agaaactcaa cgagctggac 5940
gcggatgaac aggcagacat ctgtgaatcg cttcacgacc acgctgatga gctttaccgc 6000
agctgcctcg cgcgtttcgg tgatgacggt gaaaacctct gacacatgca gctcccggag 6060
acggtcacag cttgtctgta agcggtgccg ggagcagaca agcccgtcag ggcgcgtcag 6120
cgggtgttgg cgggtgtcgg ggcgcagcca tgacccagtc acgtagcgat agcggagtgt 6180
atactggctt aactatgcgg catcagagca gattgtactg agagtgcacc atatgcggtg 6240
tgaaataccg cacagatgcg taaggagaaa ataccgcatc aggcgctctt ccgcttcctc 6300
gctcactgac tcgctgcgct cggtcgttcg gctgcggcga gcggtatcag ctcactcaaa 6360
ggcggtaata cggttatcca cagaatcagg ggataacgca ggaaagaaca tgtgagcaaa 6420
aggccagcaa aaggccagga accgtaaaaa ggccgcgttg ctggcgtttt tccataggct 6480
ccgcccccct gacgagcatc acaaaaatcg acgctcaagt cagaggtggc gaaacccgac 6540
aggactataa agataccagg cgtttccccc tggaagctcc ctcgtgcgct ctcctgttcc 6600
gaccctgccg cttaccggat acctgtccgc ctttctccct tcgggaagcg tggcgctttc 6660

-continued

```
tcatagctca cgctgtaggt atctcagttc ggtgtaggtc gttcgctcca agctgggctg   6720

tgtgcacgaa ccccccgttc agcccgaccg ctgcgcctta tccggtaact atcgtcttga   6780

gtccaacccg gtaagacacg acttatcgcc actggcagca gccactggta acaggattag   6840

cagagcgagg tatgtaggcg gtgctacaga gttcttgaag tggtggccta actacggcta   6900

cactagaagg acagtatttg gtatctgcgc tctgctgaag ccagttacct tcggaaaaag   6960

agttggtagc tcttgatccg gcaaacaaac caccgctggt agcggtggtt tttttgtttg   7020

caagcagcag attacgcgca gaaaaaaagg atctcaagaa gatcctttga tcttttctac   7080

ggggtctgac gctcagtgga acgaaaactc acgttaaggg attttggtca tgagattatc   7140

aaaaaggatc ttcacctaga tccttttaaa ttaaaaatga agttttaaat caatctaaag   7200

tatatatgag taaacttggt ctgacagtta ccaatgctta atcagtgagg cacctatctc   7260

agcgatctgt ctatttcgtt catccatagt tgcctgactc cccgtcgtgt agataactac   7320

gatacgggag ggcttaccat ctggccccag tgctgcaatg ataccgcgag acccacgctc   7380

accggctcca gatttatcag caataaacca gccagccgga agggccgagc gcagaagtgg   7440

tcctgcaact ttatccgcct ccatccagtc tattaattgt tgccgggaag ctagagtaag   7500

tagttcgcca gttaatagtt tgcgcaacgt tgttgccatt gctgcaggca tcgtggtgtc   7560

acgctcgtcg tttggtatgg cttcattcag ctccggttcc caacgatcaa ggcgagttac   7620

atgatccccc atgttgtgca aaaaagcggt tagctccttc ggtcctccga tcgttgtcag   7680

aagtaagttg gccgcagtgt tatcactcat ggttatggca gcactgcata attctcttac   7740

tgtcatgcca tccgtaagat gcttttctgt gactggtgag tactcaacca agtcattctg   7800

agaatagtgt atgcggcgac cgagttgctc ttgcccggcg tcaacacggg ataataccgc   7860

gccacatagc agaactttaa aagtgctcat cattggaaaa cgttcttcgg ggcgaaaact   7920

ctcaaggatc ttaccgctgt tgagatccag ttcgatgtaa cccactcgtg cacccaactg   7980

atcttcagca tcttttactt tcaccagcgt ttctgggtga gcaaaaacag gaaggcaaaa   8040

tgccgcaaaa aagggaataa gggcgacacg gaaatgttga atactcatac tcttcctttt   8100

tcaatattat tgaagcattt atcagggtta ttgtctcatg agcggataca tatttgaatg   8160

tatttagaaa aataaacaaa taggggttcc gcgcacattt ccccgaaaag tgccacctga   8220

cgtctaagaa accattatta tcatgacatt aacctataaa aataggcgt atcacgaggc   8280

cctttcgtct tcaagaattc tcatgtttga cagcttatca tcgatccact tgtatatttg   8340

gatgaatttt tgaggaattc tgaaccagtc ctaaaacgag taaataggac cggcaattct   8400

tcaagcaata aacaggaata ccaattatta aaagataact tagtcagatc gtacaataaa   8460

gctttgaaga aaaatgcgcc ttattcaatc tttgcataaa aaaatggccc aaaatctcac   8520

attggaagac atttgatgac ctcatttctt tcaatgaagg gcctaacgga gttgactaat   8580

gttgtgggaa attggaccga taagcgtgct tctgccgtgg ccaggacaac gtatactcat   8640

cagataacag caatacctga tcactacttc gcactagttt ctcggtacta tgcatatgat   8700

ccaatatcaa aggaaatgat agcattgaag gatgagacta atccaattga ggagtggcag   8760

catatagaac agctaaaggg tagtgctgaa ggaagcatac gataccccgc atggaatggg   8820

ataatatcac aggaggtact agactacctt tcatcctaca taaatagacg catataagta   8880

cgcatttaag cataaacacg cactatgccg ttcttctcat gtatatatat atacaggcaa   8940

cacgcagata taggtgcgac gtgaacagtg agctgtatgt gcgcagctcg cgttgcattt   9000

tcggaagcgc tcgttttcgg aaacgctttg aagttcctat tccgaagttc ctattctcta   9060
```

-continued

```
gaaagtatag gaacttcaga gcgcttttga aaaccaaaag cgctctgaag acgcactttc   9120
aaaaaaccaa aaacgcaccg gactgtaacg agctactaaa atattgcgaa taccgcttcc   9180
acaaacattg ctcaaaagta tctctttgct atatatctct gtgctatatc cctatataac   9240
catcccatcc acctttcgct ccttgaactt gcatctaaac tcgacctcta catttttat   9300
gtttatctct agtattacct cttagacaaa aaaattgtag taagaactat tcatagagtt   9360
aatcgaaaac aatacgaaaa tgtaaacatt tcctatacgt agtatataga gacaaaatag   9420
aagaaaccgt tcataatttt ctgaccaatg aagaatcatc aacgctatca ctttctgttc   9480
acaaagtatg cgcaatccac atcggtatag aatataatcg gggatgcctt tatcttgaaa   9540
aaatgcaccc gcagcttcgc tagtaatcag taaacgcggg aagtggagtc aggctttttt   9600
tatggaagag aaaatagaca ccaaagtagc cttcttctaa ccttaacgga cctacagtgc   9660
aaaaagttat caagagactg cattatagag cgcacaaagg agaaaaaaag taatctaaga   9720
tgctttgtta gaaaaatagc gctctcggga tgcatttttg tagaacaaaa aagaagtata   9780
gattcttgtt ggtaaaatag cgctctcgcg ttgcatttct gttctgtaaa aatgcagctc   9840
agattctttg tttgaaaaat tagcgctctc gcgttgcatt tttgttttac aaaaatgaag   9900
cacagattct tcgttggtaa aatagcgctt tcgcgttgca tttctgttct gtaaaaatgc   9960
agctcagatt ctttgtttga aaaattagcg ctctcgcgtt gcatttttgt tctacaaaat  10020
gaagcacaga tgcttcgtta acaaagatat gctattgaag tgcaagatgg aaacgcagaa  10080
aatgaaccgg ggatgcgacg tgcaagatta cctatgcaat agatgcaata gtttctccag  10140
gaaccgaaat acatacattg tcttccgtaa agcgctagac tatatattat tatacaggtt  10200
caaatatact atctgtttca gggaaaactc ccaggttcgg atgttcaaaa ttcaatgatg  10260
ggtaacaagt acgatcgtaa atctgtaaaa cagtttgtcg gatattaggc tgtatctcct  10320
caaagcgtat tcgaatatca ttgagaagct gcattttttt tttttttttt tttttttttt  10380
tttttatata tatttcaagg atataccatt gtaatgtctg cccctaagaa gatcgtcgtt  10440
ttgccaggtg accacgttgg tcaagaaatc acagccgaag ccattaaggt tcttaaagct  10500
atttctgatg ttcgttccaa tgtcaagttc gatttcgaaa atcatttaat tggtggtgct  10560
gctatcgatg ctacaggtgt cccacttcca gatgaggcgc tggaagcctc caagaaggtt  10620
gatgccgttt tgttaggtgc tgtgggtggt cctaaatggg gtaccggtag tgttagacct  10680
gaacaaggtt tactaaaaat ccgtaaagaa cttcaattgt acgccaactt aagaccatgt  10740
aactttgcat ccgactctct tttagactta tctccaatca agccacaatt tgctaaaggt  10800
actgacttcg ttgttgtcag agaattagtg ggaggtattt actttggtaa gagaaaggaa  10860
gacgatggtg atggtgtcgc ttgggatagt gaacaataca ccgttccaga agtgcaaaga  10920
atcacaagaa tggccgcttt catggcccta caacatgagc caccattgcc tatttggtcc  10980
ttggataaag ctaatgtttt ggcctcttca agattatgga gaaaaactgt ggaggaaacc  11040
atcaagaacg aattccctac attgaaggtt caacatcaat tgattgattc tgccgccatg  11100
atcctagtta agaacccaac ccacctaaat ggtattataa tcaccagcaa catgtttggt  11160
gatatcatct ccgatgaagc ctccgttatc ccaggttcct tgggtttgtt gccatctgcg  11220
tccttggcct ctttgccaga caagaacacc gcatttggtt tgtacgaacc atgccacggt  11280
tctgctccag atttgccaaa gaataaggtt gaccctatcg ccactatctt gtctgctgca  11340
atgatgttga aattgtcatt gaacttgcct gaagaaggta aggccattga agatgcagtt  11400
```

-continued

```
aaaaaggttt tggatgcagg tatcagaact ggtgatttag gtggttccaa cagtaccacc  11460
gaagtcggtg atgctgtcgc cgaagaagtt aagaaaatcc ttgcttaaaa agattctctt  11520
tttttatgat atttgtacaa aaaaaaaaaa aaaaaaaaaa aaaaaaaaaa aaaaaaaaaa  11580
aaaatgcagc gtcacatcgg ataataatga tggcagccat tgtagaagtg ccttttgcat  11640
ttctagtctc tttctcggtc tagctagttt tactacatcg cgaagataga atcttagatc  11700
acactgcctt tgctgagctg gatcatatga gtaacaaaag agtggtaagg cctcgttaaa  11760
ggacaaggac ctgagcggaa gtgtatcgta aagtagacgg agtatactag tatagtctat  11820
agtccgtgga attctaagtg ccagctttat aatgtcattc tccttactac agacccgcct  11880
gaaagtagac acatcatcat cagtaagctt tgacaaaaag cattgagtag ctaactcttc  11940
tatgcaatct atagctgttt tataaggcat tcaatggaca gattgaggtt tttgaaacat  12000
actagtgaaa ttagccttaa tcccttctcg aagttaatca tgcattatgg tgtaaaaaat  12060
gcaactcgcg ttgctctact ttttcccgaa tttccaaata cgcagctggg gtgattgctc  12120
gatttcgtaa cgaaagtttt gtttataaaa accgcgaaaa ccttctgtaa cagatagatt  12180
tttacagcgc tgatatacaa tgacatcagc tgtaatggaa aataactgaa atatgaatgg  12240
cgagagactg cttgcttgta ttaagcaatg tattatgcag cacttccaac ctatggtgta  12300
cgatgaaagt aggtgtgtaa tcgagacgac aagggggact tttccagttc ctgatcatta  12360
taagaaatac aaaacgttag catttgcatt tgttggacat gtactgaata cagacgacac  12420
accggtaatt gaaaaagaac tggattggcc tgatcctgca ctagtgtaca atacaattgt  12480
cgatcgaatc ataaatcacc cagaattatc acagtttata tcggttgcat ttattagtca  12540
gttaaaggcc accatcggag agggtttaga tattaatgta aaaggcacgc taaaccgcag  12600
gggaaagggt atcagaaggc ctaaaggcgt attttttaga tacatggaat ctccatttgt  12660
caatacaaag gtcactgcat tcttctctta tcttcgagat tataataaaa ttgcctcaga  12720
atatcacaat aatactaaat tcattctcac gttttcatgt caagcatatt gggcatctgg  12780
cccaaacttc tccgccttga agaatgttat ttggtgctcc ataattcatg aatacatttc  12840
taagtttgtg gaaagagaac aggataaagg tcatatagga gatcaggagc taccgcctga  12900
agaggaccct tctcgtgaac taaacaatgt acaacatgaa gtcaatagtt taacggaaca  12960
agatgcggag gcggatgaag gattgtgggg tgaaatagat tcattatgtg aaaaatggca  13020
gtctgaagcg gagagtcaaa ctgaggcgga gataatagcc gacaggataa ttggaaatag  13080
ccagaggatg gcgaacctca aaattcgtcg tacaaagttc aaaagtgtct tgtatcatat  13140
actaaaggaa ctaattcaat ctcagggaac cgtaaaggtt tatcgcggta gtagtttttc  13200
acacgattcg ataaagataa gcttacatta tgaagagcag catattacag ccgtatgggt  13260
ctacttgata gtaaaatttg aagagcattg gaagcctgtt gatgtagagg tcgagtttag  13320
atgcaagttc aaggagcgaa aggtggatgg gtaggttata tagggatata gcacagagat  13380
atatagcaaa gagatacttt tgaggcaatg tttgtggaag cggtattcgc aatattttag  13440
tagctcgtta cagtccggtg cgtttttggt tttttgaaag tgcgtcttca gagcgctttt  13500
ggttttcaaa agcgctctga agttcctata ctttctagag aataggaact tcggaatagg  13560
aacttcaaag cgtttccgaa aacgagcgct tccgaaaatg caacgcgagc tgcgcacata  13620
cagctcactg ttcacgtcgc acctatatct gcgtgttgcc tgtatatata tatacatgag  13680
aagaacggca tagtgcgtgt ttatgcttaa atgcgtactt atatgcgtct atttatgtag  13740
gatgaaaggt agtctagtac ctcctgtgat attatcccat tccatgcggg gtatcgtatg  13800
```

-continued

```
cttccttcag cactaccctt tagctgttct atatgctgcc actcctcaat tggattagtc  13860
tcatccttca atgcattcat ttcctttgat attggatcat accctagaag tattacgtga  13920
ttttctgccc cttaccctcg ttgctactct cctttttttc gtgggaaccg ctttagggcc  13980
ctcagtgatg gtgttttgta atttatatgc tcctcttgca tttgtgtctc tacttcttgt  14040
tcgcctggag ggaacttctt catttgtatt agcatggttc acttcagtcc ttccttccaa  14100
ctcactcttt ttttgctgta aacgattctc tgccgccagt tcattgaaac tattgaatat  14160
atcctttaga gattccggga tgaataaatc acctattaaa gcagcttgac gatctggtgg  14220
aactaaagta agcaattggg taacgacgct tacgagcttc ataacatctt cttccgttgg  14280
agctggtggg actaataact gtgtacaatc catttttctc atgagcattt cggtagctct  14340
cttcttgtct ttctcgggca atcttcctat tattatagca atagatttgt atagttgctt  14400
tctattgtct aacagcttgt tattctgtag catcaaatct atggcagcct gacttgcttc  14460
ttgtgaagag agcataccat ttccaatcga agatacgctg gaatcttctg cgctagaatc  14520
aagaccatac ggcctaccgg ttgtgagaga ttccatgggc cttatgacat atcctggaaa  14580
gagtagctca tcagacttac gtttactctc tatatcaata tctacatcag gagcaatcat  14640
ttcaataaac agccgacata catcccagac gctataagct gtacgtgctt ttaccgtcag  14700
attcttggct gtttcaatgt cgtccatttt ggttttcttt taccagtatt gttcgtttga  14760
taatgtattc ttgcttatta cattataaaa tctgtgcaga tcacatgtca aaacaacttt  14820
ttatcacaag atagtaccgc aaaacgaacc tgcgggccgt ctaaaaatta aggaaaagca  14880
gcaaaggtgc atttttaaaa tatgaaatga agataccgca gtaccaatta ttttcgcagt  14940
acaaataatg cgcggccggt gcatttttcg aaagaacgcg agacaaacag gacaattaaa  15000
gttagttttt cgagttagcg tgtttgaata ctgcaagata caagataaat agagtagttg  15060
aaactagata tcaattgcac acaagatcgg cgctaagcat gccacaattt ggtatattat  15120
gtaaaacacc acctaaggtg cttgttcgtc agtttgtgga aaggtttgaa agaccttcag  15180
gtgagaaaat agcattatgt gctgctgaac taacctattt atgttggatg attacacata  15240
acggaacagc aatcaagaga gccacattca tgagctataa tactatcata agcaattcgc  15300
tgagtttcga tattgtcaat aaatcactcc agtttaaata caagacgcaa aaagcaacaa  15360
ttctggaagc ctcattaaag aaattgattc ctgcttggga atttacaatt attccttact  15420
atggacaaaa acatcaatct gatatcactg atattgtaag tagtttgcaa ttacagttcg  15480
aatcatcgga agaagcagat aagggaaata gccacagtaa aaaaatgcta aagcacttct  15540
aagtgagggt gaaagcatct gggagatcac tgagaaaata ctaaattcgt ttgagtatac  15600
ttcgagattt acaaaaacaa aaactttata ccaattcctc ttcctagcta ctttcatcaa  15660
ttgtggaaga ttcagcgata ttaagaacgt tgatccgaaa tcatttaaat tagtccaaaa  15720
taagtatctg ggagtaataa tccagtgttt agtgacagag acaaagacaa gcgttagtag  15780
gcacatatac ttctttagcg caaggggtag                                  15810
```

<210> SEQ ID NO 45
<211> LENGTH: 3928
<212> TYPE: DNA
<213> ORGANISM: Artificial Sequence
<220> FEATURE:
<223> OTHER INFORMATION: Description of Artificial Sequence: Vector
      pBKS-E2sH6 sequence

<400> SEQUENCE: 45

-continued

```
cacctaaatt gtaagcgtta atattttgtt aaaattcgcg ttaaattttt gttaaatcag     60
ctcatttttt aaccaatagg ccgaaatcgg caaaatccct tataaatcaa aagaatagac    120
cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga accctaaagg    300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gaggtcgacg gtatcgataa gcttgcatgc ctgcagttaa ttaactatta    720
gtgatggtgg tgatggtgtc tgccctcgat cacctgccac tctgttgtag acagcagcag    780
cgggctaagc tctgatctat ccctgtcctc caagtcacaa cgctctcctc gagtccaatt    840
gcatgcggct tcgaacctgt gctccacgcc ccccacgtac atcctaacct tgaagatggt    900
gaagttgaca gtgcaggggt agtgccagag cctatatggg taatgaacca tacacctagg    960
tgtcagccag ggcccagaac cgcatctggc gtaggtggcc tcggggtgct tccgaaaaca   1020
gtcagtgggg caggtcaagg tgttgttgcc ggcccccccg atgttgcacg gggggccccc   1080
acacgtcttg gtgaacccag tgccattcat ccatgtacag ccgaaccagt tgcctcgcgg   1140
cggccgcgtg ttgttgagaa tcagcacatc cgagtcgttc gccccccagt tatacgtggg   1200
gacaccaaac cgatcggtcg tccccaccac aacagggctc ggggtgaagc aatacactgg   1260
accgcacacc tgagacgcgg gtacaatacc acacggtcga ggcgcgtagt gccagcagta   1320
gggcctctgg tccgagctgt taggctcagt gtaagtgagg ggaccccacc cctgagcgaa   1380
cttgtcgatg gagcgacagc tggccaagcg ctctgggcat ccagacgagt tgaatttgtg   1440
tttgtagaat agtgcggcaa agaaccctgt ttggagggag tcgttgcagt tcagggcagt   1500
cctgttgatg tgccaactgc cgttggtgtt tacgagctgg attttctgag ccgacccggg   1560
gctaaagagg gacacaaggc ccctggtatc ggaggctgct gcccctcctg acacgcgggt   1620
atggtaccgg gccccccctc gaggtcgacg gtatcgataa gcttgatatc gaattcctgc   1680
agcccggggg atccactagt tctagagcgg ccgccaccgc ggtggagctc cagcttttgt   1740
tccctttagt gagggttaat ttcgagcttg gcgtaatcat ggtcatagct gtttcctgtg   1800
tgaaattgtt atccgctcac aattccacac aacatacgag ccggaagcat aaagtgtaaa   1860
gcctggggtg cctaatgagt gagctaactc acattaattg cgttgcgctc actgcccgct   1920
ttccagtcgg gaaacctgtc gtgccagctg cattaatgaa tcggccaacg cgcggggaga   1980
ggcggtttgc gtattgggcg ctcttccgct tcctcgctca ctgactcgct gcgctcggtc   2040
gttcggctgc ggcgagcggt atcagctcac tcaaaggcgg taatacggtt atccacagaa   2100
tcaggggata acgcaggaaa gaacatgtga gcaaaaggcc agcaaaaggc caggaaccgt   2160
aaaaaggccg cgttgctggc gtttttccat aggctccgcc cccctgacga gcatcacaaa   2220
aatcgacgct caagtcagag gtggcgaaac ccgacaggac tataaagata ccaggcgttt   2280
ccccctggaa gctccctcgt gcgctctcct gttccgaccc tgccgcttac cggatacctg   2340
```

-continued

```
tccgcctttc tcccttcggg aagcgtggcg ctttctcata gctcacgctg taggtatctc   2400
agttcggtgt aggtcgttcg ctccaagctg ggctgtgtgc acgaaccccc cgttcagccc   2460
gaccgctgcg ccttatccgg taactatcgt cttgagtcca acccggtaag acacgactta   2520
tcgccactgg cagcagccac tggtaacagg attagcagag cgaggtatgt aggcggtgct   2580
acagagttct tgaagtggtg gcctaactac ggctacacta gaaggacagt atttggtatc   2640
tgcgctctgc tgaagccagt taccttcgga aaaagagttg gtagctcttg atccggcaaa   2700
caaaccaccg ctggtagcgg tggttttttt gtttgcaagc agcagattac gcgcagaaaa   2760
aaaggatctc aagaagatcc tttgatcttt tctacggggt ctgacgctca gtggaacgaa   2820
aactcacgtt aagggatttt ggtcatgaga ttatcaaaaa ggatcttcac ctagatcctt   2880
ttaaattaaa aatgaagttt taaatcaatc taaagtatat atgagtaaac ttggtctgac   2940
agttaccaat gcttaatcag tgaggcacct atctcagcga tctgtctatt tcgttcatcc   3000
atagttgcct gactccccgt cgtgtagata actacgatac gggagggctt accatctggc   3060
cccagtgctg caatgatacc gcgagaccca cgctcaccgg ctccagattt atcagcaata   3120
aaccagccag ccggaagggc cgagcgcaga agtggtcctg caactttatc cgcctccatc   3180
cagtctatta attgttgccg ggaagctaga gtaagtagtt cgccagttaa tagtttgcgc   3240
aacgttgttg ccattgctac aggcatcgtg gtgtcacgct cgtcgtttgg tatggcttca   3300
ttcagctccg gttcccaacg atcaaggcga gttacatgat cccccatgtt gtgcaaaaaa   3360
gcggttagct ccttcggtcc tccgatcgtt gtcagaagta agttggccgc agtgttatca   3420
ctcatggtta tggcagcact gcataattct cttactgtca tgccatccgt aagatgcttt   3480
tctgtgactg gtgagtactc aaccaagtca ttctgagaat agtgtatgcg gcgaccgagt   3540
tgctcttgcc cggcgtcaat acgggataat accgcgccac atagcagaac tttaaaagtg   3600
ctcatcattg gaaaacgttc ttcggggcga aaactctcaa ggatcttacc gctgttgaga   3660
tccagttcga tgtaacccac tcgtgcaccc aactgatctt cagcatcttt tactttcacc   3720
agcgtttctg ggtgagcaaa aacaggaagg caaaatgccg caaaaaaggg aataagggcg   3780
acacggaaat gttgaatact catactcttc ctttttcaat attattgaag catttatcag   3840
ggttattgtc tcatgagcgg atacatattt gaatgtattt agaaaaataa acaaataggg   3900
gttccgcgca catttccccg aaaagtgc                                      3928
```

<210> SEQ ID NO 46
<211> LENGTH: 6104
<212> TYPE: DNA
<213> ORGANISM: Artificial Sequence
<220> FEATURE:
<223> OTHER INFORMATION: Description of Artificial Sequence: Vector pYIG5HCCL-22aH6 sequence

<400> SEQUENCE: 46

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gaatttaata    240
cgactcacta tagggaattc gaggatcctt caatatgcgc acatacgctg ttatgttcaa    300
ggtcccttcg tttaagaacg aaagcggtct tccttttgag ggatgtttca agttgttcaa    360
atctatcaaa tttgcaaatc cccagtctgt atctagagcg ttgaatcggt gatgcgattt    420
```

-continued

```
gttaattaaa ttgatggtgt caccattacc aggtctagat ataccaatgg caaactgagc    480
acaacaatac cagtccggat caactggcac catctctccc gtagtctcat ctaatttttc    540
ttccggatga ggttccagat ataccgcaac acctttatta tggtttccct gagggaataa    600
tagaatgtcc cattcgaaat caccaattct aaacctgggc gaattgtatt tcgggtttgt    660
taactcgttc cagtcaggaa tgttccacgt gaagctatct tccagcaaag tctccacttc    720
ttcatcaaat tgtggagaat actcccaatg ctcttatcta tgggacttcc gggaaacaca    780
gtaccgatac ttcccaattc gtcttcagag ctcattgttt gtttgaagag actaatcaaa    840
gaatcgtttt ctcaaaaaaa ttaatatctt aactgatagt ttgatcaaag gggcaaaacg    900
taggggcaaa caaacggaaa aatcgtttct caaattttct gatgccaaga actctaacca    960
gtcttatcta aaaattgcct tatgatccgt ctctccggtt acagcctgtg taactgatta   1020
atcctgcctt tctaatcacc attctaatgt tttaattaag ggattttgtc ttcattaacg   1080
gctttcgctc ataaaaatgt tatgacgttt tgcccgcagg cgggaaacca tccacttcac   1140
gagactgatc tcctctgccg gaacaccggg catctccaac ttataagttg gagaaataag   1200
agaatttcag attgagagaa tgaaaaaaaa aaaccctgaa aaaaaaggtt gaaaccagtt   1260
ccctgaaatt attcccctac ttgactaata agtatataaa gacggtaggt attgattgta   1320
attctgtaaa tctatttctt aaacttctta aattctactt ttatagttag tctttttttt   1380
agttttaaaa caccaagaac ttagtttcga ataaacacac ataaacaaac accatgagat   1440
ttccttcaat ttttactgca gttttattcg cagcatcctc cgcattagct gctccagtca   1500
acactacaac agaagatgaa acggcacaaa ttccggctga agctgtcatc ggttactcag   1560
atttagaagg ggatttcgat gttgctgttt tgccattttc caacagcaca aataacgggt   1620
tattgtttat aaatactact attgccagca ttgctgctaa agaagaaggg gtatctctag   1680
ataaaaggca tacccgcgtg tcaggagggg cagcagcctc cgataccagg ggccttgtgt   1740
ccctctttag ccccgggtcg gctcagaaaa tccagctcgt aaacaccaac ggcagttggc   1800
acatcaacag gactgccctg aactgcaacg actccctcca aacagggttc tttgccgcac   1860
tattctacaa acacaaattc aactcgtctg gatgcccaga gcgcttggcc agctgtcgct   1920
ccatcgacaa gttcgctcag gggtggggtc ccctcactta cactgagcct aacagctcgg   1980
accagaggcc ctactgctgg cactacgcgc ctcgaccgtg tggtattgta cccgcgtctc   2040
aggtgtgcgg tccagtgtat tgcttcaccc cgagccctgt tgtggtgggg acgaccgatc   2100
ggtttggtgt ccccacgtat aactgggggg cgaacgactc ggatgtgctg attctcaaca   2160
acacgcggcc gccgcgaggc aactggttcg gctgtacatg gatgaatggc actgggttca   2220
ccaagacgtg tgggggcccc ccgtgcaaca tcgggggggc cggcaacaac accttgacct   2280
gccccactga ctgttttcgg aagcaccccg aggccactta cgccagatgc ggttctgggc   2340
cctggctgac acctaggtgt atggttcatt acccatatag gctctggcac taccccctgca   2400
ctgtcaactt caccatcttc aaggttagga tgtacgtggg gggcgtggag cacaggttcg   2460
aagccgcatg caattggact cgaggagagc gttgtgactt ggaggacagg gatagatcag   2520
agcttagctc gctgctgctg tctacaacag agtggcaggt gatcgagggc agacaccatc   2580
accaccatca ctaatagtta attaacgatc tcgacttggt tgaacacgtt gccaaggctt   2640
aagtgaattt actttaaagt cttgcattta aataaatttt ctttttatag ctttatgact   2700
tagtttcaat ttatatacta ttttaatgac attttcgatt cattgattga aagctttgtg   2760
tttttcttg atgcgctatt gcattgttct tgtctttttc gccacatgta atatctgtag    2820
```

-continued tagatacctg atacattgtg gatgctgagt gaaattttag ttaataatgg aggcgctctt 2880
aataattttg ggatattgg cttttttttt taaagtttac aaatgaattt tttccgccag 2940
gataacgatt ctgaagttac tcttagcgtt cctatcggta cagccatcaa atcatgccta 3000
taaatcatgc ctatatttgc gtgcagtcag tatcatctac atgaaaaaaa ctcccgcaat 3060
ttcttataga atacgttgaa aattaaatgt acgcgccaag ataagataac atatatctag 3120
ctagatgcag taatatacac agattcccgc ggacgtggga aggaaaaaat tagataacaa 3180
aatctgagtg atatggaaat tccgctgtat agctcatatc tttcccttca acaccagaaa 3240
tgtaaaaatc ttgttacgaa ggatcttttt gctaatgttt ctcgctcaat cctcatttct 3300
tccctacgaa gagtcaaatc tacttgtttt ctgccggtat caagatccat atcttctagt 3360
ttcaccatca aagtccaatt tctagtatac agtttatgtc ccaacgtaac agacaatcaa 3420
aattggaaag gataagtatc cttcaaagaa tgattctgcg ctggctcctg aaccgcctaa 3480
tgggaacaga gaagtccaaa acgatgctat aagaaccaga aataaaacga taaaaccata 3540
ccaggatcca agcttggcac tggccgtcgt tttacaacgt cgtgactggg aaaaccctgg 3600
cgttacccaa cttaatcgcc ttgcagcaca tccccctttc gccagctggc gtaatagcga 3660
agaggcccgc accgatcgcc cttcccaaca gttgcgcagc ctgaatggcg aatgggaaat 3720
tgtaaacgtt aatattttgt taaaattcgc gttaaatttt tgttaaatca gctcattttt 3780
taaccaatag gccgaaatcg gcaaaatccc ttataaatca aaagaataga ccgagatagg 3840
gttgagtgtt gttccagttt ggaacaagag tccactatta aagaacgtgg actccaacgt 3900
caaagggcga aaaaccgtct atcagggcga tggcccacta cgtgaaccat caccctaatc 3960
aagttttttg gggtcgaggt gccgtaaagc actaaatcgg aaccctaaag ggagcccccg 4020
atttagagct tgacggggaa agccggcgaa cgtggcgaga aaggaaggga agaaagcgaa 4080
aggagcgggc gctagggcgc tggcaagtgt agcggtcacg ctgcgcgtaa ccaccacacc 4140
cgccgcgctt aatgcgccgc tacagggcgc gtcaggtggc acttttcggg gaaatgtgcg 4200
cggaacccct atttgtttat ttttctaaat acattcaaat atgtatccgc tcatgagaca 4260
ataaccctga taaatgcttc aataatattg aaaaaggaag agtatgagta ttcaacattt 4320
ccgtgtcgcc cttattccct tttttgcggc attttgcctt cctgtttttg ctcacccaga 4380
aacgctggtg aaagtaaaag atgctgaaga tcagttgggt gcacgagtgg gttacatcga 4440
actggatctc aacagcggta agatccttga gagttttcgc cccgaagaac gttttccaat 4500
gatgagcact tttaaagttc tgctatgtgg cgcggtatta tcccgtattg acgccgggca 4560
agagcaactc ggtcgccgca tacactattc tcagaatgac ttggttgagt actcaccagt 4620
cacagaaaag catcttacgg atggcatgac agtaagagaa ttatgcagtg ctgccataac 4680
catgagtgat aacactgcgg ccaacttact tctgacaacg atcggaggac cgaaggagct 4740
aaccgctttt ttgcacaaca tgggggatca tgtaactcgc cttgatcgtt gggaaccgga 4800
gctgaatgaa gccataccaa acgacgagcg tgacaccacg atgcctgtag caatggcaac 4860
aacgttgcgc aaactattaa ctggcgaact acttactcta gcttcccggc aacaattaat 4920
agactggatg gaggcggata aagttgcagg accacttctg cgctcggccc ttccggctgg 4980
ctggtttatt gctgataaat ctggagccgg tgagcgtggg tctcgcggta tcattgcagc 5040
actggggcca gatggtaagc cctcccgtat cgtagttatc tacacgacgg ggagtcaggc 5100
aactatggat gaacgaaata gacagatcgc tgagataggt gcctcactga ttaagcattg 5160

-continued

```
gtaactgtca gaccaagttt actcatatat actttagatt gatttaaaac ttcattttta   5220

atttaaaagg atctaggtga agatcctttt tgataatctc atgaccaaaa tcccttaacg   5280

tgagttttcg ttccactgag cgtcagaccc cgtagaaaag atcaaaggat cttcttgaga   5340

tccttttttt ctgcgcgtaa tctgctgctt gcaaacaaaa aaaccaccgc taccagcggt   5400

ggtttgtttg ccggatcaag agctaccaac tctttttccg aaggtaactg gcttcagcag   5460

agcgcagata ccaaatactg tccttctagt gtagccgtag ttaggccacc acttcaagaa   5520

ctctgtagca ccgcctacat acctcgctct gctaatcctg ttaccagtgg ctgctgccag   5580

tggcgataag tcgtgtctta ccgggttgga ctcaagacga tagttaccgg ataaggcgca   5640

gcggtcgggc tgaacggggg gttcgtgcac acagcccagc ttggagcgaa cgacctacac   5700

cgaactgaga tacctacagc gtgagcattg agaaagcgcc acgcttcccg aagggagaaa   5760

ggcggacagg tatccggtaa gcggcagggt cggaacagga gagcgcacga gggagcttcc   5820

agggggaaac gcctggtatc tttatagtcc tgtcgggttt cgccacctct gacttgagcg   5880

tcgatttttg tgatgctcgt caggggggcg gagcctatgg aaaaacgcca gcaacgcggc   5940

cctttttacgg ttcctggcct tttgctggcc ttttgctcac atgttctttc ctgcgttatc   6000

ccctgattct gtggataacc gtattaccgc ctttgagtga gctgataccg ctcgccgcag   6060

ccgaacgacc gagcgcagcg agtcagtgag cgaggaagcg gaag                     6104
```

<210> SEQ ID NO 47
<211> LENGTH: 16301
<212> TYPE: DNA
<213> ORGANISM: Artificial Sequence
<220> FEATURE:
<223> OTHER INFORMATION: Description of Artificial Sequence: Vector pYYIGSE2H6 sequence

<400> SEQUENCE: 47

```
atcgataagc ttttcaattc aattcatcat ttttttttta ttcttttttt tgatttcggt     60

ttctttgaaa tttttttgat tcggtaatct ccgaacagaa ggaagaacga aggaaggagc    120

acagacttag attggtatat atacgcatat gtagtgttga agaaacatga aattgcccag    180

tattcttaac ccaactgcac agaacaaaaa cctgcaggaa acgaagataa atcatgtcga    240

aagctacata taaggaacgt gctgctactc atcctagtcc tgttgctgcc aagctattta    300

atatcatgca cgaaaagcaa acaaacttgt gtgcttcatt ggatgttcgt accaccaagg    360

aattactgga gttagttgaa gcattaggtc ccaaaatttg tttactaaaa acacatgtgg    420

atatcttgac tgatttttcc atggagggca cagttaagcc gctaaaggca ttatccgcca    480

agtacaattt tttactcttc gaagacagaa aatttgctga cattggtaat acagtcaaat    540

tgcagtactc tgcgggtgta tacagaatag cagaatgggc agacattacg aatgcacacg    600

gtgtggtggg cccaggtatt gttagcggtt tgaagcaggc ggcagaagaa gtaacaaagg    660

aacctagagg ccttttgatg ttagcagaat tgtcatgcaa gggctcccta tctactggag    720

aatatactaa gggtactgtt gacattgcga agagcgacaa agattttgtt atcggcttta    780

ttgctcaaag agacatgggt ggaagagatg aaggttacga ttggttgatt atgacacccg    840

gtgtgggttt agatgacaag ggagacgcat tgggtcaaca gtatagaacc gtggatgatg    900

tggtctctac aggatctgac attattattg ttggaagagg actatttgca aagggaaggg    960

atgctaaggt agagggtgaa cgttacagaa aagcaggctg ggaagcatat ttgagaagat   1020

gcggccagca aaactaaaaa actgtattat aagtaaatgc atgtatacta aactcacaaa   1080
```

-continued

```
ttagagcttc aatttaatta tatcagttat tacccgggaa tctcggtcgt aatgattttt   1140
ataatgacga aaaaaaaaaa attggaaaga aaaagcttta atgcggtagt ttatcacagt   1200
taaattgcta acgcagtcag gcaccgtgta tgaaatctaa caatgcgctc atcgtcatcc   1260
tcggcaccgt caccctggat gctgtaggca taggcttggt tatgccggta ctgccgggcc   1320
tcttgcggga tatcgtccat tccgacagca tcgccagtca ctatggcgtg ctgctagcgc   1380
tatatgcgtt gatgcaattt ctatgcgcac ccgttctcgg agcactgtcc gaccgctttg   1440
gccgccgccc agtcctgctc gcttcgctac ttggagccac tatcgactac gcgatcatgg   1500
cgaccacacc cgtcctgtgg atccttcaat atgcgcacat acgctgttat gttcaaggtc   1560
ccttcgttta agaacgaaag cggtcttcct tttgagggat gtttcaagtt gttcaaatct   1620
atcaaatttg caaatcccca gtctgtatct agagcgttga atcggtgatg cgatttgtta   1680
attaaattga tggtgtcacc attaccaggt ctagatatac caatggcaaa ctgagcacaa   1740
caataccagt ccggatcaac tggcaccatc tctcccgtag tctcatctaa tttttcttcc   1800
ggatgaggtt ccagatatac cgcaacacct ttattatggt ttccctgagg gaataataga   1860
atgtcccatt cgaaatcacc aattctaaac ctgggcgaat tgtatttcgg gtttgttaac   1920
tcgttccagt caggaatgtt ccacgtgaag ctatcttcca gcaaagtctc cacttcttca   1980
tcaaattgtg gagaatactc ccaatgctct tatctatggg acttccggga aacacagtac   2040
cgatacttcc caattcgtct tcagagctca ttgtttgttt gaagagacta atcaaagaat   2100
cgttttctca aaaaaattaa tatcttaact gatagtttga tcaaaggggc aaaacgtagg   2160
ggcaaacaaa cggaaaaatc gtttctcaaa ttttctgatg ccaagaactc taaccagtct   2220
tatctaaaaa ttgccttatg atccgtctct ccggttacag cctgtgtaac tgattaatcc   2280
tgcctttcta atcaccattc taatgtttta attaagggat tttgtcttca ttaacggctt   2340
tcgctcataa aaatgttatg acgttttgcc cgcaggcggg aaaccatcca cttcacgaga   2400
ctgatctcct ctgccggaac accgggcatc tccaacttat aagttggaga aataagagaa   2460
tttcagattg agagaatgaa aaaaaaaaac cctgaaaaaa aaggttgaaa ccagttccct   2520
gaaattattc ccctacttga ctaataagta tataaagacg gtaggtattg attgtaattc   2580
tgtaaatcta tttcttaaac ttcttaaatt ctacttttat agttagtctt ttttttagtt   2640
ttaaaacacc aagaacttag tttcgaataa acacacataa acaaacacca tgagatttcc   2700
ttcaattttt actgcagttt tattcgcagc atcctccgca ttagctgctc cagtcaacac   2760
tacaacagaa gatgaaacgg cacaaattcc ggctgaagct gtcatcggtt actcagattt   2820
agaaggggat ttcgatgttg ctgttttgcc attttccaac agcacaaata acgggttatt   2880
gtttataaat actactattg ccagcattgc tgctaaagaa gaaggggtat ctctagataa   2940
aaggcatacc cgcgtgtcag gaggggcagc agcctccgat accaggggcc ttgtgtccct   3000
ctttagcccc gggtcggctc agaaaatcca gctcgtaaac accaacggca gttggcacat   3060
caacaggact gccctgaact gcaacgactc cctccaaaca gggttctttg ccgcactatt   3120
ctacaaacac aaattcaact cgtctggatg cccagagcgc ttggccagct gtcgctccat   3180
cgacaagttc gctcaggggt ggggtcccct cacttacact gagcctaaca gctcggacca   3240
gaggccctac tgctggcact acgcgcctcg accgtgtggt attgtacccg cgtctcaggt   3300
gtgcggtcca gtgtattgct tcaccccgag ccctgttgtg gtggggacga ccgatcggtt   3360
tggtgtcccc acgtataact gggggcgaa cgactcggat gtgctgattc tcaacaacac   3420
gcggccgccg cgaggcaact ggttcggctg tacatggatg aatggcactg ggttcaccaa   3480
```

-continued

```
gacgtgtggg ggccccccgt gcaacatcgg gggggccggc aacaacacct tgacctgccc   3540
cactgactgt tttcggaagc accccgaggc cacttacgcc agatgcggtt ctgggccctg   3600
gctgacacct aggtgtatgg ttcattaccc atataggctc tggcactacc cctgcactgt   3660
caacttcacc atcttcaagg ttaggatgta cgtgggggc gtggagcaca ggttcgaagc    3720
cgcatgcaat tggactcgag gagagcgttg tgacttggag gacagggata gatcagagct   3780
tagctcgctg ctgctgtcta caacagagtg gcaggtgatc gagggcagac accatcacca   3840
ccatcactaa tagttaatta acgatctcga cttggttgaa cacgttgcca aggcttaagt   3900
gaatttactt taaagtcttg catttaaata aattttcttt ttatagcttt atgacttagt   3960
ttcaatttat atactatttt aatgacattt tcgattcatt gattgaaagc tttgtgtttt   4020
ttcttgatgc gctattgcat tgttcttgtc tttttcgcca catgtaatat ctgtagtaga   4080
tacctgatac attgtggatg ctgagtgaaa ttttagttaa taatggaggc gctcttaata   4140
attttgggga tattggcttt ttttttaaa gtttacaaat gaatttttc cgccaggata      4200
acgattctga agttactctt agcgttccta tcggtacagc catcaaatca tgcctataaa   4260
tcatgcctat atttgcgtgc agtcagtatc atctacatga aaaaaactcc cgcaatttct   4320
tatagaatac gttgaaaatt aaatgtacgc gccaagataa gataacatat atctagctag   4380
atgcagtaat atacacagat tcccgcggac gtgggaagga aaaaattaga taacaaaatc   4440
tgagtgatat ggaaattccg ctgtatagct catatctttc ccttcaacac cagaaatgta   4500
aaaatcttgt tacgaaggat ctttttgcta atgtttctcg ctcaatcctc atttcttccc   4560
tacgaagagt caaatctact tgttttctgc cggtatcaag atccatatct tctagtttca   4620
ccatcaaagt ccaatttcta gtatacagtt tatgtcccaa cgtaacagac aatcaaaatt   4680
ggaaaggata agtatccttc aaagaatgat tctgcgctgg ctcctgaacc gcctaatggg   4740
aacagagaag tccaaaacga tgctataaga accagaaata aaacgataaa accataccag   4800
gatcctctac gccggacgca tcgtggccgg catcaccggc gccacaggtg cggttgctgg   4860
cccctatatc gccgacatca ccgatgggga agatcgggct cgccacttcg ggctcatgag   4920
cgcttgtttc ggcgtgggta tggtggcagg ccccgtggcc gggggactgt tgggcgccat   4980
ctccttgcat gcaccattcc ttgcggcggc ggtgctcaac ggcctcaacc tactactggg   5040
ctgcttccta atgcaggagt cgcataaggg agagcgtcga ccgatgccct tgagagcctt   5100
caacccagtc agctccttcc ggtgggcgcg gggcatgact atcgtcgccg cacttatgac   5160
tgtcttcttt atcatgcaac tcgtaggaca ggtgccggca gcgctctggg tcattttcgg   5220
cgaggaccgc tttcgctgga gcgcgacgat gatcggcctg tcgcttgcgg tattcggaat   5280
cttgcacgcc ctcgctcaag ccttcgtcac tggtcccgcc accaaacgtt tcggcgagaa   5340
gcaggccatt atcgccggca tggcggccga cgcgctgggc tacgtcttgc tggcgttcgc   5400
gacgcgaggc tggatggcct tccccattat gattcttctc gcttccggcg gcatcgggat   5460
gcccgcgttg caggccatgc tgtccaggca ggtagatgac gaccatcagg gacagcttca   5520
aggatcgctc gcggctctta ccagcctaac ttcgatcact ggaccgctga tcgtcacggc   5580
gatttatgcc gcctcggcga gcacatggaa cgggttggca tggattgtag gcgccgccct   5640
ataccttgtc tgcctccccg cgttgcgtcg cggtgcatgg agccgggcca cctcgacctg   5700
aatggaagcc ggcggcacct cgctaacgga ttcaccactc caagaattgg agccaatcaa   5760
ttcttgcgga gaactgtgaa tgcgcaaacc aacccttggc agaacatatc catcgcgtcc   5820
```

-continued

```
gccatctcca gcagccgcac gcggcgcatc tcgggcagcg ttgggtcctg gccacgggtg   5880
cgcatgatcg tgctcctgtc gttgaggacc cggctaggct ggcggggttg ccttactggt   5940
tagcagaatg aatcaccgat acgcgagcga acgtgaagcg actgctgctg caaaacgtct   6000
gcgacctgag caacaacatg aatggtcttc ggtttccgtg tttcgtaaag tctggaaacg   6060
cggaagtcag cgccctgcac cattatgttc cggatctgca tcgcaggatg ctgctggcta   6120
ccctgtggaa cacctacatc tgtattaacg aagcgctggc attgaccctg agtgattttt   6180
ctctggtccc gccgcatcca taccgccagt tgtttaccct cacaacgttc cagtaaccgg   6240
gcatgttcat catcagtaac ccgtatcgtg agcatcctct ctcgtttcat cggtatcatt   6300
acccccatga acagaaattc ccccttacac ggaggcatca agtgaccaaa caggaaaaaa   6360
ccgcccttaa catggcccgc tttatcagaa gccagacatt aacgcttctg gagaaactca   6420
acgagctgga cgcggatgaa caggcagaca tctgtgaatc gcttcacgac cacgctgatg   6480
agctttaccg cagctgcctc gcgcgtttcg gtgatgacgg tgaaaacctc tgacacatgc   6540
agctcccgga gacggtcaca gcttgtctgt aagcggtgcc gggagcagac aagcccgtca   6600
gggcgcgtca gcgggtgttg gcgggtgtcg gggcgcagcc atgacccagt cacgtagcga   6660
tagcggagtg tatactggct taactatgcg gcatcagagc agattgtact gagagtgcac   6720
catatgcggt gtgaaatacc gcacagatgc gtaaggagaa aataccgcat caggcgctct   6780
tccgcttcct cgctcactga ctcgctgcgc tcggtcgttc ggctgcggcg agcggtatca   6840
gctcactcaa aggcggtaat acggttatcc acagaatcag gggataacgc aggaaagaac   6900
atgtgagcaa aaggccagca aaaggccagg aaccgtaaaa aggccgcgtt gctggcgttt   6960
ttccataggc tccgcccccc tgacgagcat cacaaaaatc gacgctcaag tcagaggtgg   7020
cgaaacccga caggactata aagataccag gcgtttcccc ctggaagctc cctcgtgcgc   7080
tctcctgttc cgaccctgcc gcttaccgga tacctgtccg cctttctccc ttcgggaagc   7140
gtggcgcttt ctcatagctc acgctgtagg tatctcagtt cggtgtaggt cgttcgctcc   7200
aagctgggct gtgtgcacga accccccgtt cagcccgacc gctgcgcctt atccggtaac   7260
tatcgtcttg agtccaaccc ggtaagacac gacttatcgc cactggcagc agccactggt   7320
aacaggatta gcagagcgag gtatgtaggc ggtgctacag agttcttgaa gtggtggcct   7380
aactacggct acactagaag gacagtattt ggtatctgcg ctctgctgaa gccagttacc   7440
ttcggaaaaa gagttggtag ctcttgatcc ggcaaacaaa ccaccgctgg tagcggtggt   7500
tttttgttt gcaagcagca gattacgcgc agaaaaaaag gatctcaaga agatcctttg   7560
atcttttcta cggggtctga cgctcagtgg aacgaaaact cacgttaagg gattttggtc   7620
atgagattat caaaaaggat cttcacctag atccttttaa attaaaaatg aagttttaaa   7680
tcaatctaaa gtatatatga gtaaacttgg tctgacagtt accaatgctt aatcagtgag   7740
gcacctatct cagcgatctg tctatttcgt tcatccatag ttgcctgact ccccgtcgtg   7800
tagataacta cgatacggga gggcttacca tctggcccca gtgctgcaat gataccgcga   7860
gacccacgct caccggctcc agatttatca gcaataaacc agccagccgg aagggccgag   7920
cgcagaagtg gtcctgcaac tttatccgcc tccatccagt ctattaattg ttgccgggaa   7980
gctagagtaa gtagttcgcc agttaatagt ttgcgcaacg ttgttgccat tgctgcaggc   8040
atcgtggtgt cacgctcgtc gtttggtatg gcttcattca gctccggttc ccaacgatca   8100
aggcgagtta catgatcccc catgttgtgc aaaaaagcgg ttagctcctt cggtcctccg   8160
atcgttgtca gaagtaagtt ggccgcagtg ttatcactca tggttatggc agcactgcat   8220
```

-continued aattctctta ctgtcatgcc atccgtaaga tgcttttctg tgactggtga gtactcaacc 8280
aagtcattct gagaatagtg tatgcggcga ccgagttgct cttgcccggc gtcaacacgg 8340
gataataccg cgccacatag cagaacttta aaagtgctca tcattggaaa acgttcttcg 8400
gggcgaaaac tctcaaggat cttaccgctg ttgagatcca gttcgatgta acccactcgt 8460
gcacccaact gatcttcagc atcttttact ttcaccagcg tttctgggtg agcaaaaaca 8520
ggaaggcaaa atgccgcaaa aaagggaata agggcgacac ggaaatgttg aatactcata 8580
ctcttccttt ttcaatatta ttgaagcatt tatcagggtt attgtctcat gagcggatac 8640
atatttgaat gtatttagaa aaataaacaa ataggggttc cgcgcacatt tccccgaaaa 8700
gtgccacctg acgtctaaga aaccattatt atcatgacat taacctataa aaataggcg 8760
tatcacgagg ccctttcgtc ttcaagaatt ctcatgtttg acagcttatc atcgatccac 8820
ttgtatattt ggatgaattt ttgaggaatt ctgaaccagt cctaaaacga gtaaatagga 8880
ccggcaattc ttcaagcaat aaacaggaat accaattatt aaaagataac ttagtcagat 8940
cgtacaataa agctttgaag aaaaatgcgc cttattcaat ctttgcataa aaaaatggcc 9000
caaaatctca cattggaaga catttgatga cctcatttct ttcaatgaag ggcctaacgg 9060
agttgactaa tgttgtggga aattggaccg ataagcgtgc ttctgccgtg gccaggacaa 9120
cgtatactca tcagataaca gcaatacctg atcactactt cgcactagtt tctcggtact 9180
atgcatatga tccaatatca aaggaaatga tagcattgaa ggatgagact aatccaattg 9240
aggagtggca gcatatagaa cagctaaagg gtagtgctga aggaagcata cgataccccg 9300
catggaatgg gataatatca caggaggtac tagactacct ttcatcctac ataaatagac 9360
gcatataagt acgcatttaa gcataaacac gcactatgcc gttcttctca tgtatatata 9420
tatacaggca acacgcagat ataggtgcga cgtgaacagt gagctgtatg tgcgcagctc 9480
gcgttgcatt ttcggaagcg ctcgttttcg gaaacgcttt gaagttccta ttccgaagtt 9540
cctattctct agaaagtata ggaacttcag agcgcttttg aaaaccaaaa gcgctctgaa 9600
gacgcacttt caaaaaacca aaaacgcacc ggactgtaac gagctactaa aatattgcga 9660
ataccgcttc cacaaacatt gctcaaaagt atctctttgc tatatatctc tgtgctatat 9720
ccctatataa ccatcccatc cacctttcgc tccttgaact tgcatctaaa ctcgacctct 9780
acatttttta tgtttatctc tagtattacc tcttagacaa aaaaattgta gtaagaacta 9840
ttcatagagt taatcgaaaa caatacgaaa atgtaaacat ttcctatacg tagtatatag 9900
agacaaaata gaagaaaccg ttcataattt tctgaccaat gaagaatcat caacgctatc 9960
actttctgtt cacaaagtat gcgcaatcca catcggtata gaatataatc ggggatgcct 10020
ttatcttgaa aaaatgcacc cgcagcttcg ctagtaatca gtaaacgcgg gaagtggagt 10080
caggcttttt ttatggaaga gaaaatagac accaaagtag ccttcttcta accttaacgg 10140
acctacagtg caaaaagtta tcaagagact gcattataga gcgcacaaag gagaaaaaaa 10200
gtaatctaag atgctttgtt agaaaaatag cgctctcggg atgcattttt gtagaacaaa 10260
aaagaagtat agattcttgt tggtaaaata gcgctctcgc gttgcatttc tgttctgtaa 10320
aaatgcagct cagattcttt gtttgaaaaa ttagcgctct cgcgttgcat ttttgtttta 10380
caaaaatgaa gcacagattc ttcgttggta aaatagcgct ttcgcgttgc atttctgttc 10440
tgtaaaaatg cagctcagat tctttgtttg aaaaattagc gctctcgcgt tgcatttttg 10500
ttctacaaaa tgaagcacag atgcttcgtt aacaaagata tgctattgaa gtgcaagatg 10560

-continued

```
gaaacgcaga aaatgaaccg gggatgcgac gtgcaagatt acctatgcaa tagatgcaat  10620
agtttctcca ggaaccgaaa tacatacatt gtcttccgta aagcgctaga ctatatatta  10680
ttatacaggt tcaaatatac tatctgtttc agggaaaact cccaggttcg gatgttcaaa  10740
attcaatgat gggtaacaag tacgatcgta aatctgtaaa acagtttgtc ggatattagg  10800
ctgtatctcc tcaaagcgta ttcgaatatc attgagaagc tgcatttttt tttttttttt  10860
tttttttttt ttttttatat atatttcaag gatataccat tgtaatgtct gcccctaaga  10920
agatcgtcgt tttgccaggt gaccacgttg gtcaagaaat cacagccgaa gccattaagg  10980
ttcttaaagc tatttctgat gttcgttcca atgtcaagtt cgatttcgaa aatcatttaa  11040
ttggtggtgc tgctatcgat gctacaggtg tcccacttcc agatgaggcg ctggaagcct  11100
ccaagaaggt tgatgccgtt ttgttaggtg ctgtgggtgg tcctaaatgg ggtaccggta  11160
gtgttagacc tgaacaaggt ttactaaaaa tccgtaaaga acttcaattg tacgccaact  11220
taagaccatg taactttgca tccgactctc ttttagactt atctccaatc aagccacaat  11280
ttgctaaagg tactgacttc gttgttgtca gagaattagt gggaggtatt tactttggta  11340
agagaaagga agacgatggt gatggtgtcg cttgggatag tgaacaatac accgttccag  11400
aagtgcaaag aatcacaaga atggccgctt tcatggccct acaacatgag ccaccattgc  11460
ctatttggtc cttggataaa gctaatgttt tggcctcttc aagattatgg agaaaaactg  11520
tggaggaaac catcaagaac gaattcccta cattgaaggt tcaacatcaa ttgattgatt  11580
ctgccgccat gatcctagtt aagaacccaa cccacctaaa tggtattata atcaccagca  11640
acatgtttgg tgatatcatc tccgatgaag cctccgttat cccaggttcc ttgggtttgt  11700
tgccatctgc gtccttggcc tctttgccag acaagaacac cgcatttggt ttgtacgaac  11760
catgccacgg ttctgctcca gatttgccaa agaataaggt tgaccctatc gccactatct  11820
tgtctgctgc aatgatgttg aaattgtcat tgaacttgcc tgaagaaggt aaggccattg  11880
aagatgcagt taaaaaggtt ttggatgcag gtatcagaac tggtgattta ggtggttcca  11940
acagtaccac cgaagtcggt gatgctgtcg ccgaagaagt taagaaaatc cttgcttaaa  12000
aagattctct ttttttatga tatttgtaca aaaaaaaaaa aaaaaaaaaa aaaaaaaaaa  12060
aaaaaaaaaa aaaaatgcag cgtcacatcg gataataatg atggcagcca ttgtagaagt  12120
gccttttgca tttctagtct ctttctcggt ctagctagtt ttactacatc gcgaagatag  12180
aatcttagat cacactgcct ttgctgagct ggatcatatg agtaacaaaa gagtggtaag  12240
gcctcgttaa aggacaagga cctgagcgga agtgtatcgt aaagtagacg gagtatacta  12300
gtatagtcta tagtccgtgg aattctaagt gccagcttta taatgtcatt ctccttacta  12360
cagacccgcc tgaaagtaga cacatcatca tcagtaagct ttgacaaaaa gcattgagta  12420
gctaactctt ctatgcaatc tatagctgtt ttataaggca ttcaatggac agattgaggt  12480
ttttgaaaca tactagtgaa attagcctta atcccttctc gaagttaatc atgcattatg  12540
gtgtaaaaaa tgcaactcgc gttgctctac tttttcccga atttccaaat acgcagctgg  12600
ggtgattgct cgatttcgta acgaaagttt tgtttataaa aaccgcgaaa accttctgta  12660
acagatagat ttttacagcg ctgatataca atgacatcag ctgtaatgga aaataactga  12720
aatatgaatg gcgagagact gcttgcttgt attaagcaat gtattatgca gcacttccaa  12780
cctatggtgt acgatgaaag taggtgtgta atcgagacga caagggggac ttttccagtt  12840
cctgatcatt ataagaaata caaaacgtta gcatttgcat ttgttggaca tgtactgaat  12900
acagacgaca caccggtaat tgaaaaagaa ctggattggc ctgatcctgc actagtgtac  12960
```

-continued

```
aatacaattg tcgatcgaat cataaatcac ccagaattat cacagtttat atcggttgca  13020
tttattagtc agttaaaggc caccatcgga gagggtttag atattaatgt aaaaggcacg  13080
ctaaaccgca ggggaaaggg tatcagaagg cctaaaggcg tattttttag atacatggaa  13140
tctccatttg tcaatacaaa ggtcactgca ttcttctctt atcttcgaga ttataataaa  13200
attgcctcag aatatcacaa taatactaaa ttcattctca cgttttcatg tcaagcatat  13260
tgggcatctg gcccaaactt ctccgccttg aagaatgtta tttggtgctc cataattcat  13320
gaatacattt ctaagtttgt ggaaagagaa caggataaag gtcatatagg agatcaggag  13380
ctaccgcctg aagaggaccc ttctcgtgaa ctaaacaatg tacaacatga agtcaatagt  13440
ttaacggaac aagatgcgga ggcggatgaa ggattgtggg gtgaaataga ttcattatgt  13500
gaaaaatggc agtctgaagc ggagagtcaa actgaggcgg agataatagc cgacaggata  13560
attggaaata gccagaggat ggcgaacctc aaaattcgtc gtacaaagtt caaaagtgtc  13620
ttgtatcata tactaaagga actaattcaa tctcagggaa ccgtaaaggt ttatcgcggt  13680
agtagttttt cacacgattc gataaagata agcttacatt atgaagagca gcatattaca  13740
gccgtatggg tctacttgat agtaaaattt gaagagcatt ggaagcctgt tgatgtagag  13800
gtcgagttta gatgcaagtt caaggagcga aaggtggatg ggtaggttat atagggatat  13860
agcacagaga tatatagcaa agagatactt ttgaggcaat gtttgtggaa gcggtattcg  13920
caatatttta gtagctcgtt acagtccggt gcgtttttgg ttttttgaaa gtgcgtcttc  13980
agagcgcttt tggttttcaa aagcgctctg aagttcctat actttctaga gaataggaac  14040
ttcggaatag gaacttcaaa gcgtttccga aaacgagcgc ttccgaaaat gcaacgcgag  14100
ctgcgcacat acagctcact gttcacgtcg cacctatatc tgcgtgttgc ctgtatatat  14160
atatacatga gaagaacggc atagtgcgtg tttatgctta aatgcgtact tatatgcgtc  14220
tatttatgta ggatgaaagg tagtctagta cctcctgtga tattatccca ttccatgcgg  14280
ggtatcgtat gcttccttca gcactaccct ttagctgttc tatatgctgc cactcctcaa  14340
ttggattagt ctcatccttc aatgcattca tttcctttga tattggatca taccctagaa  14400
gtattacgtg attttctgcc ccttaccctc gttgctactc tcctttttttt cgtgggaacc  14460
gctttagggc cctcagtgat ggtgttttgt aatttatatg ctcctcttgc atttgtgtct  14520
ctacttcttg ttcgcctgga gggaacttct tcatttgtat tagcatggtt cacttcagtc  14580
cttccttcca actcactctt tttttgctgt aaacgattct ctgccgccag ttcattgaaa  14640
ctattgaata tatcctttag agattccggg atgaataaat cacctattaa agcagcttga  14700
cgatctggtg gaactaaagt aagcaattgg gtaacgacgc ttacgagctt cataacatct  14760
tcttccgttg gagctggtgg gactaataac tgtgtacaat ccatttttct catgagcatt  14820
tcggtagctc tcttcttgtc tttctcgggc aatcttccta ttattatagc aatagatttg  14880
tatagttgct ttctattgtc taacagcttg ttattctgta gcatcaaatc tatggcagcc  14940
tgacttgctt cttgtgaaga gagcatacca tttccaatcg aagatacgct ggaatcttct  15000
gcgctagaat caagaccata cggcctaccg gttgtgagag attccatggg ccttatgaca  15060
tatcctggaa agagtagctc atcagactta cgtttactct ctatatcaat atctacatca  15120
ggagcaatca tttcaataaa cagccgacat acatcccaga cgctataagc tgtacgtgct  15180
tttaccgtca gattcttggc tgtttcaatg tcgtccattt tggttttctt ttaccagtat  15240
tgttcgtttg ataatgtatt cttgcttatt acattataaa atctgtgcag atcacatgtc  15300
```

-continued aaaacaactt tttatcacaa gatagtaccg caaaacgaac ctgcgggccg tctaaaaatt 15360
aaggaaaagc agcaaaggtg catttttaaa atatgaaatg aagataccgc agtaccaatt 15420
attttcgcag tacaaataat gcgcggccgg tgcatttttc gaaagaacgc gagacaaaca 15480
ggacaattaa agttagtttt tcgagttagc gtgtttgaat actgcaagat acaagataaa 15540
tagagtagtt gaaactagat atcaattgca cacaagatcg gcgctaagca tgccacaatt 15600
tggtatatta tgtaaaacac cacctaaggt gcttgttcgt cagtttgtgg aaaggtttga 15660
aagaccttca ggtgagaaaa tagcattatg tgctgctgaa ctaacctatt tatgttggat 15720
gattacacat aacggaacag caatcaagag agccacattc atgagctata atactatcat 15780
aagcaattcg ctgagtttcg atattgtcaa taaatcactc cagtttaaat acaagacgca 15840
aaaagcaaca attctggaag cctcattaaa gaaattgatt cctgcttggg aatttacaat 15900
tattccttac tatggacaaa aacatcaatc tgatatcact gatattgtaa gtagtttgca 15960
attacagttc gaatcatcgg aagaagcaga taagggaaat agccacagta aaaaaatgct 16020
aaagcacttc taagtgaggg tgaaagcatc tgggagatca ctgagaaaat actaaattcg 16080
tttgagtata cttcgagatt tacaaaaaca aaaactttat accaattcct cttcctagct 16140
actttcatca attgtggaag attcagcgat attaagaacg ttgatccgaa atcatttaaa 16200
ttagtccaaa ataagtatct gggagtaata atccagtgtt tagtgacaga gacaaagaca 16260
agcgttagta ggcacatata cttctttagc gcaaggggta g 16301

<210> SEQ ID NO 48
<211> LENGTH: 4989
<212> TYPE: DNA
<213> ORGANISM: Artificial Sequence
<220> FEATURE:
<223> OTHER INFORMATION: Description of Artificial Sequence: Vector pYIG7 sequence

<400> SEQUENCE: 48
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gaatttaata 240
cgactcacta tagggaattc ggatccttca atatgcgcac atacgctgtt atgttcaagg 300
tcccttcgtt taagaacgaa agcggtcttc cttttgaggg atgtttcaag ttgttcaaat 360
ctatcaaatt tgcaaatccc cagtctgtat ctagagcgtt gaatcggtga tgcgatttgt 420
taattaaatt gatggtgtca ccattaccag gtctagatat accaatggca aactgagcac 480
aacaatacca gtccggatca actggcacca tctctcccgt agtctcatct aatttttctt 540
ccggatgagg ttccagatat accgcaacac ctttattatg gtttccctga gggaataata 600
gaatgtccca ttcgaaatca ccaattctaa acctgggcga attgtatttc gggtttgtta 660
actcgttcca gtcaggaatg ttccacgtga agctatcttc cagcaaagtc tccacttctt 720
catcaaattg tggagaatac tcccaatgct cttatctatg ggacttccgg gaaacacagt 780
accgatactt cccaattcgt cttcagagct cattgtttgt ttgaagagac taatcaaaga 840
atcgttttct caaaaaaatt aatatcttaa ctgatagttt gatcaaaggg gcaaaacgta 900
ggggcaaaca aacggaaaaa tcgtttctca aattttctga tgccaagaac tctaaccagt 960
cttatctaaa aattgcctta tgatccgtct ctccggttac agcctgtgta actgattaat 1020

-continued

```
cctgcctttc taatcaccat tctaatgttt taattaaggg attttgtctt cattaacggc   1080
tttcgctcat aaaaatgtta tgacgttttg cccgcaggcg ggaaaccatc cacttcacga   1140
gactgatctc ctctgccgga acaccgggca tctccaactt ataagttgga gaaataagag   1200
aatttcagat tgagagaatg aaaaaaaaaa accctgaaaa aaaaggttga aaccagttcc   1260
ctgaaattat tcccctactt gactaataag tatataaaga cggtaggtat tgattgtaat   1320
tctgtaaatc tatttcttaa acttcttaaa ttctactttt atagttagtc tttttttag    1380
ttttaaaaca ccaagaactt agtttcgaat aaacacacat aaacaaacac catgaggtct   1440
ttgctaatac tagtgctttg cttcctgccc ctggctgctc tgggggtacc agatctcgac   1500
ttggttgaac acgttgccaa ggcttaagtg aatttacttt aaagtcttgc atttaaataa   1560
atttctttt tatagcttta tgacttagtt tcaatttata tactatttta atgacatttt   1620
cgattcattg attgaaagct ttgtgttttt tcttgatgcg ctattgcatt gttcttgtct   1680
ttttcgccac atgtaatatc tgtagtagat acctgataca ttgtggatgc tgagtgaaat   1740
tttagttaat aatggaggcg ctcttaataa ttttggggat attggctttt tttttaaag    1800
tttacaaatg aattttttcc gccaggataa cgattctgaa gttactctta gcgttcctat   1860
cggtacagcc atcaaatcat gcctataaat catgcctata tttgcgtgca gtcagtatca   1920
tctacatgaa aaaaactccc gcaatttctt atagaatacg ttgaaaatta aatgtacgcg   1980
ccaagataag ataacatata tctagctaga tgcagtaata tacacagatt cccgcggacg   2040
tgggaaggaa aaaattagat aacaaaatct gagtgatatg gaaattccgc tgtatagctc   2100
atatctttcc cttcaacacc agaaatgtaa aaatcttgtt acgaaggatc tttttgctaa   2160
tgtttctcgc tcaatcctca tttcttccct acgaagagtc aaatctactt gttttctgcc   2220
ggtatcaaga tccatatctt ctagtttcac catcaaagtc caatttctag tatacagttt   2280
atgtcccaac gtaacagaca atcaaaattg gaaaggataa gtatccttca aagaatgatt   2340
ctgcgctggc tcctgaaccg cctaatggga acagagaagt ccaaaacgat gctataagaa   2400
ccagaaataa aacgataaaa ccataccagg atccaagctt ggcactggcc gtcgttttac   2460
aacgtcgtga ctgggaaaac cctggcgtta cccaacttaa tcgccttgca gcacatcccc   2520
ctttcgccag ctggcgtaat agcgaagagg cccgcaccga tcgcccttcc caacagttgc   2580
gcagcctgaa tggcgaatgg gaaattgtaa acgttaatat tttgttaaaa ttcgcgttaa   2640
atttttgtta aatcagctca ttttttaacc aataggccga aatcggcaaa atcccttata   2700
aatcaaaaga atagaccgag atagggttga gtgttgttcc agtttggaac aagagtccac   2760
tattaaagaa cgtggactcc aacgtcaaag ggcgaaaaac cgtctatcag ggcgatggcc   2820
cactacgtga accatcaccc taatcaagtt ttttggggtc gaggtgccgt aaagcactaa   2880
atcggaaccc taaagggagc ccccgattta gagcttgacg gggaaagccg gcgaacgtgg   2940
cgagaaagga agggaagaaa gcgaaaggag cgggcgctag ggcgctggca agtgtagcgg   3000
tcacgctgcg cgtaaccacc acacccgccg cgcttaatgc gccgctacag ggcgcgtcag   3060
gtggcacttt tcggggaaat gtgcgcggaa cccctatttg tttatttttc taaatacatt   3120
caaatatgta tccgctcatg agacaataac cctgataaat gcttcaataa tattgaaaaa   3180
ggaagagtat gagtattcaa catttccgtg tcgcccttat tccctttttt gcggcatttt   3240
gccttcctgt ttttgctcac ccagaaacgc tggtgaaagt aaaagatgct gaagatcagt   3300
tgggtgcacg agtgggttac atcgaactgg atctcaacag cggtaagatc cttgagagtt   3360
ttcgccccga agaacgtttt ccaatgatga gcacttttaa agttctgcta tgtggcgcgg   3420
```

-continued tattatcccg tattgacgcc gggcaagagc aactcggtcg ccgcatacac tattctcaga 3480
atgacttggt tgagtactca ccagtcacag aaaagcatct tacggatggc atgacagtaa 3540
gagaattatg cagtgctgcc ataaccatga gtgataacac tgcggccaac ttacttctga 3600
caacgatcgg aggaccgaag gagctaaccg cttttttgca caacatgggg gatcatgtaa 3660
ctcgccttga tcgttgggaa ccggagctga atgaagccat accaaacgac gagcgtgaca 3720
ccacgatgcc tgtagcaatg gcaacaacgt tgcgcaaact attaactggc gaactactta 3780
ctctagcttc ccggcaacaa ttaatagact ggatggaggc ggataaagtt gcaggaccac 3840
ttctgcgctc ggcccttccg gctggctggt ttattgctga taaatctgga gccggtgagc 3900
gtgggtctcg cggtatcatt gcagcactgg ggccagatgg taagccctcc cgtatcgtag 3960
ttatctacac gacggggagt caggcaacta tggatgaacg aaatagacag atcgctgaga 4020
taggtgcctc actgattaag cattggtaac tgtcagacca agtttactca tatatacttt 4080
agattgattt aaaacttcat ttttaattta aaaggatcta ggtgaagatc ctttttgata 4140
atctcatgac caaaatccct taacgtgagt tttcgttcca ctgagcgtca gaccccgtag 4200
aaaagatcaa aggatcttct tgagatcctt tttttctgcg cgtaatctgc tgcttgcaaa 4260
caaaaaaacc accgctacca gcggtggttt gtttgccgga tcaagagcta ccaactcttt 4320
ttccgaaggt aactggcttc agcagagcgc agataccaaa tactgtcctt ctagtgtagc 4380
cgtagttagg ccaccacttc aagaactctg tagcaccgcc tacatacctc gctctgctaa 4440
tcctgttacc agtggctgct gccagtggcg ataagtcgtg tcttaccggg ttggactcaa 4500
gacgatagtt accggataag gcgcagcggt cgggctgaac ggggggttcg tgcacacagc 4560
ccagcttgga gcgaacgacc tacaccgaac tgagatacct acagcgtgag cattgagaaa 4620
gcgccacgct tcccgaaggg agaaaggcgg acaggtatcc ggtaagcggc agggtcggaa 4680
caggagagcg cacgagggag cttccagggg gaaacgcctg gtatctttat agtcctgtcg 4740
ggtttcgcca cctctgactt gagcgtcgat ttttgtgatg ctcgtcaggg gggcggagcc 4800
tatggaaaaa cgccagcaac gcggcctttt tacggttcct ggccttttgc tggccttttg 4860
ctcacatgtt ctttcctgcg ttatcccctg attctgtgga taaccgtatt accgcctttg 4920
agtgagctga taccgctcgc cgcagccgaa cgaccgagcg cagcgagtca gtgagcgagg 4980
aagcggaag 4989

<210> SEQ ID NO 49
<211> LENGTH: 5422
<212> TYPE: DNA
<213> ORGANISM: Artificial Sequence
<220> FEATURE:
<223> OTHER INFORMATION: Description of Artificial Sequence: Vector pYIG7E1 sequence

<400> SEQUENCE: 49
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gaatttaata 240
cgactcacta tagggaattc ggatccttca atatgcgcac atacgctgtt atgttcaagg 300
tcccttcgtt taagaacgaa agcggtcttc cttttgaggg atgtttcaag ttgttcaaat 360
ctatcaaatt tgcaaatccc cagtctgtat ctagagcgtt gaatcggtga tgcgatttgt 420

-continued

```
taattaaatt gatggtgtca ccattaccag gtctagatat accaatggca aactgagcac    480
aacaatacca gtccggatca actggcacca tctctcccgt agtctcatct aatttttctt    540
ccggatgagg ttccagatat accgcaacac ctttattatg gtttccctga gggaataata    600
gaatgtccca ttcgaaatca ccaattctaa acctgggcga attgtatttc gggtttgtta    660
actcgttcca gtcaggaatg ttccacgtga agctatcttc cagcaaagtc tccacttctt    720
catcaaattg tggagaatac tcccaatgct cttatctatg ggacttccgg gaaacacagt    780
accgatactt cccaattcgt cttcagagct cattgtttgt ttgaagagac taatcaaaga    840
atcgttttct caaaaaaatt aatatcttaa ctgatagttt gatcaaaggg gcaaaacgta    900
ggggcaaaca aacggaaaaa tcgtttctca aattttctga tgccaagaac tctaaccagt    960
cttatctaaa aattgcctta tgatccgtct ctccggttac agcctgtgta actgattaat   1020
cctgcctttc taatcaccat tctaatgttt taattaaggg attttgtctt cattaacggc   1080
tttcgctcat aaaaatgtta tgacgttttg cccgcaggcg ggaaaccatc cacttcacga   1140
gactgatctc ctctgccgga acaccgggca tctccaactt ataagttgga gaaataagag   1200
aatttcagat tgagagaatg aaaaaaaaaa accctgaaaa aaaaggttga aaccagttcc   1260
ctgaaattat tcccctactt gactaataag tatataaaga cggtaggtat tgattgtaat   1320
tctgtaaatc tatttcttaa acttcttaaa ttctactttt atagttagtc tttttttag   1380
ttttaaaaca ccaagaactt agtttcgaat aaacacacat aaacaaacac catgaggtct   1440
ttgctaatac tagtgctttg cttcctgccc ctggctgctc tggggtatga ggtgcgcaac   1500
gtgtccggga tgtaccatgt cacgaacgac tgctccaact caagcattgt gtatgaggca   1560
gcggacatga tcatgcacac ccccgggtgc gtgccctgcg ttcgggagaa caactcttcc   1620
cgctgctggg tagcgctcac ccccacgctc gcagctagga acgccagcgt ccccaccacg   1680
acaatacgac gccacgtcga tttgctcgtt ggggcggctg ctttctgttc cgctatgtac   1740
gtgggggacc tctgcggatc tgtcttcctc gtctcccagc tgttcaccat ctcgcctcgc   1800
cggcatgaga cggtgcagga ctgcaattgc tcaatctatc ccggccacat aacgggtcac   1860
cgtatggctt gggatatgat gatgaactgg taatagaccc ttctcacctc ggccgataag   1920
ctcagatctc gacttggttg aacacgttgc caaggcttaa gtgaatttac tttaaagtct   1980
tgcatttaaa taaattttct ttttatagct ttatgactta gtttcaattt atatactatt   2040
ttaatgacat tttcgattca ttgattgaaa gctttgtgtt ttttcttgat gcgctattgc   2100
attgttcttg tctttttcgc cacatgtaat atctgtagta gatacctgat acattgtgga   2160
tgctgagtga aattttagtt aataatggag gcgctcttaa taattttggg gatattggct   2220
ttttttttta aagtttacaa atgaattttt tccgccagga taacgattct gaagttactc   2280
ttagcgttcc tatcggtaca gccatcaaat catgcctata aatcatgcct atatttgcgt   2340
gcagtcagta tcatctacat gaaaaaaact cccgcaattt cttatagaat acgttgaaaa   2400
ttaaatgtac gcgccaagat aagataacat atatctagct agatgcagta atatacacag   2460
attcccgcgg acgtgggaag gaaaaaatta gataacaaaa tctgagtgat atggaaattc   2520
cgctgtatag ctcatatctt tcccttcaac accagaaatg taaaaatctt gttacgaagg   2580
atctttttgc taatgtttct cgctcaatcc tcatttcttc cctacgaaga gtcaaatcta   2640
cttgttttct gccggtatca agatccatat cttctagttt caccatcaaa gtccaatttc   2700
tagtatacag tttatgtccc aacgtaacag acaatcaaaa ttggaaagga taagtatcct   2760
```

-continued

```
tcaaagaatg attctgcgct ggctcctgaa ccgcctaatg ggaacagaga agtccaaaac   2820
gatgctataa gaaccagaaa taaaacgata aaaccatacc aggatccaag cttggcactg   2880
gccgtcgttt tacaacgtcg tgactgggaa aaccctggcg ttacccaact taatcgcctt   2940
gcagcacatc ccccttttcgc cagctggcgt aatagcgaag aggcccgcac cgatcgccct   3000
tcccaacagt tgcgcagcct gaatggcgaa tgggaaattg taaacgttaa tattttgtta   3060
aaattcgcgt taaatttttg ttaaatcagc tcatttttta accaataggc cgaaatcggc   3120
aaaatccctt ataaatcaaa agaatagacc gagatagggt tgagtgttgt tccagtttgg   3180
aacaagagtc cactattaaa gaacgtggac tccaacgtca aagggcgaaa aaccgtctat   3240
cagggcgatg gcccactacg tgaaccatca ccctaatcaa gtttttgggg gtcgaggtgc   3300
cgtaaagcac taaatcggaa ccctaaaggg agcccccgat ttagagcttg acggggaaag   3360
ccggcgaacg tggcgagaaa ggaagggaag aaagcgaaag gagcgggcgc tagggcgctg   3420
gcaagtgtag cggtcacgct gcgcgtaacc accacacccg ccgcgcttaa tgcgccgcta   3480
cagggcgcgt caggtggcac ttttcgggga aatgtgcgcg gaacccctat ttgtttattt   3540
ttctaaatac attcaaatat gtatccgctc atgagacaat aaccctgata aatgcttcaa   3600
taatattgaa aaaggaagag tatgagtatt caacatttcc gtgtcgccct tattcccttt   3660
tttgcggcat tttgccttcc tgtttttgct cacccagaaa cgctggtgaa agtaaaagat   3720
gctgaagatc agttgggtgc acgagtgggt tacatcgaac tggatctcaa cagcggtaag   3780
atccttgaga gttttcgccc cgaagaacgt tttccaatga tgagcacttt taaagttctg   3840
ctatgtggcg cggtattatc ccgtattgac gccgggcaag agcaactcgg tcgccgcata   3900
cactattctc agaatgactt ggttgagtac tcaccagtca cagaaaagca tcttacggat   3960
ggcatgacag taagagaatt atgcagtgct gccataacca tgagtgataa cactgcggcc   4020
aacttacttc tgacaacgat cggaggaccg aaggagctaa ccgctttttt gcacaacatg   4080
ggggatcatg taactcgcct tgatcgttgg gaaccggagc tgaatgaagc cataccaaac   4140
gacgagcgtg acaccacgat gcctgtagca atggcaacaa cgttgcgcaa actattaact   4200
ggcgaactac ttactctagc ttcccggcaa caattaatag actggatgga ggcggataaa   4260
gttgcaggac cacttctgcg ctcggccctt ccggctggct ggtttattgc tgataaatct   4320
ggagccggtg agcgtgggtc tcgcggtatc attgcagcac tggggccaga tggtaagccc   4380
tcccgtatcg tagttatcta cacgacgggg agtcaggcaa ctatggatga acgaaataga   4440
cagatcgctg agataggtgc ctcactgatt aagcattggt aactgtcaga ccaagtttac   4500
tcatatatac tttagattga tttaaaactt catttttaat ttaaaaggat ctaggtgaag   4560
atcctttttg ataatctcat gaccaaaatc ccttaacgtg agttttcgtt ccactgagcg   4620
tcagaccccg tagaaaagat caaaggatct tcttgagatc ctttttttct gcgcgtaatc   4680
tgctgcttgc aaacaaaaaa accaccgcta ccagcggtgg tttgtttgcc ggatcaagag   4740
ctaccaactc tttttccgaa ggtaactggc ttcagcagag cgcagatacc aaatactgtc   4800
cttctagtgt agccgtagtt aggccaccac ttcaagaact ctgtagcacc gcctacatac   4860
ctcgctctgc taatcctgtt accagtggct gctgccagtg gcgataagtc gtgtcttacc   4920
gggttggact caagacgata gttaccggat aaggcgcagc ggtcgggctg aacggggggt   4980
tcgtgcacac agcccagctt ggagcgaacg acctacaccg aactgagata cctacagcgt   5040
gagcattgag aaagcgccac gcttcccgaa gggagaaagg cggacaggta tccggtaagc   5100
ggcagggtcg gaacaggaga gcgcacgagg gagcttccag ggggaaacgc ctggtatctt   5160
```

-continued tatagtcctg tcgggtttcg ccacctctga cttgagcgtc gatttttgtg atgctcgtca 5220
ggggggcgga gcctatggaa aaacgccagc aacgcggcct ttttacggtt cctggccttt 5280
tgctggcctt ttgctcacat gttctttcct gcgttatccc ctgattctgt ggataaccgt 5340
attaccgcct ttgagtgagc tgataccgct cgccgcagcc gaacgaccga gcgcagcgag 5400
tcagtgagcg aggaagcgga ag 5422

<210> SEQ ID NO 50
<211> LENGTH: 15621
<212> TYPE: DNA
<213> ORGANISM: Artificial Sequence
<220> FEATURE:
<223> OTHER INFORMATION: Description of Artificial Sequence: Vector
pSY1YIG7E1s sequence

<400> SEQUENCE: 50
atcgataagc ttttcaattc aattcatcat ttttttttta ttcttttttt tgatttcggt 60
ttctttgaaa tttttttgat tcggtaatct ccgaacagaa ggaagaacga aggaaggagc 120
acagacttag attggtatat atacgcatat gtagtgttga agaaacatga aattgcccag 180
tattcttaac ccaactgcac agaacaaaaa cctgcaggaa acgaagataa atcatgtcga 240
aagctacata taaggaacgt gctgctactc atcctagtcc tgttgctgcc aagctattta 300
atatcatgca cgaaaagcaa acaaacttgt gtgcttcatt ggatgttcgt accaccaagg 360
aattactgga gttagttgaa gcattaggtc ccaaaatttg tttactaaaa acacatgtgg 420
atatcttgac tgatttttcc atggagggca cagttaagcc gctaaaggca ttatccgcca 480
agtacaattt tttactcttc gaagacagaa aatttgctga cattggtaat acagtcaaat 540
tgcagtactc tgcgggtgta tacagaatag cagaatgggc agacattacg aatgcacacg 600
gtgtggtggg cccaggtatt gttagcggtt tgaagcaggc ggcagaagaa gtaacaaagg 660
aacctagagg ccttttgatg ttagcagaat tgtcatgcaa gggctcccta tctactggag 720
aatatactaa gggtactgtt gacattgcga agagcgacaa agattttgtt atcggcttta 780
ttgctcaaag agacatgggt ggaagagatg aaggttacga ttggttgatt atgacacccg 840
gtgtgggttt agatgacaag ggagacgcat tgggtcaaca gtatagaacc gtggatgatg 900
tggtctctac aggatctgac attattattg ttggaagagg actatttgca aagggaaggg 960
atgctaaggt agagggtgaa cgttacagaa aagcaggctg ggaagcatat ttgagaagat 1020
gcggccagca aaactaaaaa actgtattat aagtaaatgc atgtatacta aactcacaaa 1080
ttagagcttc aatttaatta tatcagttat tacccgggaa tctcggtcgt aatgattttt 1140
ataatgacga aaaaaaaaaa attggaaaga aaaagcttta atgcggtagt ttatcacagt 1200
taaattgcta acgcagtcag gcaccgtgta tgaaatctaa caatgcgctc atcgtcatcc 1260
tcggcaccgt caccctggat gctgtaggca taggcttggt tatgccggta ctgccgggcc 1320
tcttgcggga tatcgtccat tccgacagca tcgccagtca ctatggcgtg ctgctagcgc 1380
tatatgcgtt gatgcaattt ctatgcgcac ccgttctcgg agcactgtcc gaccgctttg 1440
gccgccgccc agtcctgctc gcttcgctac ttggagccac tatcgactac gcgatcatgg 1500
cgaccacacc cgtcctgtgg atcctggtat ggttttatcg ttttatttct ggttcttata 1560
gcatcgtttt ggacttctct gttcccatta ggcggttcag gagccagcgc agaatcattc 1620
tttgaaggat acttatcctt tccaattttg attgtctgtt acgttgggac ataaactgta 1680
tactagaaat tggactttga tggtgaaact agaagatatg gatcttgata ccggcagaaa 1740

-continued

```
acaagtagat ttgactcttc gtagggaaga aatgaggatt gagcgagaaa cattagcaaa   1800
aagatccttc gtaacaagat ttttacattt ctggtgttga agggaaagat atgagctata   1860
cagcggaatt tccatatcac tcagattttg ttatctaatt ttttccttcc cacgtccgcg   1920
ggaatctgtg tatattactg catctagcta gatatatgtt atcttatctt ggcgcgtaca   1980
tttaattttc aacgtattct ataagaaatt gcgggagttt ttttcatgta gatgatactg   2040
actgcacgca aatataggca tgatttatag gcatgatttg atggctgtac cgataggaac   2100
gctaagagta acttcagaat cgttatcctg gcggaaaaaa ttcatttgta aactttaaaa   2160
aaaaaagcca atatccccaa aattattaag agcgcctcca ttattaacta aaatttcact   2220
cagcatccac aatgtatcag gtatctacta cagatattac atgtggcgaa aaagacaaga   2280
acaatgcaat agcgcatcaa gaaaaaacac aaagctttca atcaatgaat cgaaaatgtc   2340
attaaaatag tatataaatt gaaactaagt cataaagcta taaaaagaaa atttatttaa   2400
atgcaagact ttaaagtaaa ttcacttaag ccttggcaac gtgttcaacc aagtcgagat   2460
ctgagcttat cggccgaggt gagaagggtc tattaccagt tcatcatcat atcccaagcc   2520
atacggtgac ccgttatgtg gccgggatag attgagcaat tgcagtcctg caccgtctca   2580
tgccggcgag gcgagatggt gaacagctgg gagacgagga agacagatcc gcagaggtcc   2640
cccacgtaca tagcggaaca gaaagcagcc gccccaacga gcaaatcgac gtggcgtcgt   2700
attgtcgtgg tggggacgct ggcgttccta gctgcgagcg tgggggtgag cgctacccag   2760
cagcgggaag agttgttctc ccgaacgcag ggcacgcacc cgggggtgtg catgatcatg   2820
tccgctgcct catacacaat gcttgagttg gagcagtcgt tcgtgacatg gtacatcccg   2880
gacacgttgc gcacctcata ccccagagca gccaggggca ggaagcaaag cactagtatt   2940
agcaaagacc tcatggtgtt tgtttatgtg tgtttattcg aaactaagtt cttggtgttt   3000
taaaactaaa aaaaagacta actataaaag tagaatttaa gaagtttaag aaatagattt   3060
acagaattac aatcaatacc taccgtcttt atatacttat tagtcaagta ggggaataat   3120
ttcagggaac tggtttcaac cttttttttc agggtttttt tttttcattc tctcaatctg   3180
aaattctctt atttctccaa cttataagtt ggagatgccc ggtgttccgg cagaggagat   3240
cagtctcgtg aagtggatgg tttcccgcct gcgggcaaaa cgtcataaca tttttatgag   3300
cgaaagccgt taatgaagac aaaatccctt aattaaaaca ttagaatggt gattagaaag   3360
gcaggattaa tcagttacac aggctgtaac cggagagacg gatcataagg caatttttag   3420
ataagactgg ttagagttct tggcatcaga aaatttgaga aacgattttt ccgtttgttt   3480
gcccctacgt tttgcccctt tgatcaaact atcagttaag atattaattt ttttgagaaa   3540
acgattcttt gattagtctc ttcaaacaaa caatgagctc tgaagacgaa ttgggaagta   3600
tcggtactgt gtttcccgga agtcccatag ataagagcat tgggagtatt ctccacaatt   3660
tgatgaagaa gtggagactt tgctggaaga tagcttcacg tggaacattc ctgactggaa   3720
cgagttaaca aacccgaaat acaattcgcc caggtttaga attggtgatt tcgaatggga   3780
cattctatta ttccctcagg gaaaccataa taaaggtgtt gcggtatatc tggaacctca   3840
tccggaagaa aaattagatg agactacggg agagatggtg ccagttgatc cggactggta   3900
ttgttgtgct cagtttgcca ttggtatatc tagacctggt aatggtgaca ccatcaattt   3960
aattaacaaa tcgcatcacc gattcaacgc tctagataca gactggggat ttgcaaattt   4020
gatagatttg aacaacttga aacatccctc aaaaggaaga ccgctttcgt tcttaaacga   4080
```

-continued

```
agggaccttg aacataacag cgtatgtgcg catattgaag gatcctctac gccggacgca   4140
tcgtggccgg catcaccggc gccacaggtg cggttgctgg cccctatatc gccgacatca   4200
ccgatgggga agatcgggct cgccacttcg ggctcatgag cgcttgtttc ggcgtgggta   4260
tggtggcagg ccccgtggcc gggggactgt tgggcgccat ctccttgcat gcaccattcc   4320
ttgcggcggc ggtgctcaac ggcctcaacc tactactggg ctgcttccta atgcaggagt   4380
cgcataaggg agagcgtcga ccgatgccct tgagagcctt caacccagtc agctccttcc   4440
ggtgggcgcg gggcatgact atcgtcgccg cacttatgac tgtcttcttt atcatgcaac   4500
tcgtaggaca ggtgccggca gcgctctggg tcattttcgg cgaggaccgc tttcgctgga   4560
gcgcgacgat gatcggcctg tcgcttgcgg tattcggaat cttgcacgcc ctcgctcaag   4620
ccttcgtcac tggtcccgcc accaaacgtt tcggcgagaa gcaggccatt atcgccggca   4680
tggcggccga cgcgctgggc tacgtcttgc tggcgttcgc gacgcgaggc tggatggcct   4740
tccccattat gattcttctc gcttccggcg gcatcgggat gcccgcgttg caggccatgc   4800
tgtccaggca ggtagatgac gaccatcagg gacagcttca aggatcgctc gcggctctta   4860
ccagcctaac ttcgatcact ggaccgctga tcgtcacggc gatttatgcc gcctcggcga   4920
gcacatggaa cgggttggca tggattgtag gcgccgccct ataccttgtc tgcctccccg   4980
cgttgcgtcg cggtgcatgg agccgggcca cctcgacctg aatggaagcc ggcggcacct   5040
cgctaacgga ttcaccactc caagaattgg agccaatcaa ttcttgcgga gaactgtgaa   5100
tgcgcaaacc aacccttggc agaacatatc catcgcgtcc gccatctcca gcagccgcac   5160
gcggcgcatc tcgggcagcg ttgggtcctg gccacgggtg cgcatgatcg tgctcctgtc   5220
gttgaggacc cggctaggct ggcggggttg ccttactggt tagcagaatg aatcaccgat   5280
acgcgagcga acgtgaagcg actgctgctg caaaacgtct gcgacctgag caacaacatg   5340
aatggtcttc ggtttccgtg tttcgtaaag tctggaaacg cggaagtcag cgccctgcac   5400
cattatgttc cggatctgca tcgcaggatg ctgctggcta ccctgtggaa cacctacatc   5460
tgtattaacg aagcgctggc attgaccctg agtgattttt ctctggtccc gccgcatcca   5520
taccgccagt tgtttaccct cacaacgttc cagtaaccgg gcatgttcat catcagtaac   5580
ccgtatcgtg agcatcctct ctcgtttcat cggtatcatt acccccatga acagaaattc   5640
ccccttacac ggaggcatca agtgaccaaa caggaaaaaa ccgcccttaa catggcccgc   5700
tttatcagaa gccagacatt aacgcttctg gagaaactca acgagctgga cgcggatgaa   5760
caggcagaca tctgtgaatc gcttcacgac cacgctgatg agctttaccg cagctgcctc   5820
gcgcgtttcg gtgatgacgg tgaaaacctc tgacacatgc agctcccgga gacggtcaca   5880
gcttgtctgt aagcggtgcc gggagcagac aagcccgtca gggcgcgtca gcgggtgttg   5940
gcgggtgtcg gggcgcagcc atgacccagt cacgtagcga tagcggagtg tatactggct   6000
taactatgcg gcatcagagc agattgtact gagagtgcac catatgcggt gtgaaatacc   6060
gcacagatgc gtaaggagaa aataccgcat caggcgctct tccgcttcct cgctcactga   6120
ctcgctgcgc tcggtcgttc ggctgcggcg agcggtatca gctcactcaa aggcggtaat   6180
acggttatcc acagaatcag gggataacgc aggaaagaac atgtgagcaa aaggccagca   6240
aaaggccagg aaccgtaaaa aggccgcgtt gctggcgttt ttccataggc tccgcccccc   6300
tgacgagcat cacaaaaatc gacgctcaag tcagaggtgg cgaaacccga caggactata   6360
aagataccag gcgtttcccc ctggaagctc cctcgtgcgc tctcctgttc cgaccctgcc   6420
gcttaccgga tacctgtccg cctttctccc ttcgggaagc gtggcgcttt ctcatagctc   6480
```

-continued acgctgtagg tatctcagtt cggtgtaggt cgttcgctcc aagctgggct gtgtgcacga 6540
accccccgtt cagcccgacc gctgcgcctt atccggtaac tatcgtcttg agtccaaccc 6600
ggtaagacac gacttatcgc cactggcagc agccactggt aacaggatta gcagagcgag 6660
gtatgtaggc ggtgctacag agttcttgaa gtggtggcct aactacggct acactagaag 6720
gacagtattt ggtatctgcg ctctgctgaa gccagttacc ttcggaaaaa gagttggtag 6780
ctcttgatcc ggcaaacaaa ccaccgctgg tagcggtggt ttttttgttt gcaagcagca 6840
gattacgcgc agaaaaaaag gatctcaaga agatcctttg atcttttcta cggggtctga 6900
cgctcagtgg aacgaaaact cacgttaagg gattttggtc atgagattat caaaaaggat 6960
cttcacctag atccttttaa attaaaaatg aagttttaaa tcaatctaaa gtatatatga 7020
gtaaacttgg tctgacagtt accaatgctt aatcagtgag gcacctatct cagcgatctg 7080
tctatttcgt tcatccatag ttgcctgact ccccgtcgtg tagataacta cgatacggga 7140
gggcttacca tctggcccca gtgctgcaat gataccgcga gacccacgct caccggctcc 7200
agatttatca gcaataaacc agccagccgg aagggccgag cgcagaagtg gtcctgcaac 7260
tttatccgcc tccatccagt ctattaattg ttgccgggaa gctagagtaa gtagttcgcc 7320
agttaatagt ttgcgcaacg ttgttgccat tgctgcaggc atcgtggtgt cacgctcgtc 7380
gtttggtatg gcttcattca gctccggttc ccaacgatca aggcgagtta catgatcccc 7440
catgttgtgc aaaaaagcgg ttagctcctt cggtcctccg atcgttgtca gaagtaagtt 7500
ggccgcagtg ttatcactca tggttatggc agcactgcat aattctctta ctgtcatgcc 7560
atccgtaaga tgcttttctg tgactggtga gtactcaacc aagtcattct gagaatagtg 7620
tatgcggcga ccgagttgct cttgcccggc gtcaacacgg gataataccg cgccacatag 7680
cagaacttta aaagtgctca tcattggaaa acgttcttcg gggcgaaaac tctcaaggat 7740
cttaccgctg ttgagatcca gttcgatgta acccactcgt gcacccaact gatcttcagc 7800
atcttttact ttcaccagcg tttctgggtg agcaaaaaca ggaaggcaaa atgccgcaaa 7860
aaagggaata agggcgacac ggaaatgttg aatactcata ctcttccttt ttcaatatta 7920
ttgaagcatt tatcagggtt attgtctcat gagcggatac atatttgaat gtatttagaa 7980
aaataaacaa ataggggttc cgcgcacatt tccccgaaaa gtgccacctg acgtctaaga 8040
aaccattatt atcatgacat taacctataa aaataggcg tatcacgagg ccctttcgtc 8100
ttcaagaatt ctcatgtttg acagcttatc atcgatccac ttgtatattt ggatgaattt 8160
ttgaggaatt ctgaaccagt cctaaaacga gtaaatagga ccggcaattc ttcaagcaat 8220
aaacaggaat accaattatt aaaagataac ttagtcagat cgtacaataa agctttgaag 8280
aaaaatgcgc cttattcaat ctttgcataa aaaaatggcc caaaatctca cattggaaga 8340
catttgatga cctcatttct ttcaatgaag ggcctaacgg agttgactaa tgttgtggga 8400
aattggaccg ataagcgtgc ttctgccgtg gccaggacaa cgtatactca tcagataaca 8460
gcaatacctg atcactactt cgcactagtt tctcggtact atgcatatga tccaatatca 8520
aaggaaatga tagcattgaa ggatgagact aatccaattg aggagtggca gcatatagaa 8580
cagctaaagg gtagtgctga aggaagcata cgataccccg catggaatgg gataatatca 8640
caggaggtac tagactacct ttcatcctac ataaatagac gcatataagt acgcatttaa 8700
gcataaacac gcactatgcc gttcttctca tgtatatata tatacaggca acacgcagat 8760
ataggtgcga cgtgaacagt gagctgtatg tgcgcagctc gcgttgcatt ttcggaagcg 8820

-continued

```
ctcgttttcg gaaacgcttt gaagttccta ttccgaagtt cctattctct agaaagtata   8880
ggaacttcag agcgcttttg aaaaccaaaa gcgctctgaa gacgcacttt caaaaaacca   8940
aaaacgcacc ggactgtaac gagctactaa aatattgcga ataccgcttc cacaaacatt   9000
gctcaaaagt atctctttgc tatatatctc tgtgctatat ccctatataa ccatcccatc   9060
cacctttcgc tccttgaact tgcatctaaa ctcgacctct acatttttta tgtttatctc   9120
tagtattacc tcttagacaa aaaaattgta gtaagaacta ttcatagagt taatcgaaaa   9180
caatacgaaa atgtaaacat ttcctatacg tagtatatag agacaaaata gaagaaaccg   9240
ttcataattt tctgaccaat gaagaatcat caacgctatc actttctgtt cacaaagtat   9300
gcgcaatcca catcggtata gaatataatc ggggatgcct ttatcttgaa aaaatgcacc   9360
cgcagcttcg ctagtaatca gtaaacgcgg gaagtggagt caggcttttt ttatggaaga   9420
gaaaatagac accaaagtag ccttcttcta accttaacgg acctacagtg caaaaagtta   9480
tcaagagact gcattataga gcgcacaaag gagaaaaaaa gtaatctaag atgctttgtt   9540
agaaaaatag cgctctcggg atgcattttt gtagaacaaa aaagaagtat agattcttgt   9600
tggtaaaata gcgctctcgc gttgcatttc tgttctgtaa aaatgcagct cagattcttt   9660
gtttgaaaaa ttagcgctct cgcgttgcat ttttgtttta caaaaatgaa gcacagattc   9720
ttcgttggta aaatagcgct ttcgcgttgc atttctgttc tgtaaaaatg cagctcagat   9780
tctttgtttg aaaaattagc gctctcgcgt tgcatttttg ttctacaaaa tgaagcacag   9840
atgcttcgtt aacaaagata tgctattgaa gtgcaagatg gaaacgcaga aaatgaaccg   9900
gggatgcgac gtgcaagatt acctatgcaa tagatgcaat agtttctcca ggaaccgaaa   9960
tacatacatt gtcttccgta aagcgctaga ctatatatta ttatacaggt tcaaatatac  10020
tatctgtttc agggaaaact cccaggttcg gatgttcaaa attcaatgat gggtaacaag  10080
tacgatcgta aatctgtaaa acagtttgtc ggatattagg ctgtatctcc tcaaagcgta  10140
ttcgaatatc attgagaagc tgcatttttt tttttttttt tttttttttt ttttttatat  10200
atatttcaag gatataccat tgtaatgtct gcccctaaga agatcgtcgt tttgccaggt  10260
gaccacgttg gtcaagaaat cacagccgaa gccattaagg ttcttaaagc tatttctgat  10320
gttcgttcca atgtcaagtt cgatttcgaa aatcatttaa ttggtggtgc tgctatcgat  10380
gctacaggtg tcccacttcc agatgaggcg ctggaagcct ccaagaaggt tgatgccgtt  10440
ttgttaggtg ctgtgggtgg tcctaaatgg ggtaccggta gtgttagacc tgaacaaggt  10500
ttactaaaaa tccgtaaaga acttcaattg tacgccaact taagaccatg taactttgca  10560
tccgactctc ttttagactt atctccaatc aagccacaat ttgctaaagg tactgacttc  10620
gttgttgtca gagaattagt gggaggtatt tactttggta agagaaagga agacgatggt  10680
gatggtgtcg cttgggatag tgaacaatac accgttccag aagtgcaaag aatcacaaga  10740
atggccgctt tcatggccct acaacatgag ccaccattgc ctatttggtc cttggataaa  10800
gctaatgttt tggcctcttc aagattatgg agaaaaactg tggaggaaac catcaagaac  10860
gaattcccta cattgaaggt tcaacatcaa ttgattgatt ctgccgccat gatcctagtt  10920
aagaacccaa cccacctaaa tggtattata atcaccagca acatgtttgg tgatatcatc  10980
tccgatgaag cctccgttat cccaggttcc ttgggtttgt tgccatctgc gtccttggcc  11040
tctttgccag acaagaacac cgcatttggt ttgtacgaac catgccacgg ttctgctcca  11100
gatttgccaa agaataaggt tgaccctatc gccactatct tgtctgctgc aatgatgttg  11160
aaattgtcat tgaacttgcc tgaagaaggt aaggccattg aagatgcagt taaaaaggtt  11220
```

-continued

```
ttggatgcag gtatcagaac tggtgattta ggtggttcca acagtaccac cgaagtcggt  11280
gatgctgtcg ccgaagaagt taagaaaatc cttgcttaaa aagattctct ttttttatga  11340
tatttgtaca aaaaaaaaaa aaaaaaaaaa aaaaaaaaaa aaaaaaaaaa aaaaatgcag  11400
cgtcacatcg gataataatg atggcagcca ttgtagaagt gccttttgca tttctagtct  11460
ctttctcggt ctagctagtt ttactacatc gcgaagatag aatcttagat cacactgcct  11520
ttgctgagct ggatcatatg agtaacaaaa gagtggtaag gcctcgttaa aggacaagga  11580
cctgagcgga agtgtatcgt aaagtagacg gagtatacta gtatagtcta tagtccgtgg  11640
aattctaagt gccagcttta taatgtcatt ctccttacta cagacccgcc tgaaagtaga  11700
cacatcatca tcagtaagct ttgacaaaaa gcattgagta gctaactctt ctatgcaatc  11760
tatagctgtt ttataaggca ttcaatggac agattgaggt ttttgaaaca tactagtgaa  11820
attagcctta atcccttctc gaagttaatc atgcattatg gtgtaaaaaa tgcaactcgc  11880
gttgctctac tttttcccga atttccaaat acgcagctgg ggtgattgct cgatttcgta  11940
acgaaagttt tgtttataaa aaccgcgaaa accttctgta acagatagat ttttacagcg  12000
ctgatataca atgacatcag ctgtaatgga aaataactga aatatgaatg gcgagagact  12060
gcttgcttgt attaagcaat gtattatgca gcacttccaa cctatggtgt acgatgaaag  12120
taggtgtgta atcgagacga caagggggac ttttccagtt cctgatcatt ataagaaata  12180
caaaacgtta gcatttgcat ttgttggaca tgtactgaat acagacgaca caccggtaat  12240
tgaaaaagaa ctggattggc ctgatcctgc actagtgtac aatacaattg tcgatcgaat  12300
cataaatcac ccagaattat cacagtttat atcggttgca tttattagtc agttaaaggc  12360
caccatcgga gagggtttag atattaatgt aaaaggcacg ctaaaccgca ggggaaaggg  12420
tatcagaagg cctaaaggcg tattttttag atacatggaa tctccatttg tcaatacaaa  12480
ggtcactgca ttcttctctt atcttcgaga ttataataaa attgcctcag aatatcacaa  12540
taatactaaa ttcattctca cgttttcatg tcaagcatat tgggcatctg gcccaaactt  12600
ctccgccttg aagaatgtta tttggtgctc cataattcat gaatacattt ctaagtttgt  12660
ggaaagagaa caggataaag gtcatatagg agatcaggag ctaccgcctg aagaggaccc  12720
ttctcgtgaa ctaaacaatg tacaacatga agtcaatagt ttaacggaac aagatgcgga  12780
ggcggatgaa ggattgtggg gtgaaataga ttcattatgt gaaaaatggc agtctgaagc  12840
ggagagtcaa actgaggcgg agataatagc cgacaggata attggaaata gccagaggat  12900
ggcgaacctc aaaattcgtc gtacaaagtt caaaagtgtc ttgtatcata tactaaagga  12960
actaattcaa tctcagggaa ccgtaaaggt ttatcgcggt agtagttttt cacacgattc  13020
gataaagata agcttacatt atgaagagca gcatattaca gccgtatggg tctacttgat  13080
agtaaaattt gaagagcatt ggaagcctgt tgatgtagag gtcgagttta gatgcaagtt  13140
caaggagcga aaggtggatg ggtaggttat atagggatat agcacagaga tatatagcaa  13200
agagatactt ttgaggcaat gtttgtggaa gcggtattcg caatatttta gtagctcgtt  13260
acagtccggt gcgtttttgg ttttttgaaa gtgcgtcttc agagcgcttt tggttttcaa  13320
aagcgctctg aagttcctat actttctaga gaataggaac ttcggaatag gaacttcaaa  13380
gcgtttccga aaacgagcgc ttccgaaaat gcaacgcgag ctgcgcacat acagctcact  13440
gttcacgtcg cacctatatc tgcgtgttgc ctgtatatat atatacatga gaagaacggc  13500
atagtgcgtg tttatgctta aatgcgtact tatatgcgtc tatttatgta ggatgaaagg  13560
```

-continued

```
tagtctagta cctcctgtga tattatccca ttccatgcgg ggtatcgtat gcttccttca  13620
gcactaccct ttagctgttc tatatgctgc cactcctcaa ttggattagt ctcatccttc  13680
aatgcattca tttcctttga tattggatca taccctagaa gtattacgtg attttctgcc  13740
ccttaccctc gttgctactc tcctttttt cgtgggaacc gctttagggc cctcagtgat  13800
ggtgttttgt aatttatatg ctcctcttgc atttgtgtct ctacttcttg ttcgcctgga  13860
gggaacttct tcatttgtat tagcatggtt cacttcagtc cttccttcca actcactctt  13920
tttttgctgt aaacgattct ctgccgccag ttcattgaaa ctattgaata tatcctttag  13980
agattccggg atgaataaat cacctattaa agcagcttga cgatctggtg gaactaaagt  14040
aagcaattgg gtaacgacgc ttacgagctt cataacatct tcttccgttg gagctggtgg  14100
gactaataac tgtgtacaat ccatttttct catgagcatt tcggtagctc tcttcttgtc  14160
tttctcgggc aatcttccta ttattatagc aatagatttg tatagttgct ttctattgtc  14220
taacagcttg ttattctgta gcatcaaatc tatggcagcc tgacttgctt cttgtgaaga  14280
gagcatacca tttccaatcg aagatacgct ggaatcttct gcgctagaat caagaccata  14340
cggcctaccg gttgtgagag attccatggg ccttatgaca tatcctggaa agagtagctc  14400
atcagactta cgtttactct ctatatcaat atctacatca ggagcaatca tttcaataaa  14460
cagccgacat acatcccaga cgctataagc tgtacgtgct tttaccgtca gattcttggc  14520
tgtttcaatg tcgtccattt tggttttctt ttaccagtat tgttcgtttg ataatgtatt  14580
cttgcttatt acattataaa atctgtgcag atcacatgtc aaaacaactt tttatcacaa  14640
gatagtaccg caaaacgaac ctgcgggccg tctaaaaatt aaggaaaagc agcaaaggtg  14700
catttttaaa atatgaaatg aagataccgc agtaccaatt attttcgcag tacaaataat  14760
gcgcggccgg tgcatttttc gaaagaacgc gagacaaaca ggacaattaa agttagtttt  14820
tcgagttagc gtgtttgaat actgcaagat acaagataaa tagagtagtt gaaactagat  14880
atcaattgca cacaagatcg gcgctaagca tgccacaatt tggtatatta tgtaaaacac  14940
cacctaaggt gcttgttcgt cagtttgtgg aaaggtttga aagaccttca ggtgagaaaa  15000
tagcattatg tgctgctgaa ctaacctatt tatgttggat gattacacat aacggaacag  15060
caatcaagag agccacattc atgagctata atactatcat aagcaattcg ctgagtttcg  15120
atattgtcaa taaatcactc cagtttaaat acaagacgca aaaagcaaca attctggaag  15180
cctcattaaa gaaattgatt cctgcttggg aatttacaat tattccttac tatggacaaa  15240
aacatcaatc tgatatcact gatattgtaa gtagtttgca attacagttc gaatcatcgg  15300
aagaagcaga taagggaaat agccacagta aaaaaatgct aaagcacttc taagtgaggg  15360
tgaaagcatc tgggagatca ctgagaaaat actaaattcg tttgagtata cttcgagatt  15420
tacaaaaaca aaaactttat accaattcct cttcctagct actttcatca attgtggaag  15480
attcagcgat attaagaacg ttgatccgaa atcatttaaa ttagtccaaa ataagtatct  15540
gggagtaata atccagtgtt tagtgacaga gacaaagaca agcgttagta ggcacatata  15600
cttctttagc gcaaggggta g                                            15621
```

<210> SEQ ID NO 51

<211> LENGTH: 3593

<212> TYPE: DNA

-continued

<213> ORGANISM: Artificial Sequence

<220> FEATURE:

<223> OTHER INFORMATION: Description of Artificial Sequence: Vector pPICZalphaA sequence

<400> SEQUENCE: 51

```
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagctgaa ttcacgtggc ccagccggcc gtctcggatc ggtacctcga gccgcggcgg   1260
ccgccagctt tctagaacaa aaactcatct cagaagagga tctgaatagc gccgtcgacc   1320
atcatcatca tcatcattga gtttgtagcc ttagacatga ctgttcctca gttcaagttg   1380
ggcacttacg agaagaccgg tcttgctaga ttctaatcaa gaggatgtca gaatgccatt   1440
tgcctgagag atgcaggctt catttttgat acttttttat ttgtaaccta tatagtatag   1500
gatttttttt gtcattttgt ttcttctcgt acgagcttgc tcctgatcag cctatctcgc   1560
agctgatgaa tatcttgtgg taggggtttg ggaaaatcat tcgagtttga tgtttttctt   1620
ggtatttccc actcctcttc agagtacaga agattaagtg agaccttcgt ttgtgcggat   1680
cccccacaca ccatagcttc aaaatgtttc tactcctttt ttactcttcc agattttctc   1740
ggactccgcg catcgccgta ccacttcaaa acacccaagc acagcatact aaattttccc   1800
tctttcttcc tctagggtgt cgttaattac ccgtactaaa ggtttggaaa agaaaaaaga   1860
gaccgcctcg tttctttttc ttcgtcgaaa aaggcaataa aaatttttat cacgtttctt   1920
tttcttgaaa tttttttttt tagttttttt ctctttcagt gacctccatt gatatttaag   1980
ttaataaacg gtcttcaatt tctcaagttt cagtttcatt tttcttgttc tattacaact   2040
ttttttactt cttgttcatt agaaagaaag catagcaatc taatctaagg ggcggtgttg   2100
```

-continued

```
acaattaatc atcggcatag tatatcggca tagtataata cgacaaggtg aggaactaaa   2160
ccatggccaa gttgaccagt gccgttccgg tgctcaccgc gcgcgacgtc gccggagcgg   2220
tcgagttctg gaccgaccgg ctcgggttct cccgggactt cgtggaggac gacttcgccg   2280
gtgtggtccg ggacgacgtg accctgttca tcagcgcggt ccaggaccag gtggtgccgg   2340
acaacaccct ggcctgggtg tgggtgcgcg gcctggacga gctgtacgcc gagtggtcgg   2400
aggtcgtgtc cacgaacttc cgggacgcct ccgggccggc catgaccgag atcggcgagc   2460
agccgtgggg gcgggagttc gccctgcgcg acccggccgg caactgcgtg cacttcgtgg   2520
ccgaggagca ggactgacac gtccgacggc ggcccacggg tcccaggcct cggagatccg   2580
tcccccttt cctttgtcga tatcatgtaa ttagttatgt cacgcttaca ttcacgccct   2640
ccccccacat ccgctctaac cgaaaaggaa ggagttagac aacctgaagt ctaggtccct   2700
atttattttt ttatagttat gttagtatta agaacgttat ttatatttca aatttttctt   2760
ttttttctgt acagacgcgt gtacgcatgt aacattatac tgaaaacctt gcttgagaag   2820
gttttgggac gctcgaaggc tttaatttgc aagctggaga ccaacatgtg agcaaaaggc   2880
cagcaaaagg ccaggaaccg taaaaaggcc gcgttgctgg cgtttttcca taggctccgc   2940
ccccctgacg agcatcacaa aaatcgacgc tcaagtcaga ggtggcgaaa cccgacagga   3000
ctataaagat accaggcgtt tccccctgga agctccctcg tgcgctctcc tgttccgacc   3060
ctgccgctta ccggatacct gtccgccttt ctcccttcgg gaagcgtggc gctttctcaa   3120
tgctcacgct gtaggtatct cagttcggtg taggtcgttc gctccaagct gggctgtgtg   3180
cacgaacccc ccgttcagcc cgaccgctgc gccttatccg gtaactatcg tcttgagtcc   3240
aacccggtaa gacacgactt atcgccactg gcagcagcca ctggtaacag gattagcaga   3300
gcgaggtatg taggcggtgc tacagagttc ttgaagtggt ggcctaacta cggctacact   3360
agaaggacag tatttggtat ctgcgctctg ctgaagccag ttaccttcgg aaaaagagtt   3420
ggtagctctt gatccggcaa acaaaccacc gctggtagcg gtggtttttt tgtttgcaag   3480
cagcagatta cgcgcagaaa aaaggatctc caagaagatc ctttgatctt ttctacgggg   3540
tctgacgctc agtggaacga aaactcacgt taagggattt tggtcatgag atc          3593
```

<210> SEQ ID NO 52
<211> LENGTH: 3547
<212> TYPE: DNA
<213> ORGANISM: Artificial Sequence
<220> FEATURE:
<223> OTHER INFORMATION: Description of Artificial Sequence: Vector
      pPICZalphaD' sequence

<400> SEQUENCE: 52

```
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
```

-continued

```
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaaggga   1080
tttcgatgtt gctgttttgc cattttccaa cagcacaaat aacgggttat tgtttataaa   1140
tactactatt gccagcattg ctgctaaaga agaaggggta tctctcgaga aaagggggccc   1200
gaattcgcat gcggccgcca gctttctaga acaaaaactc atctcagaag aggatctgaa   1260
tagcgccgtc gaccatcatc atcatcatca ttgagtttgt agccttagac atgactgttc   1320
ctcagttcaa gttgggcact tacgagaaga ccggtcttgc tagattctaa tcaagaggat   1380
gtcagaatgc catttgcctg agagatgcag gcttcatttt tgatactttt ttatttgtaa   1440
cctatatagt ataggatttt ttttgtcatt ttgtttcttc tcgtacgagc ttgctcctga   1500
tcagcctatc tcgcagctga tgaatatctt gtggtagggg tttgggaaaa tcattcgagt   1560
ttgatgtttt tcttggtatt tcccactcct cttcagagta cagaagatta agtgagacct   1620
tcgtttgtgc ggatccccca cacaccatag cttcaaaatg tttctactcc ttttttactc   1680
ttccagattt tctcggactc cgcgcatcgc cgtaccactt caaaacaccc aagcacagca   1740
tactaaattt tccctctttc ttcctctagg gtgtcgttaa ttacccgtac taaaggtttg   1800
gaaaagaaaa aagagaccgc ctcgtttctt tttcttcgtc gaaaaaggca ataaaaattt   1860
ttatcacgtt tctttttctt gaaatttttt tttttagttt ttttctcttt cagtgacctc   1920
cattgatatt taagttaata aacggtcttc aatttctcaa gtttcagttt catttttctt   1980
gttctattac aacttttttt acttcttgtt cattagaaag aaagcatagc aatctaatct   2040
aaggggcggt gttgacaatt aatcatcggc atagtatatc ggcatagtat aatacgacaa   2100
ggtgaggaac taaaccatgg ccaagttgac cagtgccgtt ccggtgctca ccgcgcgcga   2160
cgtcgccgga gcggtcgagt tctggaccga ccggctcggg ttctcccggg acttcgtgga   2220
ggacgacttc gccggtgtgg tccgggacga cgtgaccctg ttcatcagcg cggtccagga   2280
ccaggtggtg ccggacaaca ccctggcctg ggtgtgggtg cgcggcctgg acgagctgta   2340
cgccgagtgg tcggaggtcg tgtccacgaa cttccgggac gcctccgggc cggccatgac   2400
cgagatcggc gagcagccgt gggggcggga gttcgccctg cgcgacccgg ccggcaactg   2460
cgtgcacttc gtggccgagg agcaggactg acacgtccga cggcggccca cgggtcccag   2520
gcctcggaga tccgtccccc ttttcctttg tcgatatcat gtaattagtt atgtcacgct   2580
tacattcacg ccctcccccc acatccgctc taaccgaaaa ggaaggagtt agacaacctg   2640
aagtctaggt ccctatttat ttttttatag ttatgttagt attaagaacg ttatttatat   2700
ttcaaatttt tctttttttt ctgtacagac gcgtgtacgc atgtaacatt atactgaaaa   2760
ccttgcttga gaaggttttg ggacgctcga aggctttaat ttgcaagctg gagaccaaca   2820
tgtgagcaaa aggccagcaa aaggccagga accgtaaaaa ggccgcgttg ctggcgtttt   2880
```

-continued

```
tccataggct ccgcccccct gacgagcatc acaaaaatcg acgctcaagt cagaggtggc   2940

gaaacccgac aggactataa agataccagg cgtttccccc tggaagctcc ctcgtgcgct   3000

ctcctgttcc gaccctgccg cttaccggat acctgtccgc ctttctccct tcgggaagcg   3060

tggcgctttc tcaatgctca cgctgtaggt atctcagttc ggtgtaggtc gttcgctcca   3120

agctgggctg tgtgcacgaa ccccccgttc agcccgaccg ctgcgcctta tccggtaact   3180

atcgtcttga gtccaacccg gtaagacacg acttatcgcc actggcagca gccactggta   3240

acaggattag cagagcgagg tatgtaggcg gtgctacaga gttcttgaag tggtggccta   3300

actacggcta cactagaagg acagtatttg gtatctgcgc tctgctgaag ccagttacct   3360

tcggaaaaag agttggtagc tcttgatccg gcaaacaaac caccgctggt agcggtggtt   3420

tttttgtttg caagcagcag attacgcgca gaaaaaaagg atctcaagaa gatcctttga   3480

tcttttctac ggggtctgac gctcagtgga acgaaaactc acgttaaggg attttggtca   3540

tgagatc                                                             3547
```

<210> SEQ ID NO 53
<211> LENGTH: 3558
<212> TYPE: DNA
<213> ORGANISM: Artificial Sequence
<220> FEATURE:
<223> OTHER INFORMATION: Description of Artificial Sequence: Vector
      pPICZalphaE' sequence

<400> SEQUENCE: 53

```
agatctaaca tccaaagacg aaaggttgaa tgaaaccttt ttgccatccg acatccacag     60

gtccattctc acacataagt gccaaacgca acaggagggg atacactagc agcagaccgt    120

tgcaaacgca ggacctccac tcctcttctc ctcaacaccc acttttgcca tcgaaaaacc    180

agcccagtta ttgggcttga ttggagctcg ctcattccaa ttccttctat taggctacta    240

acaccatgac tttattagcc tgtctatcct ggcccccctg gcgaggttca tgtttgttta    300

tttccgaatg caacaagctc cgcattacac ccgaacatca ctccagatga gggctttctg    360

agtgtggggt caaatagttt catgttcccc aaatggccca aaactgacag tttaaacgct    420

gtcttggaac ctaatatgac aaaagcgtga tctcatccaa gatgaactaa gtttggttcg    480

ttgaaatgct aacggccagt tggtcaaaaa gaaacttcca aaagtcggca taccgtttgt    540

cttgtttggt attgattgac gaatgctcaa aaataatctc attaatgctt agcgcagtct    600

ctctatcgct tctgaacccc ggtgcacctg tgccgaaacg caaatgggga aacacccgct    660

ttttggatga ttatgcattg tctccacatt gtatgcttcc aagattctgg tgggaatact    720

gctgatagcc taacgttcat gatcaaaatt taactgttct aacccctact tgacagcaat    780

atataaacag aaggaagctg ccctgtctta aacctttttt tttatcatca ttattagctt    840

actttcataa ttgcgactgg ttccaattga caagcttttg attttaacga cttttaacga    900

caacttgaga agatcaaaaa acaactaatt attcgaaacg atgagatttc cttcaatttt    960

tactgctgtt ttattcgcag catcctccgc attagctgct ccagtcaaca ctacaacaga   1020

agatgaaacg gcacaaattc cggctgaagc tgtcatcggt tactcagatt tagaagggga   1080

tttcgatgtt gctgttttgc cattttccaa cagcacaaat aacgggttat tgtttataaa   1140

tactactatt gccagcattg ctgctaaaga agaaggggta tctctcgaga aaagagaggc   1200

tgaagcctgc agcatatgct cgaggccgcc agctttctag aacaaaaact catctcagaa   1260

gaggatctga atagcgccgt cgaccatcat catcatcatc attgagtttg tagccttaga   1320
```

-continued catgactgtt cctcagttca agttgggcac ttacgagaag accggtcttg ctagattcta 1380
atcaagagga tgtcagaatg ccatttgcct gagagatgca ggcttcattt ttgatacttt 1440
tttatttgta acctatatag tataggattt tttttgtcat tttgtttctt ctcgtacgag 1500
cttgctcctg atcagcctat ctcgcagctg atgaatatct tgtggtaggg gtttgggaaa 1560
atcattcgag tttgatgttt ttcttggtat ttcccactcc tcttcagagt acagaagatt 1620
aagtgagacc ttcgtttgtg cggatccccc acacaccata gcttcaaaat gtttctactc 1680 ctttttttact cttccagatt ttctcggact ccgcgcatcg ccgtaccact tcaaaacacc 1740
caagcacagc atactaaatt ttccctcttt cttcctctag ggtgtcgtta attacccgta 1800
ctaaaggttt ggaaaagaaa aaagagaccg cctcgtttct ttttcttcgt cgaaaaaggc 1860
aataaaaatt tttatcacgt ttcttttttct tgaaattttt ttttttagtt tttttctctt 1920
tcagtgacct ccattgatat ttaagttaat aaacggtctt caatttctca agtttcagtt 1980
tcatttttct tgttctatta caactttttt tacttcttgt tcattagaaa gaaagcatag 2040
caatctaatc taaggggcgg tgttgacaat taatcatcgg catagtatat cggcatagta 2100
taatacgaca aggtgaggaa ctaaaccatg gccaagttga ccagtgccgt tccggtgctc 2160
accgcgcgcg acgtcgccgg agcggtcgag ttctggaccg accggctcgg gttctcccgg 2220
gacttcgtgg aggacgactt cgccggtgtg gtccgggacg acgtgaccct gttcatcagc 2280
gcggtccagg accaggtggt gccggacaac accctggcct gggtgtgggt gcgcggcctg 2340
gacgagctgt acgccgagtg gtcggaggtc gtgtccacga acttccggga cgcctccggg 2400
ccggccatga ccgagatcgg cgagcagccg tgggggcggg agttcgccct gcgcgacccg 2460
gccggcaact gcgtgcactt cgtggccgag gagcaggact gacacgtccg acggcggccc 2520
acgggtccca ggcctcggag atccgtcccc cttttccttt gtcgatatca tgtaattagt 2580
tatgtcacgc ttacattcac gccctccccc cacatccgct ctaaccgaaa aggaaggagt 2640
tagacaacct gaagtctagg tccctattta ttttttttata gttatgttag tattaagaac 2700
gttatttata tttcaaattt ttcttttttt tctgtacaga cgcgtgtacg catgtaacat 2760
tatactgaaa accttgcttg agaaggtttt gggacgctcg aaggctttaa tttgcaagct 2820
ggagaccaac atgtgagcaa aaggccagca aaaggccagg aaccgtaaaa aggccgcgtt 2880
gctggcgttt ttccataggc tccgcccccc tgacgagcat cacaaaaatc gacgctcaag 2940
tcagaggtgg cgaaacccga caggactata aagataccag gcgtttcccc ctggaagctc 3000
cctcgtgcgc tctcctgttc cgaccctgcc gcttaccgga tacctgtccg cctttctccc 3060
ttcgggaagc gtggcgcttt ctcaatgctc acgctgtagg tatctcagtt cggtgtaggt 3120
cgttcgctcc aagctgggct gtgtgcacga accccccgtt cagcccgacc gctgcgcctt 3180
atccggtaac tatcgtcttg agtccaaccc ggtaagacac gacttatcgc cactggcagc 3240
agccactggt aacaggatta gcagagcgag gtatgtaggc ggtgctacag agttcttgaa 3300
gtggtggcct aactacggct acactagaag gacagtattt ggtatctgcg ctctgctgaa 3360
gccagttacc ttcggaaaaa gagttggtag ctcttgatcc ggcaaacaaa ccaccgctgg 3420
tagcggtggt ttttttgttt gcaagcagca gattacgcgc agaaaaaaag gatctcaaga 3480
agatcctttg atcttttcta cggggtctga cgctcagtgg aacgaaaact cacgttaagg 3540
gattttggtc atgagatc 3558

<210> SEQ ID NO 54
<211> LENGTH: 28

-continued

<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 54
tcgagaaaag gggcccgaat tcgcatgc 28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 55
ggccgcatgc gaattcgggc cccttttc 28

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 56
tcgagaaaag agaggctgaa gcctgcagca tatgc 35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic probe or primer

<400> SEQUENCE: 57
ggccgcatat gctgcaggct tcagcctctc ttttc 35

<210> SEQ ID NO 58
<211> LENGTH: 3997
<212> TYPE: DNA
<213> ORGANISM: Artificial Sequence
<220> FEATURE:
<223> OTHER INFORMATION: Description of Artificial Sequence: Vector pPICZalphaD'E1sH6 sequence

<400> SEQUENCE: 58
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600

-continued

```
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaaggtatga   1200
ggtgcgcaac gtgtccggga tgtaccatgt cacgaacgac tgctccaact caagcattgt   1260
gtatgaggca gcggacatga tcatgcacac ccccgggtgc gtgccctgcg ttcgggagaa   1320
caactcttcc cgctgctggg tagcgctcac ccccacgctc gcagctagga acgccagcgt   1380
ccccactacg acaatacgac gccacgtcga tttgctcgtt ggggcggctg ctttctgttc   1440
cgctatgtac gtgggggatc tctgcggatc tgtcttcctc gtctcccagc tgttcaccat   1500
ctcgcctcgc cggcatgaga cggtgcagga ctgcaattgc tcaatctatc ccggccacat   1560
aacaggtcac cgtatggctt gggatatgat gatgaactgg caccaccacc atcaccatta   1620
aagatctaag cttgaatccc gcggccatgc gaattcgcat gcggccgcca gctttctaga   1680
acaaaaactc atctcagaag aggatctgaa tagcgccgtc gaccatcatc atcatcatca   1740
ttgagtttgt agccttagac atgactgttc ctcagttcaa gttgggcact tacgagaaga   1800
ccggtcttgc tagattctaa tcaagaggat gtcagaatgc catttgcctg agagatgcag   1860
gcttcatttt tgatactttt ttatttgtaa cctatatagt ataggatttt ttttgtcatt   1920
ttgtttcttc tcgtacgagc ttgctcctga tcagcctatc tcgcagctga tgaatatctt   1980
gtggtagggg tttgggaaaa tcattcgagt ttgatgtttt tcttggtatt tcccactcct   2040
cttcagagta cagaagatta agtgagacct tcgtttgtgc ggatccccca cacaccatag   2100
cttcaaaatg tttctactcc ttttttactc ttccagattt tctcggactc cgcgcatcgc   2160
cgtaccactt caaaacaccc aagcacagca tactaaattt tccctctttc ttcctctagg   2220
gtgtcgttaa ttacccgtac taaaggtttg gaaaagaaaa aagagaccgc ctcgtttctt   2280
tttcttcgtc gaaaaaggca ataaaaattt ttatcacgtt tctttttctt gaaatttttt   2340
tttttagttt ttttctcttt cagtgacctc cattgatatt taagttaata aacggtcttc   2400
aatttctcaa gtttcagttt catttttctt gttctattac aacttttttt acttcttgtt   2460
cattagaaag aaagcatagc aatctaatct aaggggcggt gttgacaatt aatcatcggc   2520
atagtatatc ggcatagtat aatacgacaa ggtgaggaac taaaccatgg ccaagttgac   2580
cagtgccgtt ccggtgctca ccgcgcgcga cgtcgccgga gcggtcgagt tctggaccga   2640
ccggctcggg ttctcccggg acttcgtgga ggacgacttc gccggtgtgg tccgggacga   2700
cgtgaccctg ttcatcagcg cggtccagga ccaggtggtg ccggacaaca ccctggcctg   2760
ggtgtgggtg cgcggcctgg acgagctgta cgccgagtgg tcggaggtcg tgtccacgaa   2820
cttccgggac gcctccgggc cggccatgac cgagatcggc gagcagccgt gggggcggga   2880
gttcgccctg cgcgacccgg ccggcaactg cgtgcacttc gtggccgagg agcaggactg   2940
```

```
acacgtccga cggcggccca cgggtcccag gcctcggaga tccgtccccc ttttcctttg   3000

tcgatatcat gtaattagtt atgtcacgct tacattcacg ccctcccccc acatccgctc   3060

taaccgaaaa ggaaggagtt agacaacctg aagtctaggt ccctatttat ttttttatag   3120

ttatgttagt attaagaacg ttatttatat ttcaaatttt tctttttttt ctgtacagac   3180

gcgtgtacgc atgtaacatt atactgaaaa ccttgcttga gaaggttttg ggacgctcga   3240

aggctttaat ttgcaagctg gagaccaaca tgtgagcaaa aggccagcaa aaggccagga   3300

accgtaaaaa ggccgcgttg ctggcgtttt tccataggct ccgcccccct gacgagcatc   3360

acaaaaatcg acgctcaagt cagaggtggc gaaacccgac aggactataa agataccagg   3420

cgtttccccc tggaagctcc ctcgtgcgct ctcctgttcc gaccctgccg cttaccggat   3480

acctgtccgc ctttctccct tcgggaagcg tggcgctttc tcaatgctca cgctgtaggt   3540

atctcagttc ggtgtaggtc gttcgctcca agctgggctg tgtgcacgaa ccccccgttc   3600

agcccgaccg ctgcgcctta tccggtaact atcgtcttga gtccaacccg gtaagacacg   3660

acttatcgcc actggcagca gccactggta acaggattag cagagcgagg tatgtaggcg   3720

gtgctacaga gttcttgaag tggtggccta actacggcta cactagaagg acagtatttg   3780

gtatctgcgc tctgctgaag ccagttacct tcggaaaaag agttggtagc tcttgatccg   3840

gcaaacaaac caccgctggt agcggtggtt tttttgtttg caagcagcag attacgcgca   3900

gaaaaaaagg atctcaagaa gatcctttga tcttttctac ggggtctgac gctcagtgga   3960

acgaaaactc acgttaaggg attttggtca tgagatc                           3997
```

<210> SEQ ID NO 59
<211> LENGTH: 4004
<212> TYPE: DNA
<213> ORGANISM: Artificial Sequence
<220> FEATURE:
<223> OTHER INFORMATION: Description of Artificial Sequence: Vector
      pPICZalphaE'E1sH6 sequence

<400> SEQUENCE: 59

```
agatctaaca tccaaagacg aaaggttgaa tgaaaccttt ttgccatccg acatccacag     60

gtccattctc acacataagt gccaaacgca acaggagggg atacactagc agcagaccgt    120

tgcaaacgca ggacctccac tcctcttctc ctcaacaccc acttttgcca tcgaaaaacc    180

agcccagtta ttgggcttga ttggagctcg ctcattccaa ttccttctat taggctacta    240

acaccatgac tttattagcc tgtctatcct ggcccccctg gcgaggttca tgtttgttta    300

tttccgaatg caacaagctc cgcattacac ccgaacatca ctccagatga gggctttctg    360

agtgtggggt caaatagttt catgttcccc aaatggccca aaactgacag tttaaacgct    420

gtcttggaac ctaatatgac aaaagcgtga tctcatccaa gatgaactaa gtttggttcg    480

ttgaaatgct aacggccagt tggtcaaaaa gaaacttcca aaagtcggca taccgtttgt    540

cttgtttggt attgattgac gaatgctcaa aaataatctc attaatgctt agcgcagtct    600

ctctatcgct tctgaacccc ggtgcacctg tgccgaaacg caaatgggga aacacccgct    660

ttttggatga ttatgcattg tctccacatt gtatgcttcc aagattctgg tgggaatact    720

gctgatagcc taacgttcat gatcaaaatt taactgttct aacccctact tgacagcaat    780

atataaacag aaggaagctg ccctgtctta aacctttttt tttatcatca ttattagctt    840

actttcataa ttgcgactgg ttccaattga caagcttttg attttaacga cttttaacga    900

caacttgaga agatcaaaaa acaactaatt attcgaaacg atgagatttc cttcaatttt    960
```

-continued

```
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagcctat gaggtgcgca acgtgtccgg gatgtaccat gtcacgaacg actgctccaa   1260
ctcaagcatt gtgtatgagg cagcggacat gatcatgcac acccccgggt gcgtgccctg   1320
cgttcgggag aacaactctt cccgctgctg ggtagcgctc acccccacgc tcgcagctag   1380
gaacgccagc gtccccacta cgacaatacg acgccacgtc gatttgctcg ttggggcggc   1440
tgctttctgt tccgctatgt acgtgggggga tctctgcgga tctgtcttcc tcgtctccca   1500
gctgttcacc atctcgcctc gccggcatga gacggtgcag gactgcaatt gctcaatcta   1560
tcccggccac ataacgggtc accgtatggc ttgggatatg atgatgaact ggcaccacca   1620
ccatcaccat taaagatcta agcttgaatc ccgcggccat ggcatatgcg gccgccagct   1680
ttctagaaca aaaactcatc tcagaagagg atctgaatag cgccgtcgac catcatcatc   1740
atcatcattg agtttgtagc cttagacatg actgttcctc agttcaagtt gggcacttac   1800
gagaagaccg gtcttgctag attctaatca agaggatgtc agaatgccat ttgcctgaga   1860
gatgcaggct tcatttttga tacttttttta tttgtaacct atatagtata ggattttttt   1920
tgtcattttg tttcttctcg tacgagcttg ctcctgatca gcctatctcg cagctgatga   1980
atatcttgtg gtaggggttt gggaaaatca ttcgagtttg atgtttttct tggtatttcc   2040
cactcctctt cagagtacag aagattaagt gagaccttcg tttgtgcgga tcccccacac   2100
accatagctt caaaatgttt ctactccttt tttactcttc cagattttct cggactccgc   2160
gcatcgccgt accacttcaa aacacccaag cacagcatac taaattttcc ctctttcttc   2220
ctctagggtg tcgttaatta cccgtactaa aggtttggaa aagaaaaaag agaccgcctc   2280
gtttcttttt cttcgtcgaa aaaggcaata aaaattttta tcacgtttct ttttcttgaa   2340
attttttttt ttagtttttt tctctttcag tgacctccat tgatatttaa gttaataaac   2400
ggtcttcaat ttctcaagtt tcagtttcat ttttcttgtt ctattacaac ttttttttact   2460
tcttgttcat tagaaagaaa gcatagcaat ctaatctaag ggcggtgtt gacaattaat   2520
catcggcata gtatatcggc atagtataat acgacaaggt gaggaactaa accatggcca   2580
agttgaccag tgccgttccg gtgctcaccg cgcgcgacgt cgccggagcg gtcgagttct   2640
ggaccgaccg gctcgggttc tcccgggact tcgtggagga cgacttcgcc ggtgtggtcc   2700
gggacgacgt gaccctgttc atcagcgcgg tccaggacca ggtggtgccg gacaacaccc   2760
tggcctgggt gtgggtgcgc ggcctggacg agctgtacgc cgagtggtcg gaggtcgtgt   2820
ccacgaactt ccgggacgcc tccgggccgg ccatgaccga gatcggcgag cagccgtggg   2880
ggcgggagtt cgccctgcgc gacccggccg gcaactgcgt gcacttcgtg gccgaggagc   2940
aggactgaca cgtccgacgg cggcccacgg gtcccaggcc tcggagatcc gtcccccttt   3000
tcctttgtcg atatcatgta attagttatg tcacgcttac attcacgccc tccccccaca   3060
tccgctctaa ccgaaaagga aggagttaga caacctgaag tctaggtccc tatttatttt   3120
tttatagtta tgttagtatt aagaacgtta tttatatttc aaatttttct tttttttctg   3180
tacagacgcg tgtacgcatg taacattata ctgaaaacct tgcttgagaa ggttttggga   3240
cgctcgaagg ctttaatttg caagctggag accaacatgt gagcaaaagg ccagcaaaag   3300
gccaggaacc gtaaaaaggc cgcgttgctg gcgtttttcc ataggctccg ccccccctgac   3360
```

-continued gagcatcaca aaaatcgacg ctcaagtcag aggtggcgaa acccgacagg actataaaga 3420
taccaggcgt ttccccctgg aagctccctc gtgcgctctc ctgttccgac cctgccgctt 3480
accggatacc tgtccgcctt tctcccttcg ggaagcgtgg cgctttctca atgctcacgc 3540
tgtaggtatc tcagttcggt gtaggtcgtt cgctccaagc tgggctgtgt gcacgaaccc 3600
cccgttcagc ccgaccgctg cgccttatcc ggtaactatc gtcttgagtc caacccggta 3660
agacacgact tatcgccact ggcagcagcc actggtaaca ggattagcag agcgaggtat 3720
gtaggcggtg ctacagagtt cttgaagtgg tggcctaact acggctacac tagaaggaca 3780
gtatttggta tctgcgctct gctgaagcca gttaccttcg gaaaaagagt tggtagctct 3840
tgatccggca aacaaaccac cgctggtagc ggtggttttt ttgtttgcaa gcagcagatt 3900
acgcgcagaa aaaaaggatc tcaagaagat cctttgatct tttctacggg gtctgacgct 3960
cagtggaacg aaaactcacg ttaagggatt ttggtcatga gatc 4004

<210> SEQ ID NO 60
<211> LENGTH: 4492
<212> TYPE: DNA
<213> ORGANISM: Artificial Sequence
<220> FEATURE:
<223> OTHER INFORMATION: Description of Artificial Sequence: Vector pPICZalphaD'E2sH6 sequence

<400> SEQUENCE: 60
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttcaatttt 960
tactgctgtt ttattcgcag catcctccgc attagctgct ccagtcaaca ctacaacaga 1020
agatgaaacg gcacaaattc cggctgaagc tgtcatcggt tactcagatt tagaagggga 1080
tttcgatgtt gctgttttgc cattttccaa cagcacaaat aacgggttat tgtttataaa 1140
tactactatt gccagcattg ctgctaaaga agaaggggta tctctcgaga aaaggcatac 1200
ccgcgtgtca ggaggggcag cagcctccga taccaggggc cttgtgtccc tctttagccc 1260
cgggtcggct cagaaaatcc agctcgtaaa caccaacggc agttggcaca tcaacaggac 1320
tgccctgaac tgcaacgact ccctccaaac agggttcttt gccgcactat tctacaaaca 1380

-continued caaattcaac tcgtctggat gcccagagcg cttggccagc tgtcgctcca tcgacaagtt 1440
cgctcagggg tggggtcccc tcacttacac tgagcctaac agctcggacc agaggcccta 1500
ctgctggcac tacgcgcctc gaccgtgtgg tattgtaccc gcgtctcagg tgtgcggtcc 1560
agtgtattgc ttcaccccga gccctgttgt ggtggggacg accgatcggt ttggtgtccc 1620
cacgtataac tgggggggcga acgactcgga tgtgctgatt ctcaacaaca cgcggccgcc 1680
gcgaggcaac tggttcggct gtacatggat gaatggcact gggttcacca agacgtgtgg 1740
gggcccccccg tgcaacatcg ggggggccgg caacaacacc ttgacctgcc ccactgactg 1800
ttttcggaag caccccgagg ccacctacgc cagatgcggt tctgggccct ggctgacacc 1860
taggtgtatg gttcattacc catataggct ctggcactac cctgcactg tcaacttcac 1920
catcttcaag gttaggatgt acgtgggggg cgtggagcac aggttcgaag ccgcatgcaa 1980
ttggactcga ggagagcgtt gtgacttgga ggacagggat agatcagagc ttagcccgct 2040
gctgctgtct acaacagagt ggcaggtgat cgagggcaga caccatcacc accatcacta 2100
atagttaatt aactgcaggc atgcaagctt atcgataccg tcgacgaatt cgcatgcggc 2160
cgccagcttt ctagaacaaa aactcatctc agaagaggat ctgaatagcg ccgtcgacca 2220
tcatcatcat catcattgag tttgtagcct tagacatgac tgttcctcag ttcaagttgg 2280
gcacttacga gaagaccggt cttgctagat tctaatcaag aggatgtcag aatgccattt 2340
gcctgagaga tgcaggcttc atttttgata ctttttttatt tgtaacctat atagtatagg 2400
atttttttttg tcattttgtt tcttctcgta cgagcttgct cctgatcagc ctatctcgca 2460
gctgatgaat atcttgtggt aggggtttgg gaaaatcatt cgagtttgat gtttttcttg 2520
gtatttccca ctcctcttca gagtacagaa gattaagtga gaccttcgtt tgtgcggatc 2580
ccccacacac catagcttca aaatgtttct actccttttt tactcttcca gattttctcg 2640
gactccgcgc atcgccgtac cacttcaaaa cacccaagca cagcatacta aattttccct 2700
ctttcttcct ctagggtgtc gttaattacc cgtactaaag gtttggaaaa gaaaaaagag 2760
accgcctcgt ttcttttttct tcgtcgaaaa aggcaataaa aatttttatc acgtttcttt 2820
ttcttgaaat tttttttttt agttttttttc tctttcagtg acctccattg atatttaagt 2880
taataaacgg tcttcaattt ctcaagtttc agtttcattt ttcttgttct attacaactt 2940
tttttacttc ttgttcatta gaaagaaagc atagcaatct aatctaaggg gcggtgttga 3000
caattaatca tcggcatagt atatcggcat agtataatac gacaaggtga ggaactaaac 3060
catggccaag ttgaccagtg ccgttccggt gctcaccgcg cgcgacgtcg ccggagcggt 3120
cgagttctgg accgaccggc tcgggttctc ccgggacttc gtggaggacg acttcgccgg 3180
tgtggtccgg gacgacgtga ccctgttcat cagcgcggtc caggaccagg tggtgccgga 3240
caacaccctg gcctgggtgt gggtgcgcgg cctggacgag ctgtacgccg agtggtcgga 3300
ggtcgtgtcc acgaacttcc gggacgcctc cgggccggcc atgaccgaga tcggcgagca 3360
gccgtggggg cgggagttcg ccctgcgcga cccggccggc aactgcgtgc acttcgtggc 3420
cgaggagcag gactgacacg tccgacggcg gcccacgggt cccaggcctc ggagatccgt 3480
ccccctttttc ctttgtcgat atcatgtaat tagttatgtc acgcttacat tcacgccctc 3540
cccccacatc cgctctaacc gaaaaggaag gagttagaca acctgaagtc taggtcccta 3600
tttatttttt tatagttatg ttagtattaa gaacgttatt tatatttcaa atttttcttt 3660
tttttctgta cagacgcgtg tacgcatgta acattatact gaaaaccttg cttgagaagg 3720

-continued

```
ttttgggacg ctcgaaggct ttaatttgca agctggagac caacatgtga gcaaaaggcc   3780

agcaaaaggc caggaaccgt aaaaaggccg cgttgctggc gtttttccat aggctccgcc   3840

cccctgacga gcatcacaaa aatcgacgct caagtcagag gtggcgaaac ccgacaggac   3900

tataaagata ccaggcgttt ccccctggaa gctccctcgt gcgctctcct gttccgaccc   3960

tgccgcttac cggatacctg tccgcctttc tcccttcggg aagcgtggcg ctttctcaat   4020

gctcacgctg taggtatctc agttcggtgt aggtcgttcg ctccaagctg ggctgtgtgc   4080

acgaaccccc cgttcagccc gaccgctgcg ccttatccgg taactatcgt cttgagtcca   4140

acccggtaag acacgactta tcgccactgg cagcagccac tggtaacagg attagcagag   4200

cgaggtatgt aggcggtgct acagagttct tgaagtggtg gcctaactac ggctacacta   4260

gaaggacagt atttggtatc tgcgctctgc tgaagccagt taccttcgga aaaagagttg   4320

gtagctcttg atccggcaaa caaaccaccg ctggtagcgg tggttttttt gtttgcaagc   4380

agcagattac gcgcagaaaa aaaggatctc aagaagatcc tttgatcttt tctacggggt   4440

ctgacgctca gtggaacgaa aactcacgtt aagggatttt ggtcatgaga tc           4492
```

```
<210> SEQ ID NO 61
<211> LENGTH: 4431
<212> TYPE: DNA
<213> ORGANISM: Artificial Sequence
<220> FEATURE:
<223> OTHER INFORMATION: Description of Artificial Sequence: Vector
      pPICZalphaE'E2sH6 sequence

<400> SEQUENCE: 61
```

```
agatctaaca tccaaagacg aaaggttgaa tgaaaccttt ttgccatccg acatccacag     60

gtccattctc acacataagt gccaaacgca acaggagggg atacactagc agcagaccgt    120

tgcaaacgca ggacctccac tcctcttctc ctcaacaccc acttttgcca tcgaaaaacc    180

agcccagtta ttgggcttga ttggagctcg ctcattccaa ttccttctat taggctacta    240

acaccatgac tttattagcc tgtctatcct ggcccccctg gcgaggttca tgtttgttta    300

tttccgaatg caacaagctc cgcattacac ccgaacatca ctccagatga gggctttctg    360

agtgtggggt caaatagttt catgttcccc aaatggccca aaactgacag tttaaacgct    420

gtcttggaac ctaatatgac aaaagcgtga tctcatccaa gatgaactaa gtttggttcg    480

ttgaaatgct aacggccagt tggtcaaaaa gaaacttcca aaagtcggca taccgtttgt    540

cttgtttggt attgattgac gaatgctcaa aaataatctc attaatgctt agcgcagtct    600

ctctatcgct tctgaacccc ggtgcacctg tgccgaaacg caaatgggga aacacccgct    660

ttttggatga ttatgcattg tctccacatt gtatgcttcc aagattctgg tgggaatact    720

gctgatagcc taacgttcat gatcaaaatt taactgttct aacccctact tgacagcaat    780

atataaacag aaggaagctg ccctgtctta aacctttttt tttatcatca ttattagctt    840

actttcataa ttgcgactgg ttccaattga caagcttttg attttaacga cttttaacga    900

caacttgaga agatcaaaaa acaactaatt attcgaaacg atgagatttc cttcaatttt    960

tactgctgtt ttattcgcag catcctccgc attagctgct ccagtcaaca ctacaacaga   1020

agatgaaacg gcacaaattc cggctgaagc tgtcatcggt tactcagatt tagaagggga   1080

tttcgatgtt gctgttttgc cattttccaa cagcacaaat aacgggttat tgtttataaa   1140

tactactatt gccagcattg ctgctaaaga agaaggggta tctctcgaga aaagagaggc   1200

tgaagcccat acccgcgtgt caggaggggc agcagcctcc gataccaggg gccttgtgtc   1260
```

-continued

```
cctctttagc cccgggtcgg ctcagaaaat ccagctcgta aacaccaacg gcagttggca   1320
catcaacagg actgccctga actgcaacga ctccctccaa acagggttct ttgccgcact   1380
attctacaaa cacaaattca actcgtctgg atgcccagag cgcttggcca gctgtcgctc   1440
catcgacaag ttcgctcagg ggtggggtcc cctcacttac actgagccta acagctcgga   1500
ccagaggccc tactgctggc actacgcgcc tcgaccgtgt ggtattgtac ccgcgtctca   1560
ggtgtgcggt ccagtgtatt gcttcacccc gagccctgtt gtggtgggga cgaccgatcg   1620
gtttggtgtc cccacgtata actgggggc gaacgactcg gatgtgctga ttctcaacaa   1680
cacgcggccg ccgcgaggca actggttcgg ctgtacatgg atgaatggca ctgggttcac   1740
caagacgtgt gggggccccc cgtgcaacat cggggggggcc ggcaacaaca ccttgacctg   1800
ccccactgac tgttttcgga agcaccccga ggccacctac gccagatgcg gttctgggcc   1860
ctggctgaca cctaggtgta tggttcatta cccatatagg ctctggcact acccctgcac   1920
tgtcaacttc accatcttca aggttaggat gtacgtgggg ggcgtggagc acaggttcga   1980
agccgcatgc aattggactc gaggagagcg ttgtgacttg gaggacaggg atagatcaga   2040
gcttagcccg ctgctgctgt ctacaacaga gtggcaggtg atcgagggca gacaccatca   2100
ccaccatcac taatagttaa ttaactgcag gcatgcaagc ttatcgatac cgtcgaccat   2160
catcatcatc atcattgagt ttgtagcctt agacatgact gttcctcagt tcaagttggg   2220
cacttacgag aagaccggtc ttgctagatt ctaatcaaga ggatgtcaga atgccatttg   2280
cctgagagat gcaggcttca tttttgatac tttttttattt gtaacctata tagtatagga   2340
ttttttttgt cattttgttt cttctcgtac gagcttgctc ctgatcagcc tatctcgcag   2400
ctgatgaata tcttgtggta ggggtttggg aaaatcattc gagtttgatg tttttcttgg   2460
tatttcccac tcctcttcag agtacagaag attaagtgag accttcgttt gtgcggatcc   2520
cccacacacc atagcttcaa aatgtttcta ctcctttttt actcttccag attttctcgg   2580
actccgcgca tcgccgtacc acttcaaaac acccaagcac agcatactaa attttccctc   2640
tttcttcctc tagggtgtcg ttaattaccc gtactaaagg tttggaaaag aaaaaagaga   2700
ccgcctcgtt tctttttctt cgtcgaaaaa ggcaataaaa atttttatca cgtttctttt   2760
tcttgaaatt ttttttttta gttttttttct ctttcagtga cctccattga tatttaagtt   2820
aataaacggt cttcaatttc tcaagtttca gtttcatttt tcttgttcta ttacaacttt   2880
ttttacttct tgttcattag aaagaaagca tagcaatcta atctaagggg cggtgttgac   2940
aattaatcat cggcatagta tatcggcata gtataatacg acaaggtgag gaactaaacc   3000
atggccaagt tgaccagtgc cgttccggtg ctcaccgcgc gcgacgtcgc cggagcggtc   3060
gagttctgga ccgaccggct cgggttctcc cgggacttcg tggaggacga cttcgccggt   3120
gtggtccggg acgacgtgac cctgttcatc agcgcggtcc aggaccaggt ggtgccggac   3180
aacaccctgg cctgggtgtg ggtgcgcggc ctggacgagc tgtacgccga gtggtcggag   3240
gtcgtgtcca cgaacttccg ggacgcctcc gggccggcca tgaccgagat cggcgagcag   3300
ccgtgggggc gggagttcgc cctgcgcgac ccggccggca actgcgtgca cttcgtggcc   3360
gaggagcagg actgacacgt ccgacggcgg cccacgggtc ccaggcctcg gagatccgtc   3420
ccccttttcc tttgtcgata tcatgtaatt agttatgtca cgcttacatt cacgccctcc   3480
ccccacatcc gctctaaccg aaaaggaagg agttagacaa cctgaagtct aggtccctat   3540
ttatttttt atagttatgt tagtattaag aacgttattt atatttcaaa tttttctttt   3600
ttttctgtac agacgcgtgt acgcatgtaa cattatactg aaaaccttgc ttgagaaggt   3660
```

```
tttgggacgc tcgaaggctt taatttgcaa gctggagacc aacatgtgag caaaaggcca   3720

gcaaaaggcc aggaaccgta aaaaggccgc gttgctggcg tttttccata ggctccgccc   3780

ccctgacgag catcacaaaa atcgacgctc aagtcagagg tggcgaaacc cgacaggact   3840

ataaagatac caggcgtttc cccctggaag ctccctcgtg cgctctcctg ttccgaccct   3900

gccgcttacc ggatacctgt ccgcctttct cccttcggga agcgtggcgc tttctcaatg   3960

ctcacgctgt aggtatctca gttcggtgta ggtcgttcgc tccaagctgg gctgtgtgca   4020

cgaacccccc gttcagcccg accgctgcgc cttatccggt aactatcgtc ttgagtccaa   4080

cccggtaaga cacgacttat cgccactggc agcagccact ggtaacagga ttagcagagc   4140

gaggtatgta ggcggtgcta cagagttctt gaagtggtgg cctaactacg gctacactag   4200

aaggacagta tttggtatct gcgctctgct gaagccagtt accttcggaa aaagagttgg   4260

tagctcttga tccggcaaac aaaccaccgc tggtagcggt ggtttttttg tttgcaagca   4320

gcagattacg cgcagaaaaa aaggatctca agaagatcct ttgatctttt ctacggggtc   4380

tgacgctcag tggaacgaaa actcacgtta agggattttg gtcatgagat c            4431
```

```
<210> SEQ ID NO 62
<211> LENGTH: 2880
<212> TYPE: DNA
<213> ORGANISM: Artificial Sequence
<220> FEATURE:
<223> OTHER INFORMATION: Description of Artificial Sequence: Vector
      pUC18MFa sequence

<400> SEQUENCE: 62
```

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagcttac    240

cccttcttct ttagcagcaa tgctggcaat agtagtattt ataaacaata acccgttatt    300

tgtgctgttg gaaaatggca aaacagcaac atcgaaatcc ccttctaaat ctgagtaacc    360

gatgacagct tcagccggaa tttgtgccgt ttcatcttct gttgtagtgt tgactggagc    420

agctaatgcg gaggatgctg cgaataaaac tgcagtaaaa attgaaggaa atctcatgaa    480

ttcactggcc gtcgttttac aacgtcgtga ctgggaaaac cctggcgtta cccaacttaa    540

tcgccttgca gcacatcccc ctttcgccag ctggcgtaat agcgaagagg cccgcaccga    600

tcgcccttcc caacagttgc gcagcctgaa tggcgaatgg cgcctgatgc ggtattttct    660

ccttacgcat ctgtgcggta tttcacaccg catatggtgc actctcagta caatctgctc    720

tgatgccgca tagttaagcc agccccgaca cccgccaaca cccgctgacg cgccctgacg    780

ggcttgtctg ctcccggcat ccgcttacag acaagctgtg accgtctccg ggagctgcat    840

gtgtcagagg ttttcaccgt catcaccgaa acgcgcgaga cgaaagggcc tcgtgatacg    900

cctattttta taggttaatg tcatgataat aatggtttct tagacgtcag gtggcacttt    960

tcggggaaat gtgcgcggaa cccctatttg tttatttttc taaatacatt caaatatgta   1020

tccgctcatg agacaataac cctgataaat gcttcaataa tattgaaaaa ggaagagtat   1080

gagtattcaa catttccgtg tcgcccttat tccctttttt gcggcatttt gccttcctgt   1140

ttttgctcac ccagaaacgc tggtgaaagt aaaagatgct gaagatcagt tgggtgcacg   1200

agtgggttac atcgaactgg atctcaacag cggtaagatc cttgagagtt ttcgccccga   1260
```

-continued agaacgtttt ccaatgatga gcacttttaa agttctgcta tgtggcgcgg tattatcccg 1320
tattgacgcc gggcaagagc aactcggtcg ccgcatacac tattctcaga atgacttggt 1380
tgagtactca ccagtcacag aaaagcatct tacggatggc atgacagtaa gagaattatg 1440
cagtgctgcc ataaccatga gtgataacac tgcggccaac ttacttctga caacgatcgg 1500
aggaccgaag gagctaaccg cttttttgca caacatgggg gatcatgtaa ctcgccttga 1560
tcgttgggaa ccggagctga atgaagccat accaaacgac gagcgtgaca ccacgatgcc 1620
tgtagcaatg gcaacaacgt tgcgcaaact attaactggc gaactactta ctctagcttc 1680
ccggcaacaa ttaatagact ggatggaggc ggataaagtt gcaggaccac ttctgcgctc 1740
ggcccttccg gctggctggt ttattgctga taaatctgga gccggtgagc gtgggtctcg 1800
cggtatcatt gcagcactgg ggccagatgg taagccctcc cgtatcgtag ttatctacac 1860
gacggggagt caggcaacta tggatgaacg aaatagacag atcgctgaga taggtgcctc 1920
actgattaag cattggtaac tgtcagacca agtttactca tatatacttt agattgattt 1980
aaaacttcat ttttaattta aaaggatcta ggtgaagatc ctttttgata atctcatgac 2040
caaaatccct taacgtgagt tttcgttcca ctgagcgtca gaccccgtag aaaagatcaa 2100
aggatcttct tgagatcctt tttttctgcg cgtaatctgc tgcttgcaaa caaaaaaacc 2160
accgctacca gcggtggttt gtttgccgga tcaagagcta ccaactcttt ttccgaaggt 2220
aactggcttc agcagagcgc agataccaaa tactgtcctt ctagtgtagc cgtagttagg 2280
ccaccacttc aagaactctg tagcaccgcc tacatacctc gctctgctaa tcctgttacc 2340
agtggctgct gccagtggcg ataagtcgtg tcttaccggg ttggactcaa gacgatagtt 2400
accggataag gcgcagcggt cgggctgaac ggggggttcg tgcacacagc ccagcttgga 2460
gcgaacgacc tacaccgaac tgagatacct acagcgtgag ctatgagaaa gcgccacgct 2520
tcccgaaggg agaaaggcgg acaggtatcc ggtaagcggc agggtcggaa caggagagcg 2580
cacgagggag cttccagggg gaaacgcctg gtatctttat agtcctgtcg ggtttcgcca 2640
cctctgactt gagcgtcgat ttttgtgatg ctcgtcaggg gggcggagcc tatggaaaaa 2700
cgccagcaac gcggcctttt tacggttcct ggccttttgc tggccttttg ctcacatgtt 2760
ctttcctgcg ttatcccctg attctgtgga taaccgtatt accgcctttg agtgagctga 2820
taccgctcgc cgcagccgaa cgaccgagcg cagcgagtca gtgagcgagg aagcggaaga 2880

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: 6X-His tag

<400> SEQUENCE: 63

His His His His His His
1 5

<210> SEQ ID NO 64
<211> LENGTH: 5
<212> TYPE: PRT
<213> ORGANISM: Hepatitis C virus

<400> SEQUENCE: 64

Val Ile Glu Gly Arg
1 5

-continued

```
<210> SEQ ID NO 65
<211> LENGTH: 4
<212> TYPE: PRT
<213> ORGANISM: Hepatitis C virus

<400> SEQUENCE: 65

Asn Asn Ser Ser
  1
```